US012203932B2

(12) United States Patent
Marvin et al.

(10) Patent No.: US 12,203,932 B2
(45) Date of Patent: *Jan. 21, 2025

(54) GENETICALLY ENCODED BIOSENSORS

(71) Applicant: Howard Hughes Medical Institute, Chevy Chase, MD (US)

(72) Inventors: Jonathan S. Marvin, Arlington, VA (US); Loren Looger, Sterling, VA (US)

(73) Assignee: Howard Hughes Medical Institute, Chevy Chase, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 18/322,480

(22) Filed: May 23, 2023

(65) Prior Publication Data
US 2024/0085411 A1  Mar. 14, 2024

Related U.S. Application Data

(60) Continuation of application No. 17/515,289, filed on Oct. 29, 2021, now Pat. No. 11,698,374, which is a division of application No. 16/902,160, filed on Jun. 15, 2020, now Pat. No. 11,162,942, which is a continuation of application No. 16/002,697, filed on Jun. 7, 2018, now Pat. No. 10,684,282, which is a continuation-in-part of application No. 15/904,574, filed on Feb. 26, 2018, now Pat. No. 10,060,920, which is a division of application No. 15/664,326, filed on Jul. 31, 2017, now Pat. No. 9,939,437, which is a division of application No. 14/350,199, filed as application No. PCT/US2012/059219 on Oct. 8, 2012, now Pat. No. 9,719,992.

(60) Provisional application No. 61/544,867, filed on Oct. 7, 2011.

(51) Int. Cl.
G01N 33/557 (2006.01)
C07K 14/195 (2006.01)
C07K 14/245 (2006.01)
C07K 14/435 (2006.01)
G01N 33/58 (2006.01)
G01N 33/68 (2006.01)

(52) U.S. Cl.
CPC ......... *G01N 33/557* (2013.01); *C07K 14/195* (2013.01); *C07K 14/245* (2013.01); *C07K 14/43595* (2013.01); *G01N 33/582* (2013.01); *G01N 33/68* (2013.01); *G01N 33/6812* (2013.01); *C07K 2319/20* (2013.01); *C07K 2319/24* (2013.01); *C07K 2319/60* (2013.01); *G01N 2400/00* (2013.01); *G01N 2458/00* (2013.01)

(58) Field of Classification Search
CPC .................................................. C07K 14/195
See application file for complete search history.

(56) References Cited

U.S. PATENT DOCUMENTS

| | | |
|---|---|---|
| 6,133,502 A | 10/2000 | Kasuga et al. |
| 6,175,057 B1 | 1/2001 | Mucke et al. |
| 6,180,849 B1 | 1/2001 | Streuli et al. |
| 9,719,992 B2 | 8/2017 | Marvin et al. |
| 9,939,437 B2 | 4/2018 | Marvin et al. |
| 10,060,920 B2 | 8/2018 | Marvin et al. |
| 10,345,297 B2 | 7/2019 | Marvin et al. |
| 2004/0118681 A1 | 6/2004 | Hellinga et al. |
| 2015/0111222 A1 | 4/2015 | Marvin et al. |
| 2018/0017553 A1 | 1/2018 | Marvin et al. |
| 2018/0209972 A1 | 7/2018 | Marvin et al. |
| 2018/0372738 A1 | 12/2018 | Marvin et al. |
| 2019/0331678 A1 | 10/2019 | Marvin et al. |

FOREIGN PATENT DOCUMENTS

| | | |
|---|---|---|
| WO | WO 2006/044612 | 4/2006 |
| WO | WO 2006/110728 | 10/2006 |

OTHER PUBLICATIONS

Andrade and Wei et al., "Adsorption of complex proteins at interfaces," Pure and Appl. Chem., 1992, 64(11):1777-1781.
Baird et al.,"Circular permutation and receptor insertion within green fluorescent proteins," Proc. Natl. Acad. Sci., USA, 1999, 96: 11241-11246.
Bao et al., "Exocytotic fusion pores are composed of both lipids and proteins.", Nat. Struct. Biol., 23: 67-73, 2016.
Belousov et al., "Genetically encoded fluorescent indicator for intracellular hydrogen peroxide," Nat. Methods, 2006, 3: 281-286.
Berg et al., "A genetically encoded fluorescent reporter of ATP:ADP ratio," Nat. Methods., 2009, 105: 365-370.
Bloom et al., "Protein stability promotes evolvability," Proc. Natl. Acad. Sci., 2006, 103: 5869-5874.
Bogner and Ludewig, "Visualization of arginine influx into plant cells using a specific FRET-sensor," J. Fluoresc., 2007, 17: 350-360.
Borghuis et al., "Two-photon imaging of nonlinear glutamate release dynamics at bipolar cell synapses in the mouse retina.", J. Neurosci., 33: 10972-85, 2013.
Brinster et al., "Expression of a microinjected immunoglobulin gene in the spleen of transgenic mice," Nature, 1983, 306: 332-336.
Brunert et al., "Cell-Type-Specific Modulation of Sensory Responses in Olfactory Bulb Circuits by Serotonergic Projections from the Raphe Nuclei.", J. Neurosci., 36: 6820-35, 2016.
Choi et al., "Evolutionary conservation in multiple faces of protein interaction," Proteins, 2009, 77(1): 14-25.
Cubitt et al., "Understanding, improving and using green fluorescent proteins," Trends Biochem., 1995, 20: 448-455.
Cuneo et al., "The crystal structure of a thermophilic glucose binding protein reveals adaptations that interconvert mono and di-saccharide binding sites," J. Mol. Biol., 2006, 362: 259-270.

(Continued)

*Primary Examiner* — Suzanne M Noakes
(74) *Attorney, Agent, or Firm* — Fish & Richardson P.C.

(57) ABSTRACT

The present disclosure provides, inter alia, genetically encoded recombinant peptide biosensors comprising analyte-binding framework portions and signaling portions, wherein the signaling portions are present within the framework portions at sites or amino acid positions that undergo a conformational change upon interaction of the framework portion with an analyte.

36 Claims, 97 Drawing Sheets

Specification includes a Sequence Listing.

(56) References Cited

OTHER PUBLICATIONS

Deuschle et al., "Construction and optimization of a family of genetically encoded metabolite sensors by semirational protein engineering," Protein Sci, 2005, 14: 2304-2314.

Deuschle et al., "Genetically encoded sensors for metabolites," Cytometry, 2005, 64: 3-9.

Dodge et al., "Co-operative action a calcium ions in transmitter release at the neuromuscular junction.", J. Physiol., 193: 419-32, 1967.

Dwyer and Hellinga, "Periplasmic binding proteins: a versatile superfamily for protein engineering," Curr. Opin. Struc. Biol., 2004, 14: 495-504.

Enger et al., "Dynamics of Ionic Shifts in Cortical Spreading Depression.", Cerebral Cortex, 25: 4469-76, 2015.

Evdokimov et al., "Structural basis for oligosaccharide recognition by Pyrococcus furiosus maltodextrin-binding protein," J. Mol. Biol., 2001, 305: 891-904.

Fallon and Quiocho, "A closed compact structure of native Ca(2+)-calmodulin," Structure, 2003, 11: 1303-1307.

Fan et al., "A periplasmic glutamate/aspartate binding protein from Shigella flexneri: Gene cloning, over-expression, purification and preliminary crystallographic studies of the recombinant protein," Protein Pept. Lett., 2006, 13:513-516.

Frommer et al., "Genetically encoded biosensors based on engineered fluorescent proteins," Chem. Soc. Rev., 2009, 38: 2833-2841.

Gautam et al., "Exploration of fluorescent protein voltage probes based on circularly permuted fluorescent proteins," Frontiers in Neuroengineering, 2009, 2(14): 1-8.

Gong et al., "Extracting consistent knowledge from highly inconsistent cancer gene data sources," BMC: Bioinformatics, 2010, 11: 76, 8 pages.

Gong et al., "Analysis and verification of the HMGB1 signaling pathway", BMC: Bioinformatics, 6: 1471-2105, 2010.

Gu et al., "A novel analytical method for in vivo phosphate tracking," FEBS Letters, 2006, 580: 5885-5893.

Guntas and Mansell, "Directed evolution of protein switches and their application to the creation of ligand-binding proteins," Proc. Natl. Acad. Sci., 2005, 102: 11224-11229.

Guntas and Ostermeier, "Creation of an allosteric enzyme by domain insertion," J. Mol. Biol., 2004, 336: 263-273.

Guntas et al., "A molecular switch created by in vitro recombination of nonhomologous genes," Chem. Biol., 2004, 11: 1483-1487.

International Preliminary Report on Patentability in International Application No. PCT/US2012/059219, mailed Apr. 17, 2014, 11 pages.

International Search Report and Written Opinion in International Application No. PCT/US2012/059219, mailed Jun. 10, 2013, 18 pages.

Invitation to Pay Additional Fees in International Application No. PCT/US2012/059219, 2013.

Jaeger et al., "Improved predictions of secondary structures for RNA," Proc. Natl. Acad. Sci. USA, 1989, 86: 7706-10.

Jiang et al., "Dysfunctional Calcium and Glutamate Signaling in Striatal Astrocytes from Huntington's Disease Model Mice.", J. Neurosci., 36: 3453-70, 2016.

Kazemipour et al., "Fast and Stable Signal Deconvolution via Compressible State-Space Models", 65(1): 74-86, 2018.

Kim and Ostermeier, "Modulation of effector affinity by hinge region mutations also modulates switching activity in an engineered allosteric TEM1 beta-lactamase switch," Arch. Biochem. Biophys., 2006, 446: 44-51.

Kuboniwa et al., "Solution structure of calcium-free calmodulin," Nat. Struc. Biol., 1996, 2: 768-776.

Markwardt et al., "An improved cerulean fluorescent protein with enhanced brightness and reduced reversible photoswitching," PLoS ONE, 2011, 6(3) e17896, 11 pages.

Martineau et al., "Genetic approach to the role of tryptophan residues in the activities and fluorescence of a bacterial periplasmic maltose-binding protein," J. Mol. Biol., 1990, 214: 337-352.

Marvin and Hellinga, "Manipulation of ligand binding affinity by exploitation of conformational coupling," Nat. Struc. Biol., 2001, 8: 795-798.

Marvin et al., "The rational design of allosteric interactions in a monomeric protein and its applications to the construction of biosensors," Proc. Natl. Acad. Sci. USA, 1997, vol. 94, pp. 4366-4371.

Marvin et al., "An optimized fluorescent probe for visualizing glutamate neurotransmission.", Nat. Methods, 10: 162-70, 2013.

Marvin, J.S. & Hellinga, H.W., "Engineering Biosensors by Introducing Fluorescent Allosterc Signal Transducers: Construction of a Novel Glucose Sensor", J. Am. Chem. Soc. 1998, 120, 7-11.

Mena et al., "Blue fluorescent proteins with enhanced brightness and photostability from a structurally targeted library.", Nat. Biotech., 24: 1569-71, 2006.

Nagai et al., "A variant of yellow fluorescent protein with fast and efficient maturation for cell-biological applications.", Nat. Biotech., 20: 87-90, 2002.

Nakai et al., "A high signal-to-noise Ca(2+) probe composed of a single green fluorescent protein," Nat. Biotechno., 2001, 19: 137-141.

Nausch et al., "Differential patterning of cGMP in vascular smooth muscle cells revealed by single GFP-linked biosensors," Proc. Natl. Acad. Sci. USA., 2008, 105: 365-370.

NCBI Reference Sequence: NP_290668.1, 2013, 2 pages.

O'Herron et al., "Neural correlates of single-vessel haemodynamic responses in vivo.", Nature, 534: 378-82, 2016.

Okumoto et al., "Detection of glutamate release from neurons by genetically encoded surface-displayed FRET nanosensors," Proc. Natl. Acad. Sci. USA., 2005, 102: 8740-8745.

Okumoto, "Imaging approach for monitoring cellular metabolites and ions using genetically encoded biosensors," Curr. Opin. Biotechnol., 2010, 21: 45-54.

Ouiocho et al., "Atomic structure and specificity of bacterial periplasmic receptors for active transport and chemotaxis: variation of common themes", Mol. Microbial., 20: 17-225, 1996.

Ouiocho et al., "Extensive features of tight oligosaccharide binding revealed in high-resolution structures of the maltodextrin transport/ chemosensory receptor.", Structure, 5: 997-1015, 1997.

Park et al., "Excitatory synaptic inputs to mouse on-off direction-selective retinal ganglion cells lack direction tuning.", J. Neurosci., 34: 3976-81, 2014.

Pedelacq et al., "Engineering and characterization of a superfolder green fluorescent protein.", Nature Biotechnol., 24: 79-88, 2006.

Peirce, "PsychoPy—Psychophysics software in Python.", J. Neurosci. Methods, 162: 8-13, 2007.

Quiocho and Ledvina, "Atomic structure and specificity of bacterial periplasmic receptors for active transport and chemotaxis: variation of common themes," Mol. Microbiol., 1996, 20: 17-25.

Quiocho et al., "Extensive features of tight oligosaccharide binding revealed in high-resolution structures of the maltodextrin transport/ chemosensory receptor," Structure, 1997, 5: 997-1015.

Raj-Ahmad et al., "Development of a helper-independent human adenovirus vector and its use in the transfer of the herpes simplex virus thymidine kinase gene.", J. Virology 57: 267-74, 1986.

Rosa et al., "Neuron-glia signaling in developing retina mediated by neurotransmitter spillover", eLife, 4: 728, 2015.

Schindelin et al., "Fiji: an open-source platform for biological-image analysis.", Nat. Methods, 9: 676-82, 2012.

Shaner et al., "Advances in fluorescent protein technology," J. Cell. Sci., 2007, 120: 4247-4260.

Sharff et al., "Crystallographic evidence of a large ligand-induced hinge-twist motion between the two domains of the maltodextrin binding protein involved in active transport and chemotaxis," Biochemistry, 1992, 31: 10657-10663.

Tainaka et al., "Design Strategies of Fluorescent Biosensors Based on Biological Macromolecular Receptors," Sensors, 2010, 10(2): 1355-1376.

Tang et al., "Developing compact multiphoton systems using femtosecond fiber lasers.", J. Biomed. Optics, 14: 030508, 2009.

(56) References Cited

OTHER PUBLICATIONS

Tian et al., "Imaging neural activity in worms, flies and mice with improved GCaMP calcium indicators," Nat. Methods, 2009, 6: 875-881.
Topell and Glockshuber, "Circular permutation of the green fluorescent protein," Methods in Molecular Biology, 2002, 183: 31-48.
Van Beugen et al., "High frequency burst firing of granule cells ensures transmission at the parallel fiber to purkinje cell synapse at the cost of temporal coding.", Frontiers in Neural Circuits, 7: 95, 2013.
Woitecki et al., "Identification of Synaptotagmin 10 as Effector of NPAS4-Mediated Protection from Excitotoxic Neurodegeneration.", J. Neurosci., 36: 2561-70, 2016.
Xie et al., "Resolution of High-Frequency Mesoscale Intracortical Maps Using the Genetically Encoded Glutamate Sensor iGluSnFR.", J. Neurosci., 36: 1261-72, 2016.
Zhang et al., "Creating new fluorescent probes for cell biology," Nat Rev Mol Cell Biol., 2002, 3: 906-908.

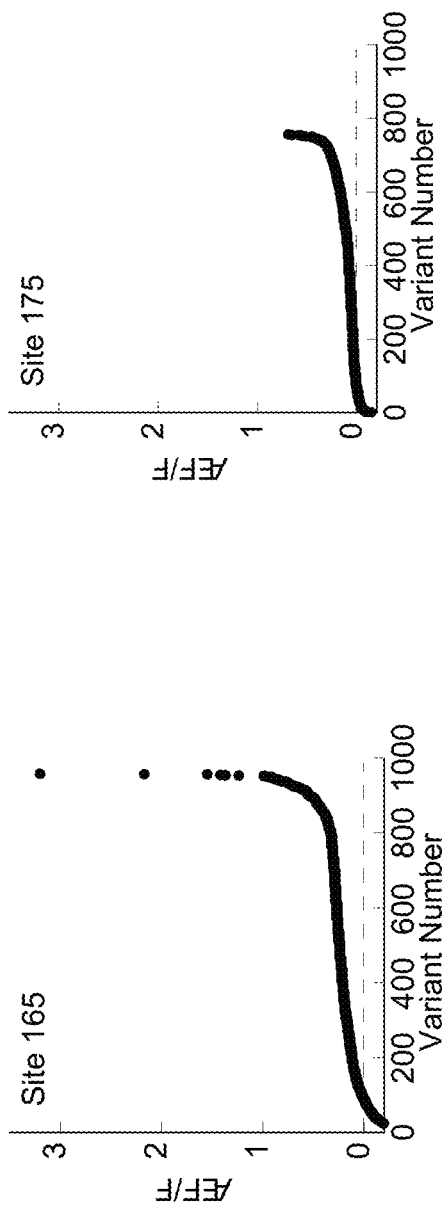
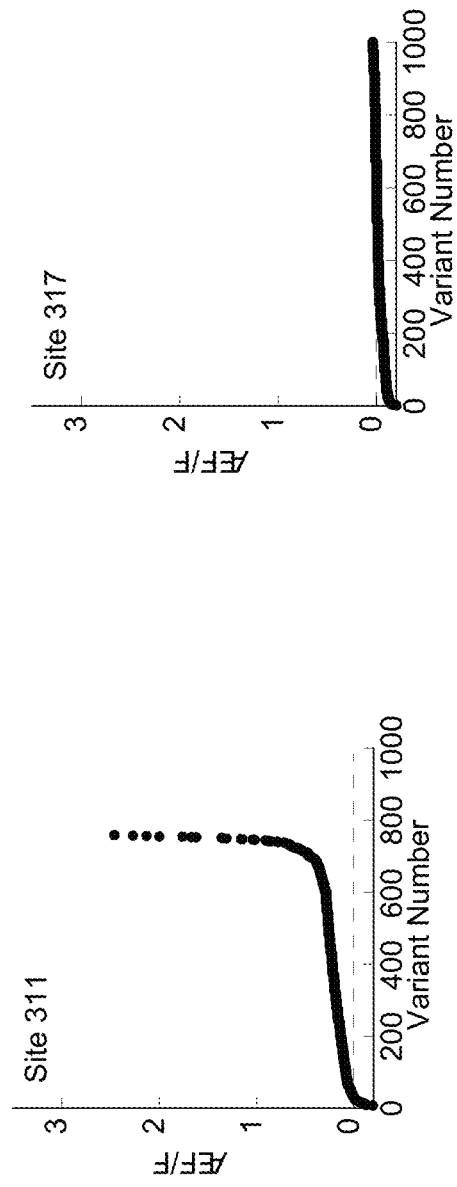
FIG. 11A
FIG. 11B
FIG. 11C
FIG. 11D

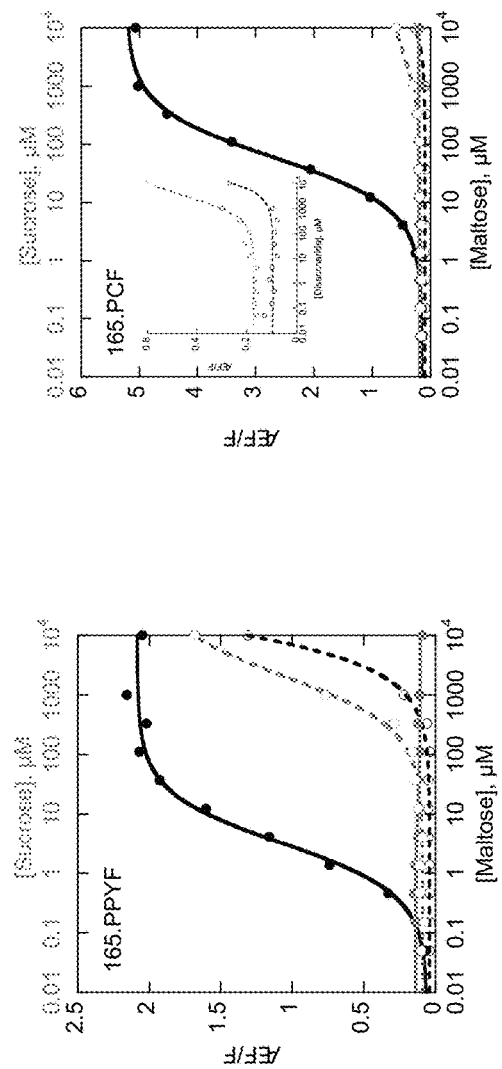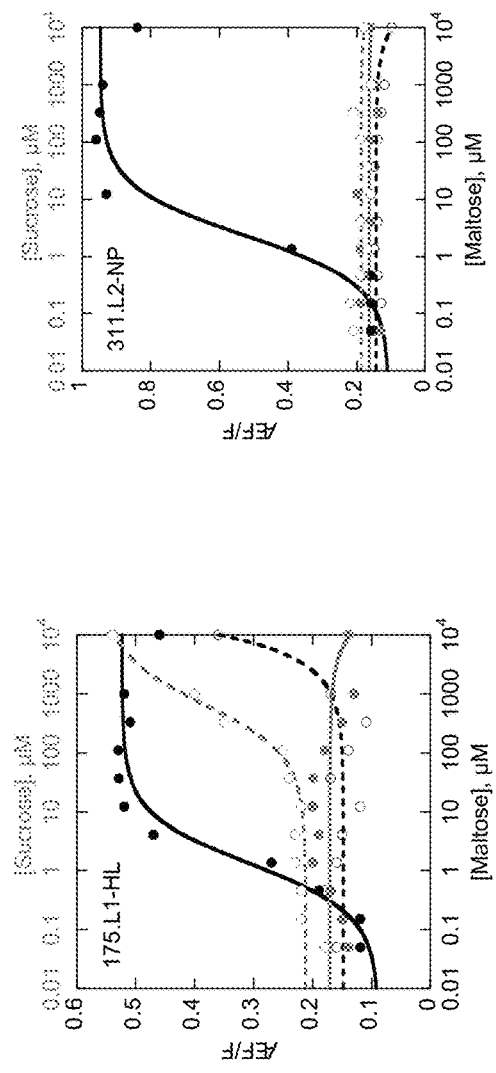
FIG. 14A  FIG. 14B  FIG. 14C  FIG. 14D

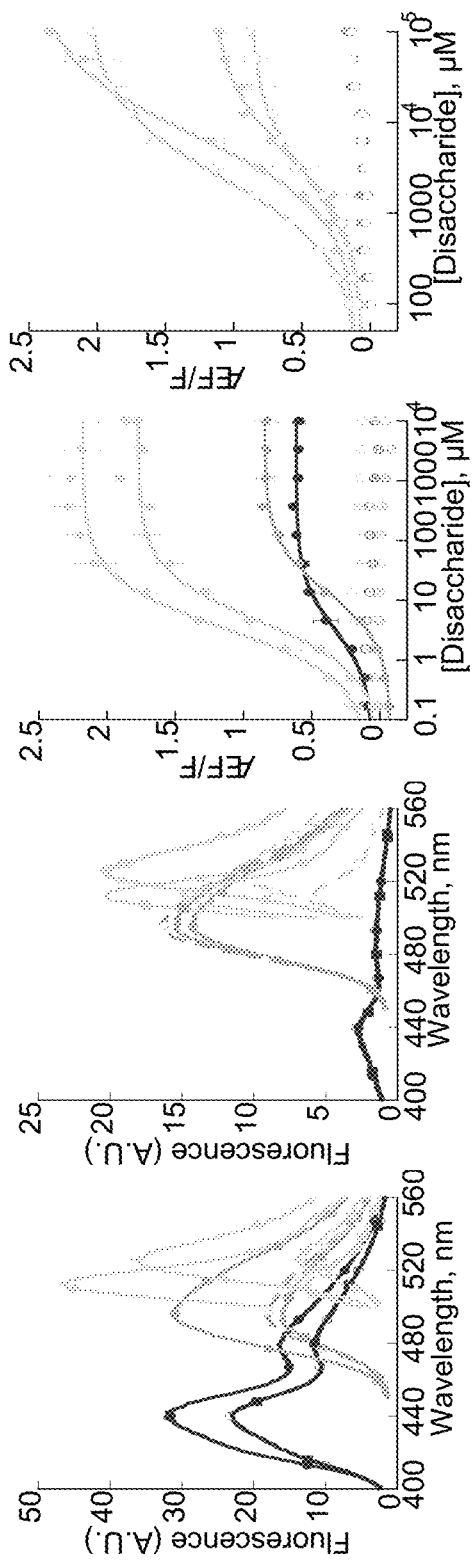

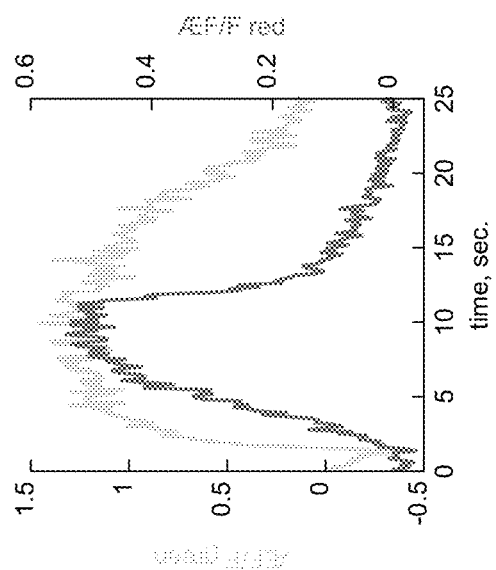
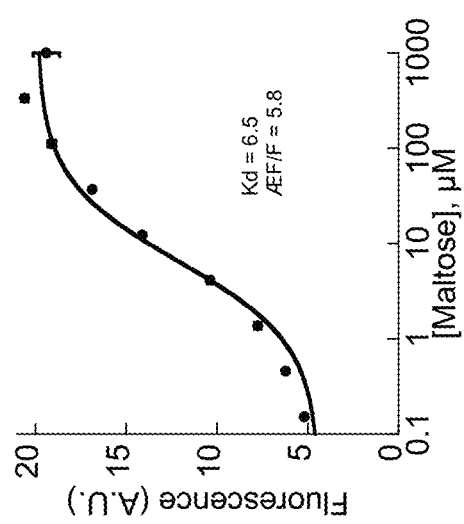
FIG. 21A
FIG. 21B

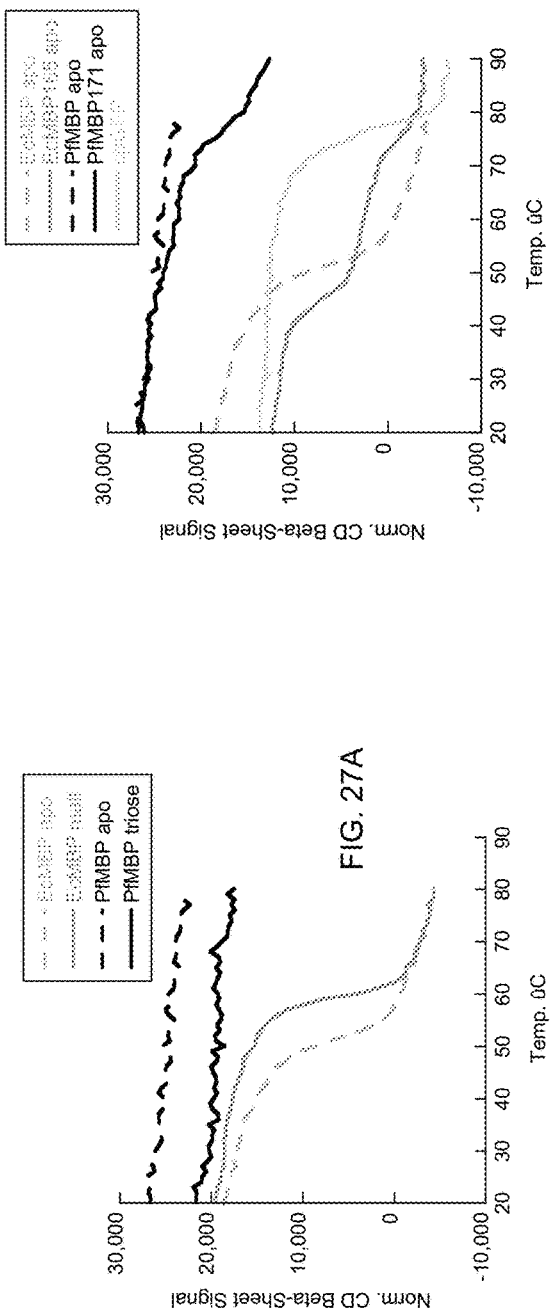
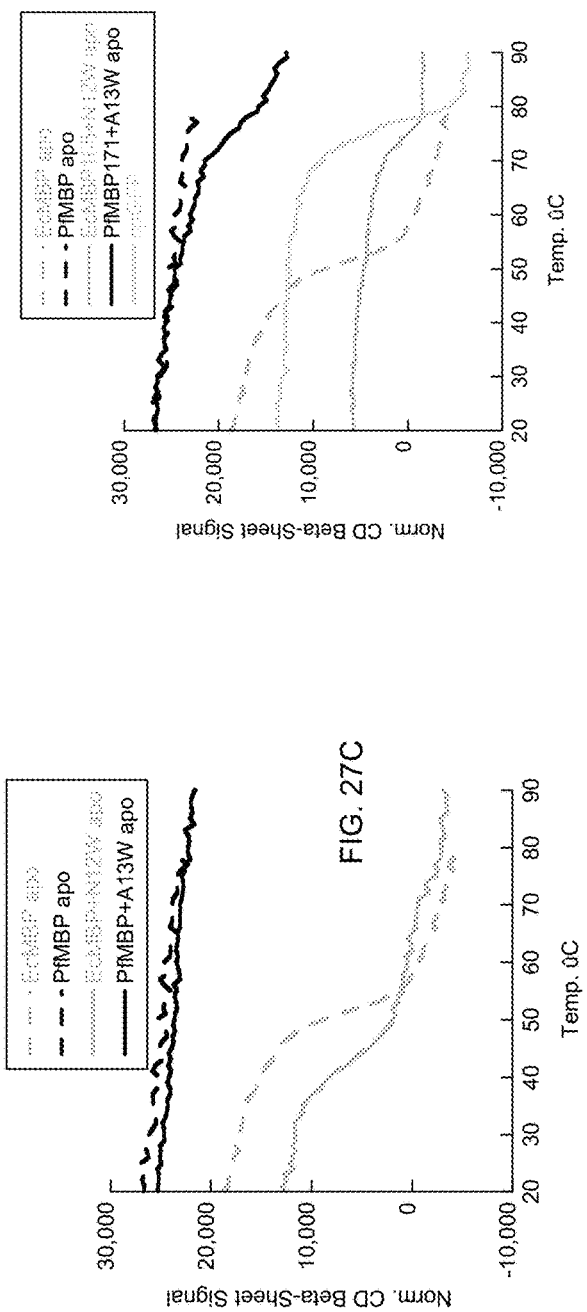
FIG. 27A
FIG. 27B
FIG. 27C
FIG. 27D

MKIKTGARIL ALSALTTMMF SASALAKIEE GKLVIWINGD
KGYNGLAEVG KKFEKDTGIK VTVEHPDKLE EKFPQVAATG
DGPDIIFWAH DRFGGYAQSG LLAEITPDKA FQDKLYPFTW
DAVRYNGKLI AYPIAVEALS LIYNKDLLPN PPKTWEEIPA
LDKELKAKGK SALMFNLQEP YFTWPLIAAD GGYAFKYENG
KYDIKDVGVD NAGAKAGLTF LVDLIKNKHM NADTDYSIAE
AAFNKGETAM TINGPWAWSN IDTSKVNYGV TVLPTFKGQP
SKPFVGVLSA GINAASPNKE LAKEFLENYL LTDEGLEAVN
KDKPLGAVAL KSYEEELAKD PRIAATMENA QKGEIMPNIP
QMSAFWYAVR TAVINAASGR QTVDEALKDA QTRITK

FIG. 41

```
MRRATYAFAL LAILVLGVVA SGCIGGGTTT
PTQTSPATQP TTTQTPTQTE TQAVECGSGK
VVIWHAMQPN ELEVFQSLAE EYMALCPEVE
IVFEQKPNLE DALKAAIPTG QGPDLFIWAH
DWIGKFAEAG LLEPIDEYVT EDLLNEFAPM
AQDAMQYKGH YYALPFAAET VAIIYNKEMV
SEPPKTFDEM KAIMEKYYDP ANEKYGIAWP
INAYFISAIA QAFGGYYFDD KTEQPGLDKP
ETIEGFKFF TEIWPYMAPT GDYNTQQSIF
LEGRAPMMVN GPWSINDVKK AGINFGVVPL
PPIIKDGKEY WPRPYGGVKL IYFAAGIKNK
DAAWKFAKWL TTSEESIKTL ALELGYIPVL
TKVLDDPEIK NDPVIYGFGQ AVQHAYLMPK
SPKMSAVWGG VDGAINEILQ DPQNADIEGI
LKKYQQEILN NMQG
```

FIG. 42

MNAKIIASLA FTSMFSLSTL LNPAYAEEQE
KALNFGIIST ESQQNLKPQW TPFLQDMEKK
LGVKVNAFFA PDYAGIIQGM RFNKVDIAWY
GNLSAMEAVD RANGQVFAQT VAADGSPGYW
SVLIVNKDSP INNLNDLLAK RKDLTFGNGD
PNSTSGFLVP GYYVFAKNNI SASDEKRTVN
AGHETNALAV ANKQVDVATN NTENLDKLKT
SAPEKLKELK VIWKSPLIPG DPIWRKNLS
ETTKDKIYDF FMNYGKTPEE KAVLERLGWA
PFRASSDLQL VPIRQLALFK EMQSVKDNKG
LNEQDKLAKT TAIQAQLDDL DRLNNALSAM
SSVSKAVQ

FIG. 43

MQLRKPATAI LALALSAGLA QADDAAPAAG
STLDKIAKNG VIVVGHRESS VPFSYYDNQQ
KVVGYSQDYS NAIVEAVKKK LNKPDLQVKL
IPITSQNRIP LLQNGTFDFE CGSTTNNVER
QKQAAFSDTI FVVGTRLLTK KGGDIKDFAN
LKDKAVVVTS GTTSEVLLNK LNEEQKMNMR
IISAKDHGDS FRTLESGRAV AFMMDDALLA
GERAKAKKPD NWEIVGKPQS QEAYGCMLRK
DDPQFKKLMD DTIAQVQTSG EAEKWFDKWF
KNPIPPKNLN MNFELSDEMK ALFKEPNDKA
LN

FIG. 44

```
MRKWLLAIGM VLGLSALAQG GKLEIFSWWA
GDEGPALEAL IRLYKQKYPG VEVINATVTG
GAGVNARAVL KTRMLGGDPP DTFQVHAGME
LIGTWVANR  MEDLSALFRQ EGWLQAFPKG
LIDLISYKGG IWSVPVNIHR SNVMWYLPAK
LKEWGVNPPR TWDEFLATCQ TLKQKGLEAP
LALGENWTQQ HLWESVALAV LGPDDWNNLW
NGKLKFTDPK AVRAWEVFGR VLDCANKDAA
GLSWQQAVDR VVQGKAAFNV MGDWAAGYMT
TTLKLKPGTD FAWAPSPGTQ GVFMMLSDSF
GLPKGAKNRQ NAINWLRLVG SKEGQDTFNP
LKGSIAARLD SDPSKYNAYG QSAMRDWRSN
RIVGSLVHGA VAPESFMSQF GTVMEIFLQT
RNPQAAANAA QAIADQVGLG RLGQ
```

FIG. 45

MIRTLSLKFM LAGAVCMATL TAGSAFAAEP
ESCGTVRFSD VGWTDITATT ATATTILEAL
GYETDVKVLS VPVTYTSLKN KDIDVFLGNW
MPTMEADIAP YREDKSVETV RENLAGAKYT
LATNAKGAEL GIKDFKDIAA HKDELDGKIY
GIEPGNDGNR LIIDMVEKGT FDLKGFEVVE
SSEQGMLAQV ARAEKSGDPI VFLGWEPHPM
NANFKLTYLS GGDDVFGPNY GGATVHTNVR
AGYTTECPNV GKLLQNLSFS LQMENEIMGK
ILNDGEDPEK AAAAWLKDNP QSIEPWLSGV
ATKDGGDGLA AVKAALGL

FIG. 46

MGGGRSTETS SSSGGDGGAT KKKVVVGTDA
AFAPFEYMQK GKIVGFDVDL LDAVMKAAGL
DYELKNIGWD PLFASLQSKE VDMGISGITI
TDERKQSYDF SDPYFEATQV ILVKQGSPVK
NALDLKGKTI GVQNATTGQE AAEKLFGKGP
HIKKFETTVV AIMELLNGGV DAVITDNAVA
NEYVKNNPNK KLQVIEDPKN FASEYYGMIF
PKNSELKAKV DEALKNVINS GKYTEIYKKW
FGKEPKLDRL

FIG. 47

MKKSLLSAVA LTAMVAFGGS AWADVVIAVG
APLTGPNAAF GAQIQKGAEQ AAKDINAAGG
INGEQIKIVL GDDVSDPKQG ISVANKFVAD
GVKFVVGHFN SGVSIPASEV YAENGILEIT
PAATNPVFTE RGLWNTFRTC GRDDQQGGIA
GKYLADHEKD AKVAIIHDKT PYGQGLADET
KKAANAAGVT EVMYEGVNVG DKDFSALISK
MKEAGVSIIY WGGLHTEAGL IIRQAADQGL
KAKLVSGDGI VSNELASIAG DAVEGTLNTF
GPDPTLRPEN KELVEKFKAA GFNPEAYTLY
SYAAMQAIAG AAKAAGSVEP EKVAEALKKG
SFPTALGEIS FDEKGDPKLP GYVMYEWKKG
PDGKFTYIQQ

FIG. 48

MNIKGKALLA GCIALAFSNM ALAEDIKVAV
VGAMSGPVAQ YGDQEFTGAE QAVADINAKG
GIKGNKLQIV KYDDACDPKQ AVAVANKVVN
DGIKYVIGHL CSSSTQPASD IYEDEGILMI
TPAATAPELT ARGYQLILRT TGLDSDQGPT
AAKYILEKVK PQRIAIVHDK QQYGEGLARA
VQDGLKKGNA NVVFFDGITA GEKDFSTLVA
RLKKENIDFV YYGGYHPEMG QILRQARAAG
LKTQFMGPEG VANVSLSNIA GESAEGLLVT
KPKNYDQVPA NKPIVDAIKA KKQDPSGAFV
WTTYAALQSL QAGLNQSDDP AEIAKYLKAN
SVDTVMGPLT WDEKGDLKGF EFGVFDWHAN
GTATDAK

FIG. 49

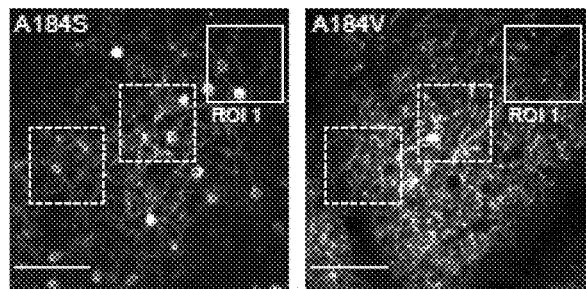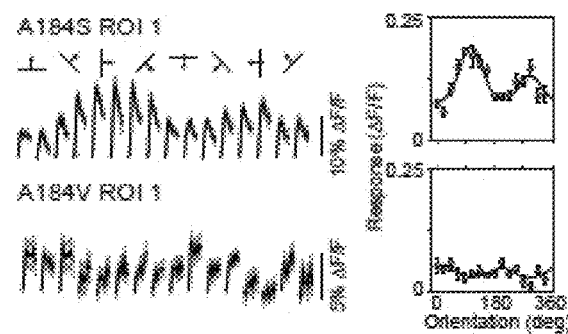
FIG. 53A | FIG. 53B
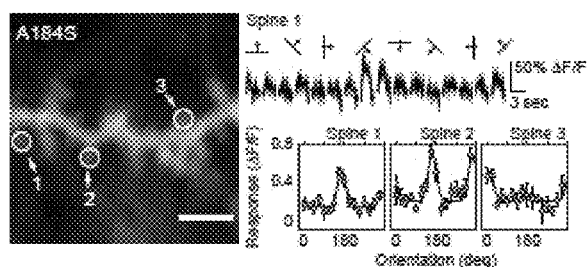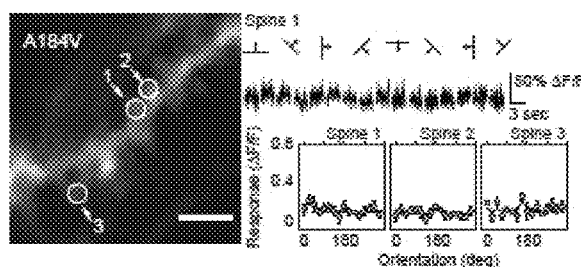
FIG. 53C | FIG. 53D FIG. 54A
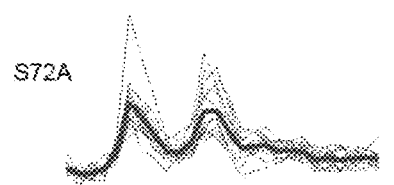
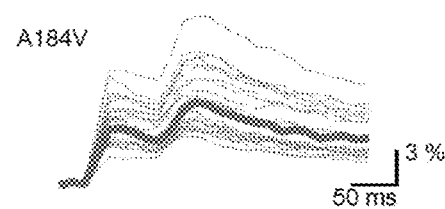
FIG. 54B
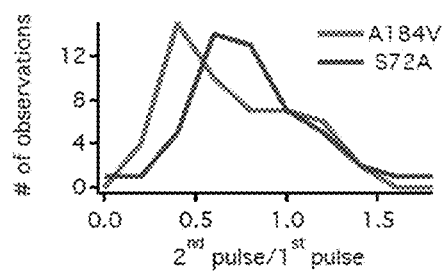

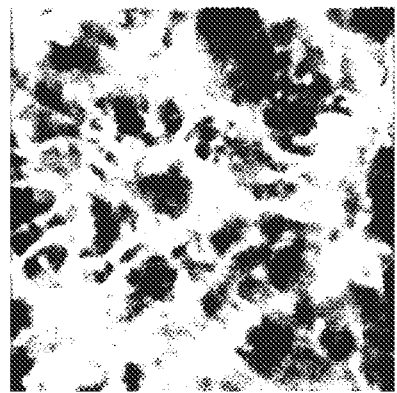
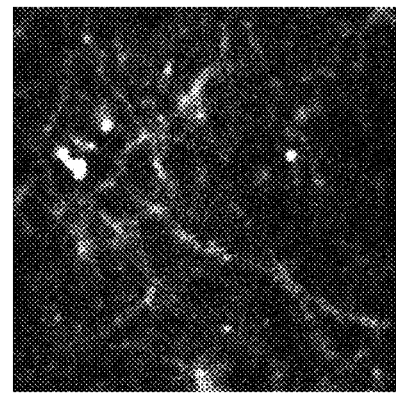
FIG. 59A  FIG. 59B
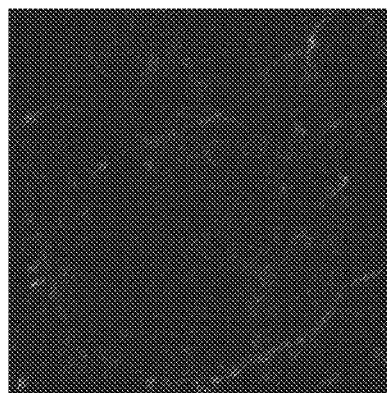
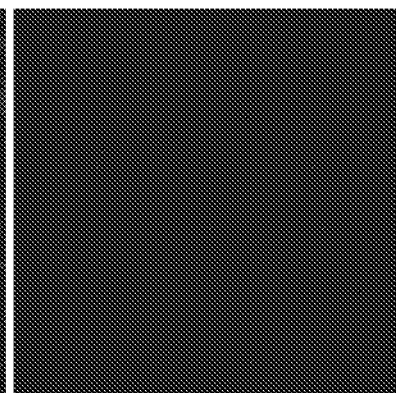
FIG. 59C  FIG. 59D FIG. 60A
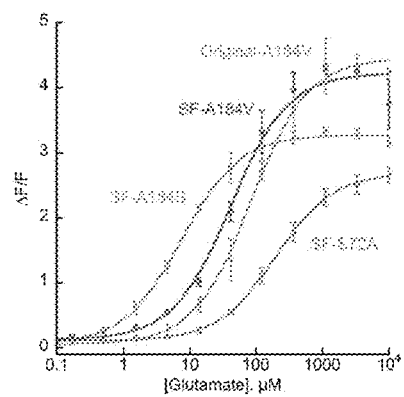
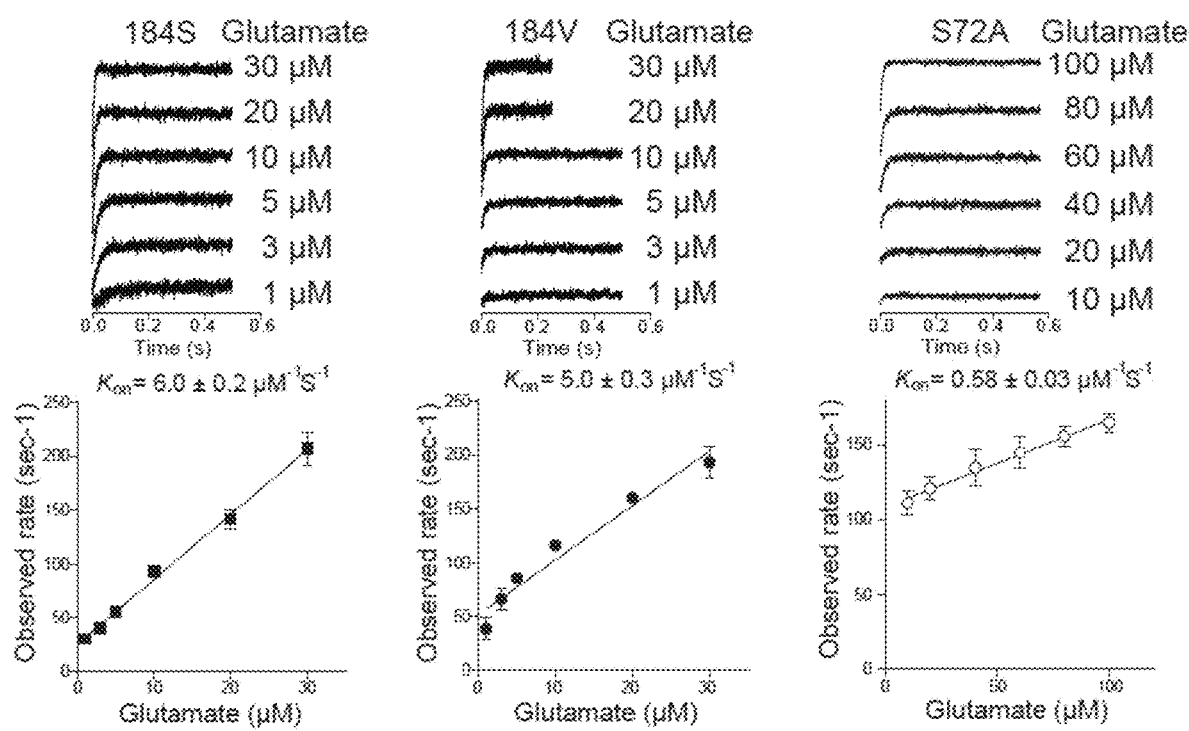
FIG. 60B

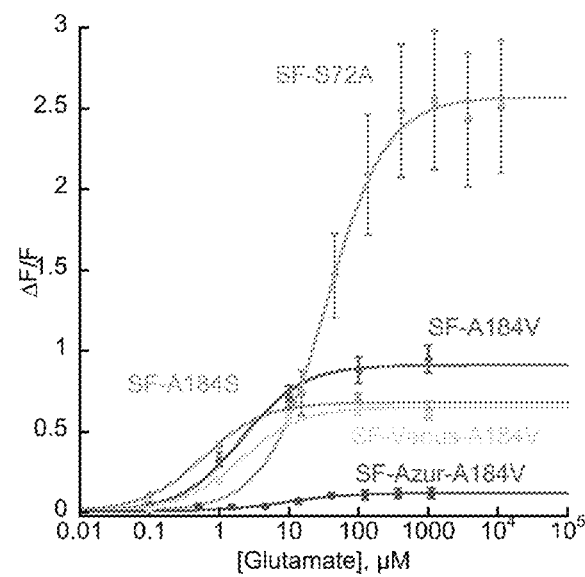
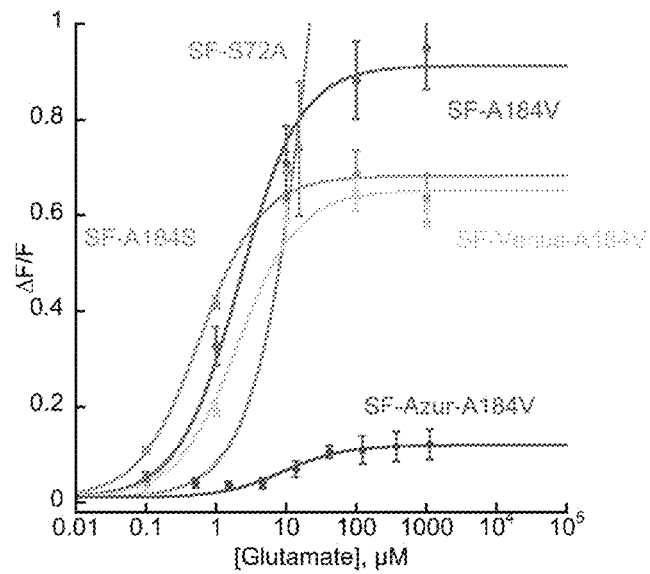
FIG. 62

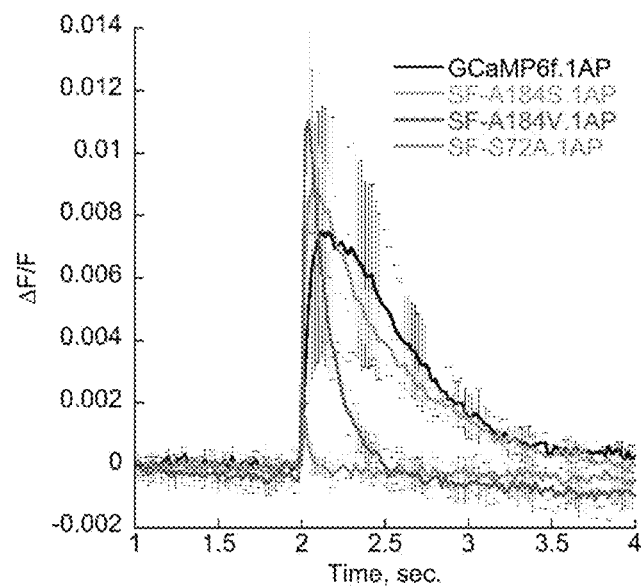
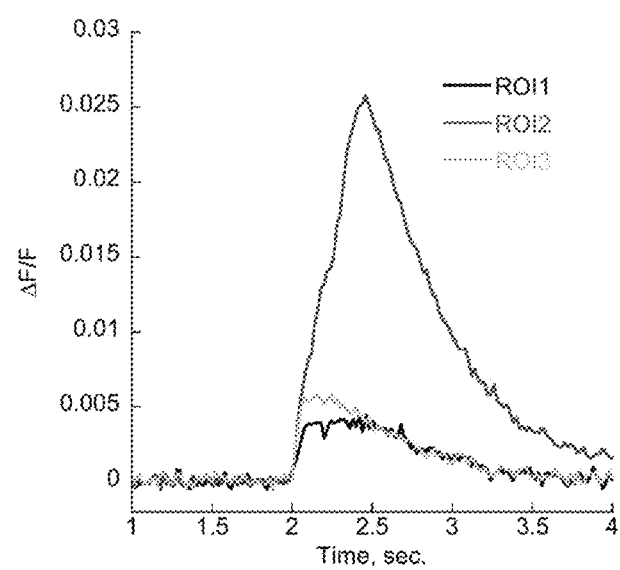
FIG. 63A

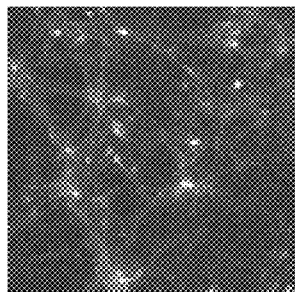 GCaMP6f
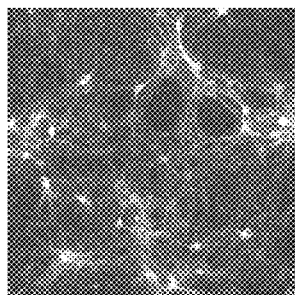 A184Sf
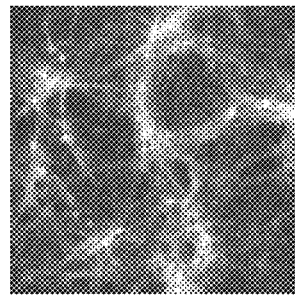 A184V
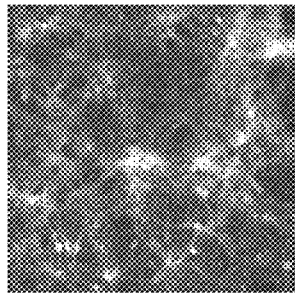 S72A
FIG. 63B

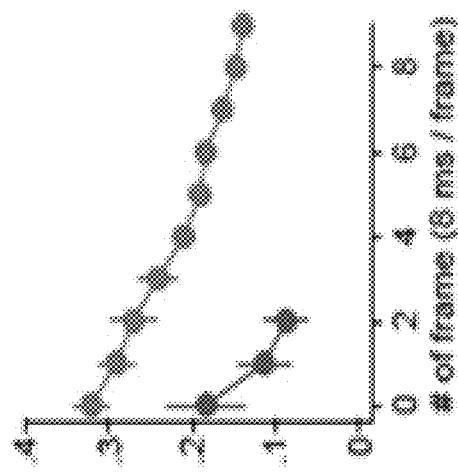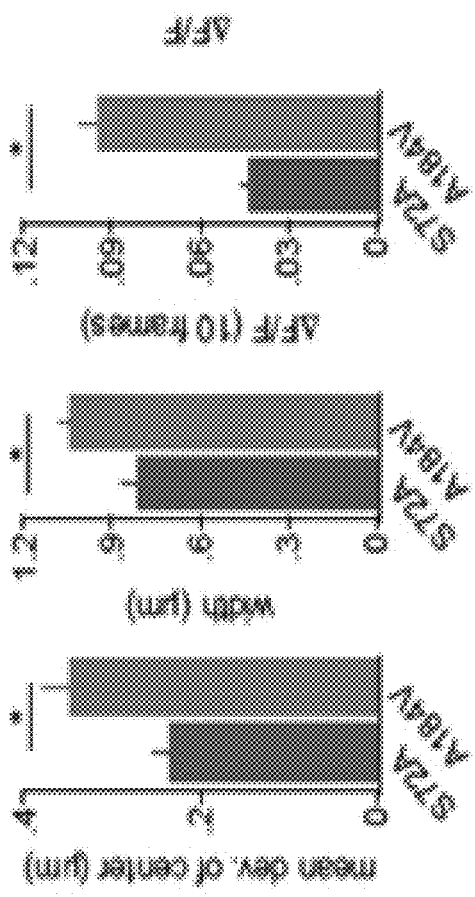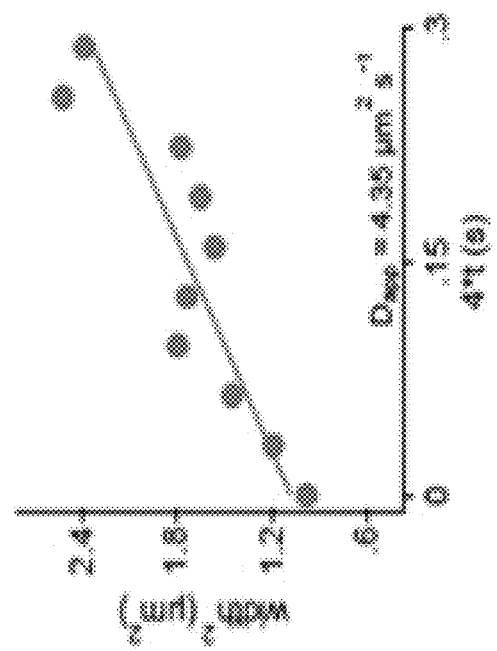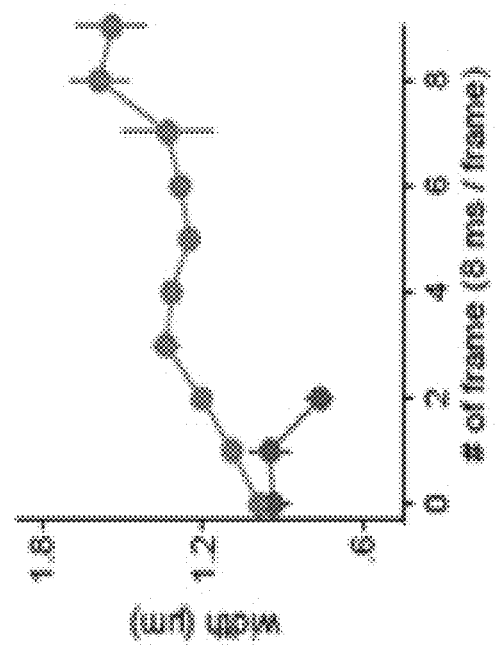
FIG. 66F  FIG. 66G  FIG. 66H  FIG. 66I  FIG. 66J IgG secretion signal
Linker
Myc epitope
PDGFR transmembrane domain 513-561

SF-iGluSnFR

METDTLLLWVLLLWVPGSTGDRS

QVDEQK
LISEEDLNAVG

QDTQEVIVVPHSLPFKVVVISAILALVVLTIISLIILIMLWQKKPR

FIG. 67A

B  SF-Venus-iGluSnFR
Mutations in GFP: T203Y and Y65G to shift the color. Mutations F46L
and S72A to increase chromophore maturation.

METDTLLLWVLLLWVPGSTGDRS

GGTGGS

QVDEQK
LISEEDLNAVG

QDTQEVIVVPHSLPFKVVVISAILALVVLTIISLIILIMLWQKKPR

FIG. 67B

SF-Azurite-iGluSnFR
Mutations in GFP: T65S and Y66H to shift the color. V150I and V224R to improve maturation and brightness.
Linker1 mutations: GltI-cpSFGFP connection from PILV▒NV to PILG▒NV
Linker2 mutations: cpSFGFP-GltI connection from YNFNN▒N to YNFNE▒N

FIG. 67C

SF-iGluSnFR.A184V (SEQ ID NO: 176)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGD
IKDFANLKDKAVVVTSGTTSEVLLNKLNEEQKMNMRIISAKDHGDSFRTLESGRAVAFMMDDVLLAGERA
KAKKPDNWEIVGKPQSQEAYGCMLRKDDPQFKKLMDDTIAQVQTSGEAEKWFDKWFKNPILVSHNYIIA
KQKNGIKANFKIRHNVEDGSVQLADHYQQNTPIGDGPVLLPDNHYLSTQSVLSKDPNEKRDHMVLLEF
VTAAGITLGMDELYKGGTGGSMVSKGEELFTGVVPILVELDGDVNGHKFSVRGEGEGDATNGKLTLKFI
CTTGKLPVPWPTLVTTLTYGVQCFSRYPDHMKQHDFFKSAMPEGYVQERTISFKDDGTYKTRAEVKFEGDTL
VNRIELKGIDFKEDGNILGHKLEYNFNSHNVYITADKQKNGIKVNFKIRHNIEDGSVQLADHYQQNTPIGDGPVLLPDNHYLSTQSALSKDPNEKRDHMVLLEFVTAAGITLGMDELYKGGTGGSMVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYKGGTGGSMVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYKLQVDEQKLISEEDLNAVG
QDTQEVIVVPHSLPFKVVVISAILALVVLTIISLIILIMLWQKKPR

SF-iGluSnFR.A184S (SEQ ID NO: 177)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGD
IKDFANLKDKAVVVTSGTTSEVLLNKLNEEQKMNMRIISAKDHGDSFRTLESGRAVAFmMDDSLLAGERA
KAKKPDNWEIVGKPQSQEAYGCMLRKDDPQFKKLMDDTIAQVQTSGEAEKWFDKWFKNPILVSHNYIIA
KQKNGIKANFKIRHNVEDGSVQLADHYQQNTPIGDGPVLLPDNHYLSTQSVLSKDPNEKRDHMVLLEF
VTAAGITLGMDELYKGGTGGSMVSKGEELFTGVVPILVELDGDVNGHKFSVSGEGEGDATYGKLTLKFICTTGKLPVPWPTLVTTLTYGVQCFSRYPDHMKQHDFFKSAMPEGYVQERTIFFKDDGNYKTRAEVKFEGDTLVNRIELKGIDFKEDGNILGHKLEYNYNSHNVYIMADKQKNGIKVNFKIRHNIEDGSVQLADHYQQNTPIGDGPVLLPDNHYLSTQSALSKDPNEKRDHMVLLEFVTAAGITLGMDELYKLQVDEQKLISEEDLNAVG
QDTQEVIVVPHSLPFKVVVISAILALVVLTIISLIILIMLWQKKPR

FIG. 70A

SF-iGluSnFR.S72A (SEQ ID NO: 178)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGD
IKDFANLKDKAVVVTSGTTPEVLLNKINEEQKMNMRIISAKDHGDSFRTLESGRAVAFMMDDVLLAGERA
KAKKPDNWEIVGKPQSQEAYGCMLRKDDPQFKKLMDDTIAQVQTSGEAEKWFDKWFKNPILVSHNYTLA
KDINGIKANEKIFENVELGSVQLADHYQQNTPIGDGPVLLPNNLYSTQSVLSKPNEKRDHMVLLEFV
TAAGITLGMDELYKGGTGGSMSKGEELFTGVVPILVELDGDVNGHKFSVSGEGEGDATNGKLTLKFIC
TTGKLPVPWPTLVTTLGYGVQCFARYPDHMKQHDFFKSAMPEGYVQERTISFKDDGTYKTRAEVKFEGDTLV
NRIELKGIDFKEDGNILGHKLEYNFNSHNVYITADKQKNGIKVNFKIRHNIEDGSVQLADHYQQNTPIGDGPV
LLPDNHYLSTQSVLSKPNEKRDHMVLLEFVTAAGITLGMDELYKGGTGGSMSKGEELFTGVVPILVELDG
DVNGHKFSVSGEGEGDATNGKLTLKFICTTGKLPVPWPTLVTTLGYGVQCFARYPDHMKQHDFFKSAM
PEGYVQERTISFKDDGTYKTRAEVKFEGDTLVNRIELKGIDFKEDGNILGHKLEYNFNSHNVYITADKQKNGIKVNFKIRHNIEDGSVQLADHYQQNTPIGDGPVLLPDNHYLSTQSVLSKPNEKRDHMVLLEFVTAAGITLGMDELYK
NRIELKGIDFKEDGNILGHKLEYNFNPLMMNFELSDEMKAFKEPNDKALKLQVDEQKLISEEDLNAVG
QDTQEVIVVPHSLPFKVVVISAILALVVLTIISLIILIMLWQKKPR

SF-Venus-iGluSnFR.A184V (SEQ ID NO: 179)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGD
IKDFANLKDKAVVVTSGTTPEVLLNKINEEQKMNMRIISAKDHGDSFRTLESGRAVAFMMDDVLLAGERA
KAKKPDNWEIVGKPQSQEAYGCMLRKDDPQFKKLMDDTIAQVQTSGEAEKWFDKWFKNPILVSHNYTLA
KDINGIKANEKIFENVELGSVQLADHYQQNTPIGDGPVLLPDNHYLSTQSVLSKPNEKRDHMVLLEFV
TAAGITLGMDELYKGGTGGSMSKGEELFTGVVPILVELDGDVNGHKFSVSGEGEGDATNGKLTLKFIC
TTGKLPVPWPTLVTTLGYGVQCFARYPDHMKQHDFFKSAMPEGYVQERTISFKDDGTYKTRAEVKFEGDTLV
NRIELKGIDFKEDGNILGHKLEYNFNPLMMNFELSDEMKAFKEPNDKALKLQVDEQKLISEEDLNAVG
QDTQEVIVVPHSLPFKVVVISAILALVVLTIISLIILIMLWQKKPR

FIG. 70B

SF-Venus-iGluSnFR.A184S (SEQ ID NO: 180)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGGD
IKDFANLKDKAVVVTSGTTSEVLLNKLNEEQKMNMRIISAKDHGDSFRTLESGRAVAFmMDDSLLAGERA
KAKKPDNWEIVGKPQSQEAYGCMLRKDDPQFKKLMDDTIAQVQTSGEAEKWFDKWFKNPILVSHGYIT
KQPNGLANEKLRINVEDSSVQLADHYQQNTPIGDGPVLLPDNHYLSYQSVLSKDPNEKRDHMVLLEFV
TAAGITLGMDELYKGGTGGSMVSKGEELFTGVVPILVELDGDVNGHKFSVRGEGEGDATNGKLTLKICT
TGKLPVPWPTLVTTLGYGVQCFSRYPDHMKQHDFFKSAMPEGYVQERTISFKDDGTYKTRAEVKFEGDT
LVNRIELKGIDFKEDGNILGHKLEYNFNSHNVYITADKQKNGIKANFKIRHNIEDGSVQLADHYQQNTPIGDGPVLLPDNHYLSYQSVLSKDPNEKRDHMVLLEFVTAAGITLGMDELYKLQVDEQKLISEEDLNAVG
QDTQEVIVVPHSLPFKVVVISAILALVVLTIISLIILIMLWQKKPR

SF-Venus-iGluSnFR.S72A (SEQ ID NO: 181)

METDTLLLWVLLLWVPGSTGDRSAAGSTLDKIAKNGVIVVGHRESSVPFSYYDNQQKVVGYSQDYSNAIV
EAVKKKLNKPDLQVKLIPITSQNRIPLLQNGTFDFECGSTTNNVERQKQAAFSDTIFVVGTRLLTKKGGD
IKDFANLKDKAVVVTSGTTSEVLLNKLNEEQKMNMRIISAKDHGDSFRTLESGRAVAFMMDDVLLAGERA
KAKKPDNWEIVGKPQSQEAYGCMLRKDDPQFKKLMDDTIAQVQTSGEAEKWFDKWFKNPILVSHGYIT
KQPNGLANEKLRINVEDSSVQLADHYQQNTPIGDGPVLLPDNHYLSYQSVLSKDPNEKRDHMVLLEFV
TAAGITLGMDELYKGGTGGSMVSKGEELFTGVVPILVELDGDVNGHKFSVRGEGEGDATNGKLTLKICT
TGKLPVPWPTLVTTLGYGVQCFSRYPDHMKQHDFFKSAMPEGYVQERTISFKDDGTYKTRAEVKFEGDT
LVNRIELKGIDFKEDGNILGHKLEYNFNSHNVYITADKQKNGIKANFKIRHNIEDGSVQLADHYQQNTPIGDGPVLLPDNHYLSYQSVLSKDPNEKRDHMVLLEFVTAAGITLGMDELYKLQVDEQKLISEEDLNAVG
QDTQEVIVVPHSLPFKVVVISAILALVVLTIISLIILIMLWQKKPR

FIG. 70C

SF-Azurite-iGluSnFR (SEQ ID NO: 182)

METDTLLLWVLLLWVPGSTGDRSAAGSTLDKIAKNGVIVVGHRESSVPFSYYDNQQKVVGYSQDYSNAIV
AVKKKLNKPDLQVKLIPITSQNRIPLLQNGTFDFECGSTTNNVERQKQAAFSDTIFVVGTRLLTRKGGD
IKDFANLKDKAVVVTSGTTSEVLLNKLNEEQKMNMRIISAKDHGDSFRTLESGRAVAFMMDDVLLAGERA
KAKKPNNWEIVGKFQSQEAYGCMLRKDDPQPKKLMDDTIAQVQTSGEABKWFDKWFKNPILGVNLITA
RQINGLKANFKIRHNVEDGSVQLADHYQQNTPIGDGPVLLPDNHYLSTQSVLSKDPNEKRDHMVLLEF
VAAGITLGMDELYKGGTGGSMSKGEELFTGVVPILVELDGDVNGHKFSVRGEGEGDATNGKLTLKFI
CTTGKLPVPWPTLVTTLSHGVQCFARYPDHMKQHDFFKSAMPEGYVQERTISFKDDGTYKTRAEVKFE
GDTLVNRIELKGIDFKEDGNILGHKLEYNFNSHNVYIMADKQKNGIKVNFKIRHNIEDGSVQLADHYQ
QNTPIGDGPVLLPDNHYLSTQSVLSKDPNEKRDHMVLLEFVTAAGITLGMDELYKGGTGGSMSKGEELFTGVVPILVELDGDVNGHKFSVRGEGEGDATNGKLTLKFI
CTTGKLPVPWPTLVTTLSHGVQCFARYPDHMKQHDFFKSAMPEGYVQERTISFKDDGTYKTRAEVKFE
GDTLVNRIELKGIDFKEDGNILGHKLEYNeqLNMNFELSDEMKALFKEPNDKALKLQVDEQKLISEEDLNAVG
QDTQEVIVVPHSLPFKVVVISAILALVVLTIISLIILIMLWQKKPR iDexSnFR (SF-GlucoseSensor)(SEQ ID NO: 183)

METDTLLLWVLLLWVPGSTGDRSKLEIFSWWAGDEGPALEALIRLYKQKYPGVEVINATVTGGAGVNARA
VLKTRMLGGDPPDTFQVAAGMELIGTWVANRMEDLSALFRQEGWLQAFPKGLIDLISYKGGIWSVPVNI
HRSNVMWYLPAKLKEWGVNPPRTWDEFLATCQTLKQKGLEAPLALGENWTQQHLWESVALAVLGPDDWNN
LWNGKLKFTDPKAVRAWEVFGRVLDCANKDAAGLSWQQAVDRVVQGKAAFNVMGDWAAGYMTTTLKLKPG
TDFAWAPSPGTQGVFMMLSDSFGLPKGAKNRQNAINWLRLVGSKEGQDTFNPLKGSIAARLDSDPSKYPA
SHNVYIMADKQKNGIKANFKIRHNVEDGSVQLADHYQQNTPIGDGPVLLPDNHYLSTQSVLSKDPNEKR
DHMVLLEFVTAAGITLGMDELYKGGTGGSMSKGEELFTGVVPILVELDGDVNGHKFSVRGEGEGDATNGK
LTLKFICTTGKLPVPWPTLVTTLSHGVQCFARYPDHMKQHDFFKSAMPEGYVQERTISFKDDGTYKTRAE
VKFEGDTLVNRIELKGIDFKEDGNILGHKLEYNFNNPNAYGQSAMRDWRSNRIVGSLVAGAVAPESFMSQF
GTVMEIFLQTRNPQAAANAAQAIADQVGLGRLGQLQVDEQKLISEEDLNAVGQDTQEVIVVPHSLPFKVV
VISAILALVVLTIISLIILIMLWQKKPR

FIG. 70D iGABASnFR (SEQ ID NO:184)

METDTLLLWVLILLWVPGSTGDRSESINFVSWGGSTQDAQKQAWADPFSKASGITVVQDGPTDYCKLRAMV
ESGNVQWDVVDVEADFAIRAAAEGLLEPLDFSVIQRDKIDPRFVSDHGVGSIIFSFVIGYNEGKLQASKP
QDWTALFDTKTYPGKRALYKWPSEGVIELALLADGVPADKLYPLDLDRAFKKLDTIKKDIVWWGGAQSQ
QLLASGEVSMGQFWNGRIHALQEDGAFVGVSWKQNLVMADILVVPKGTKNKAAAMKFLASASSAKGQDDF
SaITAYAPVNIDSVQRLDIAGVFTIADKQFNGSHANFKIRHNVEDGSVQLADHYQQNTPIGDGPVLLPD
NYLSTQSVLSKDPNEKRDHMVLLEFVTAAGITLGMDELYKGGTGGSMSKGEELFTGVVPILVELDGDVN
GHKFSVRGEGEGDATNGKLTLKFICTTGKLPVPWPTLVTTLTYGVQCFSRYPDHMKQHDFFKSAMPEGYV
QERTISFKDDGTYKTRAEVKFEGDTLVNRIELKGIDFKEDGNILGHKLEYNFNshnLAFNLFTAYVKDQITL
DFAYWAKNGPAIATRWNEWLVKLQVDLQVDEQKLISEEDLNAVGQDTQEVIVVPHSLPFKVVVISAILAL
VVLTIISLIILIMLWQKKPR iAChSnFR

SEQ ID NO: 185

MHHHHHHGYPYDVPDYAGAQPARSANDTVVVGSIIFTEGIIVANMVAEMIEAHTDLKVVRKLNLGGVNVN
FEAIKRGGANNGIDIYVEYTGHGLVDILGFPEPNVYITADKQKNGIKANFKIRHNVEDGSVQLADHYQQN
TPIGDGPVLLPDNHYLSTQSVLSKDPNEKRDHMVLLEFVTAAGITLGMDELYKGGTGGSMSKGEELFTGV
VPILVELDGDVNGHKFSVRGEGEGDATNGKLTLKFICTTGKLPVPWPTLVTTLTYGVQCFSRYPDHMKQH
DFFKSAMPEGYVQERTISFKDDGTYKTRAEVKFEGDTLVNRIELKGIDFKEDGNILGHKLEYNFPPPATT
DPEGAYETVKKEYKRKWNIVWLKPLGFNNTYTLTVKDELAKQYNLKTFSDLAKISDKLILGATMFFLEGP
DGYPGLQKLYNFKFKHTKSMDMGIRYTAIDNNEVQVIDAWATDGLLVSHKLKILEDDKAFFPPYYAAPII
RQDVLDKHPELKDVLNKLANQISLEEMQKLNYKVDGEGQDPAKVAKEFLKEKGLILQVDEQKLISEEDLN

FIG. 70E

SEQ ID NO: 186

METDTLLLWVLLLWVPGSTGDRSANDTVVVGSIIFTEGIIVANMVAEMIEAHTDLKVVRKLNLGGVNVNF
EAIKRGGANNGIDIYVEYTGHGLVDILGFPEPNVYITADKQKNGIKANFKIRHNVEDGSVQLADHYQQNT
PIGDGPVLLPDNHYLSTQSVLSKDPNEKRDHMVLLEFVTAAGITLGMDELYKGGTGGSMSKGEELFTGVV
PILVELDGDVNGHKFSVRGEGEGDATNGKLTLKFICTTGKLPVPWPTLVTTLTYGVQCFSRYPDHMKQHD
FFKSAMPEGYVQERTISFKDDGTYKTRAEVKFEGDTLVNRIELKGIDFKEDGNILGHKLEYNFPPPATTD
PEGAYETVKKEYKRKWNIVWLKPLGFNNTYTLTVKDELAKQYNLKTFSDLAKISDKLILGATMFFLEGPD
GYPGLQKLYNFKFKHTKSMDMGIRYTAIDNNEVQVIDAWATDGLLVSHKLKILEDDKAFFPPYYAAPIIR
QDVLDKHPELKDVLNKLANQISLEEMQKLNYKVDGEGQDPAKVAKEFLKEKGLILQVDEQKLISEEDLNA
VGQDTQEVIVVPHSLPFKVVVISAILALVVLTIISLIILIMLWQKKPR

FIG. 70F

Structure 1

F—S—F

Wherein:

F " is a framework portion;

S " is a first signaling portion;

"——" is an optional linker, wherein the signaling portion is present at a site within the framework portion that undergoes a conformational change upon interaction of the framework portion with an analyte

FIG. 71

GENETICALLY ENCODED BIOSENSORS

CROSS REFERENCE TO RELATED APPLICATIONS

This application is a Continuation of, and claims the benefit of priority under 35 U.S.C. § 121 to, U.S. application Ser. No. 17/515,289 filed Oct. 29, 2021, now allowed, which is a Divisional of, and claims the benefit of priority under 35 U.S.C. § 121 to, U.S. application Ser. No. 16/902,160 filed Jun. 15, 2020, which is a Continuation of, and claims priority under 35 U.S.C. § 121 to, U.S. application Ser. No. 16/002,697 filed Jun. 7, 2018, which is a Continuation-In-Part of, and claims priority under 35 U.S.C. § 120 to, U.S. application Ser. No. 15/904,574 filed Feb. 26, 2018, which is a Divisional application of, and claims the benefit of priority under 35 U.S.C. § 121 to, U.S. application Ser. No. 15/664,326 filed Jul. 31, 2017, which is a Divisional application of, and claims the benefit of priority under 35 U.S.C. § 121 to, U.S. application Ser. No. 14/350,199 filed Nov. 18, 2014, which is a U.S. National Phase application of, and claims the benefit of priority under 35 U.S.C. 371 to, International Application No. PCT/US2012/059219 filed Oct. 8, 2012, which claims the benefit of priority under 35 U.S.C. § 119(e) to U.S. Application No. 61/544,867 filed Oct. 7, 2011, all of which are incorporated by reference in their entirety.

SEQUENCE LISTING

This application contains a Sequence Listing that has been submitted electronically as an XML file named "30872-0020004_SL_ST26.XML." The XML file, created on May 23, 2023, is 288,585 bytes in size. The material in the XML file is hereby incorporated by reference in its entirety.

TECHNICAL FIELD

This disclosure relates to genetically encoded biosensors and methods for the design, production, and use of such biosensors.

BACKGROUND

Protein-based sensors that transduce microscopic binding events into macroscopically observable signals are available to allow real-time visualization of a variety of biological events and/or molecules (Frommer et al., Chem. Soc. Rev., 38:2833-2841, 2009). Such sensors can be targeted and/or expressed in living cells, tissues, and organisms, and permit imaging with minimally invasive techniques (Okumoto, Curr. Opin. Biotechnol., 21:45-54, 2010). Application of these sensors is limited by the narrow range of analytes that can be detected and/or by their inability to distinguish signal over noise.

SUMMARY

In one aspect, a recombinant peptide biosensor is provided that includes an analyte-binding framework portion and a signaling portion, wherein the signaling portion is present within the framework portion at a site or amino acid position that undergoes a conformational change upon interaction of the framework portion with a defined, specific, or selected analyte.

In one embodiment, the signaling portion is allosterically regulated by the framework portion such that signaling from the signaling portion is altered upon interaction of the framework portion with the analyte. In some embodiments, signaling by the signaling portion detectably increases upon interaction of the framework portion with the analyte. In some embodiments, signaling by the signaling portion detectably decreases upon interaction of the framework portion with the analyte. In some embodiments, signaling by the signaling portion is proportional to the level of interaction between the framework portion and the analyte.

In some embodiments, the signaling portion is a super-folder (SF) fluorescent protein (see, for example, Pedelacq et al., 2006, Nature Biotechnol., 24:79-88), a protein that exhibits robust folding, even when fused to a protein that folds poorly. In some embodiments, the SF protein is circularly permuted. In some embodiments, the SF protein is a green fluorescent protein, a yellow fluorescent protein, a red fluorescent protein, or a blue fluorescent protein.

In some embodiments, the framework portion has a first structure in the absence of an analyte and a second structure, that is detectably distinct from the first structure, in the presence of the analyte. In some embodiments, the conformational change between the first structure and the second structure allosterically regulates the signaling portion. In some embodiments, the framework portion is a periplasmic binding protein (PBP) or a variant of a PBP.

In some embodiments, the analyte-binding framework portion binds specifically to an analyte selected from the group consisting of glucose, maltose, phosphonate, glutamate, GABA, and ACh.

In another aspect, a recombinant peptide biosensor is provided that includes an amino acid sequence having at least 90% identity to a recombinant peptide biosensor selected from the group consisting of SEQ ID NOs: 176-182, wherein the recombinant peptide biosensor binds specifically to glutamate.

In one embodiment, the recombinant peptide biosensor includes a recombinant peptide biosensor selected from the group consisting of SEQ ID NOs: 176-182 comprising 10 or fewer conservative amino acid substitutions, wherein the recombinant peptide biosensor binds specifically to glutamate. In some embodiments, the recombinant peptide biosensor includes a recombinant peptide biosensor selected from the group consisting of SEQ ID NOs: 176-182.

In still another aspect, a recombinant peptide biosensor is provided that includes an amino acid sequence having at least 90% identity to a recombinant peptide biosensor having the sequence shown in SEQ ID NO: 183, wherein the recombinant peptide biosensor binds specifically to glucose.

In some embodiments, the recombinant peptide biosensor includes a recombinant peptide biosensor having the sequence shown in SEQ ID NO: 183 comprising 10 or fewer conservative amino acid substitutions, wherein the recombinant peptide biosensor binds specifically to glucose. In some embodiments, the recombinant peptide biosensor includes a recombinant peptide biosensor having the sequence shown in SEQ ID NO: 183.

In one aspect, a recombinant peptide biosensor is provided that includes an amino acid sequence having at least 90% identity to a recombinant peptide biosensor having the sequence shown in SEQ ID NO: 184, wherein the recombinant peptide biosensor binds specifically to GABA.

In one embodiment, the recombinant peptide biosensor includes a recombinant peptide biosensor having the sequence shown in SEQ ID NO: 184 comprising 10 or fewer conservative amino acid substitutions, wherein the recombinant peptide biosensor binds specifically to GABA. In one embodiment, the recombinant peptide biosensor includes a recombinant peptide biosensor having the sequence shown in SEQ ID NO: 184.

In another aspect, a recombinant peptide biosensor is provided that includes an amino acid sequence having at least 90% identity to a recombinant peptide biosensor having a sequence selected from the group consisting of SEQ ID NO: 185 and 186, wherein the recombinant peptide biosensor binds specifically to ACh.

In one embodiment, the recombinant peptide biosensor includes a recombinant peptide biosensor having a sequence selected from the group consisting of SEQ ID NO: 185 and 186 comprising 10 or fewer conservative amino acid substitutions, wherein the recombinant peptide biosensor binds specifically to ACh. In one embodiment, the recombinant peptide biosensor includes a recombinant peptide biosensor having a sequence selected from the group consisting of SEQ ID NO: 185 and 186.

In one aspect, a nucleic acid is provided that encodes a recombinant peptide biosensor as described herein.

In one aspect, a vector is provided that includes a nucleic acid as described herein.

In one aspect, a cell is provided that includes a nucleic acid as described herein.

In one aspect, a cell is provided that includes a vector as described herein.

In one aspect, a kit is provided that includes a recombinant peptide biosensor as described herein, a nucleic acid as described herein, a vector as described herein, and/or the cell as described herein.

In still another aspect, a method is provided for detecting glutamate, the method comprising detecting a level of fluorescence emitted by a recombinant peptide biosensor, the peptide biosensor having an amino acid sequence selected from the group consisting of SEQ ID NOs: 176-182, and correlating the level of fluorescence with the presence of glutamate.

In some embodiments, the recombinant peptide biosensor is expressed from a nucleic acid. In some embodiments, the method includes contacting the recombinant peptide biosensor with a sample comprising glutamate. In some embodiments, the method includes correlating the level of fluorescence with a concentration of glutamate. In some embodiments, the method includes comparing the level of fluorescence with a level of fluorescence emitted by the recombinant peptide biosensor in the presence of a sample comprising a known concentration or range of concentrations of glutamate. In some embodiments, the method is performed in vitro.

In some aspects, a method for detecting glucose is provided, the method comprising detecting a level of fluorescence emitted by a recombinant peptide biosensor, the peptide biosensor having an amino acid sequence shown in SEQ ID NO: 183, and correlating the level of fluorescence with the presence of glucose.

In some aspects, a method for detecting GABA is provided, the method comprising detecting a level of fluorescence emitted by a recombinant peptide biosensor, the peptide biosensor having an amino acid sequence shown in SEQ ID NO: 184, and correlating the level of fluorescence with the presence of GABA.

In some aspects, a method for detecting ACh is provided, the method comprising detecting a level of fluorescence emitted by a recombinant peptide biosensor, the peptide biosensor having an amino acid sequence selected from the group consisting of SEQ ID NOs: 185 and 186, and correlating the level of fluorescence with the presence of ACh.

In some aspects, a method for detecting a defined, selected, or specific analyte is provided, the method comprising detecting a level of fluorescence emitted by a recombinant peptide biosensor of claim 1; and correlating the level of fluorescence with the presence of a defined, selected, or specific analyte In some embodiments, the recombinant peptide biosensor is expressed from a nucleic acid. In some embodiments, the method includes contacting the recombinant peptide biosensor with a sample comprising the analyte. In some embodiments, the method includes correlating the level of fluorescence with a concentration of the analyte. In some embodiments, the method includes comparing the level of fluorescence with a level of fluorescence emitted by the recombinant peptide biosensor in the presence of a sample comprising a known concentration or range of concentrations of the analyte. In some embodiments, the method is performed in vitro. In some embodiments, the analyte is selected from the group consisting of glutamate, glucose, GABA, and ACh.

The present disclosure provides genetically encoded recombinant peptides containing an analyte-binding framework portion linked (e.g., operably linked) to a signaling portion, wherein the signaling portion is allosterically regulated by the framework portion upon interaction of the framework portion with an analyte (e.g., a defined, selected, and/or specific analyte). These constructs can be used as biosensors, e.g., to transduce microscopic binding events into macroscopically observable signals.

The present disclosure provides, in part, recombinant peptides for use as biosensors (e.g., recombinant peptide biosensors) that include (e.g., comprise, consist essentially of, or consist of), e.g., include at least, an analyte-binding framework portion and a signaling portion. As described in further detail herein, such signaling portions are present within the framework portion at a site or amino acid position that undergoes a conformational change (e.g., a conformational change sufficient to alter a physical and/or functional characteristic of the signaling portion, e.g., a substantial conformational change) upon interaction of the framework portion with a defined, specific, or selected analyte (e.g. such as an analyte to which the framework portion or a region thereof, and/or the biosensor, specifically binds).

For example, in some instances, the signaling portion is allosterically regulated by the framework portion such that signaling from the signaling portion is altered (e.g. wherein a first level of signaling is altered or changed to a second level of signaling that can be distinguished using routine methods of detection from the first) upon interaction of the framework portion with the analyte. In some instances, signaling by the signaling portion can detectably increase or decrease upon interaction of the framework portion with the analyte. In some instances, signaling by the signaling portion upon interaction of the biosensor with a defined, specific, or selected analyte (e.g. such as an analyte to which the framework portion or a region thereof, and/or the biosensor, specifically binds) can be proportional or can correlate with to the level of interaction between the framework portion and the analyte such that the level of interaction can be determined from the signaling or alteration thereof.

In some instances, framework portions of the biosensors disclosed herein have a first structure in the absence of an analyte and a second structure that is detectably distinct from the first structure in the presence of the analyte. In some instances, the conformational change between the first structure and the second structure allosterically regulates the signaling portion.

In some instances, framework portions of the biosensors disclosed herein can be, or can include (e.g., comprise, consist essentially of, or consist of), periplasmic binding proteins (PBP) or variants of a PBP. In some instances, exemplary PBPs or variants thereof can include, but are not limited to, peptides with at least 90% identity to a peptide selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides with at least 95% identity to a peptide selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114. In some instances, exemplary PBPs or variants thereof can include, but are not limited to, peptides selected from the group consisting of SEQ ID NO:105, SEQ ID NO: 106, SEQ ID NO:107, SEQ ID NO:108, SEQ ID NO:109, SEQ ID NO: 110, SEQ ID NO:111, SEQ ID NO:113, and SEQ ID NO:114 comprising 10 or fewer conservative amino acid substitutions. PBPs or variants thereof disclosed herein can be truncated.

In some instances, signaling portions of the biosensors disclosed herein can be or can include (e.g., comprise, consist essentially of, or consist of) one or more (e.g., one, two three, four, five, and less than ten) circularly permuted fluorescent proteins (cpFPs). Such cpFPs can be include but are not limited to, for example, green fluorescent proteins, yellow fluorescent proteins, red fluorescent proteins, and/or blue fluorescent proteins.

In some instances, biosensors disclosed herein, e.g., analyte-binding framework portions of biosensors disclosed herein, can bind (e.g., bind specifically) to glucose. Such sensors can be referred to as glucose binding biosensors or glucose biosensors.

In some instances, biosensors disclosed herein, e.g., analyte-binding framework portions of biosensors disclosed herein, can bind (e.g., bind specifically) to maltose. Such sensors can be referred to as maltose binding biosensors or maltose biosensors.

In some instances, biosensors disclosed herein, e.g., analyte-binding framework portions of biosensors disclosed herein, can bind (e.g., bind specifically) to phosphonate. Such sensors can be referred to as phosphonate binding biosensors or phosphonate biosensors.

In some instances, biosensors disclosed herein, e.g., analyte-binding framework portions of biosensors disclosed herein, can bind (e.g., bind specifically) to glutamate. Such sensors can be referred to as glutamate binding biosensors or glutamate biosensors.

In some instances, biosensors disclosed herein can include (e.g., comprise, consist essentially of, or consist of): an amino acid sequence with at least 90% identity to a recombinant peptide biosensor selected from the group consisting of SEQ ID NO: 1, 2, 3, 4, 5, 6, 7, 8, 50, 51, 52, and 53, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53 comprising 10 or fewer conservative amino acid substitutions, wherein the recombinant peptide biosensor binds specifically to maltose; and/ or a recombinant peptide biosensor selected from the group consisting of SEQ ID NO: 1, 2, 3, 4, 5, 6, 7, 8, 50, 51, 52, and 53.

In some instances, biosensors disclosed herein can include (e.g., comprise, consist essentially of, or consist of): an amino acid sequence with at least 90% identity to a recombinant peptide biosensor selected from the group consisting of SEQ ID NO: 62 and 63, wherein the recombinant peptide biosensor binds specifically to glutamate; a recombinant peptide biosensor selected from the group consisting of SEQ ID NO: 62 and 63 comprising 10 or fewer conservative amino acid substitutions, wherein the recombinant peptide biosensor binds specifically to glutamate; and/or a recombinant peptide biosensor selected from the group consisting of SEQ ID NO: 62 and 63.

In some instances, biosensors disclosed herein can include (e.g., comprise, consist essentially of, or consist of): an amino acid sequence with at least 90% identity to a recombinant peptide biosensor selected from the group consisting of SEQ ID NO: 77 and 78, wherein the recombinant peptide biosensor binds specifically to phosphonate; a recombinant peptide biosensor selected from the group consisting of SEQ ID NO: 77 and 78 comprising 10 or fewer conservative amino acid substitutions, wherein the recombinant peptide biosensor binds specifically to phosphonate; and/or a recombinant peptide biosensor selected from the group consisting of SEQ ID NO: 77 and 78.

In some instances, biosensors disclosed herein can include (e.g., comprise, consist essentially of, or consist of): an amino acid sequence with at least 90% identity to a recombinant peptide biosensor selected from the group consisting of SEQ ID NO: 91, 92, 93 and 94, wherein the recombinant peptide biosensor binds specifically to glucose; a recombinant peptide biosensor selected from the group consisting of SEQ ID NO: 91, 92, 93 and 94 comprising 10 or fewer conservative amino acid substitutions, wherein the recombinant peptide biosensor binds specifically to glucose; and/or a recombinant peptide biosensor selected from the group consisting of SEQ ID NO: 91, 92, 93 and 94.

In some instances, biosensors disclosed herein can include (e.g., comprise, consist essentially of, or consist of): SEQ ID NO:91; SEQ ID NO:92; SEQ ID NO:93; SEQ ID NO:95.

In some instances, any recombinant biosensor disclosed herein can be isolated and/or purified. The terms "isolated" or "purified," when applied to a biosensor disclosed herein includes nucleic acid proteins and peptides that are substantially free or free of other cellular material or culture medium when produced by recombinant techniques, or substantially free or free of precursors or other chemicals when chemically synthesized.

The disclosure also provides, in part, nucleic acids (e.g., isolated and/or purified nucleic acids) encoding any one or more of the recombinant peptide biosensors disclosed herein. For example, nucleic acids can encode: an amino acid sequence with at least 90% identity to a recombinant peptide biosensor selected from the group consisting of SEQ ID NO: 1, 2, 3, 4, 5, 6, 7, 8, 50, 51, 52, and 53, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53 comprising 10 or fewer conservative amino acid substitutions, wherein the recombinant peptide biosensor binds specifically to maltose; a recombinant peptide biosensor selected from the group consisting of SEQ ID NO: 1, 2, 3, 4, 5, 6, 7, 8, 50, 51, 52, and 53; an amino acid sequence with at least 90% identity to a recombinant peptide biosensor selected from the group consisting of SEQ ID NO: 62 and 63, wherein the recombinant peptide biosensor binds specifically to glutamate; a recombinant peptide biosensor selected from the group consisting of SEQ ID NO: 62 and 63 comprising 10 or fewer conservative amino acid substitutions, wherein the recombinant peptide biosensor binds specifically to glutamate; a recombinant peptide biosensor selected from the group consisting of SEQ ID NO: 62 and 63; an amino acid sequence with at least 90% identity to a recombinant peptide biosensor selected from the group consisting of SEQ ID NO: 77 and 78, wherein the recombinant peptide biosensor binds specifically to phosphonate; a recombinant peptide biosensor selected from the group consisting of SEQ ID NO: 77 and 78 comprising 10 or fewer conservative amino acid substitutions, wherein the recombinant peptide biosensor binds specifically to phosphonate; a recombinant peptide biosensor selected from the group consisting of SEQ ID NO: 77 and 78; an amino acid sequence with at least 90% identity to a recombinant peptide biosensor selected from the group consisting of SEQ ID NO: 91, 92, 93 and 94, wherein the recombinant peptide biosensor binds specifically to glucose; a recombinant peptide biosensor selected from the group consisting of SEQ ID NO: 91, 92, 93 and 94 comprising 10 or fewer conservative amino acid substitutions, wherein the recombinant peptide biosensor binds specifically to glucose; a recombinant peptide biosensor selected from the group consisting of SEQ ID NO: 91, 92, 93 and 94; and/or SEQ ID NO:91; SEQ ID NO:92; SEQ ID NO:93; SEQ ID NO:95.

In some instances, the disclosure includes vectors containing one or a plurality of the nucleic acids disclosed herein and cells containing such vectors. In some instances, the disclosure provides cells containing one or a plurality of nucleic acids disclosed herein.

In some instances, the disclosure includes kits related to the biosensors and nucleic acids disclosed herein Such kits can include or contain, for example, a biosensor, a nucleic acid encoding a biosensor, vectors, and/or cells, provided herein.

In some instances, the disclosure provides methods related to the biosensors and nucleic acids disclosed herein. Such methods can include methods of making, using, and/or selling the biosensors and nucleic acids disclosed herein. For example, methods can include methods for producing genetically encoded recombinant peptide biosensors. In such instances, methods can include, for example, selecting a framework portion that binds specifically to a target analyte and that undergoes a conformational change upon interacting binding to the target analyte, identifying a site or amino acid position within the selected framework portion where or around which the conformational change occurs, and inserting a signaling portion into the site or amino acid position. In some instances, framework portions include periplasmic binding proteins (PBPs) disclosed herein. Exemplary PBPs include PBPs that bind (e.g., bind specifically) to glucose.

In some instances, the present disclosure includes methods for detecting glucose, e.g., in a sample containing a level of glucose. Such methods can include, detecting a level of fluorescence emitted by a recombinant peptide biosensor, the peptide biosensor having an amino acid sequence selected from the group consisting of SEQ ID NO: 91, 92, 93 and 94, and correlating the level of fluorescence with the presence of glucose. In some instances, recombinant peptide biosensors used in the methods herein are expressed from nucleic acids. In some instances, methods include contacting the recombinant peptide biosensor with a test sample (e.g., a sample comprising glucose). In some instances, methods can include the level of fluorescence emitted by a biosensor (e.g., a biosensor bound to glucose) with a concentration glucose in the sample. Such correlation can include, for example, comparing the level of fluorescence with a level of fluorescence emitted by the recombinant peptide biosensor in the presence of a sample comprising a known concentration or range of concentrations of glucose. In some instance, the level of fluorescence emitted by the recombinant peptide biosensor in the presence (e.g., bound or bound specifically to) of a sample comprising a known concentration or range of concentrations of glucose is stored on an electronic database.

One of skill will appreciate that such methods can be adapted for any defined, specific, or selected analyte. For example, in some instances, the disclosure provides methods for detecting a defined, selected, or specific analyte. These methods can include detecting a level of fluorescence emitted by a recombinant peptide biosensor expressed from a nucleic acid and correlating the level of fluorescence with the presence the defined, selected, or specific analyte. In some instances, methods include contacting the recombinant peptide biosensor with a sample comprising the analyte. In some instances, methods include correlating the level of fluorescence with a concentration of the analyte. In some instances, methods include comparing the level of fluorescence with a level of fluorescence emitted by the recombinant peptide biosensor in the presence of a sample comprising a known concentration or range of concentrations of the analyte, wherein the level of fluorescence emitted by the recombinant peptide biosensor in the presence of a sample comprising a known concentration or range of concentrations of the analyte is stored on an electronic database.

In some instances, the present disclosure provides methods for detecting a defined, selected, or specific analyte, the method comprising detecting a level of fluorescence emitted by a recombinant peptide biosensor as described herein; and correlating the level of fluorescence with the presence of a defined, selected, or specific analyte. In some instances, recombinant peptide biosensors can be expressed from a nucleic acid. In some instances, methods can include contacting the recombinant peptide biosensor with a sample comprising the analyte. In some instances, methods can include correlating the level of fluorescence with a concentration of the analyte and, optionally, comparing the level of fluorescence with a level of fluorescence emitted by the recombinant peptide biosensor in the presence of a sample comprising a known concentration or range of concentrations of the analyte. In some instances, the level of fluorescence emitted by the recombinant peptide biosensor in the presence of a sample comprising a known concentration or range of concentrations of the analyte is stored on an electronic database.

Methods herein can be performed in vitro.

In some instances, the present disclosure provides compositions containing any one or a plurality of the peptide biosensors and/or nucleic acids disclosed herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

(FIG. 6B) shows backbone structural changes. The Cα dihedral is calculated from the four atoms: Cαi+2, Cαi+1, Cαi, Cαi-1. ΔDihedral is calculated as the difference in dihedrals between the closed (1ANF) and open (1OMP) states of MBP, and corrected to fall within a range of −180° to 180°. The regions near residues 175 and 311 are labeled. There is a crystallographic artifact at the N-terminus resulting in the appearance of significant structural changes.

Figure 7A:
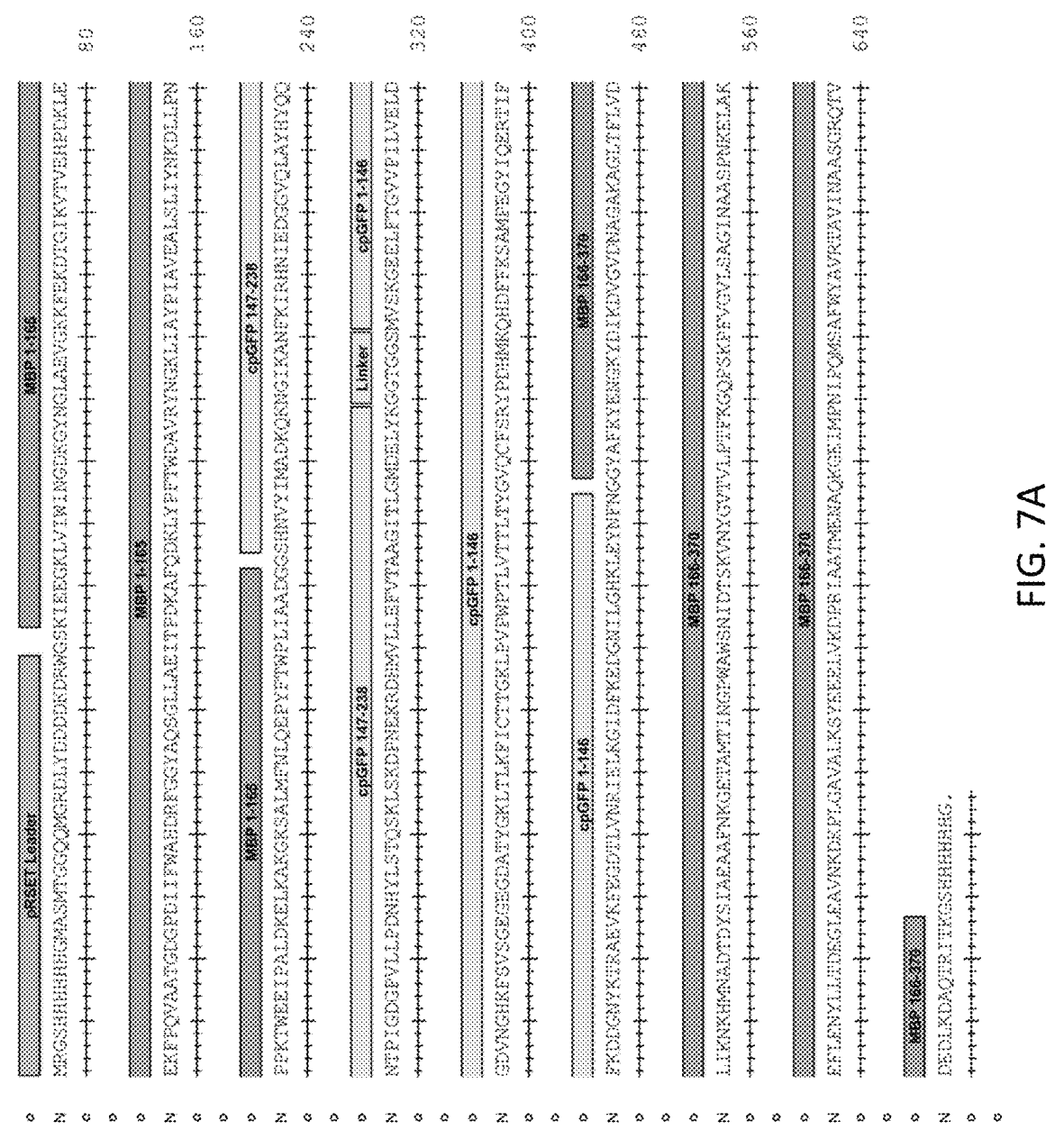
Figure 7C:
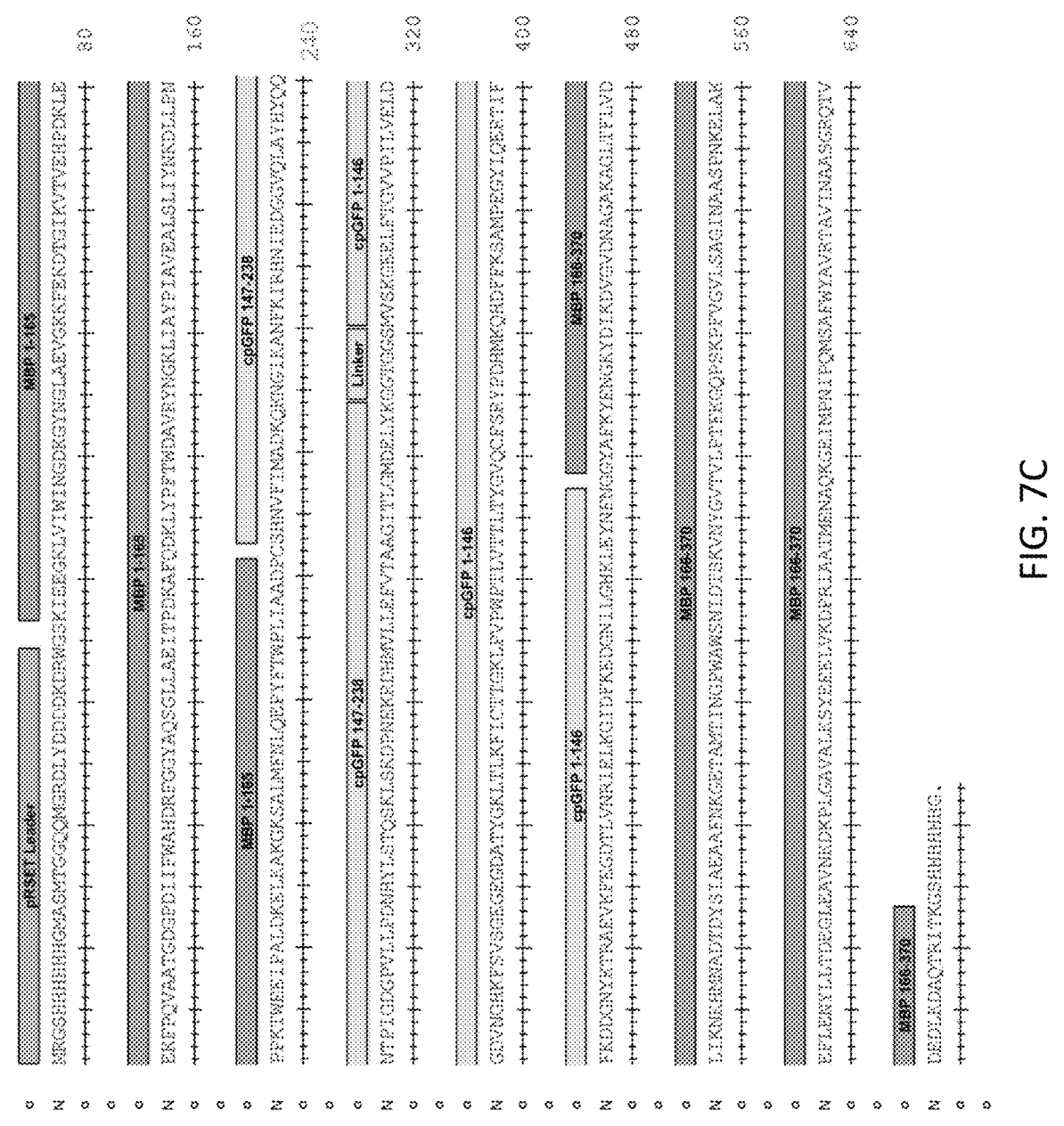

FIG. 7A|Amino acid sequence of MBP-165-cpGFP (SEQ ID NO:1).

FIG. 7C|Amino acid sequence of MBP-165-cpGFP.PCF (SEQ ID NO:3).

Figure 8A:
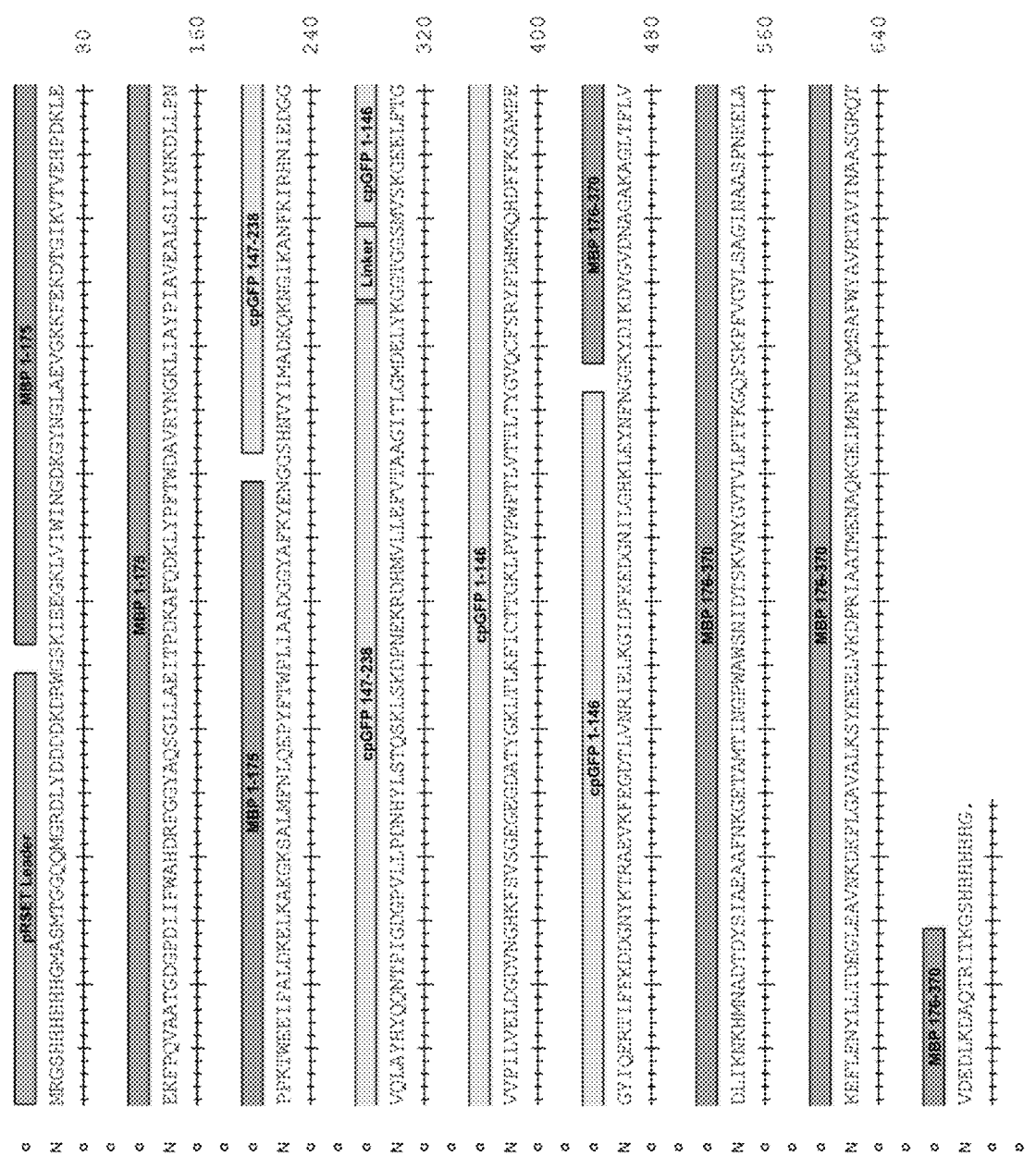
Figure 8B:
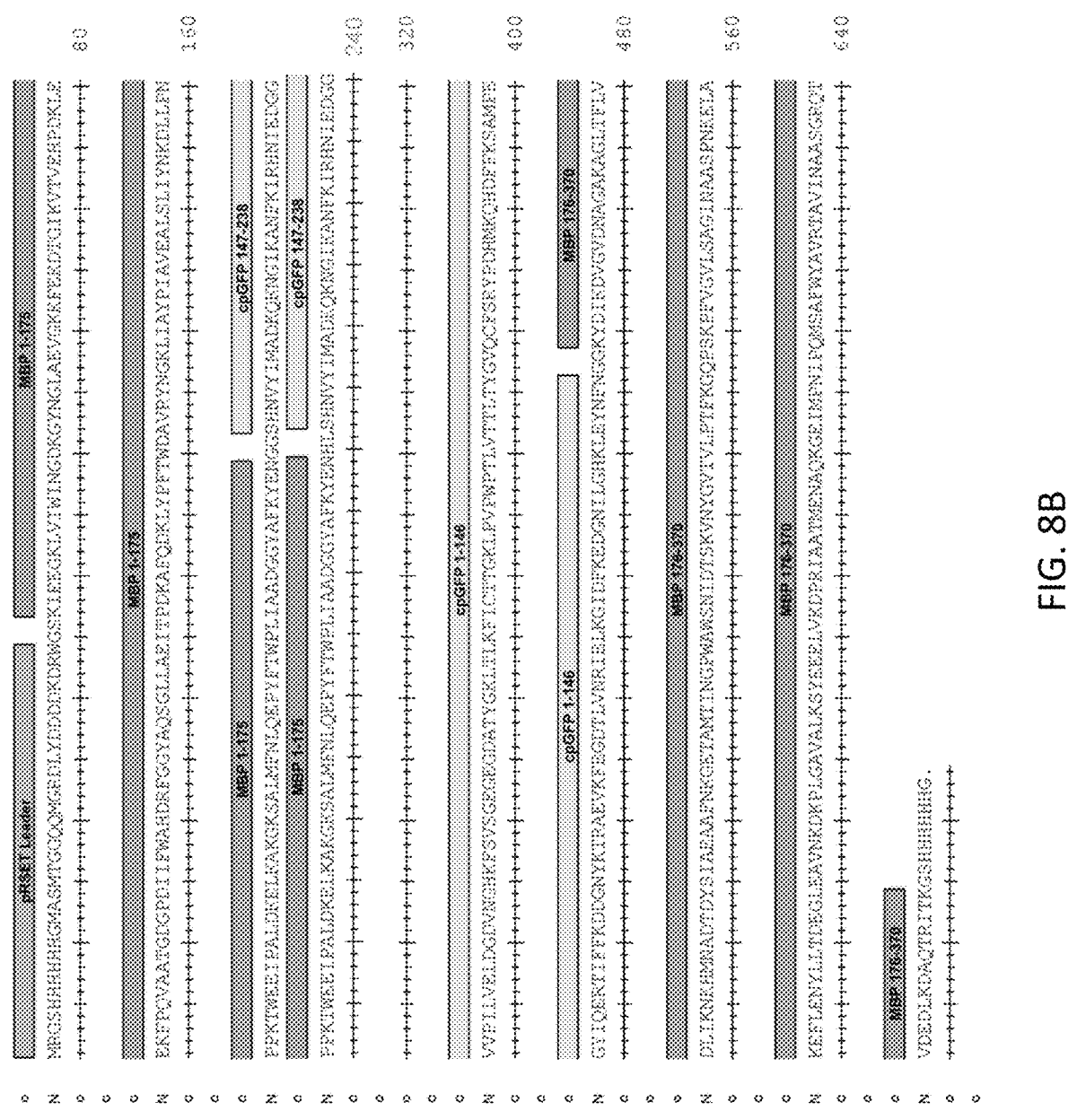

FIG. 8A|Amino acid sequence of MBP-175-cpGFP (SEQ ID NO:4).

FIG. 8B|Amino acid sequence of MBP-175-cpGFP.L1-HL (SEQ ID NO:5).

Figure 9A:
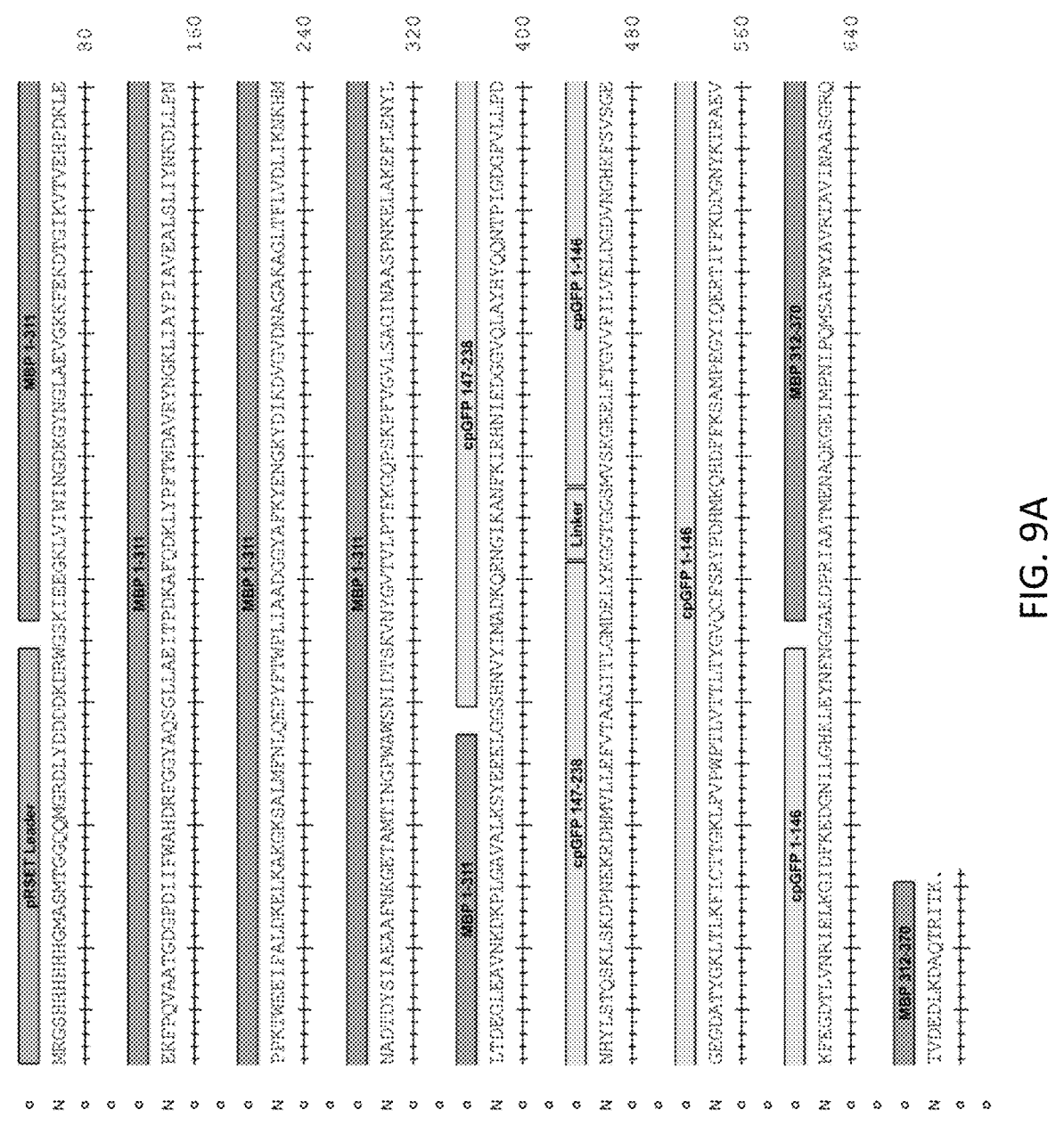
Figure 9B:
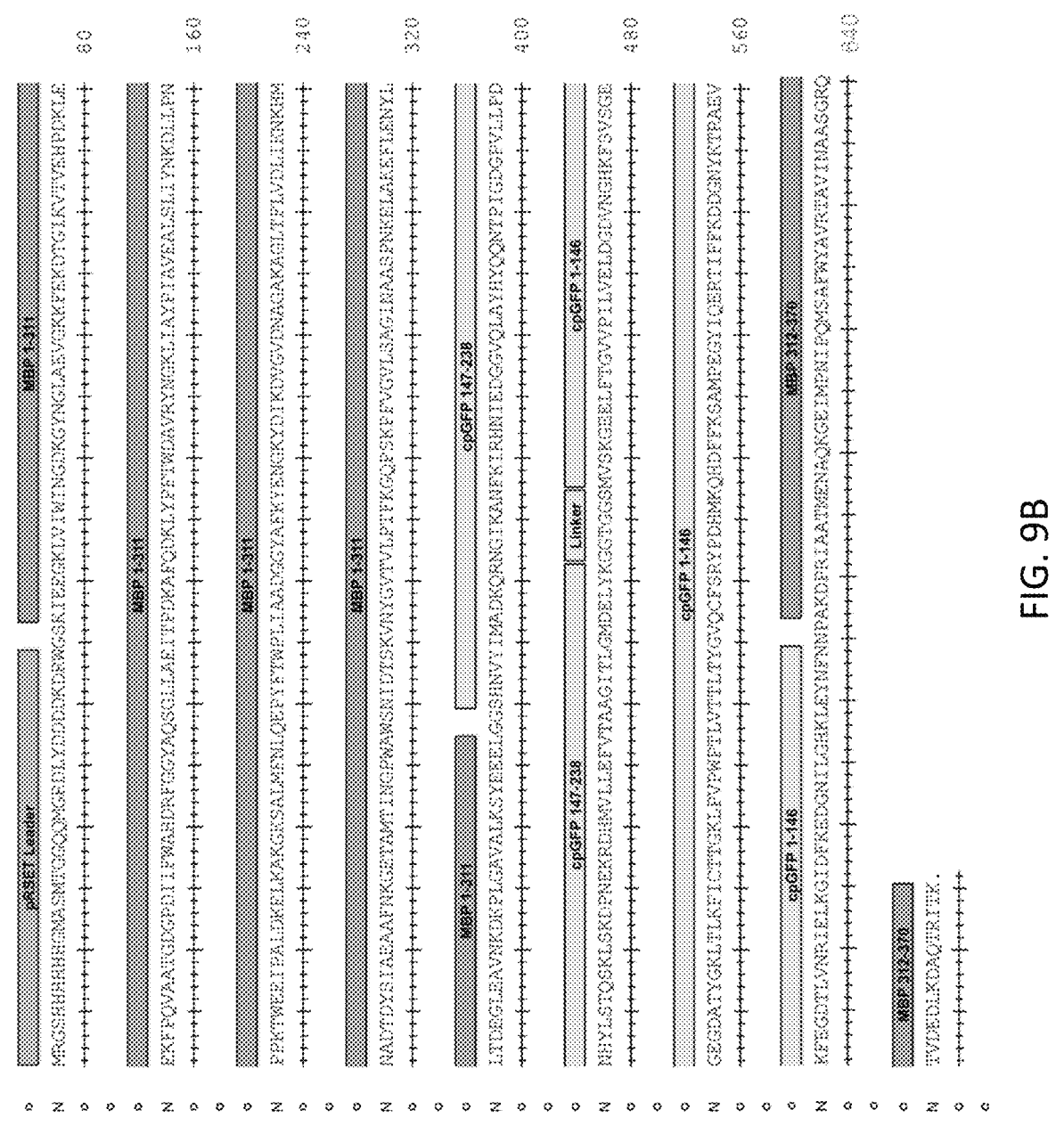

FIG. 9A|Amino acid sequence of MBP-311-cpGFP (SEQ ID NO:6).

FIG. 9B|Amino acid sequence of MBP-311-cpGFP.L2-NP (SEQ ID NO:7).

Figure 10:
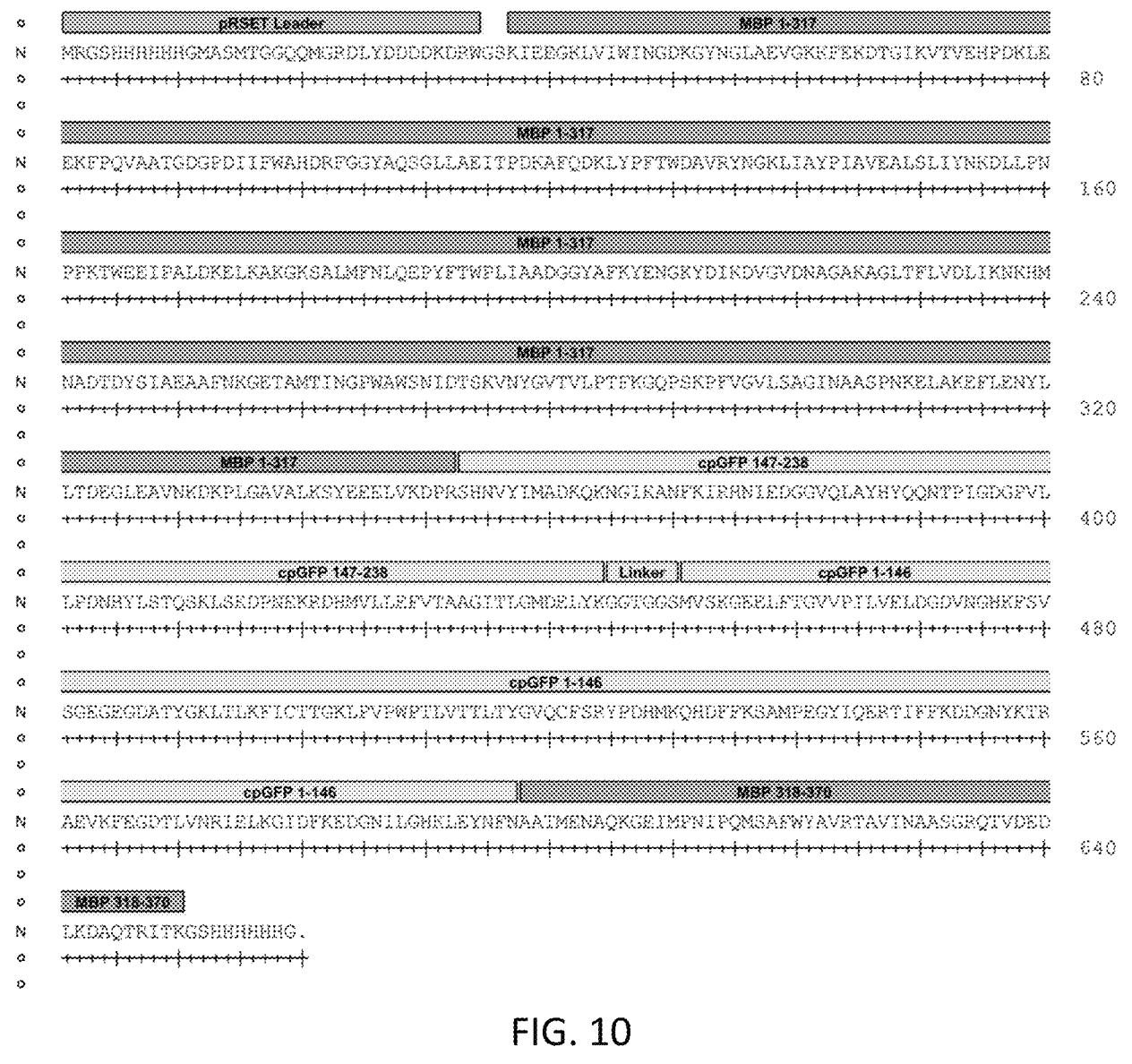

FIG. 10|Amino acid sequence of MBP-317-cpGFP (SEQ ID NO:8).

FIGS. 11A-11D|Line charts showing EcMBP plot of ΔF/F for clarified lysate screen of cpGFP linker-screens at insertion points 165, 175, 311, and 317. The horizontal dashed line at zero indicates no fluorescence change. Standard deviations in ΔF/F are less than 10% of an average ΔF (repetitions for MBP165-cpGFP.PPYF yields ΔF/F values of 2.51, 2.63, and 2.54).

FIGS. 14A-14D|Line graphs showing maltose and sucrose binding curves for wild-type and 5-7 variants of the EcMBP-cpGFP sensors. Maltose (black) and sucrose (red) binding curves for wild-type (filled, solid lines) and 5-7 variants (open, dashed lines) of the MBP-cpGFP sensors. MBP165-cpGFP.PPYF (FIG. 14A); MBP165-cpGFP.PCF (FIG. 14B); MBP175-cpGFP.L1-HL (FIG. 14C); MBP311-cpGFP.L2-NP (FIG. 14D).

FIGS. 15A-15D|Line graphs showing emission spectra for colored variants of EcMBP sensors. Fluorescence emission spectra of the MBP165-Blue, Cyan, Green, and Yellow wild-type sensors (FIG. 15A) and the 5-7 variants (FIG. 15B) in the absence of ligand (dashed lines, open circles), with 10 mM maltose (solid lines, filled circles), or 10 mM sucrose (solid lines, filed squares). Sensors were excited at 383, 433, 485, and 485 nm, respectively. Titration of maltose and sucrose in the Blue, Cyan, Green, and Yellow MBP165 wild-type sensors (FIG. 15C) and for the 5-7 variants (FIG. 15D). Filled circles are titration of maltose, open circles are titration of sucrose. For the wild-type sensors, Kds for maltose binding are: Blue 3.3 μM, Cyan 13 Green 4.5 μM, Yellow 3.3 μM. No sucrose binding is observed. For the 5-7 variants, Kd of Green is 2.4 mM (sucrose) and 7.1 mM (maltose). Kd of Yellow is 2.5 mM (sucrose) and 4.5 mM (maltose).

FIGS. 21A-21B|Graphs showing quantification of fluorescence of EcMBP-cpGFP.PPYF.T203V when displayed on the surface of HEK cells. (FIG. 21A) Concentration dependence. (FIG. 21B) Observed fluorescence after a "puff" of HBSS solution containing 1 mM maltose and 2.5 nM Alexa Fluor® 568 (Invitrogen, Carlsbad, CA).

(FIG. 23A) Emission spectra of 1 μM purified eGFP (filled circles), cpGFP (filled squares), MBP165-cpGFP.PPYF (open circles), and MBP165-cpGFP.PPYF+T203V (open squares) in the absence (dashed lines) or presence (solid lines) of 1 mM maltose. cpGFP is half as bright as eGFP, and the saturated MBP165-cpGFP.PPYF variants are about half as bright as cpGFP. (FIG. 23B) Titration of maltose for MBP165-cpGFP.PPYF (filled squares), and MBP165-cpGFP.PPYF+T203V (filled circles). Affinities for each protein are the same, but with different ΔF/F. (FIG. 23C) Emission spectra of 1 μM purified eGFP (filled circles), cpGFP (filled squares), MBP311-cpGFP.L2-NP (open circles), and MBP311-cpGFP.L2-NP+T203V (open squares) in the absence (dashed lines) or presence (solid lines) of 1 mM maltose. Note that mutation T203V decreases the fluorescence of both the apo-state and the saturated state of MBP311-cpGFP.L2-NP. (FIG. 23D) Titration of maltose for MBP311-cpGFP.L2-NP (filled squares), and MBP311-cpGFP.L2-NP+T203V (filled circles). Affinities for each protein are the same, but with ΔF/F slightly increased for the T203V variant.

FIG. 24B|Amino acid sequence of PfMBP171cpGFP.L2-FE (SEQ ID NO:51)

FIG. 25A|Amino acid sequence of PfMBP316-cpGFP (SEQ ID NO:52)

FIGS. 27A-27D|Plot of Beta-sheet circular dichroism (CD) signal as a function of temperature.

(FIG. 28A) Plot of fluorescence as a function of temperature in the presence (solid) or absence (dashed) of ligand. (FIG. 28B) Plot of ΔF/F as a function of temperature. Using the data from FIG. 27A, ΔF/F for each protein (Fbound-Fapo/Fapo) was calculated for each temperature.

FIG. 29A|Amino acid sequence of EcYbeJ253-cpGFP (SEQ ID NO:62).

FIG. 29B|Amino acid sequence of EcYbeJ253-cpGFP.L1LVL2NP (SEQ ID NO:63).

(FIG. 32A) Images of the sensor expressing HEK cells in the absence of glutamate (left), with 100 μM glutamate (center), and re-imaged after wash-out of glutamate with buffer (right). (FIG. 32B) By measuring the equilibrium ΔF/F with different concentrations of glutamate in the buffer, an in situ binding affinity (black) can be obtained. The surface displayed sensor has a higher affinity (3 μM) for glutamate than the soluble sensor (grey), which is about 90 μM.

FIG. 34A|Amino acid sequence of EcPhnD90-cpGFP (SEQ ID NO:77).

FIG. 34B|Amino acid sequence of EcPhnD90-cpGFP.L1AD+L297R+L301R (SEQ ID NO: 78).

(FIG. 36C) Analysis of the change in Cα dihedral (ΔDihedral) clearly shows that residues for which there is the greatest ΔDihedral upon going from the open to the closed state are residues 88 (ΔDihedral=-75°), 89 (ΔDihedral=123°), and 90 (ΔDihedral=52°).

FIG. 37A|Amino acid sequence of TtGBP326-cpGFP (SEQ ID NO:91).

FIG. 41|Amino acid sequence of *Escherichia* coli maltodextrin-binding protein (EcMBP) (SEQ ID NO: 105).

FIG. 42|Amino acid sequence of *Pyrococcus furiosus* maltose-binding protein (PfMBP) (SEQ ID NO: 106).

FIG. 43|Amino acid sequence of *E. coli* glutamate-binding protein (EcYbeJ) (SEQ ID NO:107).

FIG. 44|Amino acid sequence of *E. coli* phosphonate-binding protein (EcPhnD) (SEQ ID NO:108).

FIG. 45|Amino acid sequence of *Thermus thermophilus* glucose-binding protein (TtGBP) (SEQ ID NO:109).

FIG. 46|Amino acid sequence of UniProt accession number Q92N37 (SEQ ID NO: 110).

FIG. 47|Amino acid sequence of UniProt accession number D0VWX8 (SEQ ID NO:111).

FIG. 48|Amino acid sequence of UniProt accession number Q7CX36 (SEQ ID NO:112).

FIG. 49|Amino acid sequence of UniProt accession number P0AD96 (SEQ ID NO:113).

FIG. 53A-D|SF-iGluSnFR.A184S shows larger responses to visual stimuli than SF-iGluSnFR.A184V. (FIG. 53A) Two-photon standard-deviation projection of SF-iGluSnFR.A184S and A184V expressed in ferret visual cortex (A184S: 190 μm, A184V: 175 μm, scale bar 100 μm). (FIG. 53B) Trial-averaged stimulus-evoked responses (shown for ROI 1) reveal robust orientation tuning and peak amplitudes of ~30% ΔF/F for A184S. Peak responses plotted as a function of stimulus orientation show robust selectivity with the A184S variant. For the A184V variant, stimulus-evoked fluctuations are too small (~5% ΔF/F) to generate robust tuning plots. (FIG. 53C) Two-photon standard-deviation projection of an isolated dendritic segment with active spines revealed with SF-iGluSnFR.A184S. Individual dendritic spines are driven selectively and strongly by drifting gratings. Orientation tuning from peak responses shows large spine responses (30-50% ΔF/F) and, importantly, reveals that spines on a single dendritic branch can receive differently tuned excitatory input. (FIG. 53D) Same as in (FIG. 53C) for SF-iGluSnFR.A184V. Dendritic spine responses with A184V are weak and almost unresolvable.

FIG. 54A-D|SF-iGluSnFR.S72A permits resolution of multiple glutamate release events in cultured mouse embryonic hippocampal neurons. (FIG. 54A) Single (dashed) and averaged (solid) traces of SF-iGluSnFR.S72A (blue) and SF-iGluSnFR.A184V (red) response to 20 Hz paired electrical stimuli. (FIG. 54B) Histogram showing intensity second pulse to first pulse response. (FIG. 54C) The faster off-rate of S72A can be used to observe vesicle release depression. Higher concentrations of extracellular calcium can increase vesicle release, leading to vesicle exhaustion as the train of field pulses progresses. (FIG. 54D) The slow decay of A184V obscures this depression.

(FIG. 55A) Averaged response from single boutons expressing GCaMP6f (GC6f) at 2 mM $[Ca^{2+}]_{extracellular}$ (green), GC6f at 1.5 mM $[Ca^{2+}]_e$ (black), SF-iGluSnFR.A184V at 1.5 mM $[Ca^{2+}]_e$ (A184V, red) and SF-iGluSnFR.S72A at 1.5 mM $[Ca^{2+}]_e$ (S72A, blue), normalized to peak response. In parenthesis the number of trials used to calculate the average. Right, summary plots of ΔF/F0, 10-90% rise time, 50% decay time and signal-to-noise-ratio (SNR). Multiple comparisons were performed with the Kruskal-Wallis test and the Dunn's multiple comparisons test. * $P<0.05$,  $P<0.01$, ** $P<0.0001$. (FIG. 55B) Two-photon fluorescent image of granule cells and parallel fibers expressing A184V in cerebellum slice (GL—granule layer, ML—molecular layer). Yellow arrows indicate labeled soma of granule cells, and circle indicate boutons from parallel fibers. Bottom, example of single trial A184V fluorescence responses to 20 Hz electrical stimulation (red) and the average of 10 trials (purple). (FIG. 55C) Population average fluorescence responses to 20 Hz stimulation (n boutons=5 GC6f; n=17, A184V; n=3, S72A). Traces are normalized to the peak of the first response. (FIG. 55D) Population average of response to 100 Hz electrical stimulation (n boutons=9 GC6f; n=9, A184V; n=7, S72A) normalized to the maximum amplitude (left) or to the peak of the first response (middle), and average response of all the boutons. n is number of boutons. Black arrows indicate time of electrical stimulation.

(FIG. 56A) RuBi-glutamate was uncaged for 10 msec. at each of two 5 μm spots (red arrowheads) on the dendrites. Saturation denotes the glutamate transient amplitude. Yellow line indicates locations for traces shown in (FIG. 56B). (FIG. 56B) Recorded traces at nine pixels at various distances from the uncaging focus, along the yellow line in (FIG. 56A). The traces are approximate maximum likelihood solutions recovered with the FADE algorithm. (Kazemipour et al., Proceedings of the 2017 Asilomar Conference on Signals, Systems, and Computers, October 29-November 1, Pacific Grove, CA), which incorporates dynamics having arbitrarily fast rise but slow decay. This recording is of a single uncaging event, without averaging.

(FIG. 58A) 2-photon cross-section of purified, soluble iGluSnFR (grey) and SF-iGluSnFR (black) in the ligand-free (dashed line) and glutamate-saturated (solid line) state. Excitation (FIG. 58B), emission (FIG. 58C), and absorption spectra (FIG. 58D) of iGluSnFR (grey), SF-iGluSnFR (black), and cpSFGFP (green) with glutamate (solid line) and without (dashed line).

FIG. 59A-E|Representative images of (FIG. 59A) SF-iGluSnFR and (FIG. 59B) iGluSnFR in mouse somatosensory cortex taken at 0.9 μm/pixel, 0.126 nsec dwell time per μm, 80 mW power, prior to bleaching. 20 nl of AAV2/1.hSynapsin1.iGluSnFR or SF-iGluSnFR (identical virus titer, prepared by the same person) was injected three weeks before imaging. Contrast adjusted to 10 grayscales in both images to make original iGluSnFR observable. Mean signal-to-noise ratios (n=2 animals) are 66 vs. 14 (80 mW power) and 2.4 vs. 0.3 (5 mW power). (FIG. 59C) & (FIG. 59D) Representative images of SF-iGluSnFR and iGluSnFR taken with 5 mW power, which is more typical in live imaging conditions. (FIG. 59E) Bleaching of SF-iGluSnFR (black) and original iGluSnFR (grey) at 80 mW power and 10× zoom (0.09 μm/pixel, 1.26 nsec dwell time per μm).

FIG. 60A-B|In vitro binding affinity. (FIG. 60A) Titration of bacterially expressed iGluSnFR and SF-iGluSnFR and variants. Affinities ($K_d$) for original iGluSnFR, SF-iGluSnFR.A184S, SF-iGluSnFR.A184V, and SF-iGluSnFR. S72A are 84±7 µM, 7.5±0.4 µM, 41±7 µM, and 200±5 µM respectively. (FIG. 60B) Kinetics of glutamate binding by stopped-flow fluorescence spectroscopy. Equal volumes of 1 µM SF-iGluSnFR (A184S, A184V, or S72A) and glutamate (variable concentration) were mixed in an SX.18MV stopped-flow spectrometer (Applied Photophysics, Surrey, UK). Representative traces shown. Pseudo-first order analysis indicates that the on-rate of binding for SF-iGluSnFR.A184S, A184V, S72A are 6, 5, and 0.6 $µM^{-1}$ $sec^{-1}$, respectively. The off rates, as determined by the y-intercept, are 25 $sec^{-1}$, 52 $sec^{-1}$, and 108 $sec^{-1}$ respectively. Error bars are standard deviation of three measurements.

FIG. 62|Affinity of SF-iGluSnFR variants displayed on the surface of neurons. AAV2/1.hSynapsin1.SF-iGluSnFR variants (1 µl of 1E13 GC/ml) were used to infect rat hippocampal neuronal culture 3 days after culturing. After 10 days in vitro, fluorescence was monitored under continuous flow of buffer with varying concentrations of glutamate. Affinities ($K_d$) for SF-iGluSnFR.A184S, SF-iGluSnFR.A184V, and SF-iGluSnFR.S72A are 0.6, 2.1, and 34 µM respectively. Affinities for SF-Venus.A184V and SF-Azurite.A184V are 2.0 and 9 µM respectively. Bottom panel is zoom-in of top panel.

FIG. 63A-B|Rise and decay of fluorescence signal resulting from a single field stimulation (1 msec., 90 mA) in rat hippocampal culture (10 DIV, 7 DPI) in non-flowing buffer (FIG. 63B). Traces in FIG. 63A are the average of three ROIs (bottom) and three trials (top); error bars are standard deviation of those nine measurements. The large error for GCaMP6f results from back propagating action potentials, which can be seen in differences from individual ROIs.

FIG. 66A-J|Vesicle release sites can be localized by identifying the center of stimulus-evoked SF-iGluSnFR fluorescence changes. (FIGS. 66A and 66B) Representative images of SF-iGluSnFR.S72A and SF-iGluSnFR.A184V expression in primary neuron cultures. Markers indicate the centers of Gaussians fitted to fluorescence profiles calculated across identified release sites from consecutive stimulation trials (such as shown in (FIG. 66E)). Note that the scatter of the centers of the localized release sites is substantially larger for SF-iGluSnFR.A184V (16-25 stimulation trials per experiment with inter-stimulus intervals of 20-60 s, 20 frames before and 10 frames after stimulation were recorded). (FIGS. 66C and 66D) Spots of increased fluorescence as they occur immediately after electrical stimulation when neurons are expressing SF-iGluSnFR.S72A or SF-iGluSnFR.A184V. 10 frames after the stimulus were averaged and divided by an average of 5 frames before stimulation. In this way, structures, which do not change fluorescence after simulation (background/inactive dendritic segments) will become 1. The lookup table of these images was adjusted to range from 1 to 1.5. (FIG. 66E) Line profiles calculated across the response sites shown in (FIG. 66C) and (FIG. 66D) (dashed lines) and superimposed Gaussian fits (lines). The width of the fitted Gaussian profiles were 0.57 and 1.11 µm for SF-iGluSnFR.S72A and SF-iGluSnFR.A184V, respectively. (FIG. 66F) Localization is more precise for SF-iGluSnFR. S72A. For each selected responding site (n=28-53), the mean deviation of the center of the Gaussians across the stimulation trials was calculated. These values were averaged and bar graphed for each SF-iGluSnFR variant. (FIGS. 66G and 66H) Width and amplitude of fitted Gaussian functions are significantly larger for the high affinity A184V sensor. (FIG. 66I) Gaussian fits to profiles obtained from individual (not averaged) frames after stimulus reveal the persistence of the SF-iGluSnFR.A184V variant. (FIG. 66J) Left: Gaussians fitted to the SF-iGluSnFR.A184V-mediated signal progressively broaden over time indicating that also sensor molecules remote to the site of release bind glutamate. Right: Same data as on left, but plotted as width over 4*t. The data points can be approximated by a line consistent with a diffusional spread of glutamate. The slope of the fitted line estimates the apparent (A184V-slowed) diffusion coefficient (Dapp) of synaptically released glutamate to be 4.3 $µm^2/s$ in vitro. This value is orders of magnitude smaller than the diffusion coefficient of free glutamate in solution (~600-700 $µm^2/s$) indicating that A184V not only prolongs but also substantially localizes glutamate molecules at the sites of release.

FIG. 67A-C|Annotated amino acid sequences of SF-iGluSnFR (FIG. 67A), SF-Azurite-iGluSnFR (FIG. 67C), and SF-Venus-iGluSnFR (FIG. 67B). Domains colored as indicated. Affinity modulating mutations S72A and A184V/S are indicated by orange arrow. Mutations from SF-iGluSnFR to SF-Venus-iGluSnFR and SF-Azurite-iGluSnFR indicated in red.

(FIG. 68A) Titration of SF-Azurite-iGluSnFR yields a $K_d$ of 62±11 µM, error bars are standard deviation of three measurements. Excitation (FIG. 67B), emission (FIG. 67C), and absorption (FIG. 68D) spectra of SF-Azurite-iGluSnFR (light blue) and Azurite (dark blue), with glutamate (solid line) and without (dashed line).

(FIG. 69D) 2-photon spectrum with SF-iGluSnFR (black) and vertical 1030 nm markup included for reference.

FIG. 70A-F Annotated amino acid sequences of the SF biosensors disclosed herein. Affinity modulating mutations S72A and A184V/S are indicated with small case letters. For SEQ ID NOs: 176-182, each domain is indicated with underlining as follows: <u>IgG secretion signal</u>; GltI 5-253; <u>SF-GFP 147-238</u>; Linker; <u>SF-GFP1-146</u>; GM 254-279; <u>Myc epitope</u>; <u>PDGFR transmembrane domain 513-561</u>. SF-iGluSnFR.A184V (SEQ ID NO: 179); SF-iGluSnFR.A184S (SEQ ID NO: 177); SF-iGluSnFR.S72A (SEQ ID NO:178); SF-Venus-iGluSnFR.A184V (SEQ ID NO: 179; mutations at residues T203Y and Y65G to shift the color and at residues F46L and S72A to increase chromophore maturation are shown in lower case); SF-Venus-iGluSnFR.A184S (SEQ ID NO: 180; mutations at residues T203Y and Y65G to shift the color and at residues F46L and S72A to increase chromophore maturation are shown in lower case); SF-Venus-iGluSnFR.S72A (SEQ ID NO: 181; mutations at residues T203Y and Y65G to shift the color and at residues F46L and S72A to increase chromophore maturation are shown in lower case); SF-Azurite-iGluSnFR (SEQ ID NO: 182; mutations at residues T65S and Y66H to shift the color and at residues V150I and V224R to improve maturation and brightness are shown in lower case; Linker1 mutations: GltI-cpSFGFP connection from PILVSHNV (SEQ ID NO: 187) to PILGYHNV (SEQ ID NO: 188); Linker2 mutations: cpSFGFP-GltI connection from YNFNNPLN (SEQ ID NO: 189) to YNFNEQLN (SEQ ID NO: 190)); iDexSnFR (or SF-GlucoseSensor) (SEQ ID NO: 183); iGABASnFR (SEQ ID NO: 184; cpSFGFP was inserted after D276 of the Pf622 starting sequence. Insertion of cpSFGFP is after residue D276 of Pf622. Residues RS near the N-terminus encode BglII, and residues LQ at the C-terminus encode PstI. Mutations included in iGABASnFR include: affinity modulating hinge mutation: Pf622: F101L; Pf622-SFGFP interface: Pf622: N260A; Linker 1: SHNVY (SEQ ID NO: 191) of SFGFP to LAQVR (SEQ ID NO: 192) (SFGFP: S147L, H148A, N149Q, Y151R); Linker 2: SFGFP (SEQ ID NO: 193): F145W; Linker 2: SVLAP (SEQ ID NO: 194) of Pf622 to ANLAP (SEQ ID NO: 195) (Pf622: S277A, V278N); Binding site mutation: Pf622: F102G/Y. Underlining indicates the domain as follows: <u>IgG secretion signal</u>; Pf622 2-276; <u>SF-GFP147-238</u>; Linker; <u>SF-GFP1-146</u>; Pf622 277-320; <u>Myc epitope</u>; <u>PDGFR transmembrane domain 513-561</u>. Binding site mutation F102 indicated with a small case letter; and iAChSnFR (E. coli expression vector shown in SEQ ID NO:185 with the domains indicated as follows: <u>pHHM His tag leader sequence</u>; Thermoanaerobacter sp. X513 choline binding protein sequence; Linker regions; Circularly permuted super-folder EGFP; <u>Myc tag C-terminal sequence</u>; and mammalian expression vector shown in SEQ ID NO: 186 with the domains indicated as follows: <u>IgG secretion sequence leader</u>; Thermoanaerobacter sp. X513 choline binding protein sequence; <u>Linker regions</u>; <u>CircularlypermutedsuperfolderEGFP</u>; <u>PDGFR transmembrane sequence</u>).

FIG. 71 A schematic of Structure I as described herein.

DETAILED DESCRIPTION

Figure 1:
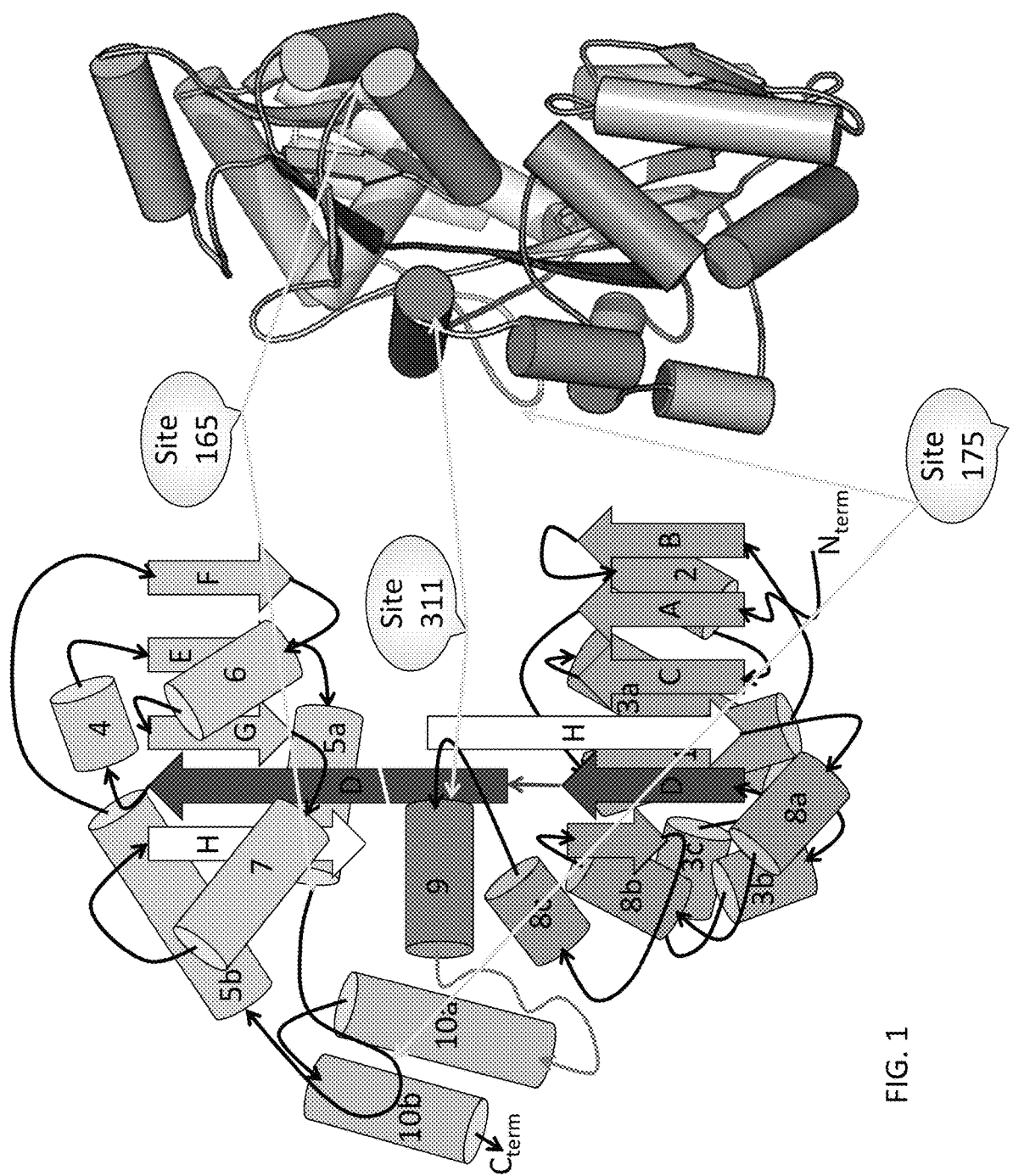
FIG. 1|Cartoon representation showing ligand bound *Escherichia coli* malto-dextrin-binding protein (EcMBP) and potential circularly-permuted fluorescent protein (cpFP) insertion sites.

The present disclosure is based, at least in part, on the discovery of structures and methods related to and useful for genetically encoded biosensors. Specifically, the disclosure provides genetically encoded recombinant or chimeric peptides for use as biosensors and methods for the design, production, and use of such biosensors. As described below, these sensors can be employed (e.g., expressed) in biological systems to detect and/or monitor a wide range of target analytes (e.g., a defined, selected, and/or specific analytes) due, in part, to the signal change generated by the sensors upon binding to their respective analyte(s), which signal change allows bound and unbound sensors to be distinguished.

While the disclosure encompasses generic biosensors and methods related thereto, examples of particular binding sensors, including biosensors for detecting maltose, sucrose, maltotriose, glutamate, phosphonate, and glucose are also disclosed.

Compositions

Provided herein are genetically encoded biosensors, i.e., nucleic acids encoding peptides, and/or the encoded peptides (e.g., isolated peptides), for use as biosensors. Biosensors herein include genetically encoded recombinant peptides containing an analyte-binding framework portion linked (e.g., operably linked) to at least one independent signaling portion, wherein the independent signaling portion is allosterically modulated or regulated by the framework portion upon interaction of the framework portion with an analyte (e.g., a defined, selected, and/or specific analyte), such that signaling from the signaling portions is altered upon interaction of the framework portion with the analyte.

In some instances, an independent signaling portion is present at a site within the framework portion that undergoes a conformational change upon interaction of the framework portion with an analyte such that the conformational change allosterically modulates or regulates signaling by the signaling portion. For example, biosensors herein can include structure I.

In some instances, signaling by the signaling portion is detectably altered upon interaction (e.g., binding) of the framework portion with an analyte. For example, signaling by the signaling portion can detectably increase or detectably decrease upon interaction (e.g., binding) of the framework portion with an analyte. In some cases, biosensors have a signal change upon binding (e.g., specific binding) to their respective analyte of at least about, for example, ±0.5, and/or an increase or decrease in signal of at least about, for example, 10%, 20%, 30%, 40%, 50%, 60%, 70%, 80%, 90%, 100%, 250%, 500%, 750%, 1000%, or more than 1000%, e.g., relative to unbound biosensor. In some increases, the level of signal change is linked to background signal. Values represented here can be converted and/or expressed into any conventional units using ordinary skill. For example, units can be expressed as 'signal change' (as used above), $\Delta F/F$ and/or as signal-to-noise ratio (e.g., $\Delta F/F$ multiplied by the square root of the number of photons collected). In some instances, signaling by a biosensor can be intensity based.

In some instances, biosensors herein are distinguishable from Förster resonance energy transfer, also known as fluorescence resonance energy transfer (FRET)-based sensors, which require donor and acceptor chromophores, e.g., that function in concert, in that they include independently functioning or detectable signaling portions. For example, in some instances, signaling by a first signaling portion of a biosensor herein is independent of signaling by a second signaling portion within the same or a distinct biosensor. As noted above, signaling portions are allosterically regulated by the framework portion to which they are linked upon interaction of the framework portion with an analyte (e.g., a defined, selected, and/or specific analyte).

Framework Portions

Framework portions include genetically encoded macromolecules (e.g., proteins or peptides) that undergo conformational alteration (e.g., a structural change) upon interaction (e.g., binding) with, or to, an analyte (e.g., an analyte-binding dependent conformational alteration). For example, genetically encoded framework portions can have a first structure in the absence of an analyte (e.g., in an unbound or open state) and a second structure, that is detectably distinct (e.g., differences in structures before and after a conformational change can be observed using methods known in the art) from the first structure, in the presence of an analyte (e.g., in a bound or closed state), e.g., under physiologic conditions. In some instances, the conformational change that occurs upon interaction with an analyte (e.g., an analyte-binding dependent conformational alteration) is detectably distinct (e.g., can be observed using methods known in the art) from a conformational change that may occur for the same protein or peptide under other physiological conditions (e.g., a change in conformation induced by altered temperature, pH, voltage, ion concentration, phosphorylation).

Methods for identifying proteins or peptides that exhibit suitable conformational characteristics and/or for observing differences in structure between structures or before and after a conformational change are known in the art and/or are described herein. Such methods can include, for example, one or more of structural analysis, crystallography, NMR, EPR using Spin label techniques, Circular Dichroism (CD), Hydrogen Exchange surface Plasmon resonance, calorimetry, and/or FRET.

In some instances, framework portions can have a first structure in the absence of an analyte (e.g., in an unbound or open state) and a second structure, that is detectably distinct (e.g., can be observed using methods known in the art) from the first structure, in the presence of an analyte (e.g., in a bound or closed state), e.g., under physiologic conditions, wherein the structural change between the open and closed state can allosterically modulate an independent signaling portion recombinantly (e.g., artificially introduced) present within the framework portion (see, e.g., Structure I).

Framework portions can also interact (e.g., bind) with at least one analyte (e.g., at least one defined, specific, and/or selected analyte). In some instances, a framework portion can interact specifically with one analyte (e.g., at least one defined, specific, and/or selected analyte). In such cases, affinity of binding between the framework binding peptide and the analyte can be high or can be controlled (e.g., with millimolar, micromolar, nanomolar, or picomolar affinity). Alternatively, the single framework binding protein can bind two or more analytes (e.g., two or more defined, specific, and/or selected analytes). In such cases, affinity of binding to the two or more analytes can be the same or distinct. For example, the affinity of binding can be greater for one analyte than it is for a second or third, etc., analyte. In some instances, binding between a framework portion and an analyte (e.g., at least one defined, specific, and/or selected analyte) have an affinity of for example, 10 mM to 1 pM.

As used herein, the term "analyte" can include naturally occurring and/or synthetic sugars, amino acids, proteins (e.g., proteins, peptides, and/or antibodies), hormones, ligands, chemicals (e.g., small molecules), pharmaceuticals, nucleic acids, cells, tissues, and combinations thereof.

In some instances, biosensors can include one, two, or more framework binding portions that bind (e.g., binds specifically) a single analyte (e.g., a single defined, specific, and/or selected analyte) or distinct analytes (e.g., two or more distinct defined, specific and/or selected analytes).

Alternatively or in addition, the framework portion can be chimeric. In such cases, a first part of the framework portion can be a first peptide or can be derived from a first peptide, and a second part of the framework portion can be a second peptide or can be derived from a second peptide, wherein the first a second peptides are combined to result in a single peptide.

Accordingly, framework portions can include macromolecules that undergo a conformational change upon interaction with an analyte. One non-limiting example of a suitable macromolecule is Calmodulin (CaM). CaM is in an extended shape in the absence of $Ca^{2+}$ and in a condensed conformation in the presence of $Ca^{2+}$ (Kuboniwa et al., Nat. Struc. Biol., 2:768-776, 1996 and Fallon and Quiocho, Structure, 11:1303-1307, 2003).

In some instances, a framework binding portion can be a bacterial protein or can be derived from a bacterial protein. Suitable bacterial proteins can include, but are not limited to, for example, periplasmic binding proteins (PBPs).

PBPs from bacteria are generally useful in the biosensors herein at least because they undergo dramatic conformational changes upon ligand binding (Ouiocho et al. Mol. Microbiol., 20:17-225, 1996). X-ray crystal structures of the apo (open) and bound (closed) forms of various PBPs reveal that these proteins have two (typically, although some have more) domains that undergo a large hinge-twist movement relative to each other in a Venus flytrap manner (Dwyer and Hellinga, Curr. Opin. Struc. Biol., 14:495-504, 2004). This conformational change has been exploited to create a number of FRET-based genetically encoded sensors (see, e.g., Deuschle et al., Pro. Sci, 14:2304-2314, 2005; Deuschle et al., Cytometry, 64:3-9, 2005; Okumoto et al., Proc. Natl. Acad. Sci. USA., 102:8740-8745, 2005; Bogner and Ludewig, J. Fluoresc., 17:350-360, 2007; and Gu et al., FEBS Letters, 580:5885-5893, 2006). In addition, the ligand-binding diversity of the PBP superfamily is large (Dwyer and Hellinga, Curr. Opin. Struc. Biol., 14:495-504, 2004).

In some instances, framework portions can include, for example, one or more of: arabinose-binding protein(s), glucose/galactose-binding protein(s), histidine-binding protein(s), maltose-binding protein(s), glutamine-binding protein(s), maltotriose-binding protein(s), RBP, ribose-binding protein(s), acetylcholine binding protein(s), choline binding protein(s), lysine binding protein(s), arginine binding protein(s), gamma aminobutyric acid (GABA) binding protein(s), ion-binding protein(s), peptide-binding protein(s), lactate-binding protein(s), histamine-binding protein(s), and/or Leucine/Isoleucine/Valine binding protein(s), including full length proteins, fragments, and/or variants thereof.

In some instances, exemplary framework portions can include: SEQ ID NO:105, which is *Escherichia* coli maltodextrin-binding protein (EcMBP) (UniProt accession number P0AEX9); SEQ ID NO: 106, which is *Pyrococcus Furiosus* maltotriose-binding protein (PfMBP) (UniProt accession number P58300); SEQ ID NO:107, which is *E. coli* glutamate-binding protein (EcYbeJ) (UniProt accession number Q1R3F7); SEQ ID NO:108, which is *E. coli* phosphonate-binding protein (EcPhnD) (UniProt accession number P37902); and/or SEQ ID NO:109, which is *Thermus thermophilus* glucose-binding protein (TtGBP) (UniProt accession number Q72KX2, including full length proteins, fragments, and/or variants thereof.

In some instances, exemplary framework portions can include SEQ ID NO: 110 (UniProt accession number Q92N37); SEQ ID NO:111 (UniProt accession number D0VWx8, SEQ ID NO:112 (UniProt accession number Q7CX36), and/or SEQ ID NO:113 (UniProt accession number P0AD96, including full length proteins, fragments, and/or variants thereof.

In some embodiments, exemplary framework portions can include residues 24-272 and 517-542 of SEQ ID NO: 176 (SF-iGluSnFR.A184V); residues 24-272 and 517-542 of SEQ ID NO: 177 (SF-iGluSnFR.A184S); residues 24-272 and 517-542 of SEQ ID NO: 178 (SF-iGluSnFR.S72A); residues 24-272 and 517-542 of SEQ ID NO: 179 (SF-Venus-iGluSnFR.A184V); residues 24-272 and 517-542 of SEQ ID NO: 180 (SF-Venus-iGluSnFR.A184S); residues 24-272 and 517-542 of SEQ ID NO: 181 (SF-Venus-iGluSnFR.S72A); residues 24-271 and 519-541 of SEQ ID NO: 182 (SF-Azurite-iGluSnFR); residues 24-350 and 595-664 of SEQ ID NO: 183 (iDexSnFR or SF-GlucoseSensor); residues 24-298 and 543-586 of SEQ ID NO: 184 (iGABASnFR); residues 25-99 and 348-545 of SEQ ID NO: 185 (iAChSnFR E. coli expression sequence); or residues 24-98 and 347-544 of SEQ ID NO: 186 (iAChSnFR mammalian expression sequence).

In some instances, framework portions, or biosensors, do not include signal peptides, or portions of signal peptides, that would otherwise be present in the peptide from which the framework portion is derived.

Signaling Portions

Biosensors herein include one or more genetically encoded signaling portions (e.g., independent signaling portions) within the amino acid sequence of a framework portion at a site(s) within the framework portion that undergo(es) a conformational change upon interaction of the framework portion with an analyte (e.g., a defined, specific, and/or selected analyte).

Signaling portions (e.g., independent signaling portions) include genetically encoded molecules (e.g., peptides or proteins) that can be allosterically induced to emit a detectable signal (e.g., an analyte-binding dependent signal).

In some instances, the detectable signal is detectably distinct (e.g., can be distinguished using methods known in the art and/or disclosed herein) from a signal emitted by the molecule prior to allosteric inducement (e.g., signaling portions can emit a detectable signal in two detectably distinct states. For example, first signal can be emitted in unbound state and a second signal can be emitted in bound state). As noted above, in some instances, the detectable signal is proportional to the degree of allosteric inducement. In some instances, if two or more signaling portions are present in a biosensor, then two or more detectably distinct signals can be emitted by the biosensor.

In some instances, a genetically encoded independent signaling portion is a genetically encoded fluorescent protein (FP), e.g., a macromolecule containing a functional group (e.g., a fluorophore) that absorbs energy of a specific wavelength and re-emits energy at a different (but equally specific) wavelength, including, for example, circularly permuted FP (cpFP). In some instances, a signaling portion is a "superfolder" FP (e.g., Pedelacq et al., 2006, Nat. Biotech., 24:79-88), e.g., a circularly permuted SF FP.

As used herein, the term "fluorophore" relates to a functional group in a molecule which will absorb energy of a specific wavelength and re-emit energy at a different (but equally specific) wavelength. In some instances, fluorophore containing molecules include fluorescent proteins. The fluorophore in green fluorescent protein (GFP) includes Ser-Tyr-Gly sequence (i.e., Ser65-dehydroTyr66-Gly67), which is post-translationally modified to a 4-(p-hydroxybenzylidene)-imidazolidin-5. Exemplary genetically encoded fluorescent proteins include, but are not limited to, fluorescent proteins from coelenterate marine organisms, e.g., *Aequorea victoria, Trachyphyllia geoffroyi*, coral of the *Discosoma* genus, *Renilla mulleri, Anemonia sulcata, Heteractis crispa, Entacmaea quadricolor*, and/or GFP (including the variants S65T and EGFP, *Renilla mulleri* GFP), cyan fluorescent protein (CFP), including Cerulean, and mCerulean3 (described by Markwardt et al., PLoS ONE, 6(3) e17896.doi:10.1371/journal.pone.0017896), CGFP (CFP with Thr203Tyr: Has an excitation and emission wavelength that is intermediate between CFP and EGFP), yellow fluorescent protein (YFP, e.g., GFP-Ser65Gly/Ser72Ala/Thr203Tyr; YFP (e.g., GFP-Ser65Gly/Ser72Ala/Thr203Tyr) with Val68Leu/Gln69Lys); Citrine (i.e., YFP-Val68Leu/Gln69Met), Venus (i.e., YFP-Phe46Leu/Phe64Leu/Met153Thr/Val163Ala/Ser175Gly), PA-GFP (i.e., GFP-Val/163Ala/Thr203His), Kaede), red fluorescent protein (RFP, e.g., long wavelength fluorescent protein, e.g., DsRed (DsRed1, DsRed2, DsRed-Express, mRFP1, drFP583, dsFP593, asFP595), eqFP611, and/or other fluorescent proteins known in the art (see, e.g., Zhang et al., Nature Reviews, Molecular and Cellular Biology, 3:906-908, 2002).

As set forth above, in some instances, fluorophore containing molecules include fluorescent proteins that can be or that are circularly permutated. Circular permutation methods are known in the art (see, e.g., Baird et al., Proc. Natl. Acad. Sci., 96:11241-11246, 1999; Topell and Glockshuber, Methods in Molecular Biology, 183:31-48, 2002) as are "superfolder" (SF) proteins (e.g., Pedelacq et al., 2006, Nat. Biotech., 24:79-88) (e.g., circularly permuted SF proteins).

In some instances, single-FP sensors have a number of advantages: they preserve spectral bandwidth for multi-analyte imaging; their saturated states may be nearly as bright as the parental FP, and their ligand-free states may be arbitrarily dim, providing large theoretical fluorescence increases. This allows for much greater changes in fluorescence and thus increased signal-to-noise ratios and greater resistance to photobleaching artifacts (Tian et al., Nat. Methods, 6:875-881, 2009).

In some instances, issues arising from long-term effects such as gene regulation and protein expression and degradation can be identified by simply fusing the intensity-based sensor to a another fluorescent protein of different color, to serve as a reference channel.

In some instances, biosensors can include circularly permuted YFP (cpYFP) as a cpFP. cpYFP has been used as a reporter element in the creation of sensors for $H_2O_2$ (HyPer) (Belousov et al., Nat. Methods, 3:281-286, 2006), cGMP (FlincG) (Nausch et al., Proc. Natl. Acad. Sci. USA., 105: 365-370, 2008), ATP:ADP ratio (Perceval) (Berg et al., Nat. Methods., 105:365-370, 2008), and calcium ions (Nakai et al., Nat. Biotechno., 19:137-141, 2001), including full length, fragments, and/or variants thereof.

In some embodiments, exemplary sensor portions can include residues 273-516 of SEQ ID NO: 176 (SF-iGluSnFR.A184V); residues 273-516 of SEQ ID NO: 177 (SF-iGluSnFR.A184S); residues 273-516 of SEQ ID NO: 178 (SF-iGluSnFR.S72A); residues 273-516 of SEQ ID NO: 179 (SF-Venus-iGluSnFR.A184V); residues 273-516 of SEQ ID NO: 180 (SF-Venus-iGluSnFR.A184S); residues 273-516 of SEQ ID NO: 181 (SF-Venus-iGluSnFR.S72A); residues 272-518 of SEQ ID NO: 182 (SF-Azurite-iGluSnFR); residues 351-594 of SEQ ID NO: 183 (iDexSnFR or SF-GlucoseSensor); residues 299-544 of SEQ ID NO: 184 (iGABASnFR); residues 104-343 of SEQ ID NO: 185

(iAChSnFR *E. coli* expression sequence); or residues 103-342 of SEQ ID NO: 186 (iAChSnFR mammalian expression sequence).

Linker Portions

As shown in Structure I, biosensors herein can optionally include one or more genetically encoded linkers positioned between or operably linking the framework portion and the signaling portion. Linker portions can include at least one naturally occurring or synthetic amino acid (discussed below) as exemplified by SEQ ID NOs: 9-49, 54-61, 64-76, 79-90, 95-104. In some instances, linker can include one or more of SEQ ID NOs: 9-49, 54-61, 64-76, 79-90, 95-104, and/or portions of SEQ ID NOs: 9-49, 54-61, 64-76, 79-90, 95-104. For example, linkers can include, but are not limited to, one or more of: PxSHNVY (SEQ ID NO:114), xPSHNVY (SEQ ID NO:115), xxSHNVY (SEQ ID NO:116), xxSHNVF (SEQ ID NO:117), PxSHNVF (SEQ ID NO:118), PxSYNVF (SEQ ID NO:119), xxSYNVF (SEQ ID NO:120), PxSYNVF (SEQ ID NO:121), xxSYNVF (SEQ ID NO:122), PxSxNVY (SEQ ID NO:123), PxSHxVY (SEQ ID NO:124), PxSHNxY (SEQ ID NO:125), PxSHNVx (SEQ ID NO:126), FNxxY (SEQ ID NO:127), FNxY (SEQ ID NO:128), FNY (SEQ ID NO:129), FxY (SEQ ID NO:130), xxY (SEQ ID NO:131), WxY (SEQ ID NO:132), xKY, (SEQ ID NO:133), FNPxY (SEQ ID NO:134), FNxPY (SEQ ID NO:135), HNS (SEQ ID NO:136), GGS (SEQ ID NO:137), xxS (SEQ ID NO:138), xxK (SEQ ID NO:139), GGK (SEQ ID NO:140), PXS (SEQ ID NO:141), xPS (SEQ ID NO:142), Px (SEQ ID NO:143), xP (SEQ ID NO:144), IxxS (SEQ ID NO:145), NxPK (SEQ ID NO:146), NPcK (SEQ ID NO:147), PPxSH (SEQ ID NO:148), PPxxSH (SEQ ID NO:149), PPPxSH (SEQ ID NO:150), PPxPSH (SEQ ID NO:151), xxSH (SEQ ID NO:152), PPxx (SEQ ID NO:153), FNxKN (SEQ ID NO:154), FNxxKN (SEQ ID NO:155), FNxPKN (SEQ ID NO:156), FNPxKN (SEQ ID NO:157), FNxx (SEQ ID NO:158), N, ADGSSH (SEQ ID NO:159), ADxxSH (SEQ ID NO:160), ADxPSH (SEQ ID NO:161), ADPxSH (SEQ ID NO:162), ADxx (SEQ ID NO:163), ADxxSH (SEQ ID NO:164), FNPG (SEQ ID NO:165), FNxxPG (SEQ ID NO:166), xxPG (SEQ ID NO:167), FNxx (SEQ ID NO:168), FNPx (SEQ ID NO:169), KYxxSH (SEQ ID NO:170), KYPxSH (SEQ ID NO:171), KYxPSH (SEQ ID NO:172), FxxP (SEQ ID NO:173), FNxP (SEQ ID NO:174), and/or FNPx (SEQ ID NO:175), where "x" indicates any amino acid.

In some embodiments, exemplary linker portions can include residues 365-370 of SEQ ID NO: 176 (SF-iGluSnFR.A184V); residues 365-370 of SEQ ID NO: 177 (SF-iGluSnFR.A184S); residues 365-370 of SEQ ID NO: 178 (SF-iGluSnFR.S72A); residues 365-370 of SEQ ID NO: 179 (SF-Venus-iGluSnFR.A184V); residues 365-370 of SEQ ID NO: 180 (SF-Venus-iGluSnFR.A184S); residues 365-370 of SEQ ID NO: 181 (SF-Venus-iGluSnFR.S72A); residues 365-370 of SEQ ID NO: 182 (SF-Azurite-iGluSnFR); residues 443-448 of SEQ ID NO: 183 (iDexSnFR or SF-GlucoseSensor); residues 391-396 of SEQ ID NO: 184 (iGABASnFR); residues 100-103 and 344-347 of SEQ ID NO: 185 (iAChSnFR *E. coli* expression sequence); or residues 99-102 and 343-346 of SEQ ID NO: 186 (iAChSnFR mammalian expression sequence).

Exemplary Biosensor Constructs

As noted above, biosensors herein include genetically encoded biosensors, i.e., nucleic acids encoding biosensors, and/or the encoded biosensors (e.g., isolated biosensors), for use as biosensors. In some instances, nucleic acids encoding biosensors include isolated nucleic acids. In some instances, the portion of a nucleic acid encoding a biosensor can include a single reading frame encoding the biosensor. For example, a biosensor can be encoded by a portion of a nucleic acid that falls within a start codon and a stop codon. In some instances, biosensors are isolated (e.g., biosensors are substantially free of contaminating and/or non-biosensor components).

In some instances, biosensors can include, for example, one or more framework portions selected from the group consisting of: arabinose-binding protein(s), glucose/galactose-binding protein(s), histidine-binding protein(s), maltose-binding protein(s), maltotriose-binding protein(s), glutamine-binding protein(s), RBP, ribose-binding protein(s), acetylcholine binding protein(s), choline binding protein(s), lysine binding protein(s), arginine binding protein(s), gamma aminobutyric acid (GABA) binding protein(s), ion-binding protein(s), peptide-binding protein(s), lactate-binding protein(s), histamine-binding protein(s), and/or Leucine/Isoleucine/Valine binding protein(s), including full length proteins, fragments, and/or variants thereof, including full length proteins, fragments and/or variants thereof, and at least one independent signaling portion present at a site within the framework portion that undergoes a conformational change upon interaction of the framework portion with an analyte.

In some instances, biosensors can include, for example, one or more framework portions selected from the group consisting of: SEQ ID NO:105, which is *Escherichia coli* maltodextrin-binding protein (EcMBP) (UniProt accession number P0AEX9); SEQ ID NO: 106, which is *Pyrococcus Furiosus* maltose-binding protein (PfMBP) (UniProt accession number P58300); SEQ ID NO:107, which is *E. coli* glutamate-binding protein (EcYbeJ) (UniProt accession number Q1R3F7); SEQ ID NO:108, which is *E. coli* phosphonate-binding protein (EcPhnD) (UniProt accession number P37902); and/or SEQ ID NO:109, which is *Thermus thermophilus* glucose-binding protein (TtGBP) (UniProt accession number Q72KX2), including full length proteins, fragments and/or variants thereof, and at least one independent signaling portion present at a site within the framework portion that undergoes a conformational change upon interaction of the framework portion with an analyte.

In some instances, biosensors can include, for example, one or more framework portions selected from the group consisting of: SEQ ID NO: 110 (UniProt accession number Q92N37); SEQ ID NO:111 (UniProt accession number D0VWx8, SEQ ID NO:112 (UniProt accession number Q7CX36), and/or SEQ ID NO:113 (UniProt accession number P0AD96), including full length proteins, fragments and/or variants thereof, and at least one independent signaling portion present at a site within the framework portion that undergoes a conformational change upon interaction of the framework portion with an analyte.

In some instances, biosensors include any one or more:
  Maltose biosensors SEQ ID NOs: 1-8 (e.g., *Escherichia coli* maltodextrin-binding protein (EcMBP)) or SEQ ID NOs: 50-53 (e.g., *Pyrococcus furiosus* maltose-binding protein (PfMBP)), including full length proteins, fragments and/or variants thereof;
  Glutamate biosensors SEQ ID NOs: 62-63 (e.g., *E. coli* glutamate-binding protein (EcYbeJ)) or SEQ ID NOs: 176-182, including full length proteins, fragments and/or variants thereof;
  Phosphonate biosensors SEQ ID NOs: 77-78 (e.g., *E. coli* phosphonate-binding protein (EcPhnD)), including full length proteins, fragments and/or variants thereof;

Glucose biosensors SEQ ID NOs: 91-94 (e.g., *Thermus thermophilus* glucose-binding protein (TtGBP)) and SEQ ID NO: 183, including full length proteins, fragments and/or variants thereof;

GABA biosensors SEQ ID NO: 184, including full length proteins, fragments and/or variants thereof; and/or ACh biosensors SEQ ID NOs: 185 & 186, including full length proteins, fragments and/or variants thereof.

In some instances, nucleic acids encoding, and/or amino acid sequences of, any of the framework portions, signaling portions, linker portions, or the entire biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) disclosed herein can be modified to generate fragments (e.g., truncated peptides) and/or variants (e.g., peptides with a defined sequence homology to the peptides disclosed herein). Variants can include framework portions, signaling portions, linker portions, or biosensors with amino acid sequences with homology to the framework portions, signaling portions, linker portions, or biosensors disclosed herein and/or truncated forms of the framework portions, signaling portions, linker portions, or biosensors herein. In some instances, truncated forms of the framework portions, signaling portions, linker portions, or biosensors herein can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36 37, 38, 39, 40, 41, 42, 43, 44, 45, 46, 47, 48, 49, 50, 50-100, 101-150, fewer amino acids than the framework portions, signaling portions, linker portions, and/or biosensors herein, e.g., wherein the truncated biosensor variants retain at least at portion of the binding and/or signaling properties of same biosensor without truncation (e.g., at least 50%, 60%, 70%, 80%, 90%, or 100% of the binding and/or signaling properties of the same biosensor without truncation). In addition, truncations can be made at the amino-terminus, the carboxy-terminus, and/or within the body of the framework portions, signaling portions, linker portions, and/or biosensors herein.

While variants are generally observed and discussed at the amino acid level, the actual modifications are typically introduced or performed at the nucleic acid level. For example, variants with 95%, 96%, 97%, 98, or 99% sequence identity to SEQ ID NOs: 1, 2, 3, 4, 5, 6, 7, 8, 50, 51, 52, 53, 62, 63, 77, 78, 91, 92, 93, 94, and/or 176-186 can be generated by modifying the nucleic acids encoding SEQ ID NOs: 1, 2, 3, 4, 5, 6, 7, 8, 50, 51, 52, 53, 62, 63, 77, 78, 91, 92, 93, 94, and/or 176-186 using techniques (e.g., cloning techniques) known in the art and/or that are disclosed herein.

As with all peptides, polypeptides, and proteins, including fragments thereof, it is understood that modifications to the amino acid sequence can occur that do not alter the nature or function of the peptides, polypeptides, or proteins. Such modifications include conservative amino acids substitutions and are discussed in greater detail below.

The peptides, polypeptides, and proteins, including fragments thereof, provided herein are biosensors whose activity can be tested or verified, for example, using the in vitro and/or in vivo assays described herein.

In some instances, any of the framework portions, signaling portions, or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) described herein can be modified and varied so long as their desired function is maintained. For example, the polypeptides can be modified as long as the resulting variant polypeptides have the same or better characteristics as the polypeptide from which they derived. For example, the variants can have the same or better affinity for their respective analyte.

In some instances, the interacting face of a modified peptide can be the same (e.g., substantially the same) as an unmodified peptide (methods for identifying the interacting face of a peptide are known in the art (Gong et al., BMC: Bioinformatics, 6:1471-2105 (2007); Andrade and Wei et al., Pure and Appl. Chem., 64(11):1777-1781 (1992); Choi et al., Proteins: Structure, Function, and Bioinformatics, 77(1):14-25 (2009); Park et al., BMC: and Bioinformatics, 10:1471-2105 (2009)), e.g., to maintain binding to an analyte. Alternatively, amino acids within the interacting face can be modified, e.g., to decrease binding to an analyte and/or to change analyte specificity.

The interacting face of a peptide is the region of the peptide that interacts or associates with other molecules (e.g., other proteins). Generally, amino acids within the interacting face are naturally more highly conserved than those amino acids located outside the interacting face or interface regions of a protein. In some instances, an amino acid within the interacting face region of any of the framework portions or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) disclosed herein can be the same as the amino acid shown in any of the framework portions or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) disclosed herein or can be include conservative amino acid substitutions. In some instances, an amino acid within the interacting face region any of the framework portions or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) disclosed herein can be substituted with an amino acid that increases the interaction between the framework portion or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) and an analyte.

In some instances, genetically encoded biosensors can include peptides that have at least 80, 85, 90, 95, 96, 97, 98, 99 percent identity to the framework portions, signaling portions, or the biosensor sequence (e.g., SEQ ID NOs: 1, 2, 3, 4, 5, 6, 7, 8, 50, 51, 52, 53, 62, 63, 77, 78, 91, 92, 93, 94, and/or 176-186) (e.g., any amino acid sequence) described herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math, 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Amino acid sequence modifications typically fall into one or more of three classes: substitutional, insertional, or deletional modifications. Insertions include amino and/or terminal fusions as well as intra-sequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions can be made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. In some instances, substitutions can be conservative amino acid substitutions. In some instances, variants herein can include one or more conservative amino acid substitutions. For example, variants can include 1, 2, 3, 4, 5, 6, 7, 8, 9, 10, 11, 12, 13, 14, 15, 16, 17, 18, 19, 20, 20-30, 30-40, or 40-50 conservative amino acid substitutions. Alternatively, variants can include 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions. Such substitutions generally are made in accordance with the following Table 1 and are referred to as conservative substitutions. Methods for predicting tolerance to protein modification are known in the art (see, e.g., Guo et al., Proc. Natl. Acad. Sci., USA, 101(25):9205-9210 (2004)).

TABLE 1

| Conservative Amino Acid Substitutions | |
|---|---|
| Amino Acid | Substitutions (others are known in the art) |
| Ala | Ser, Gly, Cys |
| Arg | Lys, Gln, His |
| Asn | Gln, His, Glu, Asp |
| Asp | Glu, Asn, Gln |
| Cys | Ser, Met, Thr |
| Gln | Asn, Lys, Glu, Asp, Arg |
| Glu | Asp, Asn, Gln |
| Gly | Pro, Ala, Ser |
| His | Asn, Gln, Lys |
| Ile | Leu, Val, Met, Ala |
| Leu | Ile, Val, Met, Ala |
| Lys | Arg, Gln, His |
| Met | Leu, Ile, Val, Ala, Phe |
| Phe | Met, Leu, Tyr, Trp, His |
| Ser | Thr, Cys, Ala |

TABLE 1-continued

| Conservative Amino Acid Substitutions | |
|---|---|
| Amino Acid | Substitutions (others are known in the art) |
| Thr | Ser, Val, Ala |
| Trp | Tyr, Phe |
| Tyr | Trp, Phe, His |
| Val | Ile, Leu, Met, Ala, Thr |

In some instances, substitutions are not conservative. For example, an amino acid can be replaced with an amino acid that can alter some property or aspect of the peptide. In some instances, non-conservative amino acid substitutions can be made, e.g., to change the structure of a peptide, to change the binding properties of a peptide (e.g., to increase or decrease the affinity of binding of the peptide to an analyte and/or to alter increase or decrease the binding specificity of the peptide).

Modifications, including the specific amino acid substitutions, are made by known methods. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Nucleic Acids

The disclosure also features nucleic acids encoding the biosensors (e.g., SEQ ID NOs: 1, 2, 3, 4, 5, 6, 7, 8, 50, 51, 52, 53, 62, 63, 77, 78, 91, 92, 93, 94, and/or 176-186) described herein, including variants and/or fragments of the biosensors (e.g., variants and/or fragments of SEQ ID NOs: 1, 2, 3, 4, 5, 6, 7, 8, 50, 51, 52, 53, 62, 63, 77, 78, 91, 92, 93, 94, and/or 176-186). These sequences include all degenerate sequences related to the specific polypeptide sequence, i.e., all nucleic acids having a sequence that encodes one particular polypeptide sequence as well as all nucleic acids, including degenerate nucleic acids, encoding the disclosed variants and derivatives of the polypeptide sequences. Thus, while each particular nucleic acid sequence may not be written out herein, it is understood that each and every sequence is in fact disclosed and described herein through the disclosed polypeptide sequences.

In some instances, nucleic acids can encode biosensors with 95, 96, 97, 98, or 99 identity to SEQ ID NOs: 1, 2, 3, 4, 5, 6, 7, 8, 50, 51, 52, 53, 62, 63, 77, 78, 91, 92, 93, 94, and/or 176-186.

In some instances, nucleic acids can encode SEQ ID NOs: 1, 2, 3, 4, 5, 6, 7, 8, 50, 51, 52, 53, 62, 63, 77, 78, 91, 92, 93, 94, and/or 176-186 containing 1, 2, 3, 4, 5, 6, 7, 8, 9, 10, 11, 12, 13, 14, 15, 16, 17, 18, 19, 20, 20-30, 30-40, or 40-50 conservative amino acid substitutions.

In some instances, nucleic acids can encode SEQ ID NOs: 1, 2, 3, 4, 5, 6, 7, 8, 50, 51, 52, 53, 62, 63, 77, 78, 91, 92, 93, 94, and/or 176-186 containing 50 or fewer, 40 or fewer, 30 or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions Also provided herein are vectors comprising the biosensors (e.g, SEQ ID NOs: 1, 2, 3, 4, 5, 6, 7, 8, 50, 51, 52, 53, 62, 63, 77, 78, 91, 92, 93, 94, and/or 176-186) described herein, including variants and/or fragments of the biosensors (e.g, SEQ ID NOs: 1, 2, 3, 4, 5, 6, 7, 8, 50, 51, 52, 53, 62, 63, 77, 78, 91, 92, 93, 94, and/or 176-186). For example:

Vectors can include nucleic acids that encode biosensors with 95, 96, 97, 98, or 99 identity to SEQ ID NOs: 1, 2, 3, 4, 5, 6, 7, 8, 50, 51, 52, 53, 62, 63, 77, 78, 91, 92, 93, 94, and/or 176-186.

Vectors can include nucleic acids that encode SEQ ID NOs: 1, 2, 3, 4, 5, 6, 7, 8, 50, 51, 52, 53, 62, 63, 77, 78, 91, 92, 93, 94, and/or 176-186 containing 1, 2, 3, 4, 5, 6, 7, 8, 9, 10, 11, 12, 13, 14, 15, 16, 17, 18, 19, 20, 20-30, 30-40, or 40-50 conservative amino acid substitutions.

Vectors can include nucleic acids that encode SEQ ID NOs: 1, 2, 3, 4, 5, 6, 7, 8, 50, 51, 52, 53, 62, 63, 77, 78, 91, 92, 93, 94, and/or 176-186 containing 50 or fewer, 40 or fewer, or fewer, 20 or fewer, 10 or fewer, 9 or fewer, 8 or fewer, 7 or fewer, 6 or fewer, 5 or fewer, 4 or fewer, 3 or fewer, or 2 or fewer conservative amino acid substitutions Examples of suitable vectors include, but are not limited to, plasmids, artificial chromosomes, such as BACs, YACs, or PACs, and viral vectors. As used herein, vectors are agents that transport the disclosed nucleic acids into a cell without degradation and, optionally, include a promoter yielding expression of the nucleic acid molecule in the cells into which it is delivered.

Viral vectors can include, for example, Adenovirus, Adeno-associated virus, herpes virus, Vaccinia virus, Polio virus, Sindbis, and other RNA viruses, including these viruses with the HIV backbone. Any viral families which share the properties of these viruses which make them suitable for use as vectors are suitable. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating Vaccinia virus vectors.

Non-viral based vectors can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, WI), Clontech (Pal Alto, CA), Stratagene (La Jolla, CA), and Invitrogen/Life Technologies (Carlsbad, CA). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), enhancers derived from a eukaryotic cell viruses can be used. Examples of such can include the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Promoters of this type can include the CMV promoter, the SV40 promoter, the β-actin promoter, the EF1α promoter, and the retroviral long terminal repeat (LTR).

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, CT) sequences typically are expressed as a fusion with the encoded polypeptide. Such tags can be inserted anywhere within the polypeptide including at either the carboxyl or amino terminus.

The disclosure further provides cells comprising the biosensors (e.g., SEQ ID NOs: 1, 2, 3, 4, 5, 6, 7, 8, 50, 51, 52, 53, 62, 63, 77, 78, 91, 92, 93, 94, and/or 176-186) described herein, including variants and/or fragments of the biosensors (e.g., SEQ ID NOs: 1, 2, 3, 4, 5, 6, 7, 8, 50, 51, 52, 53, 62, 63, 77, 78, 91, 92, 93, 94, and/or 176-186). Cells can include, for example, eukaryotic and/or prokaryotic cells. For example, cells can include, but are not limited to cells of *E. coli, Pseudomonas, Bacillus, Streptomyces*; fungi cells such as yeasts (*Saccharomyces*, and methylotrophic yeast such as *Pichia, Candida, Hansenula*, and *Torulopsis*); and animal cells, such as CHO, R1.1, B-W and LM cells, African Green Monkey kidney cells (for example, COS 1, COS 7, BSC1, BSC40, and BMT10), insect cells (for example, Sf9), human cells and plant cells. Suitable human cells can include, for example, HeLa cells or human embryonic kidney (HEK) cells. In general, cells that can be used herein are commercially available from, for example, the American Type Culture Collection (ATCC), P.O. Box 1549, Manassas, VA 20108. See also F. Ausubel et al., Current Protocols in Molecular Biology, John Wiley & Sons, New York, NY, (1998).

Optionally, the biosensors (e.g., SEQ ID NOs: 1, 2, 3, 4, 5, 6, 7, 8, 50, 51, 52, 53, 62, 63, 77, 78, 91, 92, 93, 94, and/or 176-186) described herein, including variants and/or fragments of the biosensors (e.g., SEQ ID NOs: 1, 2, 3, 4, 5, 6, 7, 8, 50, 51, 52, 53, 62, 63, 77, 78, 91, 92, 93, 94, and/or 176-186) can be located in the genome of the cell (e.g., can be stably expressed in the cell) or can be transiently expressed in the cell.

Methods of making the provided cells are known and the method of transformation and choice of expression vector will depend on the host system selected. Transformation and transfection methods are described, e.g., in F. Ausubel et al., Current Protocols in Molecular Biology, John Wiley & Sons, New York, NY, (1998), and, as described above, expression vectors may be chosen from examples known in the art.

There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

By way of example, the provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004). The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003). The provided polypeptides can be delivered by tegument aggregates. Methods for making and using tegument aggregates are described in International Publication No. WO 2006/110728.

Also provided are transgenic animals comprising one or more cells the biosensors (e.g, SEQ ID NOs: 1, 2, 3, 4, 5, 6, 7, 8, 50, 51, 52, 53, 62, 63, 77, 78, 91, 92, 93, 94, and/or 176-186) described herein, including variants and/or fragments of the biosensors (e.g, SEQ ID NOs: 1, 2, 3, 4, 5, 6, 7, 8, 50, 51, 52, 53, 62, 63, 77, 78, 91, 92, 93, 94, and/or 176-186). As used herein, the term animal refers to non-human animals, including, mammals, amphibians and birds. Specifically, examples include sheep, feline, bovines, ovines, pigs, horses, rabbits, guinea pigs, mice, hamsters, rats, non-human primates, and the like. As used herein, transgenic animal refers to any animal, in which one or more of the cells of the animal contain a heterologous nucleic acid. The heterologous nucleic acid can be introduced using known transgenic techniques. The nucleic acid is introduced into the cell, directly or indirectly. For example, the nucleic acid can be introduced into a precursor of the cell or by way of deliberate genetic manipulation, such as by microinjection or by infection with a recombinant virus. The nucleic acid may be integrated within a chromosome, or it may be an extrachromosomally replicating DNA.

Methods for making transgenic animals using a variety of transgenes have been described in Wagner et al. (1981) Proc. Nat. Acad. Sci. USA, 78:5016-5020; Stewart et al. (1982) Science, 217:1046-1048; Constantini et al. (1981) Nature, 294:92-94; Lacy et al. (1983) Cell, 34:343-358; McKnight et al. (1983) Cell, 34:335-341; Brinstar et al. (1983) Nature, 306:332-336; Palmiter et al. (1982) Nature, 300:611-615; Palmiter et al. (1982) Cell, 29:701-710; and Palmiter et al. (1983) Science, 222:809-814. Such methods are also described in U.S. Pat. Nos. 6,175,057; 6,180,849; and 6,133,502.

By way of example, the transgenic animal can be created by introducing a nucleic acid into, for example, an embryonic stem cell, an unfertilized egg, a fertilized egg, a spermatozoon or a germinal cell containing a primordial germinal cell thereof, preferably in the embryogenic stage in the development of a non-human mammal (more preferably in the single-cell or fertilized cell stage and generally before the 8-cell phase). The nucleic acid can be introduced by known means, including, for example, the calcium phosphate method, the electric pulse method, the lipofection method, the agglutination method, the microinjection method, the particle gun method, the DEAE-dextran method and other such method. Optionally, the nucleic acid is introduced into a somatic cell, a living organ, a tissue cell or other cell by gene transformation methods. Cells including the nucleic acid may be fused with the above-described germinal cell by a commonly known cell fusion method to create a transgenic animal.

For embryonic stem (ES) cells, an ES cell line may be employed, or embryonic cells may be obtained freshly from a host, e.g., mouse, rat, guinea pig, and the like. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the nucleic acid. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected. The chimeric animals are screened for the presence of the nucleic acid, and males and females having the modification are mated to produce homozygous progeny transgenic animals.

Kits comprising one or more containers and the nucleic acid sequences, polypeptides, vectors, cells, provided herein, or combinations thereof, are also provided. For example, provided is a kit comprising (i) a nucleic acid sequence encoding a biosensor described herein (e.g, one or more of SEQ ID NOs: 1, 2, 3, 4, 5, 6, 7, 8, 50, 51, 52, 53, 62, 63, 77, 78, 91, 92, 93, 94, and/or 176-186), including variants and/or fragments of the biosensor (e.g, variants or fragments of one or more of SEQ ID NOs: 1, 2, 3, 4, 5, 6, 7, 8, 50, 51, 52, 53, 62, 63, 77, 78, 91, 92, 93, 94, and/or 176-186), (ii) a polypeptide comprising a biosensor described herein (e.g, one or more of SEQ ID NOs: 1, 2, 3, 4, 5, 6, 7, 8, 50, 51, 52, 53, 62, 63, 77, 78, 91, 92, 93, 94, and/or 176-186), including variants and/or fragments of the biosensor (e.g, variants or fragments of one or more of SEQ ID NOs: 1, 2, 3, 4, 5, 6, 7, 8, 50, 51, 52, 53, 62, 63, 77, 78, 91, 92, 93, 94, and/or 176-186), (iii) a vector comprising the nucleic acid of (i), (iv) a cell comprising the nucleic acid or (i) and/or the polypeptide of (ii), (v) a cell comprising the vector of (iii). The kit can comprise any combination of (i)-(v). Optionally, the kit further comprises reagents for using the nucleic acid or peptide biosensors, vectors, and/or cells. For example, if the kit comprises cells, the kit may also comprise cell culture medium. Optionally, the kit further comprises instructions for use. Optionally, the kit further comprises a GPCR, a GPCR-encoding nucleic acid sequence.

Design and Production/Manufacture Methods

Using the methods described herein, it is possible to design, produce, and/or adapt genetically encoded biosensors to assays for a variety of classes of analytes. The provided materials and methods facilitate the discovery of new compounds targeting a wide array of protein targets, including but not limited to: endogenous targets responsible for disease state progression, targets on pathogens for treating infectious diseases, and endogenous targets to be avoided (thus screening early for potential drug side effects and toxicity).

Methods herein provide systematic and generic approaches for the design and production of genetically encoded recombinant peptides containing an analyte-binding framework portion linked (e.g., operably linked) to a signaling portion, wherein the signaling portion is allosterically modulated or regulated by the framework portion upon interaction of the framework portion with an analyte. Generally, methods include: (i) selecting one or more target analytes; (ii) selecting a framework portion (e.g., a PBP) that interacts with (e.g., interacts specifically with) or binds to (e.g., binds specifically to) the target analyte and that undergoes a conformational change upon interacting with or binding to the analyte; (iii) identifying sites or amino acid positions within the framework portion (e.g., the PBP) where the conformational change occurs; and (iv) inserting or cloning a signaling portion into the site or amino acid position identified in (iii). Methods can, optionally, further include: (v) modifying or optimizing linker sequences between the framework portion and the signaling portion, for example, by genetic manipulation (e.g., by point mutation); (vi) modifying or optimizing analyte binding; (vii) modifying the signal generated by the biosensor; and/or (viii) cloning the biosensor into a suitable vector.

In some instances: (iii) includes identification of insertion sites by analysis of the structure (e.g., crystal structure) of the selected framework portion (e.g., the selected PBP) in one or both of its open and closed states to determine amino acid positions at which analyte-binding dependent structural changes occur. In instances where structures for both open and closed states are not available, analysis can be conducted by analogy to a structurally similar framework portion (e.g., PBP); (iv) includes cloning a signaling portion (e.g., a cpFP) at the site identified in (iii) such that the analyte-binding dependent structural change observed in (iii) will result in a conformational change in the signaling portion (e.g., the cpFP) and allosteric modulation of the signaling portion; (v) includes generating a library of mutants of biosensors with distinct linker sequences (e.g., by point mutation), screening the library of mutants to identify mutants with enhanced properties (e.g., improved signal-to-noise ratio), and selecting mutants with enhanced properties (e.g., improved signal-to-noise ratio); (vi) includes increasing or decreasing binding or affinity of the framework portion to the analyte, e.g., by modifying amino acids in the interacting face of the framework portion or regions within the framework portion that are critical for analyte binding; (vii) includes increasing or decreasing signal emission by the signaling portion and/or changing the color of the signal where the signaling portion is a FP (e.g., a cpFP). Methods including (i)-(viii) are exemplified in the Examples section herein.

Methods of Use

The disclosure further provides methods for using the biosensors disclosed herein (e.g., one or more of SEQ ID NOs: 1, 2, 3, 4, 5, 6, 7, 8, 50, 51, 52, 53, 62, 63, 77, 78, 91, 92, 93, 94, and/or 176-186), including variants and/or fragments of the biosensor (e.g., variants or fragments of one or more of SEQ ID NOs: 1, 2, 3, 4, 5, 6, 7, 8, 50, 51, 52, 53, 62, 63, 77, 78, 91, 92, 93, 94, and/or 176-186)) to detect analytes, e.g., in biological systems. Such methods can include, for example:

Use of a maltose biosensor disclosed herein (e.g., one or more of SEQ ID NOs: 1, 2, 3, 4, 5, 6, 7, 8, 50, 51, 52, and/or 53 including variants and/or fragments of SEQ ID NOs: 1, 2, 3, 4, 5, 6, 7, 8, 50, 51, 52, and/or 53) to detect maltose, e.g., in a biological system;

Use of a glutamate biosensor disclosed herein (e.g., one or more of SEQ ID NOs: 62, 63, and/or 176-182 including variants and/or fragments of SEQ ID NOs: 62, 63, and/or 176-182) to detect glutamate, e.g., in a biological system;

Use of a phosphonate biosensor disclosed herein (e.g., one or more of SEQ ID NOs: 77 and/or 78 including variants and/or fragments of SEQ ID NOs: 77 and/or 78) to detect phosphonate, e.g., in a biological system; and/or Use of a glucose biosensor disclosed herein (e.g., one or more of SEQ ID NOs: 91, 92, 93, 94, and/or 183 including variants and/or fragments of SEQ ID NOs: 91, 92, 93, 94, and/or 183) to detect glucose, e.g., in a biological system.

Use of a GABA biosensor disclosed herein (e.g., SEQ ID NO: 184 including variants and/or fragments of SEQ ID NO: 184) to detect GABA, e.g., in a biological system.

Use of an ACh biosensor disclosed herein (e.g., one or more of SEQ ID NOs: 185 and/or 186 including variants and/or fragments of SEQ ID NOs: 185 and/or 186) to detect ACh, e.g., in a biological system.

Techniques for performing such methods are known in the art and/or are exemplified herein. For example, methods can include introducing one or more biosensors into a biological system (e.g., a cell); expressing the one or more biosensors in the biological system (e.g., the cell); monitoring the signal emitted by the expressed biosensor in the biological system; and correlating the signal emitted by the expressed biosensor in the biological system with a level of the analyte in the biological system.

EXAMPLES

The invention is further described in the following examples, which do not limit the scope of the invention described in the claims.

Example 1: Maltose Indicators

Genetically encoded maltose indicators were generated using *Escherichia coli* maltodextrin-binding protein (EcMBP) as a framework and either circularly permuted β-lactamase (cpB1a) or circularly permuted fluorescent protein (cpFP) as a signal. Data describe below suggest that cpB1a and cpFP are not interchangeable.

Allosteric coupling of ligand binding to fluorescence was hypothesized to require:
  i) that the site in into which cpGFP is inserted have the capacity to transduce the global conformational change the scaffold protein (EcMBP in this example) to the local environment of the chromophore in cpGFP; and
  ii) that the local environment of the chromophore (e.g., linkers) be optimized to maximize the difference in emission between unbound (apo) and the bound (in this example maltose-bound) states.

Example 1A: Identification of cpGFP Insertion Sites in EcMBP

Potential insertion sites were identified using the crystal structures of the maltose-bound, closed form of EcMBP (Ouiocho et al., Structure, 5:997-1015, 1997) and the ligand-free, open form of EcMBP shown in FIG. 1 (Sharff et al., Biochemistry, 31:10657-10663, 1992) to guide rational design of EcMBP-cpGFP fusions that would result in maltose-dependent GFP fluorescence.

Figure 6B:
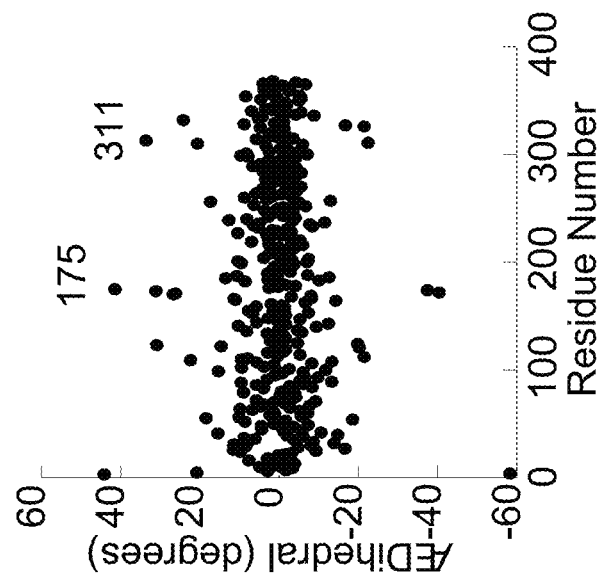
FIG. 6A-B|Changes in EcMBP upon maltose binding and locations at which circularly-permuted fluorescent protein (cpFP) was inserted are shown as colored spheres at the Cα positions. Yellow: 165-166, Green: 175-176, Cyan: 311-312, Violet: 317-318 (FIG. 6A).
Figure 6A:
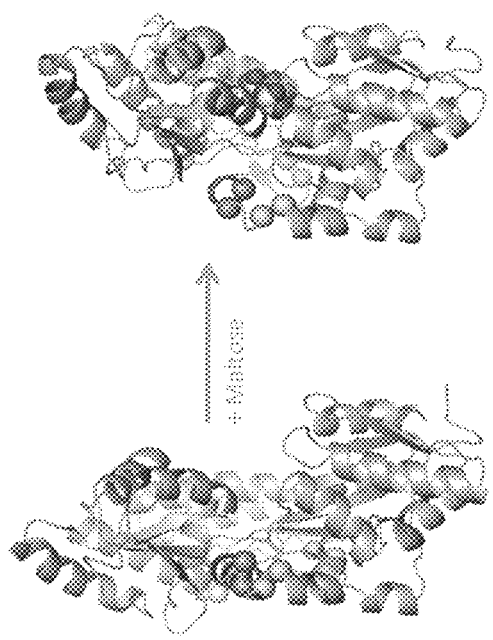
Figure 7B:
FIG. 7B|Amino acid sequence of MBP-165-cpGFP.PPYF (SEQ ID NO:2).

For (i), the change in dihedral angle (defined by the Cα atoms spanning four residues) was analyzed to identify maltose-dependent structural changes in sequentially adjacent residues (FIG. 6); this analysis showed that the Cα chain is "torqued" around residues 175 (ΔDihedral=+41°) and 311 (ΔDihedral=−22°) upon ligand binding. This sequential conformational change was predicted to be coupled to structural changes of an inserted cpGFP, resulting in maltose-dependent fluorescence for the fusion protein.

Previous studies using randomly digested and reassembled circularly permuted β-lactamase (cpB1a) and EcMBP showed maltose-dependent β-lactamase activity in proteins with insertions of cpB1a at EcMBP residues 165 and 317 (Guntas et al., Chem. Biol., 11:1483-1487, 2004; Guntas and Ostermeier, J. Mol. Biol., 336:263-273, 2004).

Since the ΔDihedral of EcMBP165 is +11° (moderate change) and EcMBP317 is +2° (no real change), four EcMBP-cpGFP templates were constructed by inserting cpGFP into EcMBP at sites 165, 175 (identified herein), 311 (identified herein), and 317 to test our predictive method and the interchangeability of cpB1a and cpGFP at sites identified from the EcMBP-cpB1a screen. These constructs were named MBP165-cpGFP, MBP175-cpGFP, MBP311-cpGFP, and MBP317-cpGFP (names were modified to encompass variants (e.g., with modified linker sequences). The cpGFP used is cpGFP146 described in Baird et al. (Proc. Natl. Acad. Sci., USA, 96:11241-11246, 1999). PCR assembly was used to construct fusion proteins with GlyGly-linkers between EcMBP and each terminus of cpGFP. The amino acid sequence of each construct is shown in FIGS. 6-9. The sequences of SEQ ID NOs:1-3 shown in FIGS. 7A-7C (i.e., MBP165-cpGFP) differ in the linker sequence between MBP 1-165 and cpGFP 147-238 (linker 1: see the line ending in amino acid 240)). The sequences of SEQ ID NOs: 4-5 shown in FIGS. 8A-8B (i.e., MBP175-cpGFP) differ in the sequence between MBP 1-175 and cpGFP 147-238 (linker 1: see the line ending in amino acid 240)). The sequences of SEQ ID NOs: 6-7 shown in FIGS. 9A-9B (i.e., MBP311-cpGFP) differ in the sequence between cpGFP 1-146 and MBP 312-370 (linker 2: see the line ending in amino acid 640)). Each construct includes 3 linkers: A linker between the C-terminus of the C-terminal portion of MBP and the N-terminus of cpGFP (i.e., linker 2), a linker between the N-terminus of cpGFP and C-terminus of the N-terminal portion of MBP, and a linker in cpGFP (i.e., linker 3).

Example 1B: Linker Optimization

Libraries of variants of SEQ ID NOs: 1-8 were generated with randomized linkers by single-stranded uracil template mutagenesis (see Kunkel et al., Methods Enzymol., 204: 125-139, 1991) using the primers listed below:

```
165 Linker 1 Primers:
                                  (SEQ ID NO: 9)
PLIAADGxxNVYIM (SEQ ID NO: 10)
PLIAADxxNVYIM (SEQ ID NO 11)
PLIAADGGxxNVYIM (SEQ ID NO: 12)
PLIAADGxPNVYIMG (SEQ ID NO: 13)
PLIAADGIxNVYIMG (SEQ ID NO: 14)
PLIAADPxSHNVYIM (SEQ ID NO: 15)
PLIAADxPSHNVYIM (SEQ ID NO: 16)
PLIAADxxSHNVYIM (SEQ ID NO: 17)
PLIAADxxSHNVFIM (SEQ ID NO: 18)
PLIAADPxSHNVFIM (SEQ ID NO: 19)
PLIAADPxSYNVFIM (SEQ ID NO: 20)
PLIAADxxSYNVFIM (SEQ ID NO: 21)
PLIAADPxSYNVFIM (SEQ ID NO: 22)
PLIAADxxSYNVFIM (SEQ ID NO: 23)
PLIAADPxSxNVYIM (SEQ ID NO: 24)
PLIAADPxSHxVYIM
```

-continued

PLIAADPxSHNxYIM (SEQ ID NO: 25)

PLIAADPxSHNVxIM (SEQ ID NO: 26)

165 Linker 2 Primers:

KLEYNFNxxYAFKYEN (SEQ ID NO: 27)

KLEYNFNxYAFKYEN (SEQ ID NO: 28)

KLEYNFNYAFKYEN (SEQ ID NO: 29)

KLEYNFxYAFKYEN (SEQ ID NO: 30)

KLEYNxxYAFKYEN (SEQ ID NO: 31)

KLEYNWxYAFKYEN (SEQ ID NO: 32)

KLEYNxKYAFKYEN (SEQ ID NO: 33)

KLEYNFNPxYAFKYEN (SEQ ID NO: 34)

KLEYNFNxPYAFKYEN (SEQ ID NO: 35)

175 Linker 1 Primers:

APKYENxxSHNVYIM (SEQ ID NO: 36)

175 Linker 2 Primers:

KLEYNFNxxKYDIKDV (SEQ ID NO: 37)

311 Linker 1 Primers:

KSYEELxxSHNVYIM (SEQ ID NO: 38)

KSYEELPxSHNVYIM (SEQ ID NO: 39)

KSYEELxPSHNVYIM (SEQ ID NO: 40)

311 Linker 2 Primers:

KLEYNFNxxAKDPRIA (SEQ ID NO: 41)

KLEYNFNPxAKDPRIA (SEQ ID NO: 42)

KLEYNFNxPAKDPRIA (SEQ ID NO: 43)

317 Linker 1 Primers:

ELAKDPRxSHNVYIM (SEQ ID NO: 44)

ELAKDPRxxSHNVYIM (SEQ ID NO: 45)

ELAKDPRxxxSHNVYIM (SEQ ID NO: 46)

317 Linker 2 Primers:

KLEYNFNxAATMENA (SEQ ID NO: 47)

KLEYNFNxxAATMENA (SEQ ID NO: 48)

KLEYNFNxxxAATMENA (SEQ ID NO: 49)

Where "x" indicates that a degenerate primer (with DNA sequence "NNS") was used to encode all 20 possible amino acids.

Figure 12:
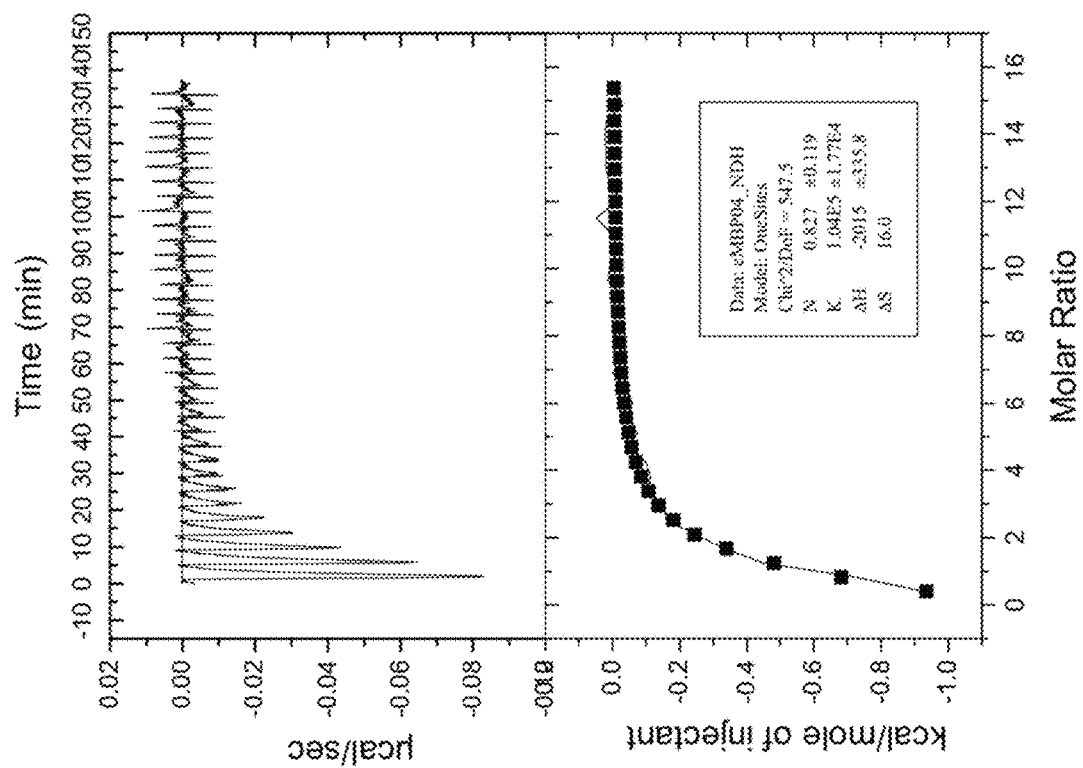
FIG. 12|Isothermal titration calorimetry (ITC) of MBP317-cpGFP with maltose.

About 400 variants were screened in semi-high-throughput fashion, measuring fluorescence intensity of clarified cell lysate in the absence and presence of 10 mM maltose. Insertion of cpGFP as MBP317, a site previously reported for cpB1a, did not show maltose-dependent fluorescence (FIG. 11) even though the framework protein still bound maltose, as determined by isothermal titration calorimetry (FIG. 12). These data demonstrate that identification of insertion sites by a method other than insertion of cpGFP (such as insertion of cpB1a) is not sufficient to identify sites that transduce ligand binding to changes in fluorescence intensity Insertion of cpGFP at residue 165 of EcMBP (EcMBP165-cpGFP), another position reported in cpB1a studies (Guntas and Ostermeier, supra) with -GlyGly-linkers flanking the cpGFP resulted in a protein in which fluorescence increased 20% ($\Delta F/F=0.2$) upon addition of saturating maltose.

Screening a fully-degenerate, length-two library ("XX") at either the EcMBP-cpGFP linker (linker 1) or the cpGFP-EcMBP linker (linker 2) yielded proteins with maltose-dependent fluorescent increases >300% or decreases >50% (FIG. 11). Many of the variants with increased $\Delta F/F$ values had linkers containing proline(s). Subsequent libraries constructed from oligonucleotides encoding XP or PX and randomization of the residues in GFP from residue 146 to 150 were screened, yielding a final variant with: a two-proline EcMBP-cpGFP linker, a two-glycine cpGFP-EcMBP linker, GFP-H148Y, and GFP-Y151F. This variant, called "EcMBP165-cpGFP.PPYF" (abbreviated PPYF (SEQ ID NO:2)) has a $\Delta F/F=2.5$, a Kd for maltose of 3 μM. Screens also identified variant EcMBP311-cpGFP.L2-NP (-AsnPro- at linker 2 (SEQ ID NO:7)), which has a $\Delta F/F$ of 1.0 and a Kd for maltose of 2 μM. This variant has an inferior maltose-dependent fluorescence increase than PPYF, but demonstrates generality of the cpFP insertion method.

EcMBP175-cpGFP was also screened with XX linkers, and a few variants with $\Delta F/F \approx 1$ were identified (FIG. 11). One mutant, with the first linker encoding HL (EcMBP175-cpGFP.L1-HL (SEQ ID NO:5)), has a $\Delta F/F=0.5$ and a Kd for maltose of 1.3 μM.

These data support that choice of insertion site by structural analysis is preferable to random insertion.

Example 1C: Modifying Ligand Binding and/or Fluorescent Properties of Sensors

One objective in the development of generic biosensors is for the framework to permit independent optimization of binding and signaling properties. Analysis of whether biosensors herein permit such optimization was tested using the high-SNR sensor PPYF, by: (i) rationally altering maltose-binding affinity; (ii) changing the ligand-binding specificity from maltose to sucrose, and (iii) creating a family of sensors in multiple colors.

Figure 13:
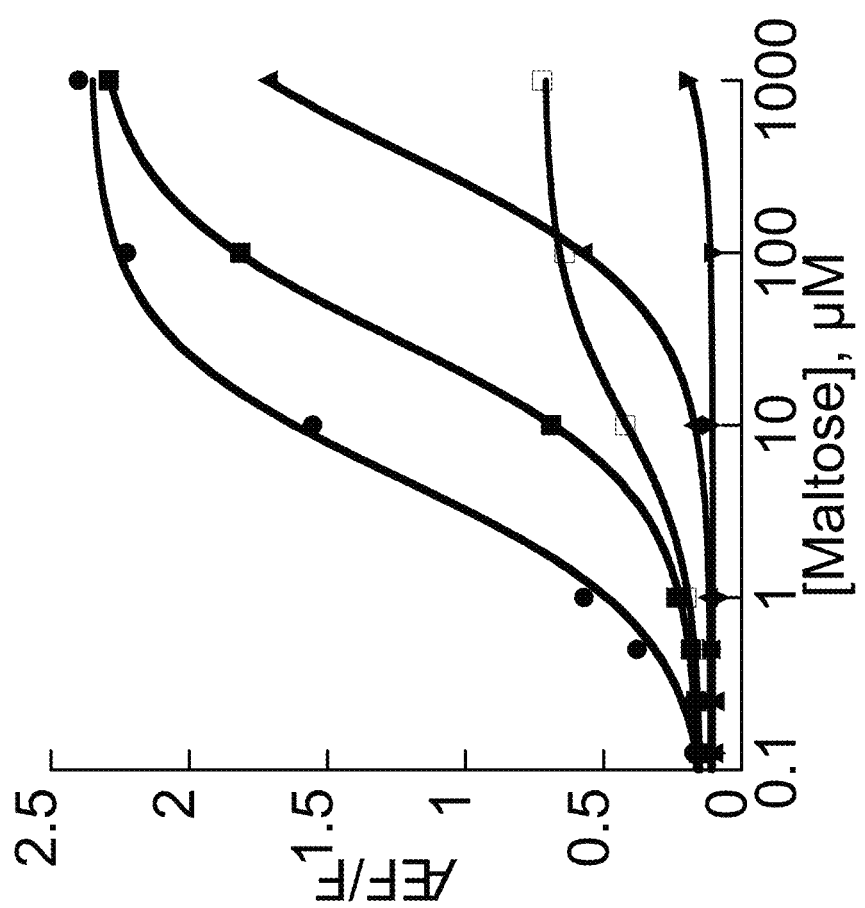
FIG. 13|Graph showing EcMBP165-cpGFP.PPYF affinity variant binding maltose-binding curves. Binding curves for affinity variants of MBP165-cpGFP.PPYF. Data is fit to a single-binding site isotherm. Curve-fit affinities are: WT binding pocket, 5 μM (●); W230A, 32 μM (■); W62A, 375 μM (▲); W340A, >1 mM (▼); 1329W, 11 μM (□).

As a first step, the impacts of mutations of three tryptophan side-chains in the maltose-binding pocket (W230, W62, and W340) were tested. These sites have previously been shown to lower the affinity of EcMBP for maltose by one, two, or three orders of magnitude, respectively, when mutated to alanine (Martineau et al., J. Mol. Biol., 214:337-352, 1990). A mutation to the hinge region, I329W, was also made to PPYF, as this has been shown to increase maltose affinity by about 2-fold in both wild-type EcMBP (Marvin and Hellinga, Nat. Struc. Biol., 8:795-798, 2001) and in the EcMBP-cpB1a switches (Guntas et al., Chem. Biol., 11:1483-1487, 2004; Kim and Ostermeier, Arch. Biochem. Biophys., 446:44-51, 2006). As shown in FIG. 13, for the PPYF sensor, the three tryptophan-to-alanine binding-pocket mutations behaved as expected, lowering affinity by between one and three orders of magnitude. In contrast, the I329W mutation did not increase affinity as expected, but rather decreased it. ΔF/F also decreased. This data suggests that the mechanism of fluorescence change in this sensor is dependent on subtle interactions between EcMBP and cpGFP that are linked to the I329W mutation.

As an alternative test for changing the ligand-binding specificity of the sensor while preserving fluorescence signaling, "5-7" mutations (D14L, K15F, W62Y, E111Y), previously shown to confer EcMBP with an affinity for sucrose (Guntas and Mansell, Proc. Natl. Acad. Sci., 102:11224-11229, 2005), were made to PPYF. As shown in FIG. 14A, the mutations conferred to the sensor about 2 mM affinity for sucrose and ~3 mM affinity for maltose. To address a discrepancy between expected (micromolar) and observed (millimolar) affinity for disaccharides, the 5-7 mutations were made to sensors with cpGFP inserted at different positions in EcMBP, and with different linker compositions. In the context of EcMBP165-cpGFP.PCF, the 5-7 mutations conferred very low (but observable) binding preference for sucrose over maltose (FIG. 14B). The trend of higher (but still weak) affinity for sucrose (~0.6 mM) over maltose (~6 mM) continued when the 5-7 mutations are made in the context of EcMBP175-cpGFP.L1-HL (FIG. 14C). In the context of EcMBP311-cpGFP.L2-NP, the 5-7 mutations appeared to eliminate all binding (FIG. 14D). The preference for sucrose over maltose of the 5-7 variants of the sensors is consistent with the binding properties of the 5-7 variants of EcMBP alone and EcMBP-cpB1a (Guntas and Mansell, Proc. Natl. Acad. Sci., 102:11224-11229, 2005). The lower affinity for both ligands of the 5-7 variants of the sensors may be the consequence of the inserted cpGFP shifting the open and closed equilibrium.

These data suggest that ligand binding and fluorescent properties of biosensors can be independently modified.

Example 1D: Modifying Sensor Color

The color of GFP can be altered by changing the amino acids that either comprise or interact with the chromophore (see Shaner et al., J. Cell. Sci. 120:4247-4260, 2007, for a review).

Using PPYF as a template, mutations Y66W (to yield a cyan variant, "cpCFP"), L64F+T65G+V68L+T203Y (yellow, "cpYFP"), and Y66H (blue, "cpBFP") mutations were made (see Cubitt et al., Trends Biochem., 20:448-455, 1995, for exemplary methods). As shown in FIG. 15, the variants exhibit fluorescence emission spectra consistent with their respective intended designs.

The ΔF/F of the color variants in response to maltose is different (in each case inferior) from the ΔF/F of 2.5 observed in PPYF-green. The EcMBP165-cpYFP.PPYF sensor, which has the same covalent chromophore structure as PPYF, has the greatest ΔF/F of the three spectral variants (FIG. 15A). EcMBP165-cpCFP.PPYF has a lower ΔF/F than the green and yellow variants, but by incorporating previously identified mutations, (L1-PC+GFP-Y151F; the resulting protein is called EcMBP165.cpCFP.PCF), a variant with ΔF/F=0.8 was obtained (FIG. 15A).

Figure 16:
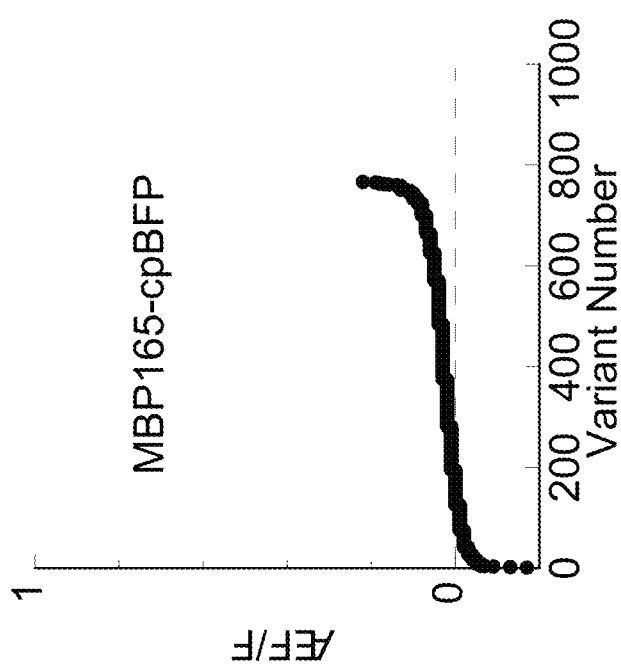
FIG. 16|Plot of ΔF/F for clarified lysate screen of MBP165-cpBFP linker-screen. The horizontal dashed line at zero indicates no fluorescence change.

The EcMBP165-cpBFP.PPYF variant, while dimly fluorescent, is not a sensor, and a screen of 800 linker variants failed to produce any variant with ΔF/F >0.2 (FIG. 16).

Since EcMBP165-cpBFP.PPYF was very dim, Azurite mutations T65S+V150I+V224R were included to increase brightness and stability, and make EcMBP165-cpAzurite a good template for linker screening. Using oligonucleotides encoding XX amino acid linkers, a variant was obtained, EcMBP165-cpAzurite.L2-FE, that had ΔF/F=0.8 (FIG. 15).

Example 1E: Modifying Sensor Color and Ligand Specificity/Affinity

The four sucrose-binding "5-7" mutations described above that conferred weak sucrose affinity in the green sensor (EcMBP165-cpGFP.PPYF) were converted to blue, cyan, and yellow maltose sensors (EcMBP165-cpAzurite.L2-FE, EcMBP165-cpCFP.PCF, and EcMBP165-cpYFP.PPYF). The green and yellow sensors showed increased fluorescence upon addition of 10 mM sucrose, but the cyan and blue proteins did not (FIG. 15A). Like the green variant, the yellow variant had no detectable sucrose affinity with the wild type binding pocket (FIG. 15C) and millimolar affinity for both sugars, with preference for sucrose over maltose (FIG. 15D).

Figure 17A:
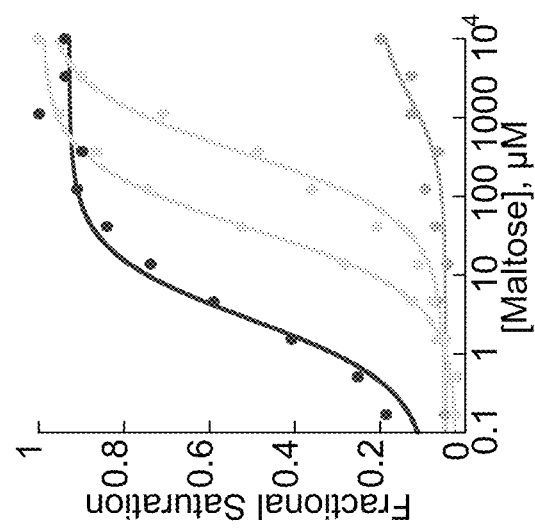
FIGS. 17A-17B|Line graphs showing maltose binding. Blue (wt binding pocket) has an affinity of 2.7 μM. Green (W230A) has an affinity of 40 μM. Yellow (W62A) has an affinity of 350 μM. Cyan (W340A) has an affinity of approximately 1.7 mM. Data is plotted at ΔF/F (FIG. 17A) or normalized to Fractional Saturation (FIG. 17B).
Figure 17B:
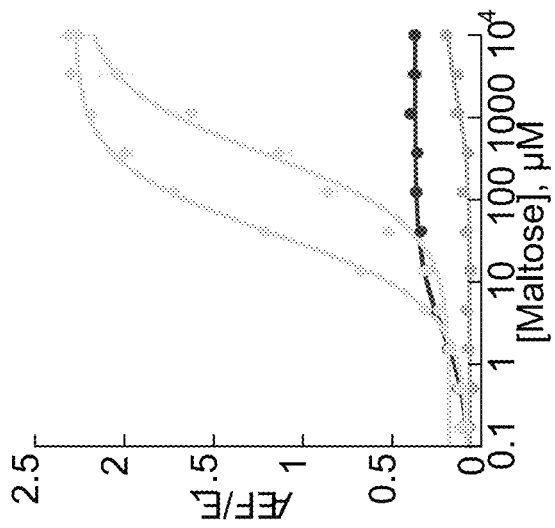

As seen in FIG. 17, as maltose concentration increased, the blue sensor increased in fluorescence first (Kd ~2.7 μM), then the green (Kd ~40 μM), then the yellow (Kd ~350 μM), and at high maltose concentrations, the cyan variant began to increase its fluorescence (Kd ~1.7 mM).

Example 1F: Imaging Bacteria

The ultimate value of genetically encoded fluorescent sensors is in their utility for observing analyte flux in living cells and organisms. In a simple proof-of-principle experiment, Escherichia coli expressing PPYF or PPYF.T203V (see "Second-generation maltose sensors" below) were imaged in the green fluorescence channel in the absence of maltose, and then re-imaged after addition of saturating maltose to the media.

Figure 18C:
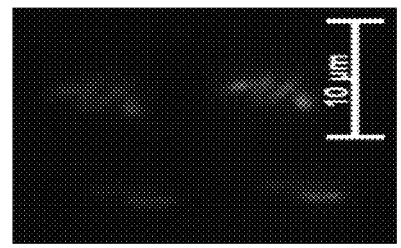
FIGS. 18A-18C|Images bacterial cells expressing (FIG. 18A) EGFP, (FIG. 18B) PPYF, or (FIG. 18C) PPYF.T203V in the absence (top) and presence (bottom) of maltose.
Figure 18B:
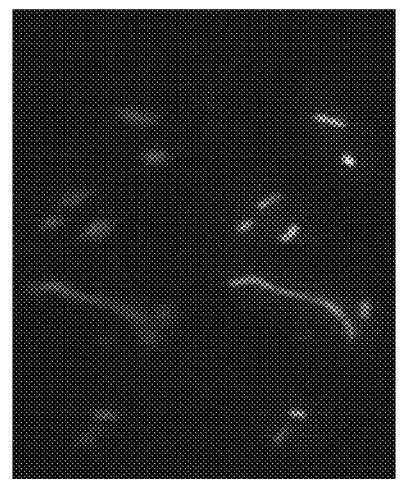
Figure 18A:
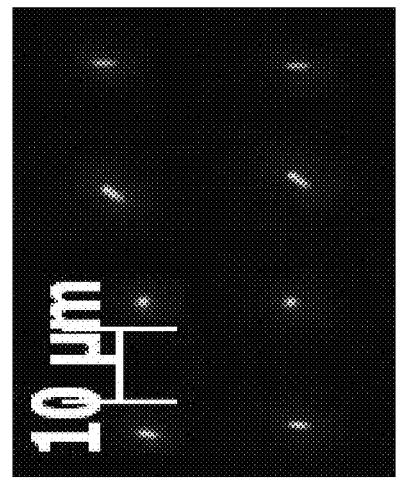

As shown in FIG. 18, bacteria expressing the sensors clearly became brighter, while control bacteria expressing EGFP appeared unchanged. Increased fluorescence was quantified by measuring the peak (gray-value) pixel intensity of each bacterium. Those expressing PPYF undergo an approximate doubling of fluorescence (bacterium-averaged ΔF/F=1.1±0.4), those expressing PPYF.T203V have slightly increased ΔF/F (ΔF/F=1.29±0.2), while those expressing EGFP have no change in fluorescence (ΔF/F=−0.01±0.05).

Example 1F: 2-Photon Imaging of Mammalian Cells

Multi-photon microscopy opened new frontiers for in vivo fluorescence imaging, in particular for neuronal activity visualization through the use of genetically encoded calcium indicators (Tian et al., Nat. Methods, 3:281-286, 2009; Denk et al., Science, 248:73-76, 1990; Denk and Svoboda, Neuron, 18:351-357, 1997).

Figures 19A, 19B:
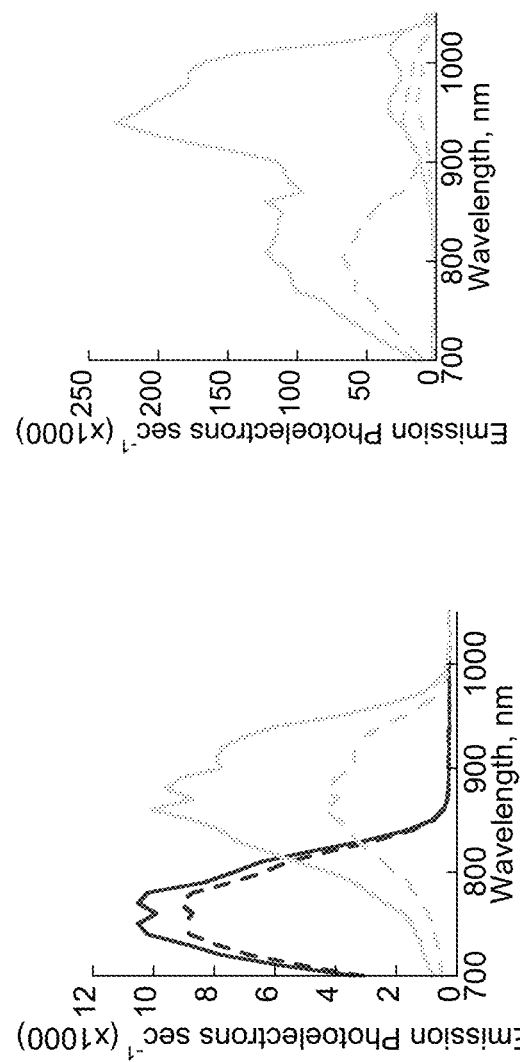
FIGS. 19A-19B|Line graphs showing EcMBP-cpGFP.PPYF.T203V 2-photon excitation spectra. MBP165-cpAzurite.L2-FE (FIG. 19A), -cpCFP.PCF (FIG. 19A), -cpGFP.PPYF (FIG. 19B), and -cpYFP.PPYF (FIG. 19B) were excited at the wavelengths indicated and emission measured through appropriate wavelength filters. Two graphs are shown to present different y-axis scales. Optimal ΔF/F values for 2-photon excitation of the spectral variants of MBP165 are: -cpAzurite, 1.1 (ex 760 nm); -cpCFP, 2.3 (ex 830-960 nm); -cpGFP, 10.0 (ex 940 nm); -cpYFP, 2.6 (ex 940 nm).

To demonstrate that the maltose sensors described herein have the potential to be used for 2-photon imaging, fluorescence excitation spectra were collected. As shown in FIG. 19, with a 535 nm bandpass emission filter (50 nm bp), EcMBP165-cpGFP.PPYF showed a 10-fold maltose-dependent increase in fluorescence when excited at 940 nm. All four spectral variants showed a significant maltose-dependent increase in 2-photon fluorescence.

Example 1G: Sub-Cloning Maltose Sensors

EcMBP165-cpGFP.PPYF.T203V (see "Second-generation maltose sensors" below) were cloned into a modified version of the pDisplay vector (Invitrogen) for extracellular display on the surface of transiently transfected human embryonic kidney (HEK293) cells.

Figures 20A, 20B, 20C:
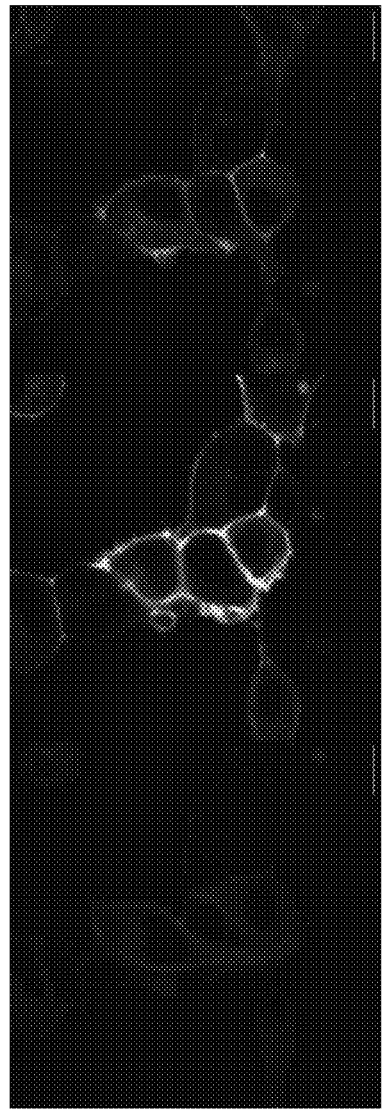
FIGS. 20A-20C|Images showing EcMBP-cpGFP.PPYF.T203V expressing HEK cells. Images of individual HEK293 cells expressing membrane displayed PPYF.T203V in the absence of maltose (FIG. 20A), in the presence of 1 mM maltose (FIG. 20B), and after washout with maltose-free buffer (FIG. 20C). Scale bars are 10 μm.

As shown in FIG. 20, the sensor localized to the plasma membrane and increased in brightness in a concentration-dependent manner when perfused with buffers of varying maltose concentration. The ΔF/F is 5.8-fold, very close to that of the soluble protein produced in E. coli, with the mid-point of the maltose-dependent fluorescence increase being 6.5 μM (FIG. 21A), very similar to the affinity determined on purified protein (5 Furthermore, the surface displayed sensor responded rapidly to a pulse of 1 mM maltose (FIG. 21A), indicating that the time course for its action is useful for transient events.

Example 1H: Crystal Structure Analysis of Maltose Sensors

Figures 22A, 22B, 22C, 22D:
FIGS. 22A-22D|Cartoon representations and close-up views of inter-domain linkers and selected amino acids of the cpGFP chromophore environment of the structure of MBP175-cpGFP.L1-HL (FIG. 22A and FIG. 22B) and MBP311-cpGFP.L2-NP (FIG. 22C and FIG. 22D) bound to maltose. The MBP domain is colored as in FIG. 1. The cpGFP domain is green and the inter-domain linkers are colored white. The cpGFP chromophore is displayed as sticks and the bound maltose as red and white spheres. Ordered water molecules are represented as red spheres. Selected hydrogen bonds are displayed as dashed black lines. β-strands 10 and 11 of cpGFP are displayed as semi-transparent for clarity. The 2Fo-Fc electron density map calculated with the displayed residues omitted from the model is shown as blue mesh.

High-resolution structures of several of the maltose sensors described above were generated. Crystallization trials were performed with EcMBP165-cpGFP.PPYF, EcMBP175-cpGFP.L1-HL, and EcMBP311-cpGFP.L2-NP in the presence and absence of excess maltose, from which both EcMBP175-cpGFP.L1-HL and EcMBP311-cpGFP.L2-NP crystallized in the presence of maltose. X-ray structures were solved to 1.9 and 2.0 Å resolution, respectively, by molecular replacement (FIGS. 22A-22C).

The structures of the cpGFP and EcMBP domains of the sensors are superimposable with published crystal structures of cpGFP (from GCaMP2; RMSD=0.36 and 0.38 Å, respectively, for comparing 221 common Ca atoms) and EcMBP-maltose (RMSD=0.43 and 0.37 Å, 370 Ca). The structure of EcMBP is largely unperturbed by insertion of the cpGFP domain; only residues around the 175 and 311 insertion sites showed any significant displacement.

GFP-H148, which H-bonds the GFP chromophore in the structure of native GFP, also directly H-bonded to the chromophore in the EcMBP175-cpGFP.L1-HL-maltose structure (FIG. 22B), although a different rotamer was observed. In the EcMBP311-cpGFP.L2-NP-maltose structure, GFP-H148 is pulled away from the chromophore and is largely replaced by the Asn from linker 2, which makes H-bond interactions to both strand 8 of the GFP barrel and the chromophore phenolate oxygen (through a water molecule, FIG. 22D). GFP-H148, meanwhile, seemed to stabilize the conformation of linker 2 of EcMBP311-cpGFP.L2-NP by H-bonding the backbone carbonyl of the linker 2 Asn. There is some solvent access to the cpGFP chromophore through the hole in the GFP barrel created by circular permutation, although the inter-domain linkers block much of the opening in both structures. Relatively few contacts are made between the cpGFP and EcMBP domains.

Figure 5:
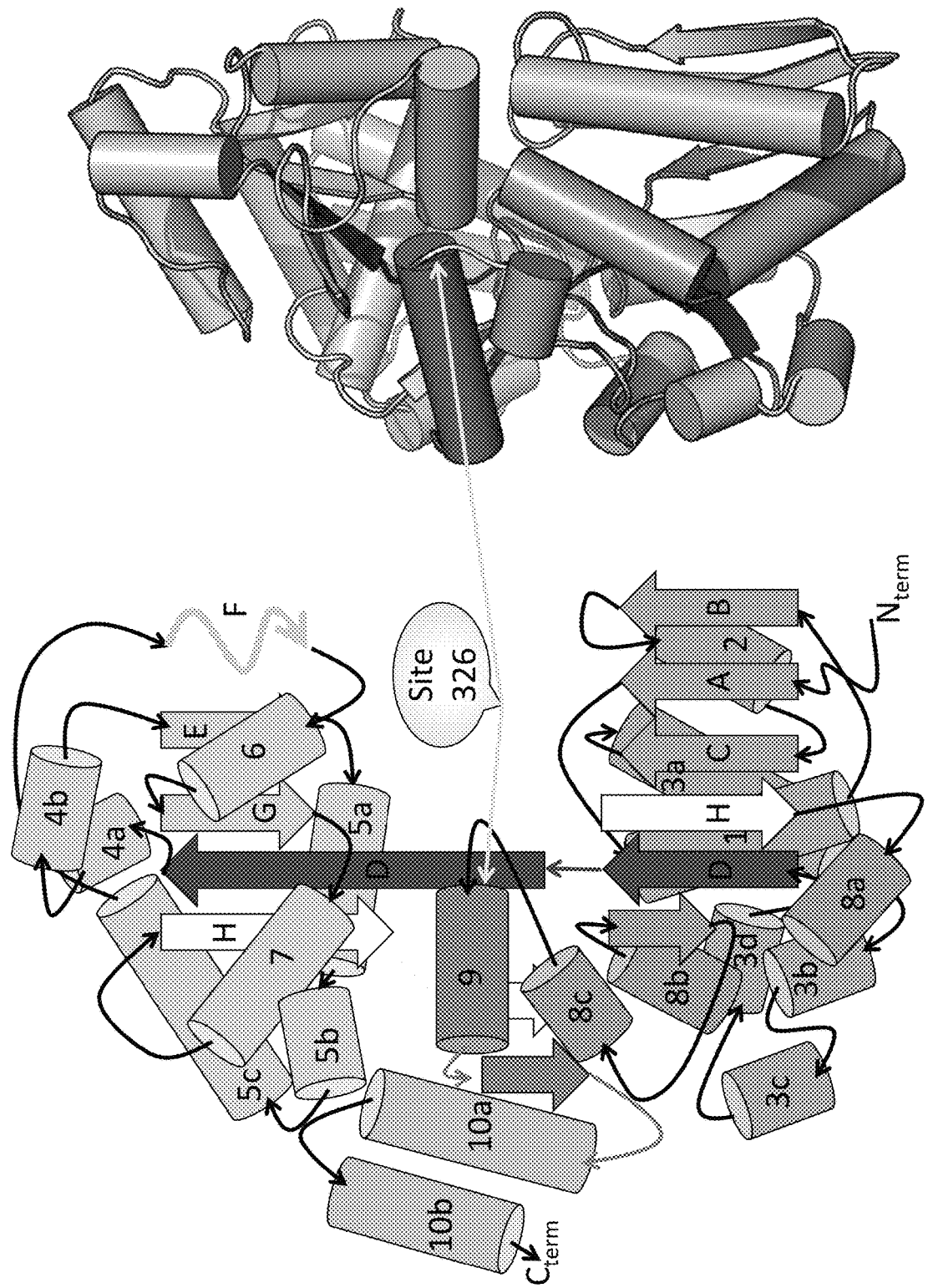
FIG. 5|Cartoon representation showing ligand bound *Thermus thermophilus* glucose binding protein (TtGBP) and potential cpFP insertion sites.

Based on the structures of two maltose-bound sensors, the sensing mechanism likely involves a shift in the relative position of linker 1 and linker 2 induced by the conformational change in the EcMBP domain associated with maltose binding (FIG. 5). The register shift of interactions between the two linkers could alter the proximity of linker 2 and nearby side-chains to the cpGFP chromophore and change the water structure in the cpGFP opening, leading to a shift in the chromophore protonation equilibrium. This might explain why rigid proline is preferred in either linker, since conformational changes upon ligand binding might be better propagated through the rigid linkers to the cpGFP chromophore environment.

Example 1I: Generation of Second-Generation Maltose Sensors

In an attempt to increase brightness and ΔF/F of GCaMP, the local environment of the chromophore was altered by randomizing residues within cpGFP, and screening for improved variants (Tian et al., nat. Methods, 6:875-881, 2009).

As shown in FIG. 23, in the context of EcMBP165-cpGFP.PPYF, the T203V mutation decreases the fluorescence emission of the apo-state by half (FIG. 23A), while saturated fluorescence and affinity are unchanged (FIG. 23B), increasing ΔF/F to 6.5. In the maltose-saturated state, PPYF itself has about a quarter the brightness of EGFP, and half the brightness of cpGFP.

Figure 23B:
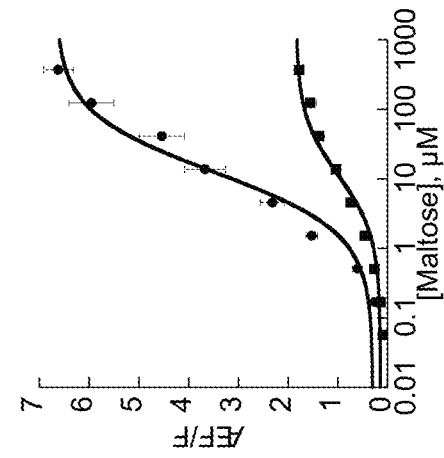
FIGS. 23A-23D|EcMBP-cpGFP: effect of T203V mutation on fluorescence.
Figure 23D:
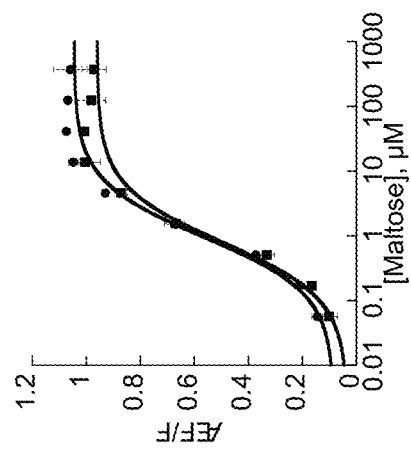
Figure 23A:
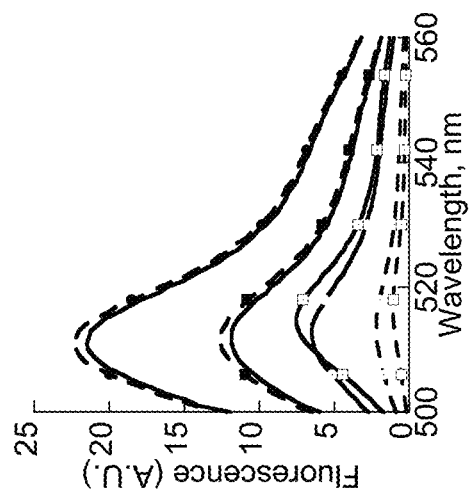
Figure 23C:
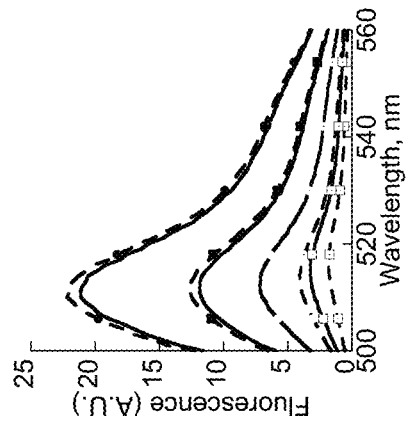

In the context of EcMBP311-cpGFP.L2-NP, the T203V mutation decreases the brightness of both the apo-state and the saturated-state equally, resulting in no significant change in ΔF/F (FIGS. 23C and D).

These results indicate that the benefits of the T203V mutation are not universally transferable, and that cpGFP-based fluorescent sensors need to be optimized individually.

Example 2: Maltotriose Indicators

Figure 2:
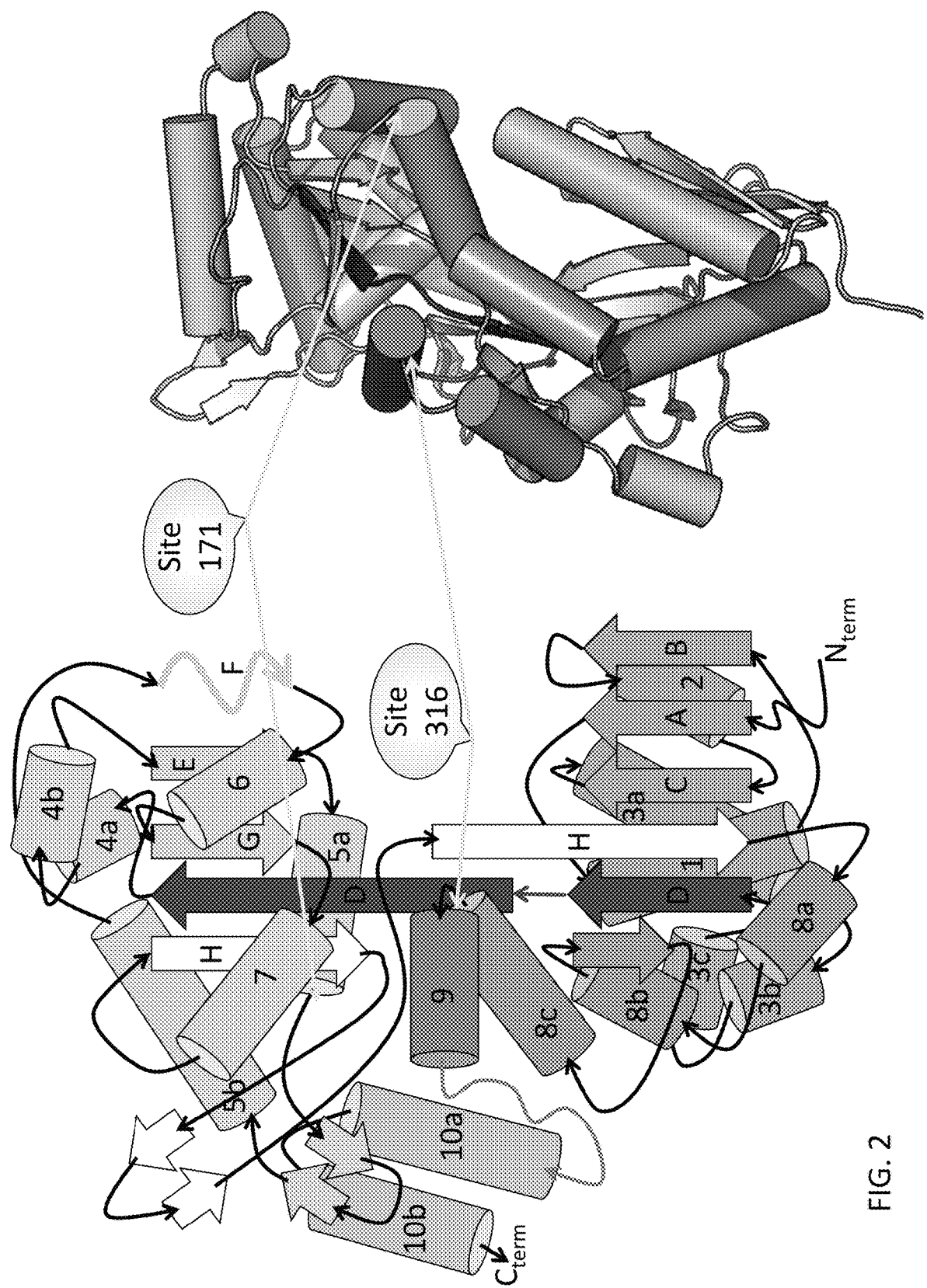
FIG. 2|Cartoon representation showing ligand bound *Pyrococcus furiosus* maltotriose binding protein (PfMBP) and potential cpFP insertion sites.

Genetically encoded maltotriose indicators were created using *Pyrococcus furiosus* maltotriose binding protein. As described below, only the structure of the ligand-bound state *P. furiosus* maltotriose binding protein (PfMBP) is available. As shown in FIGS. 1 and 2, PfMBP is homologous to EcMBP (compare FIGS. 1 and 2). Two sensors were made, PfMBP171 and PfMBP316, the insertion points for which were selected based on homology to EcMBP165 and EcMBP311, respectively. Linkers were optimized. PfMBP sensors have a ΔF/F of ~1.2.

*Pyrococcus furiosus* is a thermophilic organism. Proteins from thermophiles have been shown to be more amenable to mutation than those from mesophiles (Bloom et al., Proc. Natl. Acad. Sci., 103:5869-5874, 2006). As an alternative to developing new sensors by inserting cpGFP into PBPs, it should also be possible to generate new sensors by changing the ligand-binding specificity of an existing PBP-based sensor.

It has previously been shown that the binding sites of PBPs can be reengineered to accommodate novel ligands (Looger et al., Nature, 423:185-190, 2003). However, those re-design efforts used framework proteins from mesophiles and suffered from poor stability. We hypothesized that PfMBP, which is intrinsically more stable than EcMBP, is more tolerant of mutations. To test this hypothesis, we characterized and compared the stability of PfMBP to EcMBP, PfMBP-cpGFP sensors to EcMBP-cpGFP sensors, PfMBP binding site mutants to EcMBP binding site mutants, and PfMBP-cpGFP sensor binding site mutants to EcMBP-cpGFP sensor binding site mutants. Conclusively, the PfMBP variants were more stable than the EcMBP variants. Finally, we demonstrate that the increased thermo-stability of the PfMBP-cpGFP sensors is useful for the measurement of maltotriose at temperatures as high at 60° C., whereas the EcMBP-cpGFP sensors are only useful for the measurement of maltose at temperatures as high as 40° C.

Example 2A: Identification of cpGFP Insertion Sites in PfMBP

The ligand-bound (closed) structure of PfMBP is available (Evdokimov et al., J. Mol. Biol., 305:891-904, 2001), but the unbound structure is not. Accordingly, insertion sites for the PfMBP-cpGFP sensors were identified by homology to EcMBP.

Figure 24A:
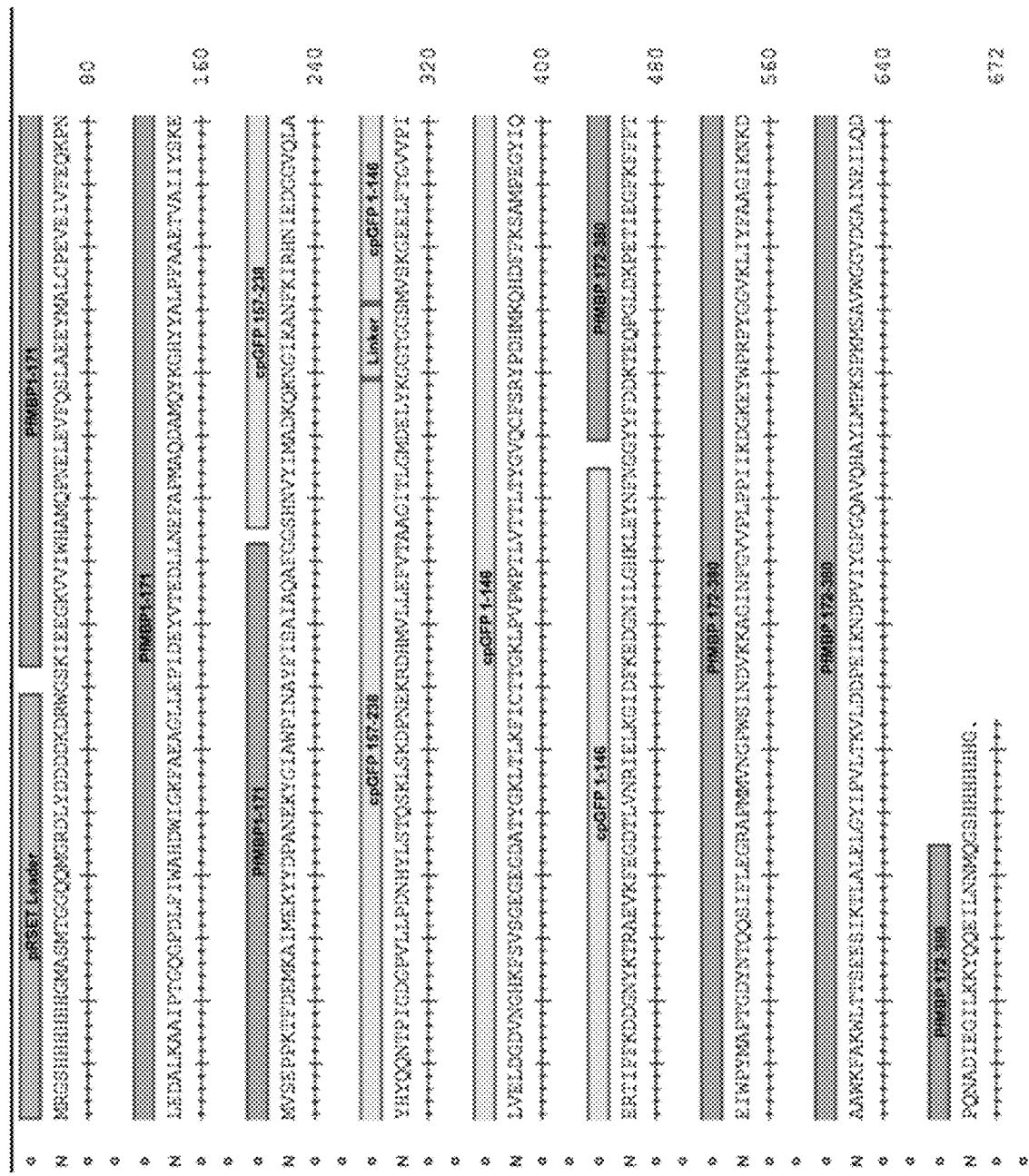
FIG. 24A|Amino acid sequence of PfMBP171-cpGFP (SEQ ID NO:50)
Figure 24B:
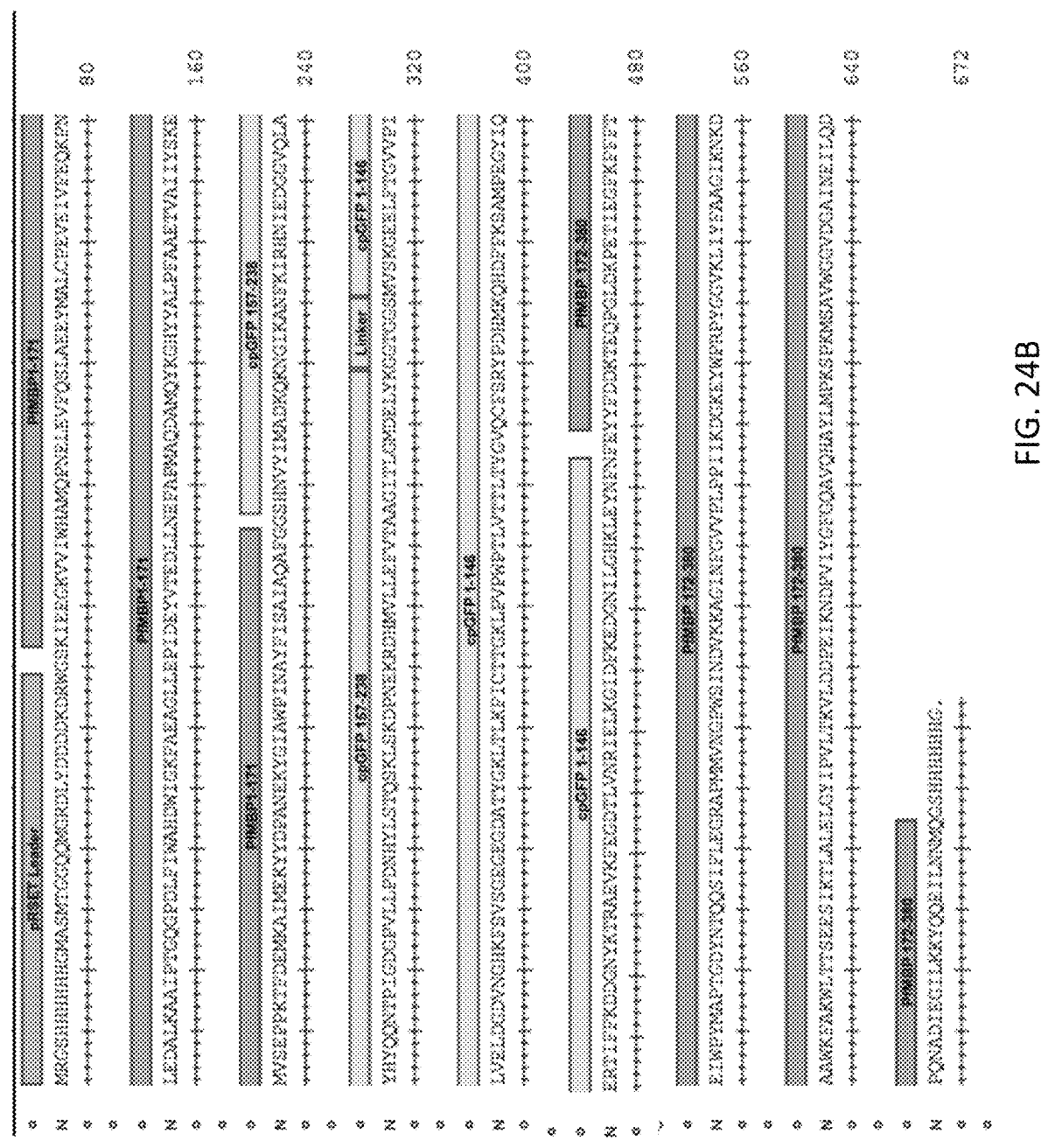
Figure 25A:
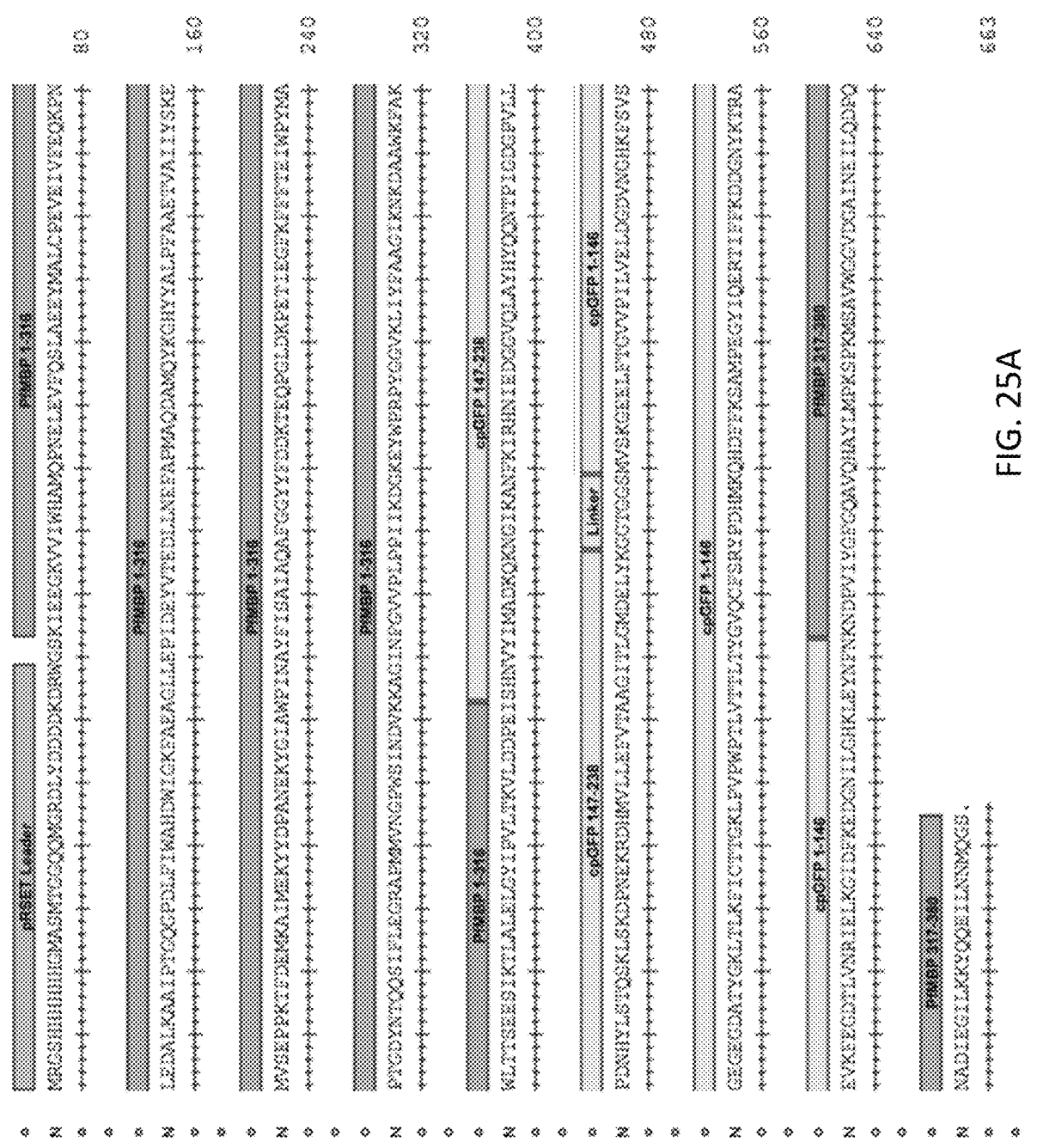
Figure 25B:
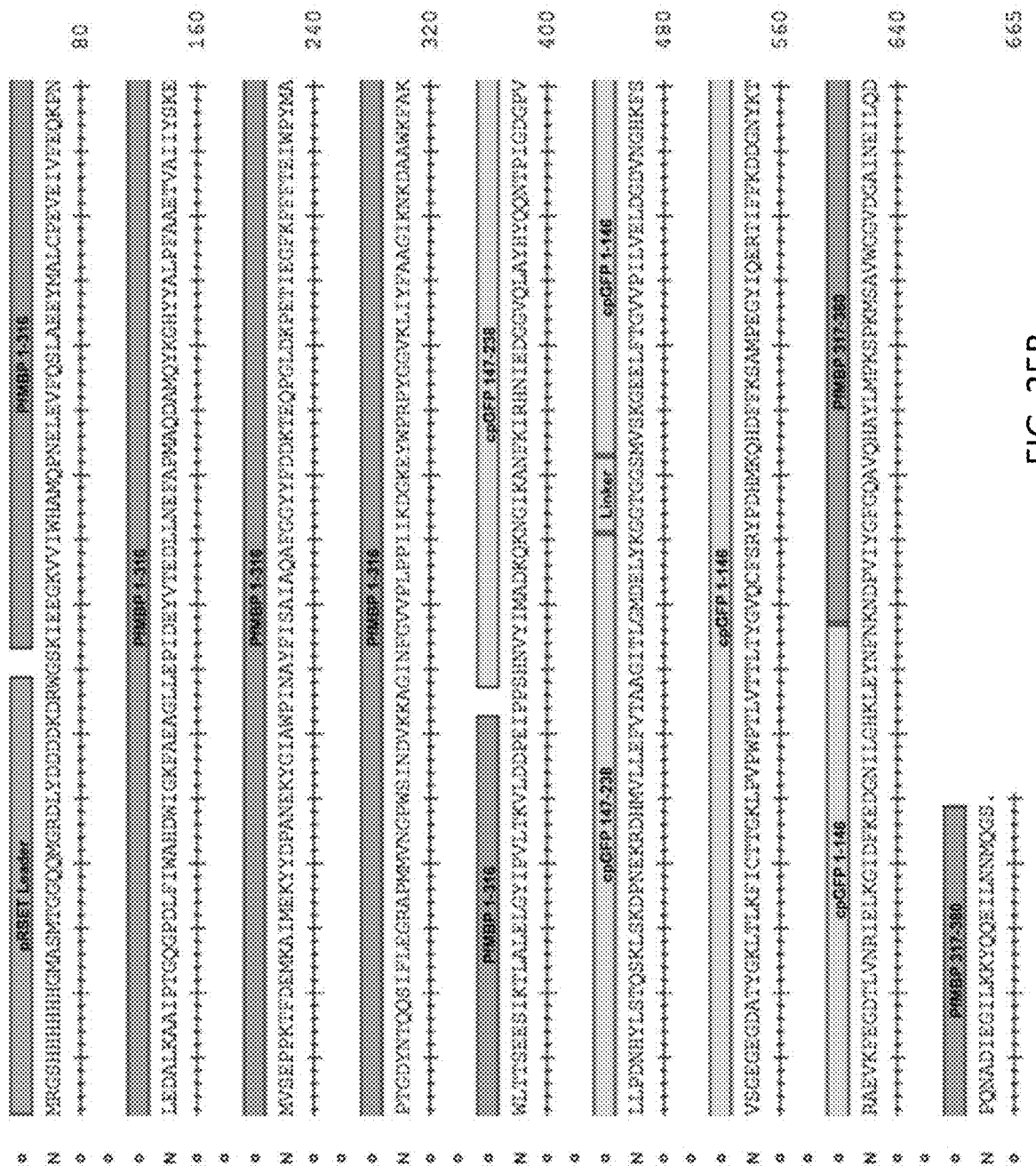
FIG. 25B|Amino acid sequence of PfMBP316-cpGFP.L1-NP (SEQ ID NO:53) FIG. 26A-26B Plot of ΔF/F for clarified lysate screen of cpGFP linker-screens at insertion points 171 (FIG. 26A) and 316 (FIG. 26B).

Sites were selected based on the structural similarities between PfMBP and EcMBP. Two sites were selected. One of these sites is EcMBP311, which is homologous to PfMBP316. This site is at juncture between the end of the cluster of helices (Helices 8a, 8b, 8c) and the start of the "equatorial" spanning helix (Helix 9). Another site that was made into a sensor in EcMBP was EcMBP165, which is homologous to PfMBP171. cpGFP was inserted into PfMBP at each of these sites. The sequences of the resulting constructs, PfMBP171-cpGFP and PfMBP316-cpGFP, are shown in FIGS. 24 and 25, respectively.

Example 2B: Linker Optimization

Libraries of variants of SEQ ID NOs: 50-53 were generated with randomized linkers by single-stranded uracil template mutagenesis using the primers listed below:

```
175 Linker 1 Primers:
                               (SEQ ID NO: 54)
AIAQAFxxSHNVYIMA (SEQ ID NO: 55)
AIAQAFPxSHNVYIMA 171 Linker 2 Primers:
                               (SEQ ID NO: 56)
KLEYNFNxxYYFDDKTE 316 Linker1 Primers
                               (SEQ ID NO: 57)
VLDDPExxHNVYIM (SEQ ID NO: 58)
VLDDPEIxxSHNVYIM 316 Linker2 Primers
                               (SEQ ID NO: 59)
KLEYNFxxNDPVIY (SEQ ID NO: 60)
KLEYNFNxPKNDPVIY (SEQ ID NO: 61)
KLEYNFNPxKNDPVIY
```

Where "x" indicates that a degenerate primer (with DNA sequence "NNS") was used to encode all 20 possible amino acids.

Several thousand variants were screened in semi-high-throughput fashion, measuring fluorescence intensity of clarified cell lysate in the absence and presence of 1 mM maltotriose.

Figures 26A, 26B:
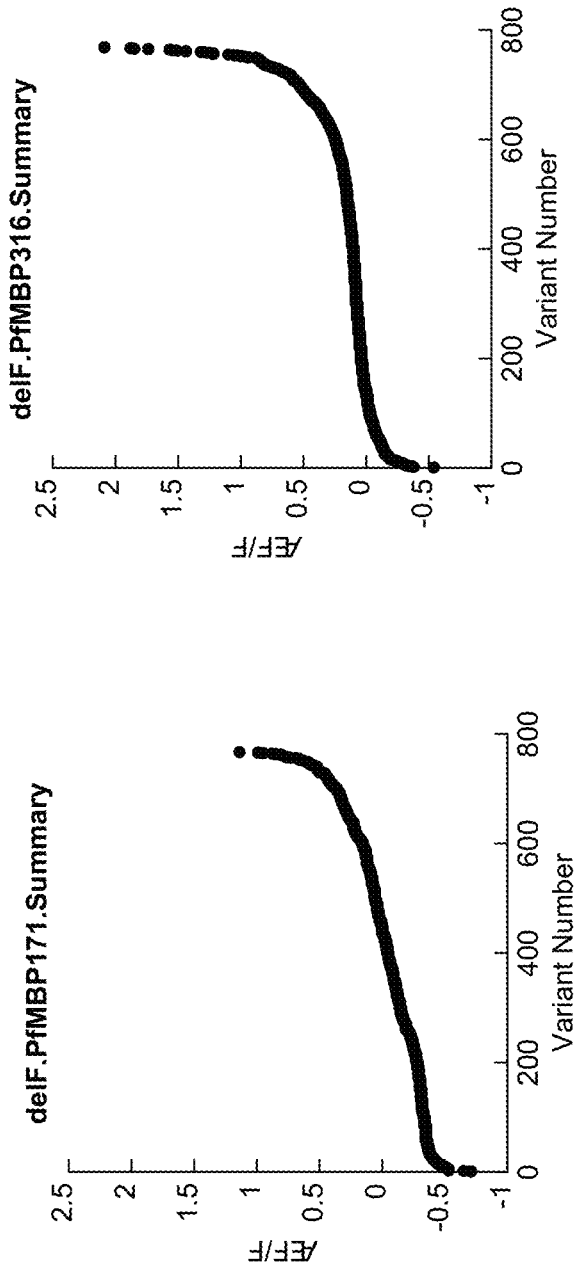

Screening a fully-degenerate, length-two library ("XX") at either the PfMBP171-cpGFP linker (linker 1) or the cpGFP-PfMBP linker (linker 2) yielded proteins with maltotriose-dependent fluorescent increases >100% or decreases >20% (FIG. 26A). A variant from this group with a GlyGly PfMBP-cpGFP linker and a PheGlu cpGFP-PfMBP linker was selected for further characterization. This variant, called "PfMBP171-cpGFP.L2FE" has a ΔF/F=1.2, a Kd for maltotriose of <1 µM.

Screening a fully-degenerate, length-two library ("XX") at either the PfMBP316-cpGFP linker (linker 1) or the cpGFP-PfMBP linker (linker 2) also yielded proteins with maltotriose-dependent fluorescent increases >100% or decreases >20% (FIG. 26B). A variant from this group with a GlyGly PfMBP-cpGFP linker and a PheGlu cpGFP-PfMBP linker was selected for further characterization. This variant, called "PfMBP316-cpGFP.L1-NP" has a ΔF/F=1.2, a Kd for maltotriose of 40 µM.

These data support that structurally homologous frameworks can be compared to identify insertion sites for cpGFP.

Example 2C: Characterization of the Thermostability of the PfMBP and PfMBP-cpGFP Compared to EcMBP and EcMBP-cpGFP Thermal stability of PfMBP171-cpGFP.L2FE was measured using circular-dichroism (CD) and compared to the original EcMBP and PfMBP binding proteins, along with cpGFP. Following the changes by means of CD allowed determination of whether different transitions happened in alpha, beta, or both kinds of structures.

Given that cpGFP is a beta barrel, strong transitions in the beta signal alone were associated with changes in this kind of structure. In the same way, transitions in both kinds of signals were associated with the binding protein structure. As shown in FIG. 27A, PfMBP is significantly more thermostable than EcMBP. In fact, while EcMBP denatured at about 50° C., PfMBP did not denature at temperatures less than 80° C. Also, the addition of maltose to EcMBP stabilized the protein by about 10° C.

As shown in FIG. 27B, the stability of the EcMBP component of the EcMBP165-cpGFP.PPYF sensor decreased from 50° C. to 45° C. with insertion of cpGFP, while the intrinsic stability of cpGFP in the sensor remained unchanged. There was little change in the stability of the PfMBP component of the PfMBP171-cpGFP.L2FE sensor with insertion of cpGFP (FIG. 27B). Moreover, PfMBP seemed to exert a small stabilizing effect over the inserted cpGFP, as shown by the change in the steepness and melting point of the curve of the soluble form and the PfMBP171-cpGFP.L2FE sensor. All the associations made between transitions and domain unfolding were supported by CD spectra taken at the beginning and the end of each temperature ramp.

Analysis of whether the PfMBP scaffold was more tolerant of mutation than the EcMBP scaffold was also performed. Proof-of-principle mutations were made to the ligand-binding sites of EcMBP and PfMBP, and their respective sensors. In EcMBP, Asn12 was mutated to Trp to result in steric clashes with the surrounding residues, and backbone, of the binding pocket. The homologous mutation in PfMBP is Ala13Trp, which would be expected to have the same effect.

As shown in FIG. 27C, N12W decreased the Tm of EcMBP from 50° C. to 40° C., while the corresponding mutation in PfMBP, A13W, had no noticeable effect. This data confirms that the thermophilic protein is more tolerant of mutations to the binding site. Furthermore, in the context of the sensors, the N12W mutation to EcMBP165-cpGFP.PPYF completely destabilized the binding protein component of the sensor (FIG. 27D), while the A13W mutation in PfMBP171-cpGFP.L2FE had no effect on stability (FIG. 27D).

Example 2D: Tolerance of PfMBP Sensor to Increased Temperature

Fluorescence of the protein in the apo and ligand-bound states at was measured at different temperatures.

Figures 28A, 28B:
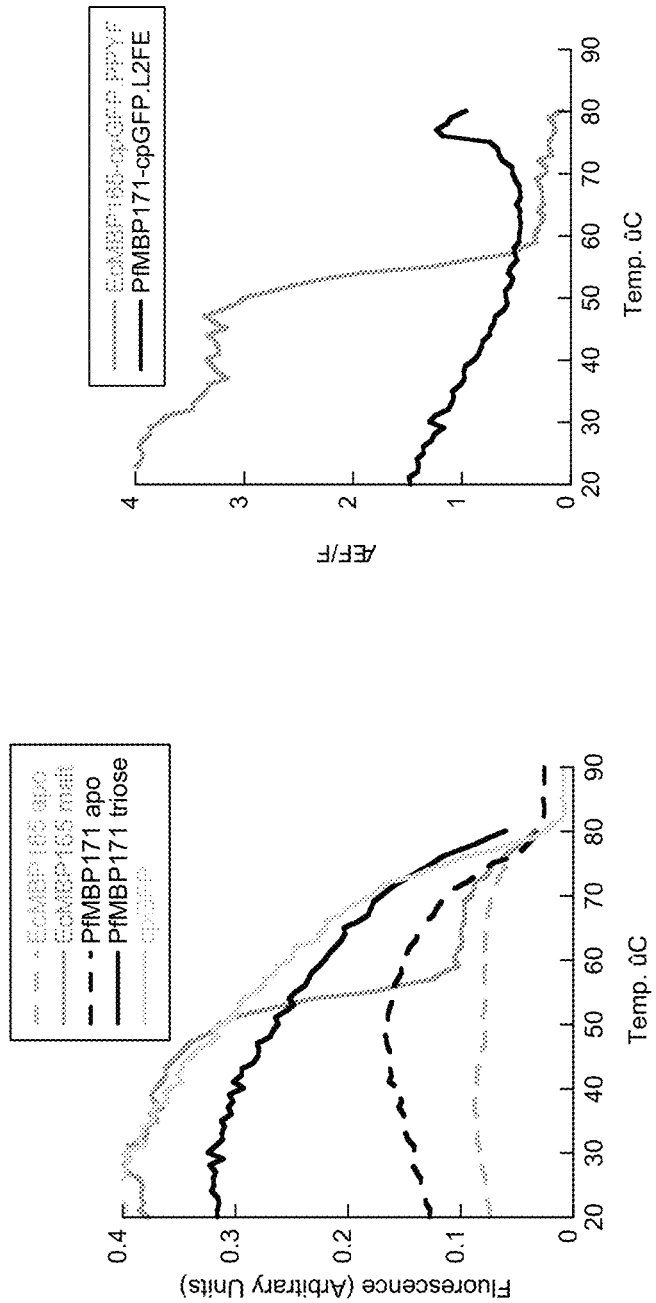
FIGS. 28A-28B|PfMBP Fluorescence vs. temperature.

As shown in FIG. 28A, fluorescence of the EcMBP165-cpGFP.PPYF sensor in the bound state was higher than it is in the apo-state at lower temperatures, by about 4-fold. However, at around 55° C. (the unfolding transition of the EcMBP component) the fluorescence of the EcMBP165-cpGFP.PPYF sensor dropped precipitously. As a result, EcMBP165-cpGFP.PPYF is unsuitable for detection of maltose at temperatures greater than 50° C. (FIG. 28B). In contrast, PfMBP171-cpGFP.L2FE retained its maltotriose binding capabilities at high temperatures (FIGS. 28A and 28B), and is limited only by the intrinsic fluorescence of the cpGFP component, which decays at about 80° C. (FIG. 28A).

Example 2E: Measurement of Maltodextrins in Hot Liquids

Figures 28C, 28D, 28E:
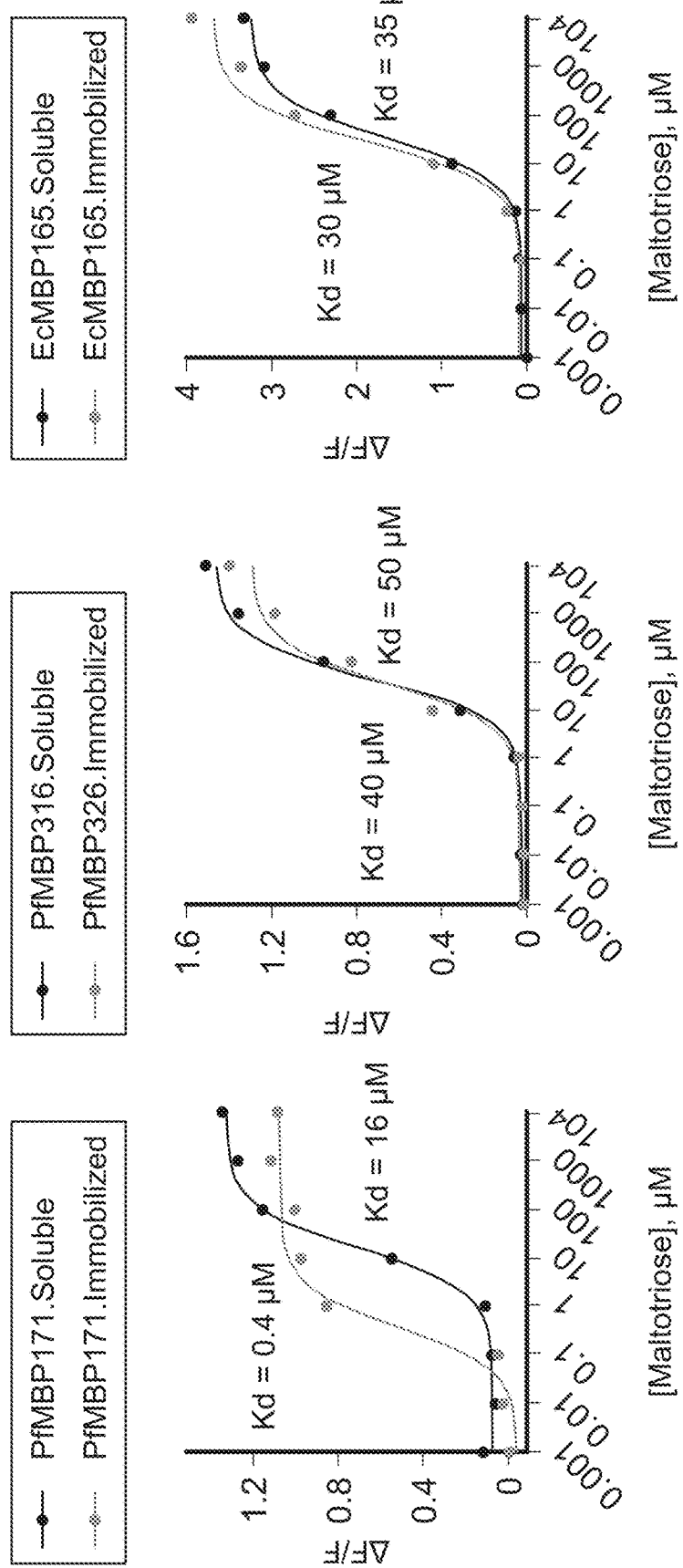
FIGS. 28C-28E|Line graphs showing the function of immobilized and soluble proteins.

To demonstrate that the soluble and immobilized sensors function similarly, PfMBP171-cpGFP.L2FE, PfMBP316-cpGFPL1XXX, and EcMBP165-cpGFP.PPYF.T203V were immobilized via their N-terminal poly-histidine tags on to the surface of Ni-NTA coated glass. In a fluorescence plate reader, the immobilized proteins performed similarly to their soluble counterparts (see FIGS. 28C, 28D, and 28F).

Next, a prototype device was constructed, with a light guide providing the excitation light and returning the fluorescent emitted light back to the photodetector, the biosensor protein immobilized to Ni-NTA coated coverslips, and the coverslip attached to the end of the light guide. The "wand" of the detector was dipped into different compositions of solutions, each with varying concentrations of maltose or maltotriose. Experiments were performed at different temperatures. PfMBP-cpGFP sensor performed better at higher temperatures (as high as 60° C.) than the EcMBP-cpGFP sensor.

Example 3: Glutamate Indicators

Figure 3:
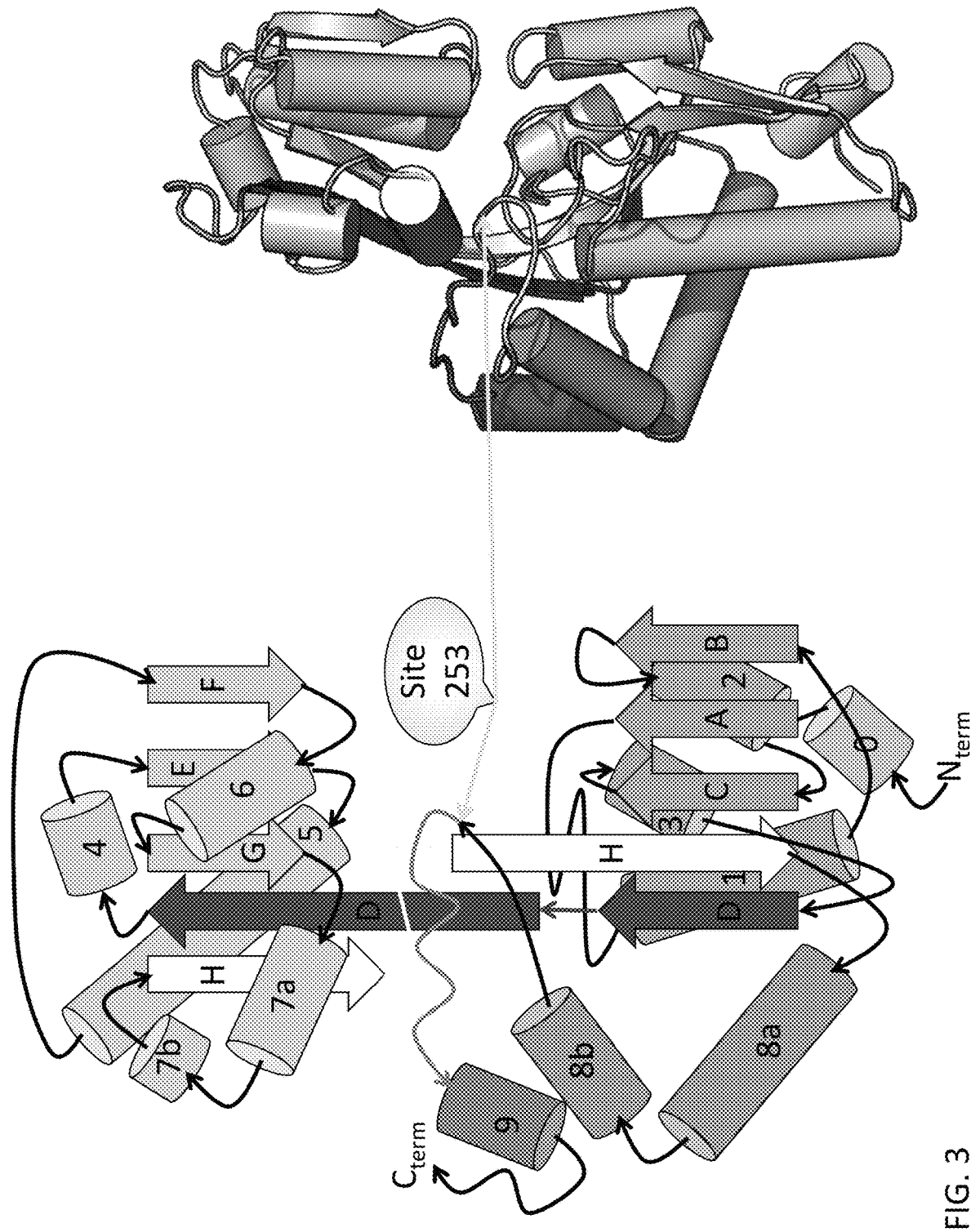
FIG. 3|Cartoon representation showing ligand bound *E. coli* glutamate-binding protein (EcYbeJ) and potential cpFP insertion sites.

Glutamate indicators were created from *Escherichia coli* glutamate-binding protein (EcYbeJ). As with PfMBP in Example 2, only the structure of the ligand-bound EcYbeJ is available. EcYbeJ is homologous to EcMBP, but to a lesser degree. The best homology match between a site in EcYbeJ and a site in a binding protein for which an intensity-based sensor has already been created is EcYbeJ253 and EcMBP311 (described herein). As shown in FIG. 3, both sites are at the junction of "Rising Helix 8" and the "Equatorial Helix/Coil." The amino acid composition of the cpGFP and EcYbeJ junction was made the same as that of the EcMBP311-cpGFP sensor (Linker 2=NP). The amino acid composition of the EcYbeJ junction and cpGFP was optimized to LV (Linker 1=LV). The variant has a ΔF/F of 5.

Example 3A: Identification of cpGFP Insertion Sites

The ligand-bound (closed) structure of *Shigella flexneri* glutamate binding protein is available (Fan et al., Protein Pept. Lett., 13:513-516, 2006). This protein has only 4 amino acid mutations relative to EcYbeJ, and is thus an appropriate model.

Insertion sites for the EcYbeJ-cpGFP sensors were identified by homology to EcMBP. Based on the topology map (FIG. 3), position 311 in EcMBP was identified as an acceptable insertion site for EcYbeJ. EcMBP311 is equivalent to EcYbeJ253. EcYbeJ253 is at juncture between the end of the cluster of helices (Helices 8a, 8b, 8c) and the start of the "equatorial" spanning helix (Helix 9). In YbeJ, the structure that is homologous to the equatorial helix is the equatorial coil (depicted in red, to match the red coloring of Helix 9).

Figure 29A:
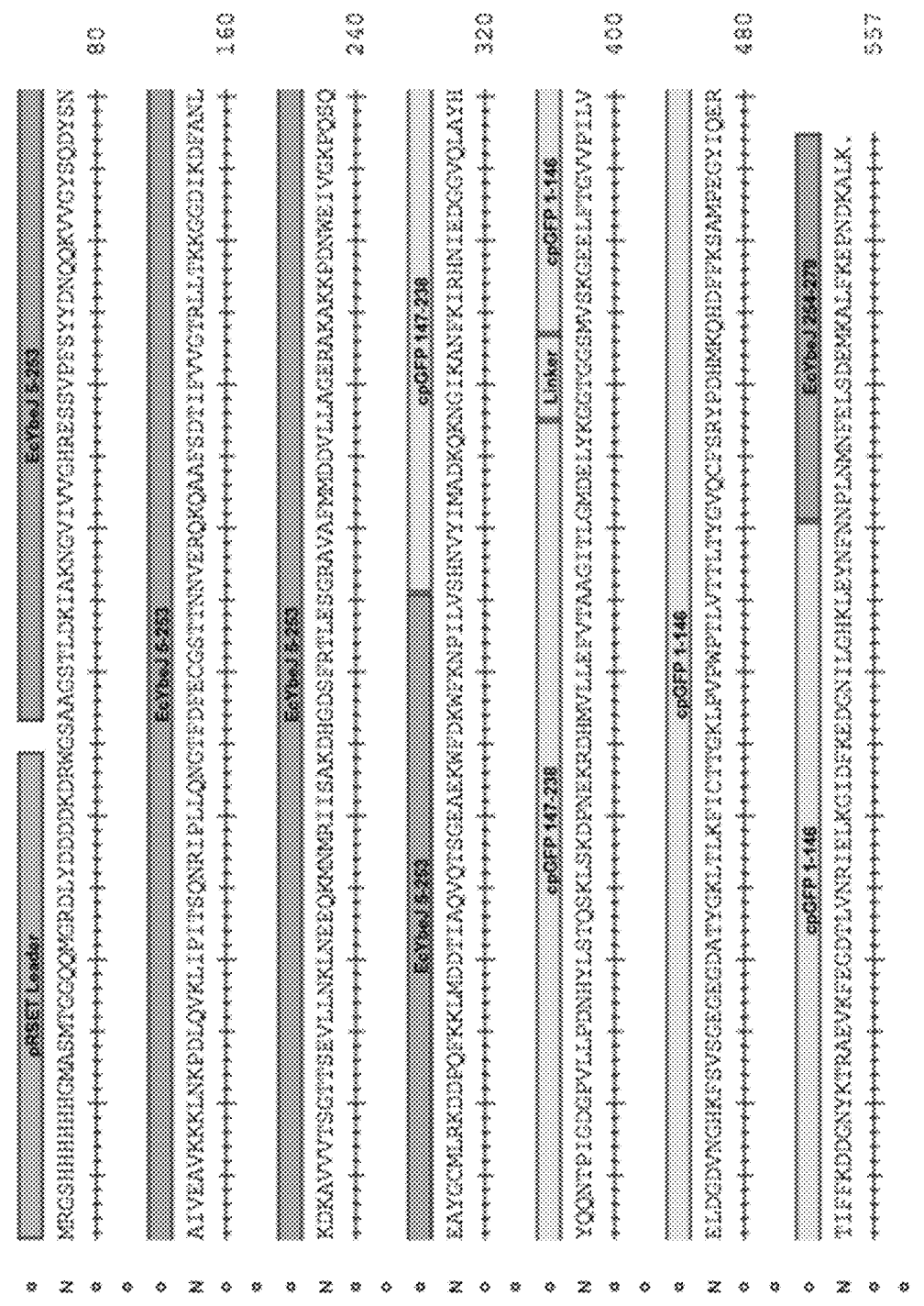
Figure 29B:
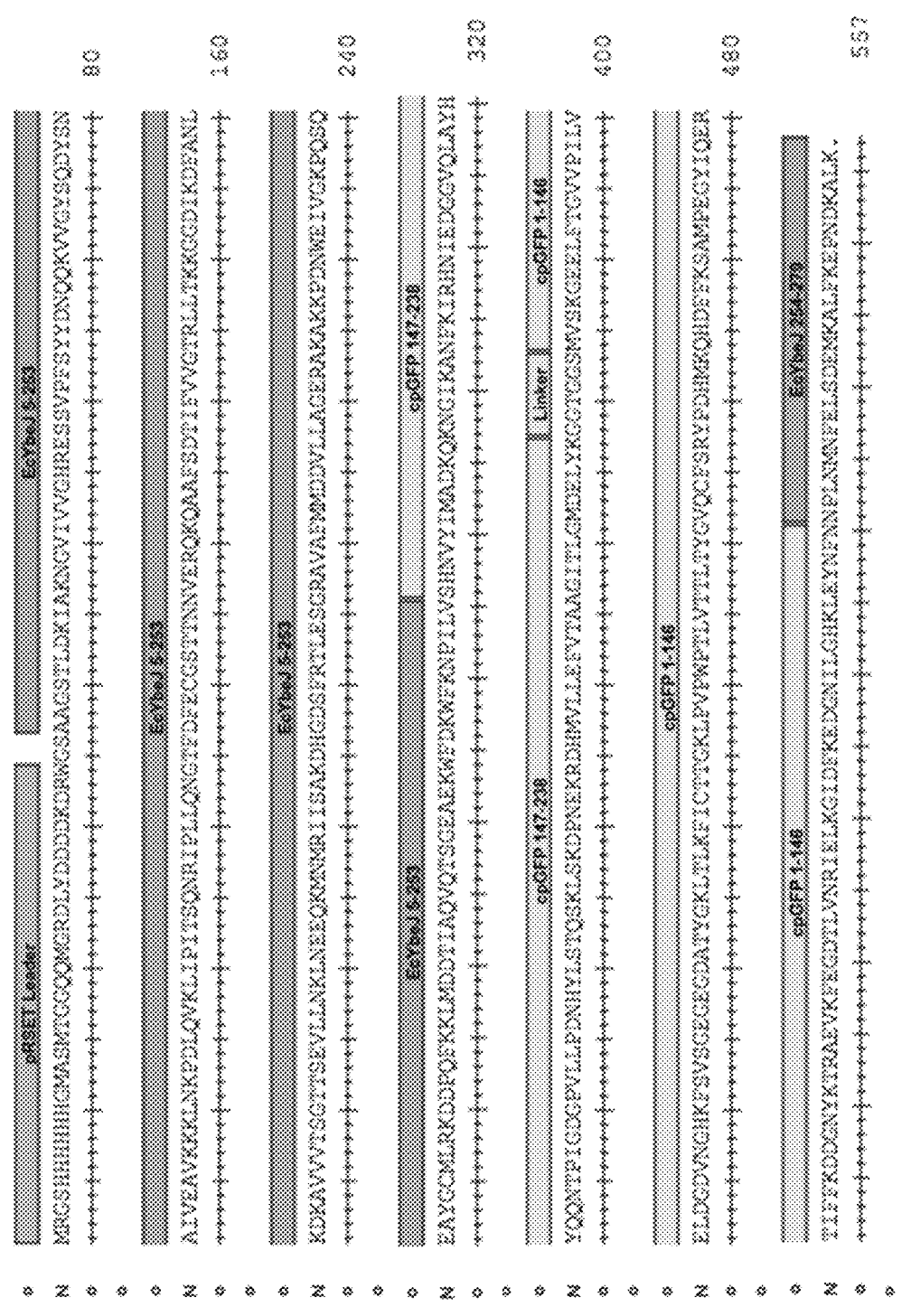

Intrinsic affinity of wild-type YbeJ for glutamate (~1 µM) was too high to permit high-throughput screening of linker libraries. Endogenous glutamate (from the growth media) saturates the sensor, making measurement of the unbound state technically challenging. A mutation to YbeJ (A184V), in the "hinge" of the protein were made. Mutation of this residue to Trp or Arg have previously been shown to decrease affinity in FRET-based sensors (see Okumoto et al., Proc. Natl. Acad. Sci., 102:8740-8745, 2005). EcYbeJ253 (A184V)-cpGFP has an affinity for glutamate of about 100 µM. All references to EcYbeJ253-cpGFP, unless otherwise noted, refer to the A184V variant. The sequences of the EcYbeJ constructs are shown in FIG. 29.

Example 3B: Linker Optimization

Libraries of variants of SEQ ID NOs: 62-63 were generated with randomized linkers by single-stranded uracil template mutagenesis using the primers listed below:

```
253 Linker 1 Primers:
                                            (SEQ ID NO: 64)
FKNPIPPxSHNVYIMA (SEQ ID NO: 65)
FKNPIPPxxSHNVYIMA (SEQ ID NO: 66)
FKNPIPPPxSHNVYIMA (SEQ ID NO: 67)
FKNPIPPxPSHNVYIMA (SEQ ID NO: 68)
KWFKNPIxxSHNVYIMA (SEQ ID NO: 69)
FKNPIPPxxNVYIMAD (SEQ ID NO: 70)
KWFKNPIxxNVYIMAD 253 Linker 2 Primers:
                                            (SEQ ID NO: 71)
KLEYNFNxKNLNMNF (SEQ ID NO: 72)
KLEYNFNxxKNLNMNF (SEQ ID NO: 73)
KLEYNFNxPKNLNMNF (SEQ ID NO: 74)
KLEYNFNPxKNLNMNF (SEQ ID NO: 75)
GHKLEYNxxLNMNF (SEQ ID NO: 76)
KLEYNFNxxLNMNF
```

Where "x" indicates that a degenerate primer (with DNA sequence "NNS") was used to encode all 20 possible amino acids.

Several thousand variants were screened in semi-highthroughput fashion, measuring fluorescence intensity of clarified cell lysate in the absence and presence of 10 mM glutamate.

Figure 30:
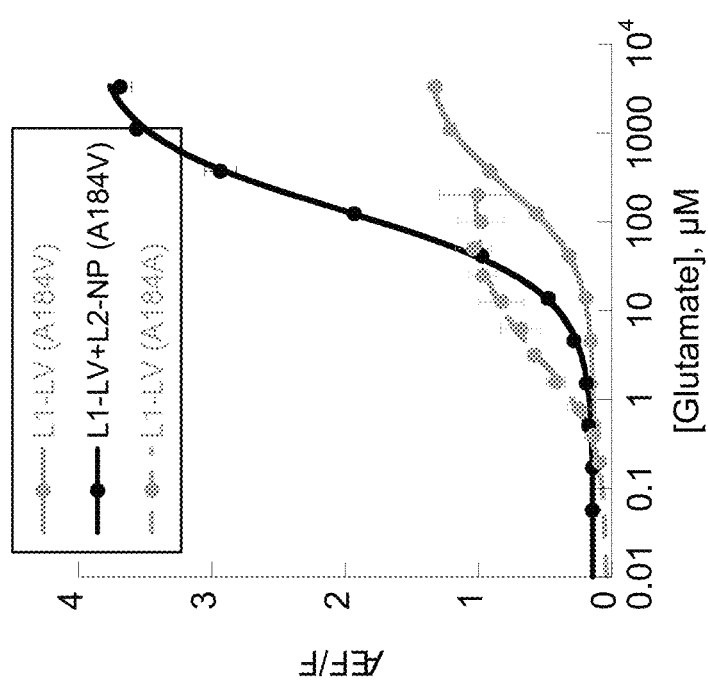
FIG. 30|EcYbeJ binding curves. Plot of ΔF/F as a function of [Glutamate], μM. The first generation sensor, EcYbeJ253.L1-LV (with the A184V) mutation (grey, solid) has an affinity for glutamate of about 100 μM and a ΔF/F of 1.2. The reversion of that affinity mutation, V184A, in the L1-LV background increases affinity to 1 (grey dashed). The second generation sensor, with the L2-NP linker optimization and the A184V mutation, has a ΔF/F of at least 4 and an affinity for glutamate of about 100 μM (black solid).

Screening a fully-degenerate, length-two library ("XX") at the EcYbeJ253-cpGFP linker (linker 1) identified a sensor with glutamate-dependent fluorescent increases of 100%. This variant has a LeuVal EcYbeJ-cpGFP linker (L1-LV) and was used as the framework for optimization of the cpGFP-EcYbeJ253 linker (linker 2). The results of that screen yielded a protein with glutamate-dependent fluorescent increase of ~500% and a linker 2 composition of AsnPro. As shown in FIG. 30, this variant, called "EcYbeJ253-cpGFP.L1LVL2NP" has a ΔF/F=5, a Kd for glutamate of 100 µM. Interestingly, the composition of the second linker, AsnPro, is the same as the linker composition of EcMBP311-cpGFP.L2NP.

Example 3C: Detection of Extracellular Glutamate

EcYbeJ253-cpGFP.L1LVL2NP was cloned into the pDisplay™ vector to allow targeting and anchoring of the sensor to the plasma membrane. The resulting construct was transfected into cultured mammalian cells (HEK293) to visualize the addition of glutamate to extracellular media. Constructs were also generated in a bacterial expression vector with the epitope tags individually and in combination.

Figure 31:
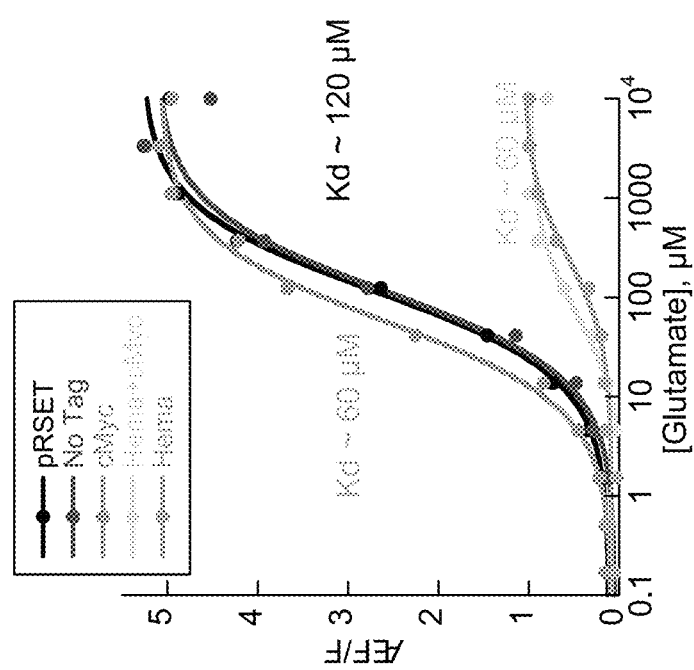
FIG. 31|EcYbeJ Hema/cMyc analysis. The effect of N- and C-terminal tags on ΔF/F and glutamate affinity were determined by expressing variously tagged versions of the EcYbeJ253.L1LVL2NP protein in bacteria. The presence of the pRSET leader sequence (black) has no effect on ΔF/F (~5) or affinity (~120 μM), when compared to the version without a tag (grey). The addition of the cMyc tag to the C-terminus retains ΔF/F and increases affinity slightly, to 60 μM. The addition of the N-terminal hemagglutinin tag, with (green) or without (orange) the cMyc tag, decreases ΔF/F substantially.
Figure 32A:
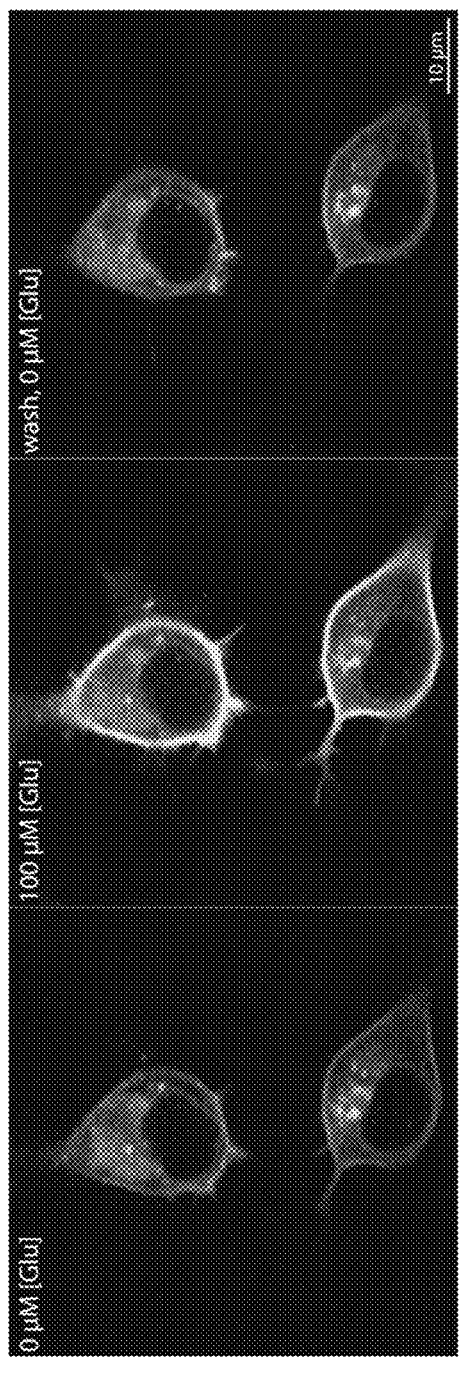
FIGS. 32A-32B|EcYbeJ253-cpGFP.L1LVL2NP.pMinDis expressed in HEK293 cells.
Figure 32B:
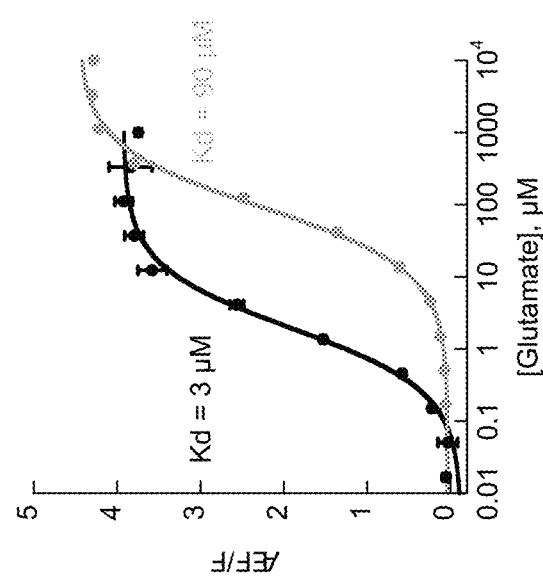

As shown in FIG. 31, the hemagglutinin tag interferes with the fluorescence change. EcYbeJ253-cpGFP.L1LVL2NP was re-cloned into a derivative of the pDisplay™ vector, lacking the hemagglutinin tag, called pMinDis (for Minimal Display). This new construct, when expressed in HEK293 cells, shows a change in fluorescence intensity under 2-photon excitation that is approximately the same as the soluble protein (see FIG. 32) with higher affinity, of about 1 (see FIG. 32).

Figure 33:
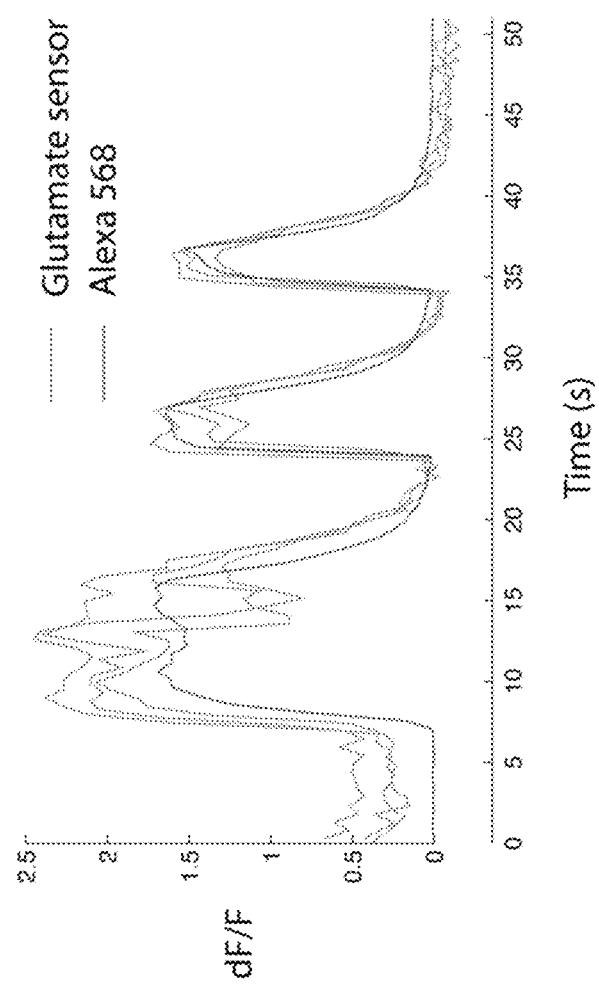
FIG. 33|EcYbeJ253-cpGFP.L1LVL2NP.pMinDis expressed in neuronal culture, and responds rapidly to added glutamate (green). Red shows signal of 2.5 nM Alexa Fluor® 568 (Invitrogen, Carlsbad, CA), also in pipette.

To demonstrate that the sensor is functional in neurons, and not just cultured HEK cells, the gene from EcYbeJ253-cpGFP.L1LVL2NP was cloned into an adeno-associated virus vector (AAV) under control of the synapsin promoter. Virus particles were generated and used to infect cultured primary hippocampus neurons from rats 7 days after culturing. 14 days after culturing (and 7 days after infection), the infected neurons were imaged under 2-photon microscopy (FIG. 33).

Example 4: Phosphonate Indicators

Figure 4:
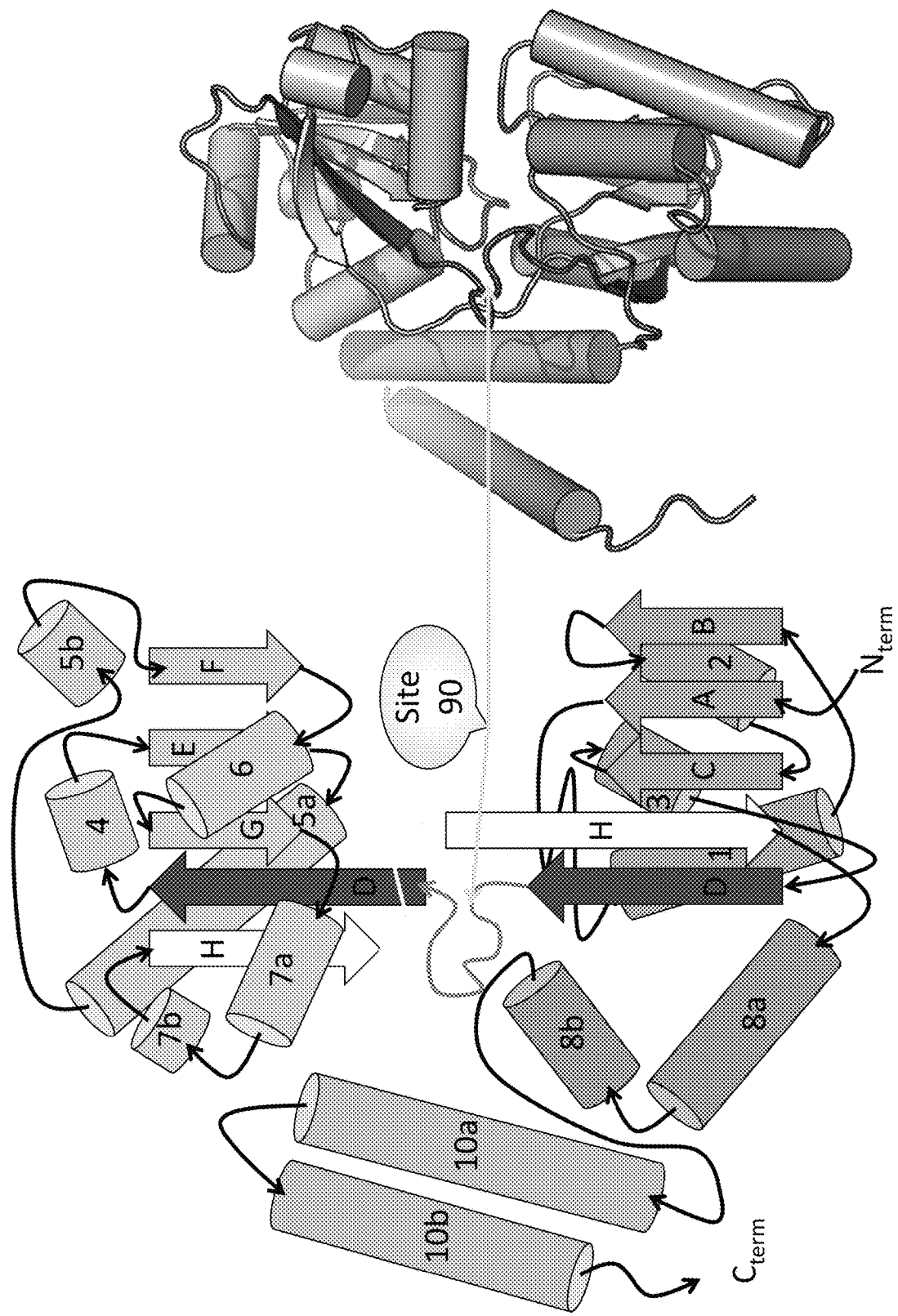
FIG. 4|Cartoon representation showing ligand bound *E. coli* phosphonate-binding protein (EcPhnD) and potential cpFP insertion sites.

An indicator for phosphonate compounds was created from *Escherichia coli* phosphonate-binding protein (EcPhnD). In this instance, only the structure of the ligand-bound state was available at the time the sensor was conceived. EcPhnD is homologous to EcMBP to a lesser degree and to EcYbeJ to a greater degree. The best homology match between a site in EcPhnD and a site in a binding protein for which an intensity-based sensor has already been created is EcPhnD90 and EcYbeJ253. There is no "Rising Helix 8" in EcPhnD, but there is an "Equatorial Helix/Coil" (FIG. 4). cpGFP was inserted at the Equatorial Helix/Coil and linkers were optimized to yield a sensor with ΔF/F of 1.2. EcPhnD is a dimmer, so, a pair of mutations (L297R+L301R) were made to convert it to a monomer. The monomer variant has a ΔF/F of 1.6.

Example 4A: Identification of cpGFP Insertion Sites in EcPhnD

Figure 34A:
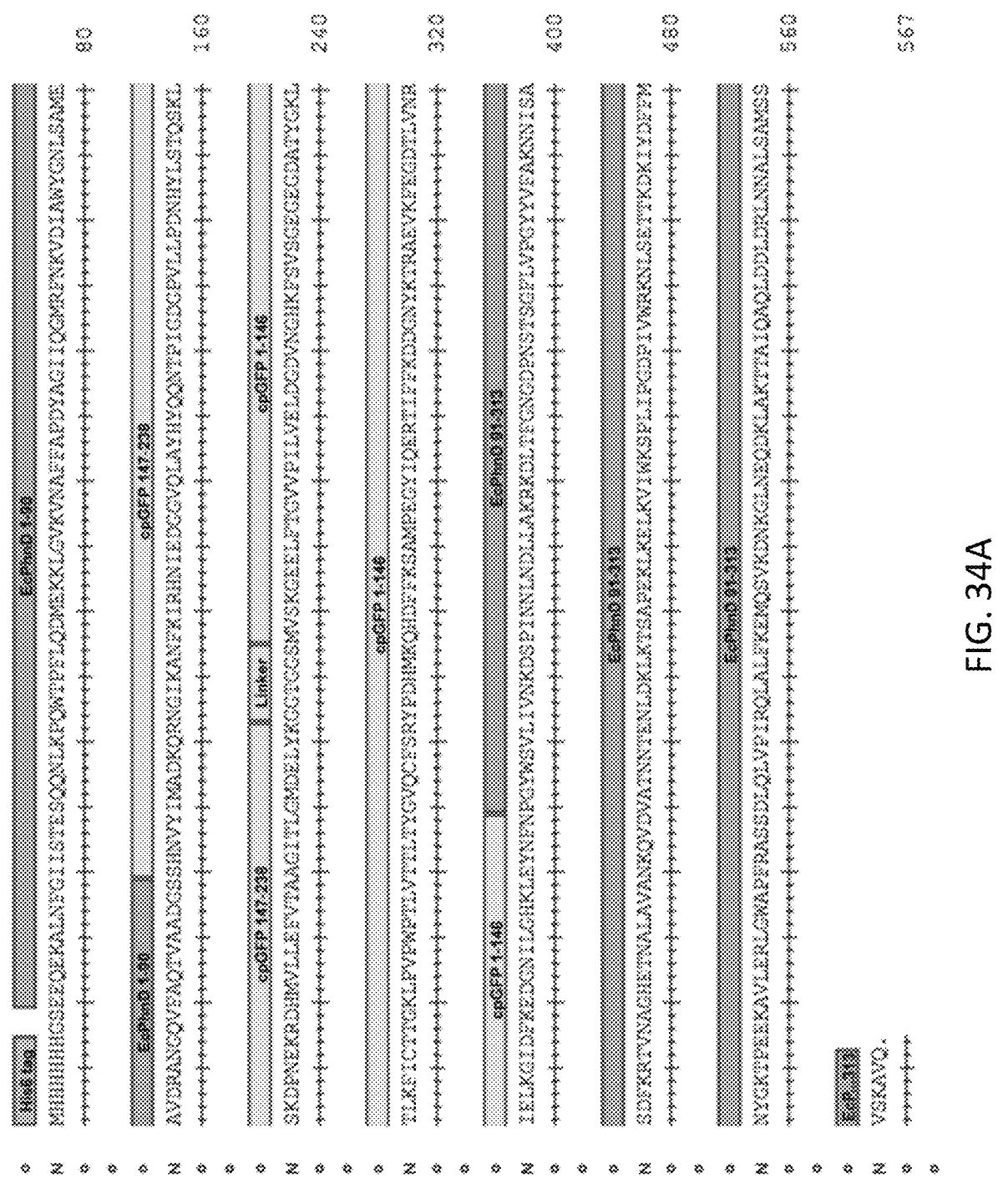
Figure 34B:
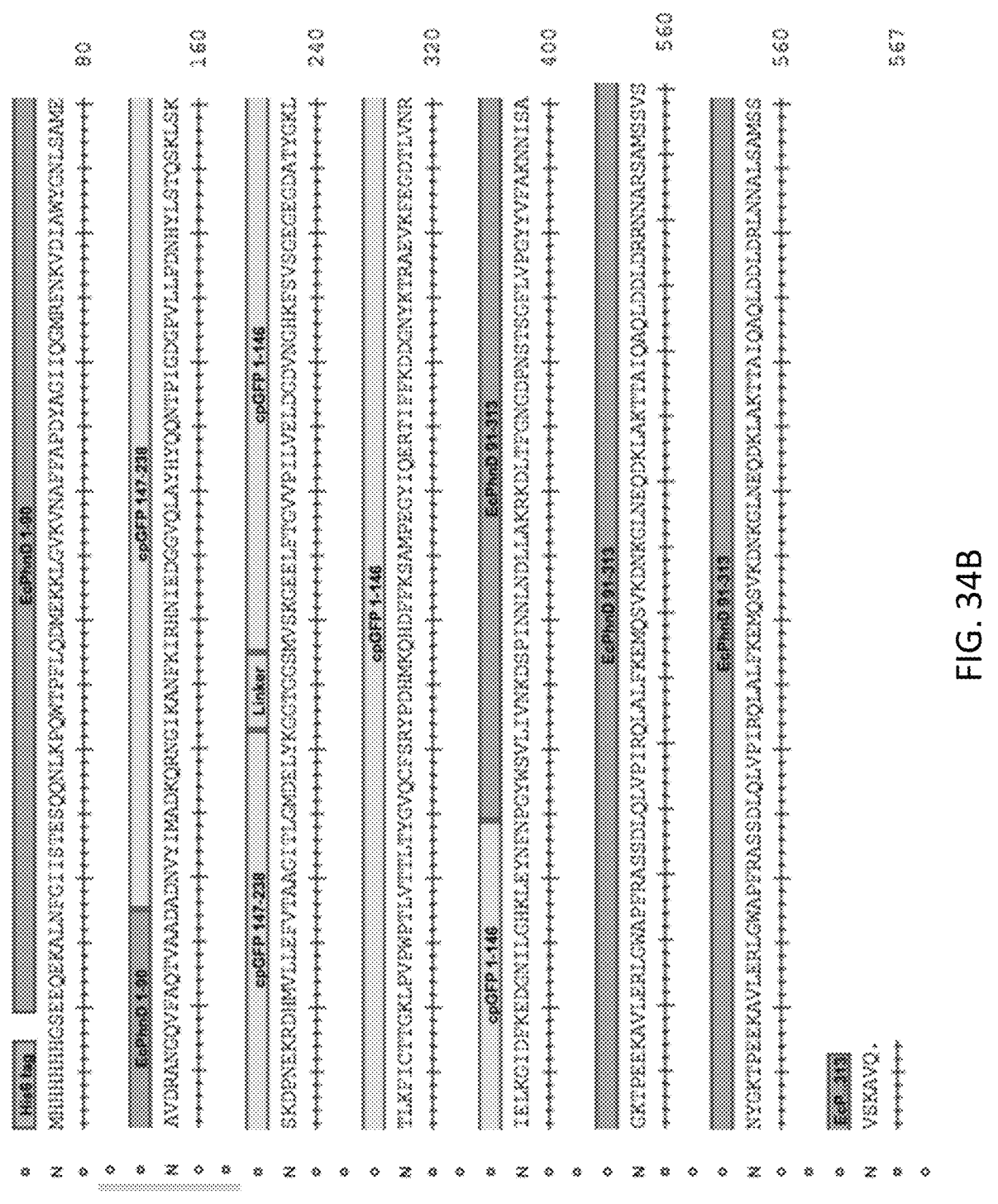

Insertion sites for the EcPhnD-cpGFP sensors were identified using the ligand-bound (closed) structure of EcPhnD by homology to EcMBP. Based on the topology map (FIG. 4), position 311 in EcMBP was identified as an acceptable insertion site in EcPhnD. EcMBP311 corresponds to EcPhnD90. This site is at the point where the rising strand (Strand D) of EcPhnD has a small bend in it that runs equatorial to the rest of the sheets in the protein. Even though it is topologically different from the "equatorial" spanning helix (Helix 9) of EcMBP its equatorial alignment is similar, and with just the closed structure at the time, in an environment that was expected to undergo significant dihedral change upon binding ligand. Sequences of EcPhnD constructs are shown in FIG. 34.

Example 4B: Linker Optimization

Libraries of variants of SEQ ID NOs: 77-78 were generated with randomized linkers by single-stranded uracil template mutagenesis using the primers listed below:

```
90 Linker 1 Primers:
                            (SEQ ID NO: 79)
QTVAADGSSHNVYIMA (SEQ ID NO: 80)
QTVAADxxSHNVYIMA (SEQ ID NO: 81)
QTVAADxPSHNVYIMA (SEQ ID NO: 82)
QTVAADPxSHNVYIMA (SEQ ID NO: 83)
QTVAADxxNVYIMA (SEQ ID NO: 84)
QTVAADxxSHNVYIMA (SEQ ID NO: 85)
VFQTVAxxSHNVYIMA 90 Linker 2 Primers:
                            (SEQ ID NO: 86)
HKLEYNFNPGYWSVLI (SEQ ID NO: 87)
HKLEYNFNxxPGYWSVLI (SEQ ID NO: 88)
HKLEYNxxPGYWSVLI (SEQ ID NO: 89)
HKLEYNFNxxYWSVLI (SEQ ID NO: 90)
HKLEYNFNPxYWSVLI
```

Where "x" indicates that a degenerate primer (with DNA sequence "NNS") was used to encode all 20 possible amino acids.

Several thousand variants were screened in semi-highthroughput fashion, measuring fluorescence intensity of clarified cell lysate in the absence and presence of 100 uM 2AEP.

Screening a number of fully-degenerate, libraries at the EcPhnD90-cpGFP linker (linker 1) yielded a protein with 2AEP-dependent fluorescent increases of >100%. This variant has a AlaAsp EcPhnD-cpGFP linker (L1-AD) and a ΔF/F of 1.2. The variant came from a linker that also deleted two residues, effectively making the insertion point of cpGFP occur after residue D88, and then skipping to residue P91 at the cpGFP-EcPhnD linker.

Figures 35A, 35B, 35C:
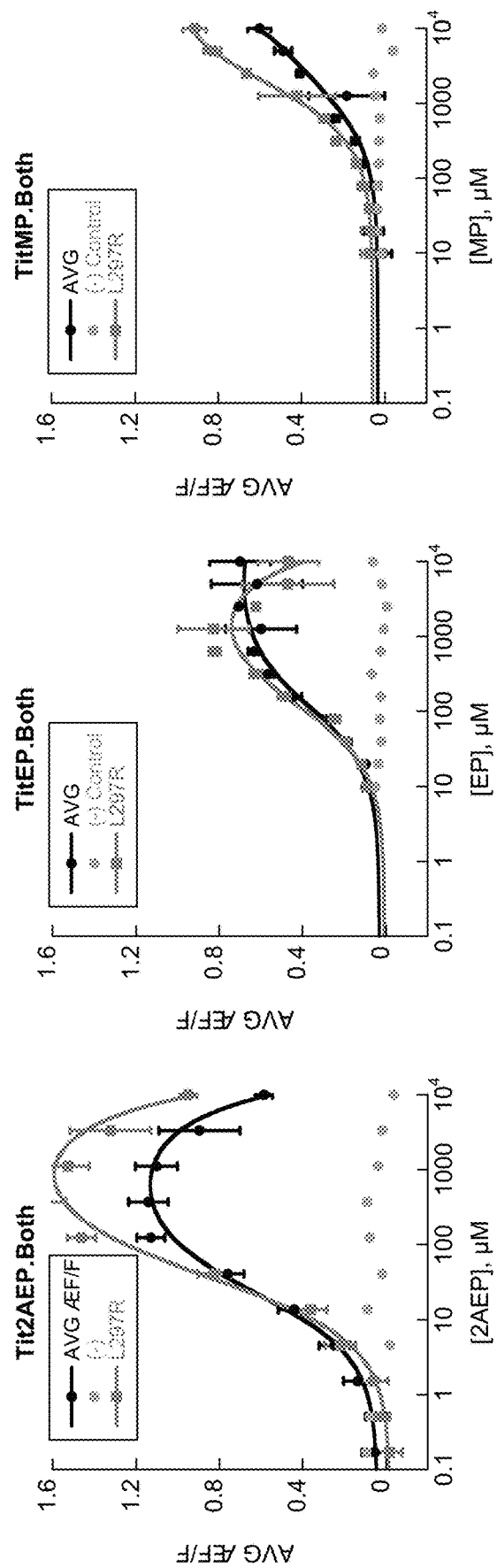
FIGS. 35A-35C|EcPhnD90-cpGFP Binding Curves. For both the L1AD and the L1AD+L297R+L301R variants, binding was determined for (FIG. 35A) 2-aminoethylphosphonate (2AEP), (FIG. 35B) methylphosphonate (MP), and (FIG. 35C) ethylphosphonate (EP).

It was observed from the crystal structure that EcPhnD forms a dimer. To disrupt the dimer inter-face and potentially simplify the observable binding behavior of the EcPhnD protein, two mutations, L297R and L301R, were introduced into the dimerization helices. These mutations were expected, by charge repulsion, to disrupt the dimer interface. As shown in FIG. 35, incorporation of L279R and L301R mutations into EcPhnD90-cpGFP.L1AD caused ΔF/F to increases to 1.6 in response to 2AEP.

Figure 36A:
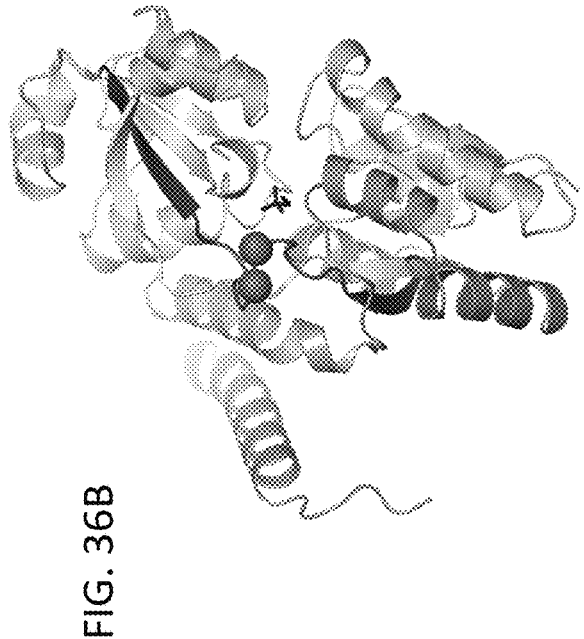
FIGS. 36A-36C|The crystal structures of the ligand-free (FIG. 36A), open state (with H157A mutation to the binding pocket) and the ligand-bound (FIG. 36B), closed state of EcPhnD clearly shows a large conformational change. Residues in between which cpGFP is inserted in EcPhnD90-cpGFP are marked by red spheres, in the equatorial strand (red).
Figure 36B:
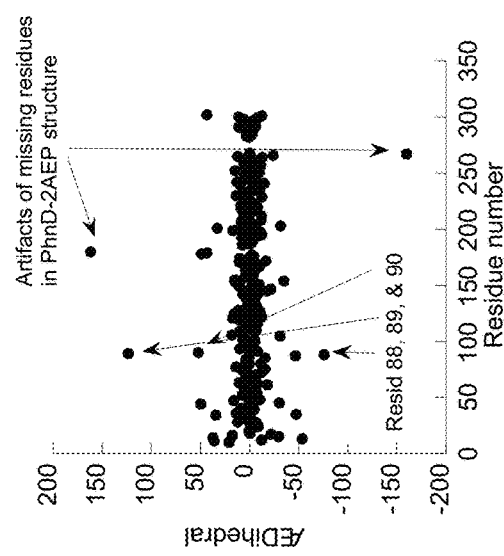
Figure 36C:
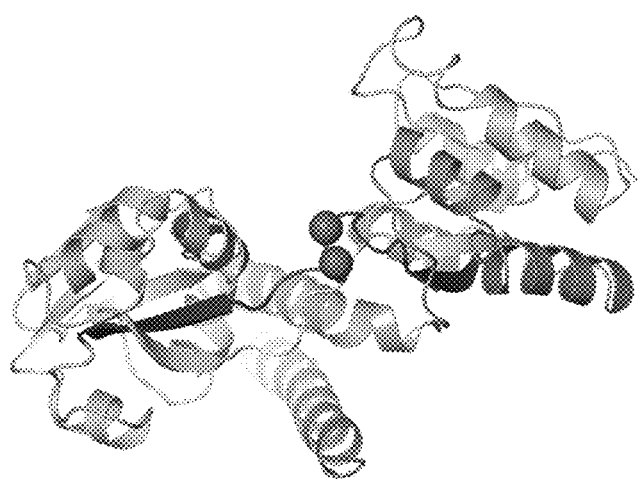

Further attempts to crystallize the open, ligand-unbound form of the protein were successful after making a mutation to the binding site, H157A, that substantially decreased affinity for phosphonate compounds. This mutant was crystallized in the absence of ligand, and the open state of the protein solved. The ΔDihedral analysis (FIG. 36) showed that the region of greatest dihedral change was the group of residues from 88-90, just one amino acid away from the site chosen by homology to the equatorial helix.

These data further indicate that ΔDihedral metric is sufficient for identifying sites in PBPs into which cpGFP can be inserted and result in intensity-based fluorescent sensors.

Example 5: Glucose Indicators

Glucose indicators were created from *Thermus thermophilus* glucose binding protein (TtGBP). In this instance, only the structure of the ligand-bound state is available. TtGBP is very homologous to EcMBP and PfMBP (compare FIG. 5 with FIGS. 1 and 2). The insertion point (TtGBP326) was chosen by homology to EcMBP311 and PfMBP316. The amino acid composition of the cpGFP and TtGBP junction was made the same as that of the EcMBP311-cpGFP and EcYbeJ253 sensors (Linker 2=NP). Linker 1 was optimized (Linker 1=PA) and the TtGBP326 sensor have a ΔF/F of ~2.5. To improve its utility for the measuring glucose concentrations in human blood, the affinity was weakened from its native ~1 μM to 1.5 mM by mutation of two residues in the binding pocket (H66A+H348A).

Example 5A: Identification of cpGFP Insertion Sites in TtGBP

Figure 37A:
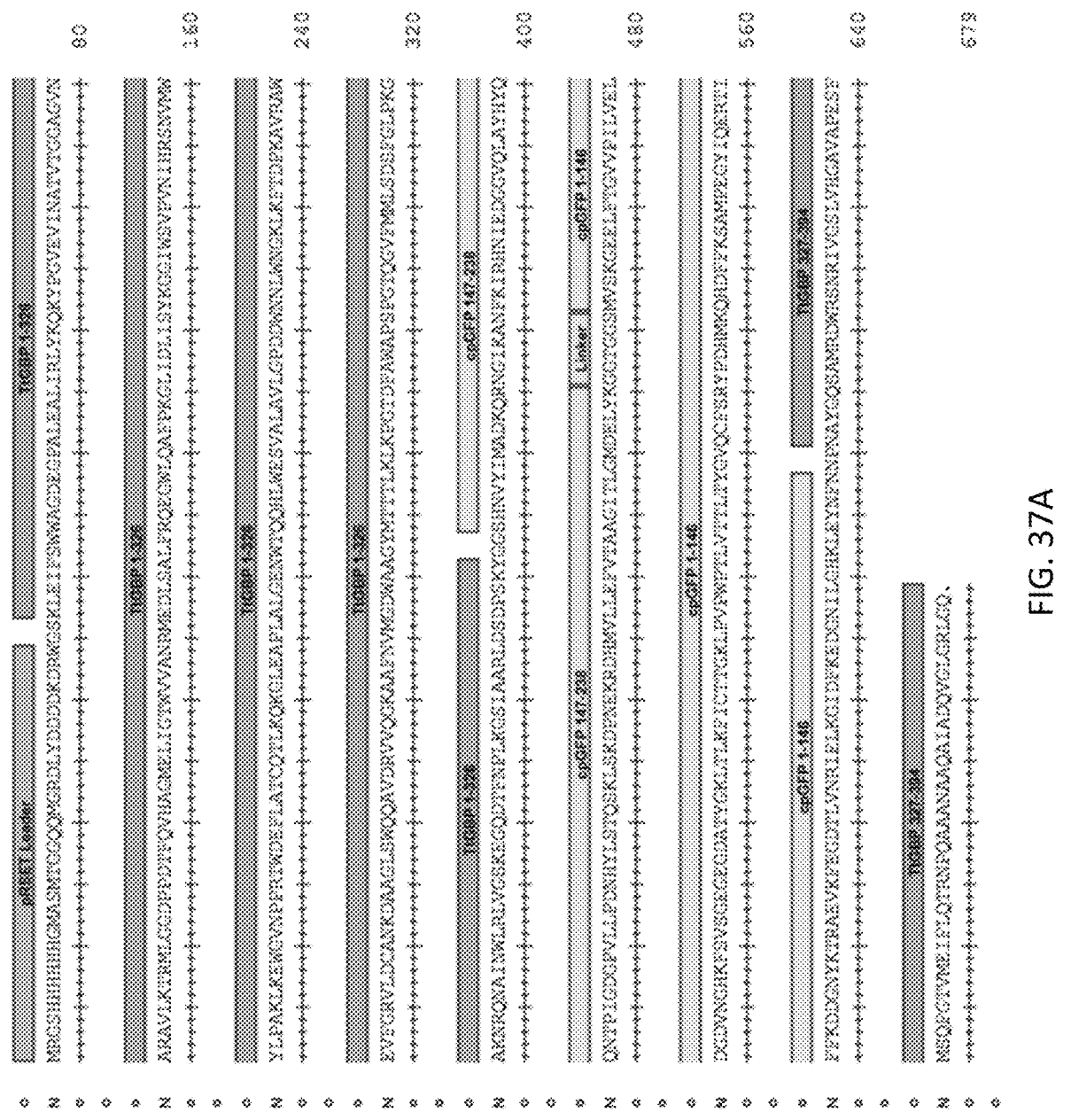
Figure 37B:
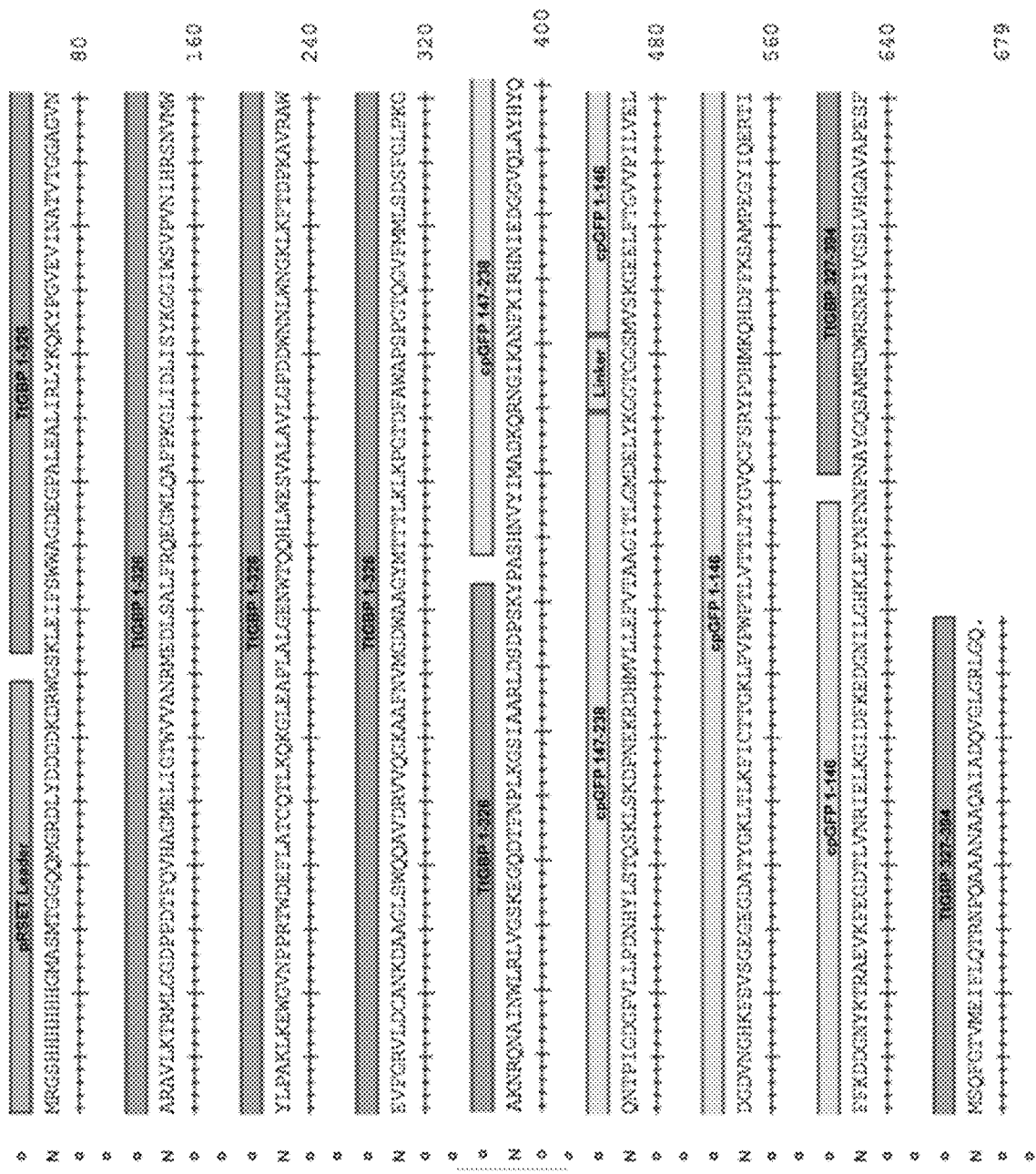
FIG. 37B|Amino acid sequence of TtGBP326.L1-PA (SEQ ID NO:92).
Figure 37C:
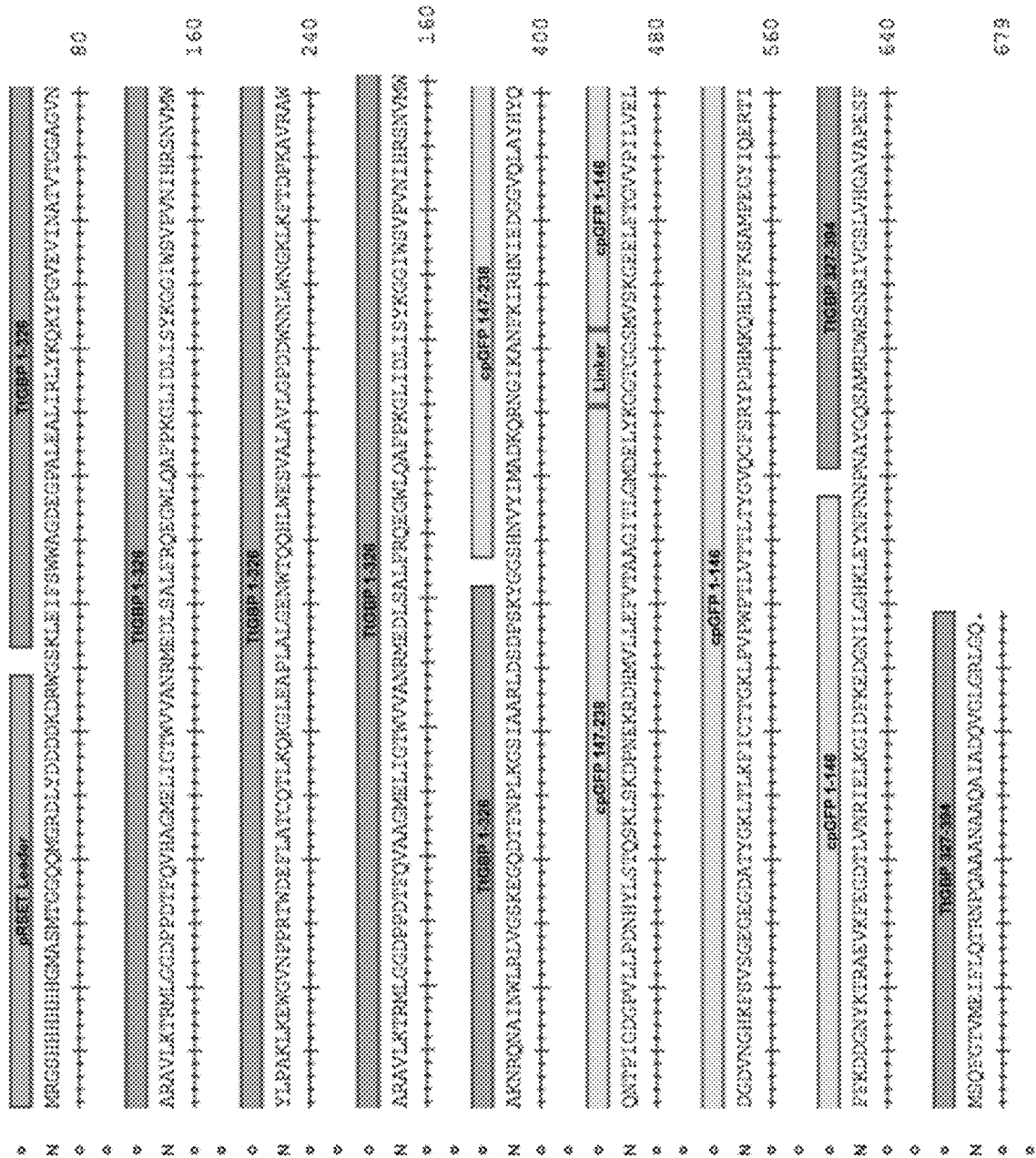
FIG. 37C|Amino acid sequence of TtGBP326.H66A (SEQ ID NO:93).
Figure 37D:
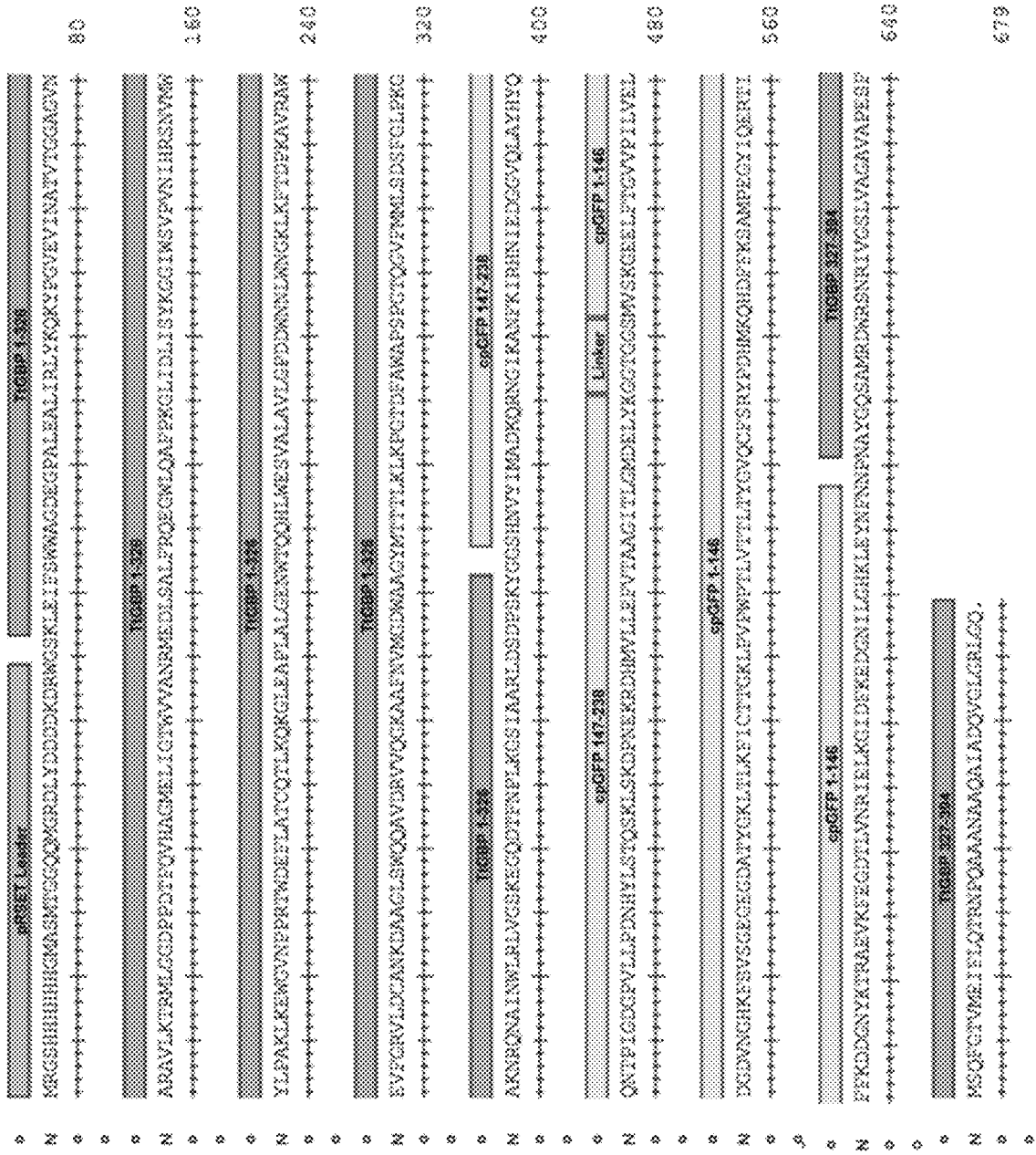
FIG. 37D|Amino acid sequence of TtGBP326.H348A (SEQ ID NO:94).

The ligand-bound (closed) structure of TtGBP is available (Cuneo et al., J. Mol. Biol., 362:259-270, 2006). Accordingly, insertion sites for the TtGBP-cpGFP sensors were identified by homology to EcMBP and PfMBP. Based on the topology map (FIG. 5), it is apparent that TtGBP, PfMBP, and EcMBP are structurally similar in the closed, ligand-bound state. Positions in EcMBP determined by the dihedral analysis (see above) were predicted to be acceptable insertion sites in TtGBP. EcMBP311 is homologous to TtGBP326. This site is at juncture between the end of the cluster of helices (Helices 8a, 8b, 8c) and the start of the "equatorial" spanning helix (Helix 9). The amino acid sequence of the TtGBP construct is shown in FIG. 37.

Example 5B: Linker Optimization

Libraries of variants of SEQ ID NO:91 were generated with randomized linkers by single-stranded uracil template mutagenesis using the primers listed below:

326 Linker 1 Primers:

```
                                      (SEQ ID NO: 95)
DSDPSKYxxSHNVYIM (SEQ ID NO: 96)
DSDPSKYPxSHNVYIM (SEQ ID NO: 97)
DSDPSKYxPSHNVYIM (SEQ ID NO: 98)
RLDSDPSxxSHNVYIM (SEQ ID NO: 99)
DSDPSKYxxNVYIM
```

326 Linker 2 Primers:

```
                                      (SEQ ID NO: 100)
KLEYNFNxxNAYGQSA (SEQ ID NO: 101)
KLEYNFxxPNAYGQSA (SEQ ID NO: 102)
GHKLEYNxxNAYGQSA (SEQ ID NO: 103)
KLEYNFNxPNAYGQSA (SEQ ID NO: 104)
KLEYNFNPxNAYGQSA
```

Where "x" indicates that a degenerate primer (with DNA sequence "NNS") was used to encode all 20 possible amino acids.

Several hundred variants were screen in semi-high-throughput fashion, measuring fluorescence intensity of clarified cell lysate in the absence and presence of 10 mM glucose.

Figure 38:
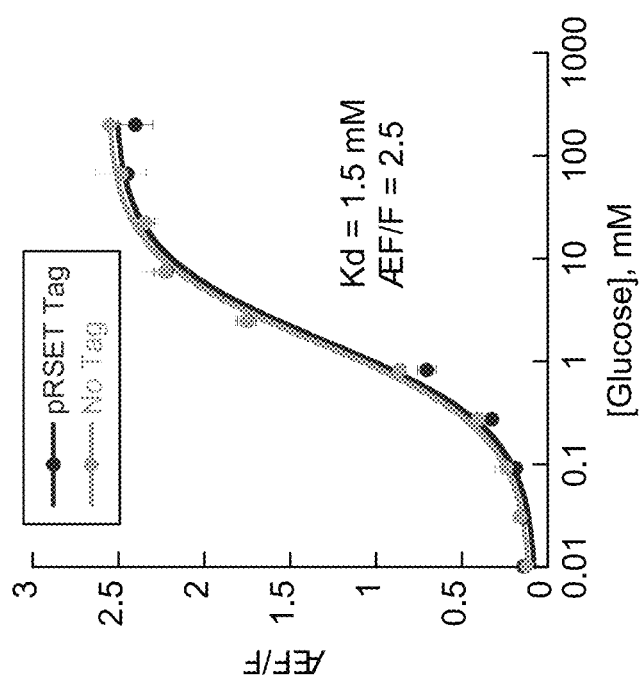
FIG. 38|TtGBP326-cpGFP Binding Curves. Plot of ΔF/F as a function of [Glucose], mM.

Linker 1 was optimized (Linker 1=PA) and the TtGBP326-cpGFP.L1PAL2NP sensor has a ΔF/F of ~2.5 (see FIG. 38). Additionally, the TtGBP sensor was tested with and without the N-terminal pRSET tag and no difference was observed. Specifically, both sensors exhibited an affinity for glucose of about 1.5 mM and a ΔF/F of 2.5. Data showing that it was possible to construct a glucose sensor by replacing the EcMBP or PfMBP with TtGBP, retaining the composition of linker 2, and optimizing the composition of linker 1, indicates that the methods for generating sensors disclosed herein can be used to generate sensors using any suitable framework.

Example 5C: Detecting Changes in Glucose Concentration in Vivo

The TtGBP326-cpGFP.L1PAL2NP sensor was cloned into a variant of the pDisplay™ vector lacking the N-terminal secretion sequence, the N-terminal hemagglutinin tag, the C-terminal cMyc tag, and the C-terminal PDGFR membrane anchoring domain.

Figure 39:
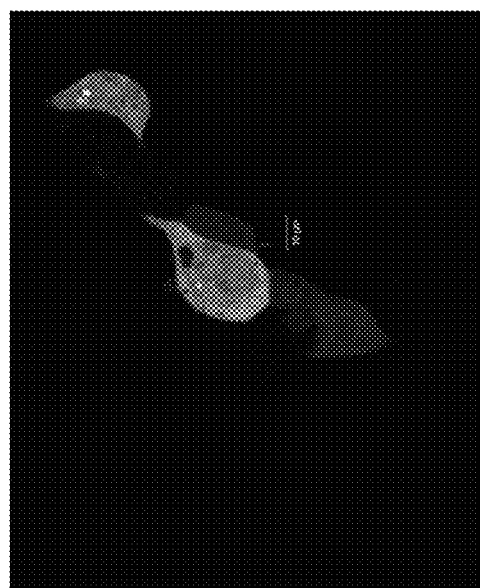
FIG. 39|An image showing TtGBP326-cpGFP expressed as a transgenic reporter of intracellular glucose in cultured human cells.

The TtGBP sensor was cloned into a mammalian expression vector (based on the pDisplay™ vector described in Example 3 above) with the secretion, epitope, and transmembrane anchoring peptides removed, thus resulting in cytosolic expression of the TtGBP326-cpGFP.L1PAL2NP+H66A+H348A sensor. The construct was transfected into HEK293 cells. As shown in FIG. 39, the TtGBP sensor was expressed in the cytosol.

Figures 40A, 40B:
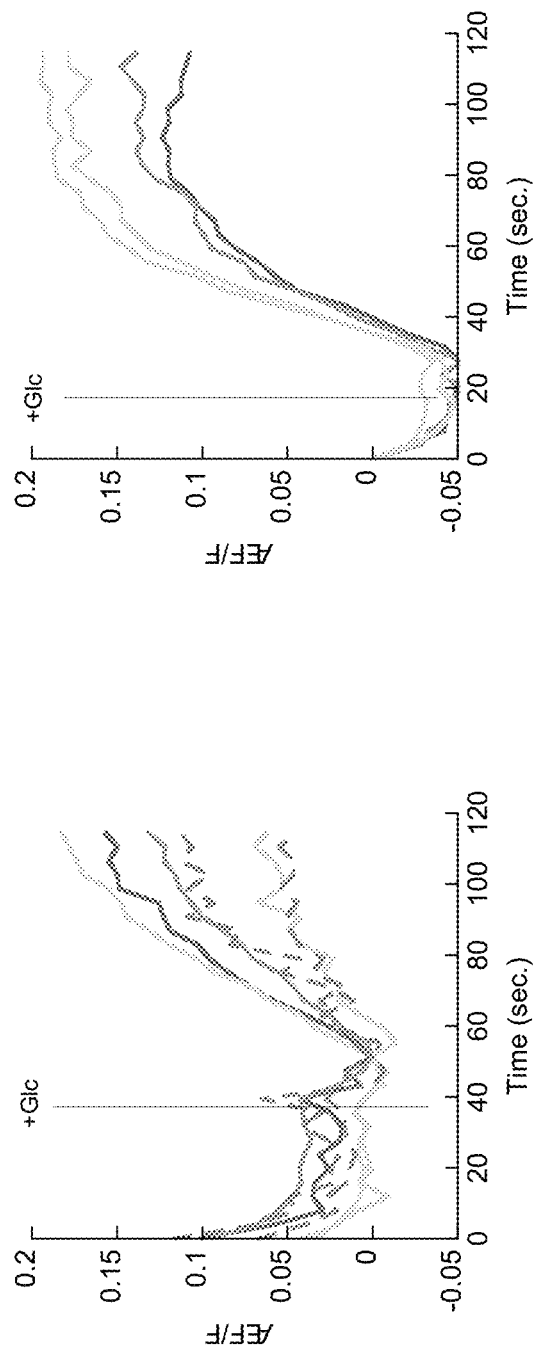
FIGS. 40A-40B|Are line graphs showing that the addition of extracellular glucose increases TtGBP326-cpGFP fluorescence in human cells.

As shown in FIG. 40, addition of 10 mM glucose to the media increases fluorescence.

Figure 50:
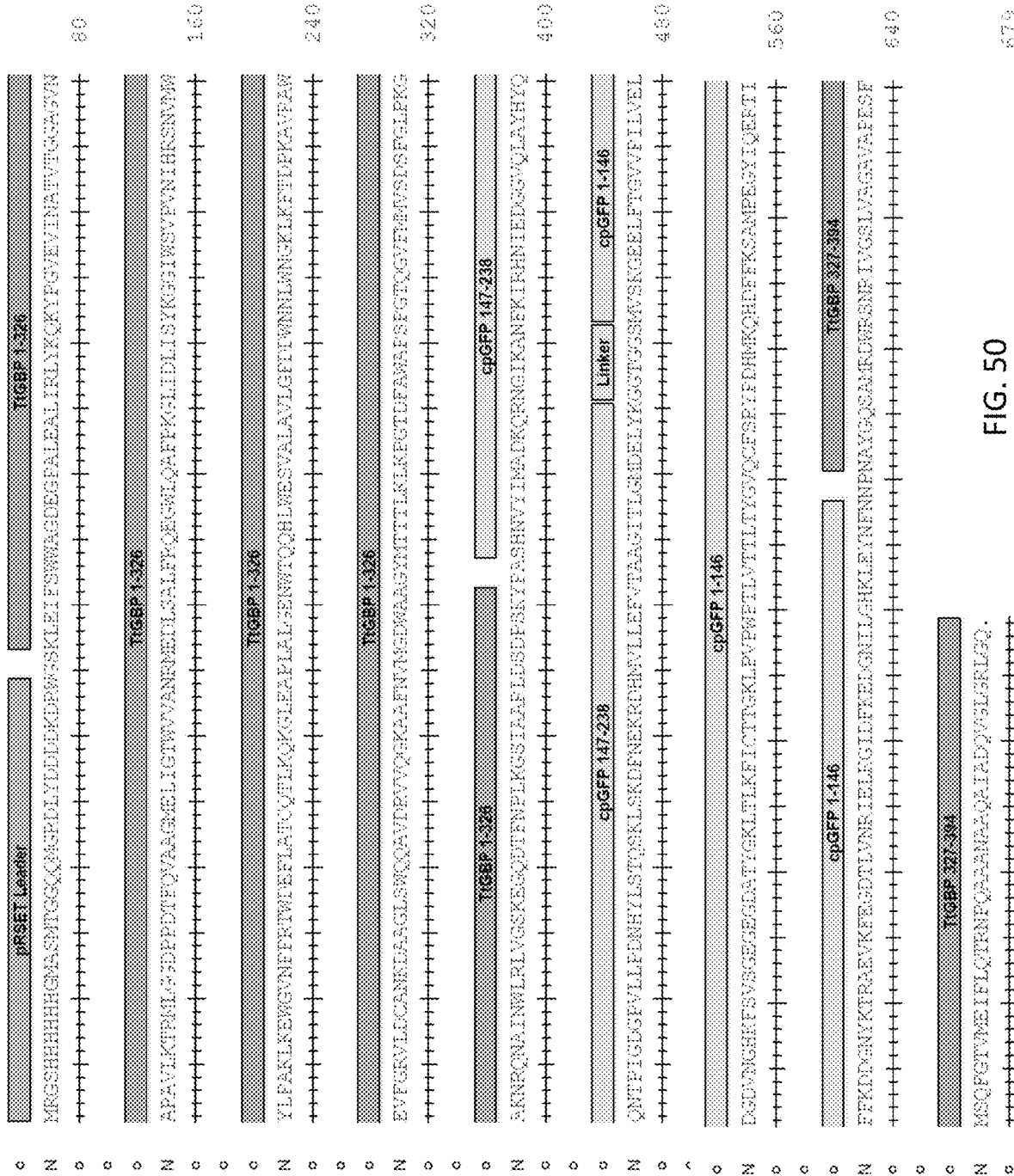
FIG. 50|Amino acid sequence of TtGBP326.L1PA.L2NP.H66A.H348A.L276V (SEQ ID NO:114).
Figure 51:
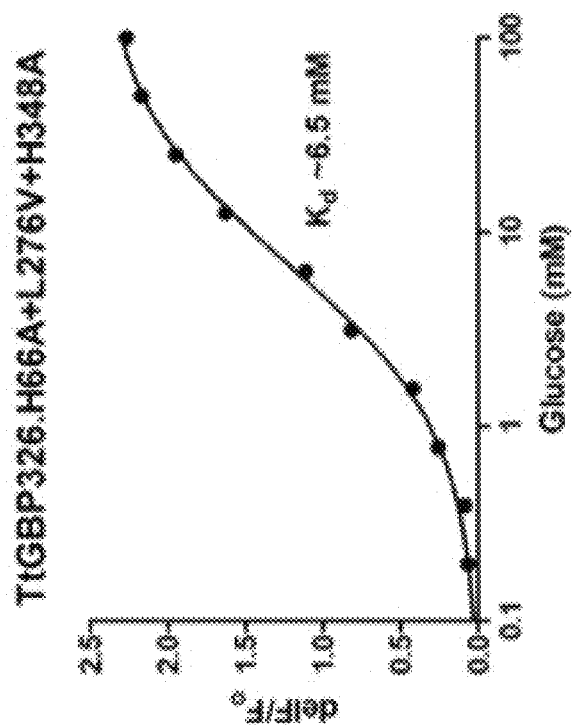
FIG. 51|A line graph showing binding of TtGBP326.L1PA.L2NP.H66A.H348A.L276V to glucose.

The TtGBP326-cpGFP.L1PAL2NP+H66A+H348A sensor was further modified by L276V mutation to produce TtGBP326.L1PA.L2NP.H66A.H348A.L276V (see FIG. 50). As shown in FIG. 51, this construct has an affinity for glucose of 6.5 mM.

Figure 52:
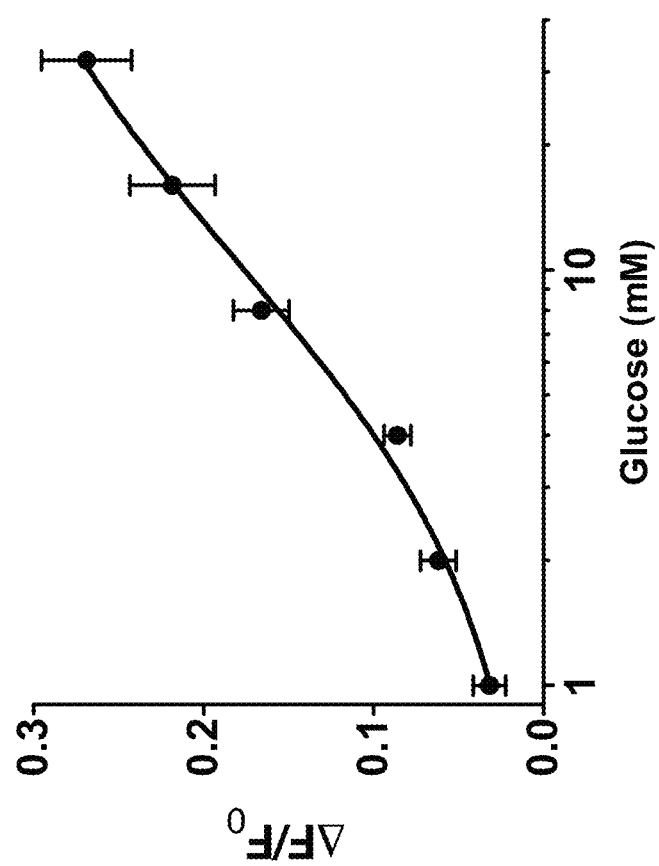
FIG. 52|A line graph showing fluorescence increase upon addition of glucose to HEK293 cells expressing TtGBP326.L1PA.H66A.H348A.L276V on their extracellular surface.

Additionally, the TtGBP326.L1P1.L2NP.G66A.H348A.L276V was cloned into the pMinDis derivative of the pDisplay vector and expressed on the extracellular surface of HEK293 cells. After exchanging the HEK293 cell media for PBS, addition of glucose to the PBS led to an increase in fluorescence (see FIG. 52).

These data indicate, in part, that the pRSET tag is not essential to the function of the sensor and that the TtGBP326-cpGFP.L1PAL2NP sensor is capable of detecting changes in the concentration of glucose inside or on the external surface of human cells.

Example 6: Stability, Affinity and Chromatic Variants of the Glutamate Sensor iGluSnFR

Example 6A: In Vivo Assessment of iGluSnFR Brightness in Apical Dendrites in Mouse Somatosensory Cortex Wildtype C57/B6 mice were purchased from the Jackson Laboratory and group housed in the Janelia animal facility. Mice were injected at 8 weeks of age with AAV2/1.hSynapsin1.iGluSnFR.A184S or SF-iGluSnFR.A184S, at identical titers ($1\times10^{13}$ genomic copies per milliliter, GC/ml), volumes (20 nl), and locations (3 mm lateral to midline, 1.4 mm caudal to bregma, and 0.3 mm below the cortical surface). After viral injection, a craniotomy (3 mm diameter) was made over the injection site, and the skull was replaced with a #1.5 Schott glass and fixed in place with dental acrylic (Lang Dental Manufacturing), which also secured a titanium head bar to the skull for head-mounting during imaging experiments.

In vivo two-photon imaging experiments were performed during a state of 'quite wakefulness', after having been habituated to head fixation the prior 2-3 days. Period water rewards were given to keep animals hydrated and passive. For comparisons of intensity and bleaching, a custom two-photon microscope emitting 960 nm light from a Coherent Chameleon ultrafast laser was used. All experiments were performed using a 25×, 1.5 NA Olympus objective immersed in water. Image acquisition was performed with ScanImage (Vidrio) software and analyzed post hoc using ImageJ (NIH). Images were acquired at a variety of speeds/zooms, and powers in order to assess the impact of pulse energy and dwell time on bleaching and intensity. Images at each setting were acquired for 5 seconds. To analyze the data, images were averaged and thresholded to create a signal (above threshold) and background mask. Signals in these masks were then averaged, and SNR was calculated from these as (signal-background)/(standard deviation of background). Bleaching percentage was calculated as the average intensity in the first 25% of the trace, divided by the last 25% of the trace.

Example 6B: Ferret Visual Cortex Assessment of SF-iGluSnFR.A184S and A184V

All procedures were approved by the Max Planck Florida Institute for Neuroscience Institutional Animal Care and Use Committee and adhered to the standards of the National Institutes of Health. Juvenile female ferrets (*Mustela putorius furo*, Marshall Farms) were used. Animals were housed in a vivarium under 16 hour light/8 hour dark cycle. The full methodological details for functional two-photon imaging of ferret visual cortex is previous described in detail (Wilson et al., 2016, Nat. Neurosci., 19:1003-9).

Briefly, juvenile female ferrets (*Mustela putorius furo*, Marshall Farms) aged P21-22 (n=2) were anesthetized with ketamine (50 mg/kg, IM) and isoflurane (1-3%) delivered in $O_2$, then intubated and artificially respirated. Atropine (0.2 mg/kg, SC) and a 1:1 mixture of lidocaine and bupivacaine administered subcutaneously in the scalp. Animals were kept at 37° C. A small craniotomy (0.8 mm) was made over the visual cortex 7-8 mm lateral and 2-3 mm anterior to lambda. AAV2/1.hSynapsin1.Cre (Penn Vector Core) was diluted in phosphate-buffered saline (Sigma) and mixed with AAV2/1.hSynapsin-FLEX.SF-iGluSnFR.A184S or A184V for expression in layer 2/3 cortical neurons. Beveled glass micropipettes were lowered into the brain and 400-500 nl of virus were injected over 5 minutes at multiple depths below the pia. Following, the craniotomy was filled with 1% w/v agarose.

After four weeks, ferrets were anesthetized with 50 mg/kg ketamine and 1-3% isoflurane. Atropine (0.2 mg/kg, SQ) and bupivacaine were administered. Animals were kept at 37 to 38° C., artificially respirated, and given intravenous fluids. Isoflurane (1-2%) was used throughout the surgical procedure to maintain a surgical plane of anesthesia. ECG, endtidal $CO_2$, external temperature, and internal temperature were continuously monitored. A custom titanium headplate was implanted on the skull at the viral injection site and the dura retracted to reveal the cortex. A custom insert with a single 4 mm coverglass (0.17 mm thickness) was placed onto the brain to gently compress the underlying cortex and dampen biological motion during imaging. The cranial window was hermetically sealed using a stainless steel retaining ring and Vetbond. Tropicamide Ophthalmic Solution and Phenylephrine Hydrochloride Ophthalmic Solution were applied and contact lenses were inserted into both eyes. Upon completion of the surgical procedure, Isoflurane was gradually reduced and pancuronium (2 mg/kg/hour) was delivered IV to immobilize the animal.

The animal was placed under the microscope 25 cm from the stimulus monitor, with the monitor subtending 130 degrees in azimuth and 74 degrees in elevation. Imaging was performed using a Bergamo II (Thorlabs) running ScanImage 5 or ScanImage 2015[19] (Vidrio Technologies) with dispersion compensated 950 nm excitation provided by an Insight DS+ (Spectraphysics). Average excitation power after the exit pupil of the objective (16×, CFI75, Nikon Instruments) ranged from 25 to 40 mW. Two-photon frame triggers from ScanImage were synchronized with stimulus information using Spike2 (CED). Visual stimuli were generated using PsychoPy (Peirce, 2007, J. Neurosci. Methods, 162:8-13). Full-field drifting square-wave gratings (16 directions, 100% contrast, 0.1 cycles/°, 4 cycles/sec., 3 sec. stimulus period followed by 2-3 sec. ISI, plus a blank) were presented to the contralateral eye in a pseudorandom sequence for 8 trials.

Images were corrected for in-plane motion using a correlation-based approach (MATLAB). ROI drawing was performed in ImageJ (Schindelin et al., 2012, Nat. Methods, 9:676-82). Fluorescence time-courses were computed as the mean of all pixels within the ROI at each time point and were extracted as described in Sage et al. (2012, ImageJ User developer Conference 1:1). Fluorescence time courses were then synchronized with stimulus information, and visually evoked responses were computed as changes in fluorescence relative to the baseline fluorescence. Peak $\Delta F/F$ responses for field ROIs and dendritic spines ROIs were computed using the Fourier analysis to calculate mean and modulation amplitudes for each stimulus presentation, which were summed together.

Example 6C: Mouse Neuronal Culture Analysis

Primary Hippocampal Neuron Cultures

Primary hippocampal neuron cultures were prepared from embryonic mice (E16) as described previously (Woitecki et al., 2016, J. Neurosci., 36:2561-70). Hippocampi were rinsed 3-5 times in Hank's Balanced Salt Solution (HBSS, Life technologies) and digested with trypsin (25 mg/ml, Life Technologies) for 20 min at 37° C. followed by DNase I (1 mg/ml; Roche). Subsequently, the tissue was dissociated using cannulas (three times 0.9 mm×40 mm; three times 0.45 mm×23 mm) and the solution was passed through a Nylon cell strainer (100 µm; BD Biosciences). The mesh was rinsed with 4-10 ml basal medium eagle (BME, Life technologies) supplemented with 0.5% glucose (Sigma-Aldrich), 10% fetal calf serum (FCS), 2% B-27, and 0.5 mM L-glutamine (all Life Technologies) to collect all cells. After counting, the cells were plated on cover slips in a 24-well cell culture plate at a density of 70,000 cells per 24-well and cultured in a humidified incubator at 37° C. and 5% $CO_2$.

Viral Vector Production

Recombinant AAV2/1 genomes were generated by large scale triple transfection of HEK293 cells as described previously (Marvin et al., 2013, Nat. Methods, 10:162-70). The adeno-associated virus (AAV) plasmid coding for SF-iGluSnFR.S72A or SF-iGluSnFR.A184V, helper plasmids encoding rep and cap genes (pRV1 and pH21), and adenoviral helper pFA6 (Stratagene) were transfected using the calcium phosphate transfection method. Cells were harvested ~72 h after transfection. To purify the virus, cell pellets were lysed in the presence of 0.5% sodium deoxycholate (Sigma) and 50 units/ml Benzonase endonuclease (Sigma). rAAV viral particles were purified from the cell lysate by HiTrap heparin HP column purification (GE Healthcare) and then concentrated using Amicon Ultra Centrifugal Filters (Millipore) until a final stock volume of 500 µl was reached.

Viral Transduction and Image Acquisition

Primary hippocampal neurons were transduced with AAV2/1.hSynapsin1.SF-iGluSnFR.S72A or with AAV2/1.hSynapsin1.SF-iGluSnFR.A184V on DIV4 and imaged on DIV13. A low amplitude field stimulation (1 msec, 20 mA, platinum bar electrodes) was applied to recruit a small fraction (~20%) of neurons. Images were acquired with an EM-CCD camera (frame time 5-50 msec) and a stabilized LED light source of cultures visualized through a coverslip with high NA objective. All experiments were performed in Tyrode's solution (1 ml/min) at RT. Low and high affinity versions of SF-iGluSnFR were expressed in a comparable manner.

Glutamate Release Site Localization

Primary hippocampal neurons were transduced with rAAV-SF-iGluSnFR.S72A or with rAAV-SF-iGluSnFR.A184V on DIV3-5 and used for experiments on DIV13-18. A low amplitude electrical field stimulation (1 msec., 20 mA, platinum bar electrodes) was applied to activate a small fraction (~20%) of neurons only. Per experiment, stimuli were applied 16-times at an inter-stimulus interval of 20-60 sec. Images were acquired with an EM-CCD camera (Hamamatsu ImagEM X1, 8 ms exposure, 125 Hz acquisition rate) attached to an inverted microscope (Nikon T1 Eclipse) using a triggered, stabilized LED light source (Cairn OptoLED with 470 nm excitation wavelength, 470/40 emission filter and 525/50 excitation filter). Cells were imaged through a coverslip with a high NA objective (Zeiss, 63×, 1.4 NA, water). All experiments were performed in saline (1 ml/min, as described above) at room temperature.

In each experiment, 30 images were acquired per stimulation trial (20 before and 10 after stimulation). Each of the 30 images was registered with StackReg Plugin in ImageJ to the first image. The image series was then normalized to the average of 5 frames before stimulation to distinguish responding sites (>1) and non-responding structures (~1). For selection of responding sites to be included in the analysis, 10 normalized images subsequent to the stimulus in the first trial were averaged. All spots of increased fluorescence (FIG. 64c,d) that reached at least 50% of the $\Delta F/F$ value of the brightest spot in the image were defined as responding sites and used for further analysis. The spatial extent of glutamate release sites was quantified by extracting a brightness profile based on a line (length: 12-30 pixels, width: 3 pixels) drawn along the underlying neurite. These profiles were calculated for each stimulation trial and each responding site in an experiment and fitted by Gaussians with Igor Pro 6.3 (Wavemetrics).

In each experiment (n=6 and 8 for S72A and A184V, respectively, each consisting of 16-25 trials) the mean deviation of the center ($X_0$ position), the average width and the average amplitude of the fitted Gaussians were calculated per response site and averaged across all experiments and statistically compared by an unpaired Mann-Whitney test, n=28 and 53 for S72A and A184V, respectively).

Example 6D: Cerebellar Parallel Fiber Analysis

Stereotaxic Injections.

To fluorescently label boutons of parallel fibers, stereotaxic injections of viral vectors expressing SF-iGluSnFR or GCaMP6f into cerebellar vermis were performed. The following vectors were used: AAV-DJ.hSynapsin.SF-iGluSnFR ($1.9 \times 10^{13}$ GC/ml), AAV2/1.hSynapsin.SF-iGluSnFR.S72A ($2.6 \times 10^{13}$ GC/ml), AAV-DJ.CAGFLEX.SF-iGluSnFR.S72A ($6.3 \times 10^{12}$ GC/ml) or AAV-DJ.hSynapsin.GCaMP6f ($1.2 \times 10^{13}$ GC/ml). Mice between 30 and 60 days old were deeply anesthetized before surgery with a mixture of hypnotic (ketamine 1.5%, Mérial) and analgesic (xylazine 0.05%, Bayer) anesthetics mixed in NaCl and injected in the peritoneum. A local anesthetic (xylocaine 2% gel, Newpharma) was applied on top of the location of the cranial incision. The anesthetized mouse was then placed on a stereotaxic frame adaptor comprising adjustable ear bars and tooth holder. The skull was then perforated at the injection site with a surgical drill. The vermis was identified using the Paxinos and Franklin mouse brain atlas. The injection of viral constructs in the vermis (100 nl; 6.5 mm caudal to bregma, lateral 0.2 mm, ventral 3.6 mm and 3.4 mm) was performed by slow infusion (100 nl/min) with steel needles (26 G×50 mm and 36 G×70 mm, Phymep) connected to a pump via a catheter and a Hamilton syringe. Injected mice were then kept 2 to 4 weeks to allow transgene expression.

Slice Preparation

All protocols were approved by the ethics committee CEEA-Paris1. Cerebellar acute slices were prepared from adult CB6F1 mice (F1 cross of BalbC and C57Bl/6J) or Gabra6 mice (B6; 129P2-Gabra6$^{tm2(cre)Wwis}$/Mmucd) of postnatal day 41 to 123. The mice were killed by rapid decapitation, after which the brains were quickly removed and placed in an ice-cold solution containing (in mM): 2.5 KCl, 0.5 $CaCl_2$, 4 $MgCl_2$, 1.25 $NaH_2PO_4$, 24 $NaHCO_3$, 25 glucose, 230 sucrose, and 0.5 ascorbic acid bubbled with 95% O2 and 5% CO$_2$. Coronal slices were cut from the dissected cerebellar vermis using a vibratome (Leica VT1200S). After preparation, the slices were incubated at 32° C. for 30 minutes in the following solution (in mM): 85 NaCl, 2.5 KCl, 0.5 CaCl$_2$, 4 MgCl$_2$, 1.25 NaH$_2$PO$_4$, 24 NaHCO$_3$, 25 glucose, 75 sucrose and 0.5 ascorbic acid. Slices were then transferred to an external recording solution containing (in mM): 125 NaCl, 2.5 KCl, 1.5 CaCl$_2$, 1.5 MgCl$_2$, 1.25 NaH$_2$PO$_4$, 25 NaHCO$_3$, glucose and 0.5 ascorbic acid, and maintained at room temperature for up to 6 hours. All slice recordings were performed at 36-38° C.

Transmitted Light and Fluorescence Imaging

Parallel fiber and boutons expressing SF-iGluSnFR or GCaMP6f were identified using an Ultima two-photon scanning scanhead (Bruker Nano Surfaces Division, Middleton, WI, USA) that was mounted on an Olympus BX61W1 microscope, equipped with a water-immersion objective (60×, 1.1 NA, Olympus Optical, Tokyo, Japan) and infrared Dodt-gradient contrast. Two-photon excitation was performed with a pulsed Ti:Sapphire laser (DeepSee, Spectra-Physics, France) tuned to 920 nm for imaging morphology, glutamate and Ca$^{2+}$ fluorescence detection.

Boutons from parallel fibers were identified by increase fluorescence as response to 100 or 300 Hz trains. The probe response was evoked with 60 µs voltage pulses 5-15 V above threshold (Digitimer Ltd, Letchworth Garden City, UK) using a patch pipette (typically with a tip resistance of 4-6 MΩ) filled with ACSF and placed in the molecular layer adjacent to labelled parallel fibers. Activation of boutons was routinely confirmed by verifying increase in fluorescence in response to 100 or 300 Hz trains of stimulation. Line-scan imaging through boutons was performed at dwell time of 0.8 µsec per pixel, for 300 to 800 msec. Individual traces were background subtracted and averaged with no smoothing or filtration for single events for SF-iGluSnFR, or background subtracted and averaged with smoothing for GCaMP6f, 20 Hz and 100 Hz trains. SNR was calculated from the peak of the fit to the fluorescent events divided by the average SD of a 20 msec baseline window. Data were analyzed and presented using custom-written macros in Igor Pro.

Example 6E: Fast Imaging of SF-Venus-iGluSnFR

Primary Rat Hippocampal Neuron Cultures

A mixed cell culture (neurons and glia) was prepared from Sprague-Dawley rat pups (Charles River Laboratories). Briefly, P0 pups were decapitated, and the brains were dissected into ice-cold neural dissection solution (NDS, 10 mM HEPES (Sigma) in HBSS (Invitrogen), pH 7.4). Hippocampi were dissected and cut into small pieces to facilitate enzyme digestion. Hippocampi pieces were transferred using a large bore pipette into a 15 ml conical tube and incubated with enzyme digest solution (Papain, Worthington Biologicals) at 37° C. for 30 min. After 30 min., the enzyme solution was removed, and Plating Media (MEM media containing 10% FBS) was added and tissue pieces were triturated resulting in mostly single cells. The cell suspension was filtered using a 45 um filter. The filtered cell suspension was centrifuged, and the resulting cell pellet was re-suspended with Plating Media and counted.

For electroporation, 1 µg of DNA was mixed with 1×10$^6$ cells using the Amaxa Nucleofector II instrument. Cells were plated onto coverslips coated with Poly-D-Lysine (Sigma) and kept at 37° C., 5% CO$_2$ in PM for ~24 hours and then in NbActiv4 (BrainBits) was added for the duration with medium exchanges every 4 days.

Glutamate Uncaging and Imaging

Rat hippocampal culture was imaged on DIV19 at room temperature in HEPES buffered Tyrode's solution (145 mM NaCl, 2.5 mM KCl, 10 mM glucose, 10 mM HEPES, 2 mM CaCl$_2$, 1 mM MgCl$_2$, pH 7.4).

Excitation was with a 1030 nm, 5 MHz, 190 fsec laser (Menlo Systems, model: Bluecut). Average power was 39 mW at the sample. Fluorescence collected at 560/80 nm with a Hamamatsu MPPC detector. The field of view is a 256 um diameter circle, 1280 pixels across. The bath contained HEPES buffered Tyrode's solution plus 10 µM NBQX and 150 µM RuBi-Glutamate (Tocris). Glutamate uncaging was performed with 420 nm fiber-coupled LEDs (Thorlabs M420F2). The tips of the fibers were imaged onto the sample plane through the same objective used for activity imaging.

Example 6F: Summary of Results

The intensity-based glutamate-sensing fluorescent reporter (iGluSnFR) (Marvin et al., 2013, Nat. Methods, 10:162-70) has become an invaluable tool for studying glutamate dynamics in diverse systems, including retina (Park et al., 2014, J. Neurosci., 34:3976-81; Borghuis et al., 2013, J. Neurosci., 33:10972-85), mouse olfactory bulb (Brunert et al., 2016, J. Neurosci., 36:6820-35) and cat visual cortex (O'Herron et al., 2016, Nature, 534:378-82). Beyond specific circuits, iGluSnFR also allows mesoscale "functional connectomic" mapping (Xie et al., 2016, J. Neurosci., 36:1261-72) and mechanistic studies of Huntington's disease (Jiang et al., 2016, J. Neurosci., 36:3453-70), synaptic spillover (Rosa et al., 2015, eLife, 4:728), cortical spreading depression (Enger et al., 2015, Cerebral Cortex, 25:4469-76) and exocytotic vesicle fusion (Bao et al., 2016, Nat. Struct. Biol., 23:67-73). However, iGluSnFR is insufficient for some applications due to poor expression (in some brain regions), and kinetics that do not match the time courses of some observations. Here, we describe variants that are functionally brighter (due to increased expression on cell membrane), have tighter or weaker affinity (resulting from slower or faster off-rates), and fluoresce blue, green, or yellow.

Figure 57:
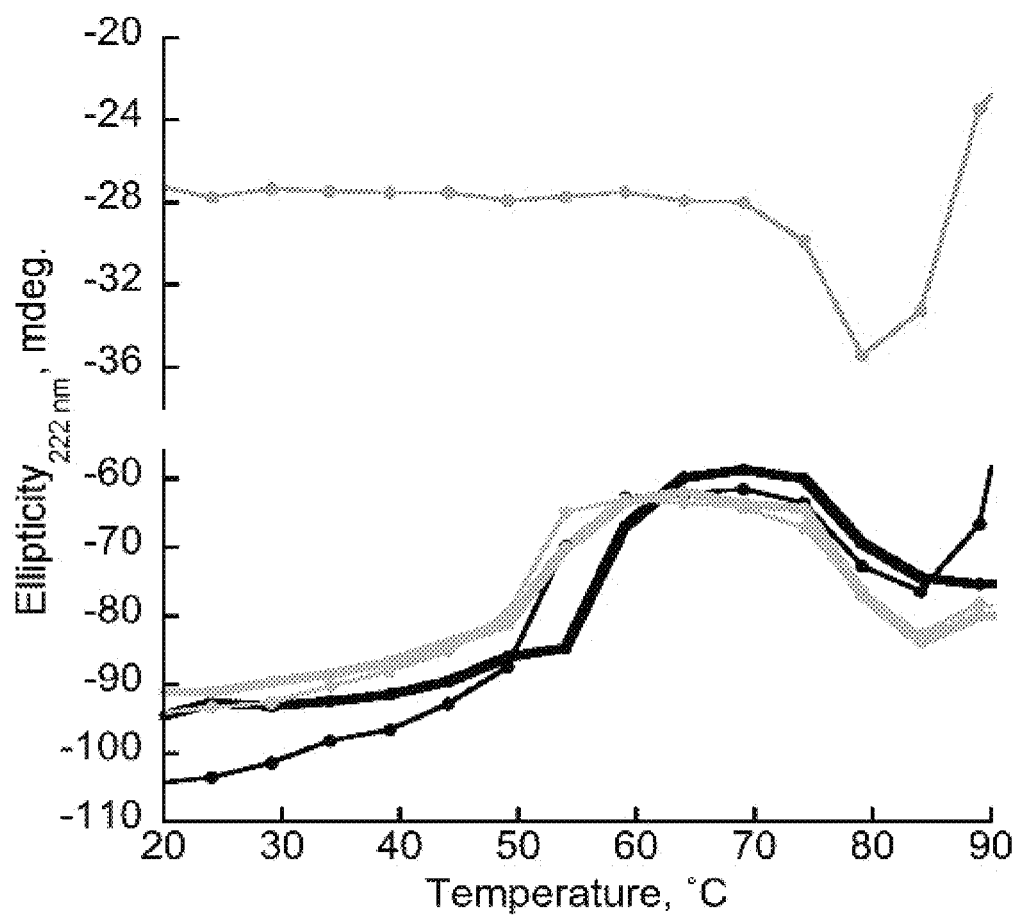
FIG. 57|Circular dichroism of iGluSnFR and SF-iGluSnFR. 20 μM purified and dialyzed protein in 0.1×PBS was analyzed by circular dichroism (Chirascan, Applied Biophysics). Grey, iGluSnFR; black, SF-iGluSnFR; green, cpSFGFP; thick line, with 1 mM glutamate; thin line, no glutamate. Spectra were collected with a 1 sec. sampling time after equilibration for 2 min at each temperature. The first unfolding transition is shifted from about 50° C. to 55° C. by inclusion of the Superfolder mutations to cpGFP. Interestingly, the second transition, at about 75° C., which parallels the transition of cpSFGFP alone, is unchanged.
Figure 58A:
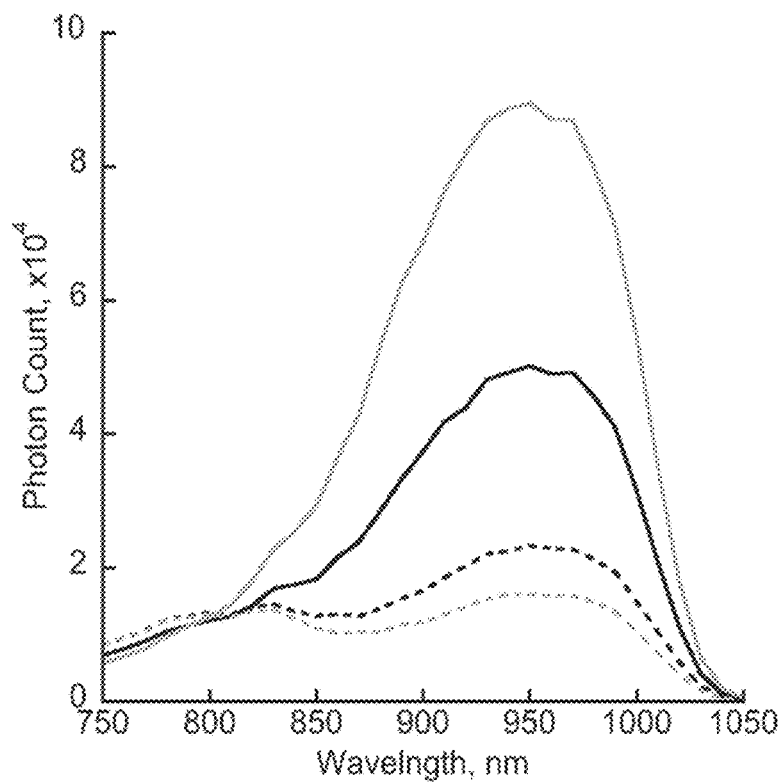
FIG. 58A-D|Spectra of SF-iGluSnFR.
Figure 58B:
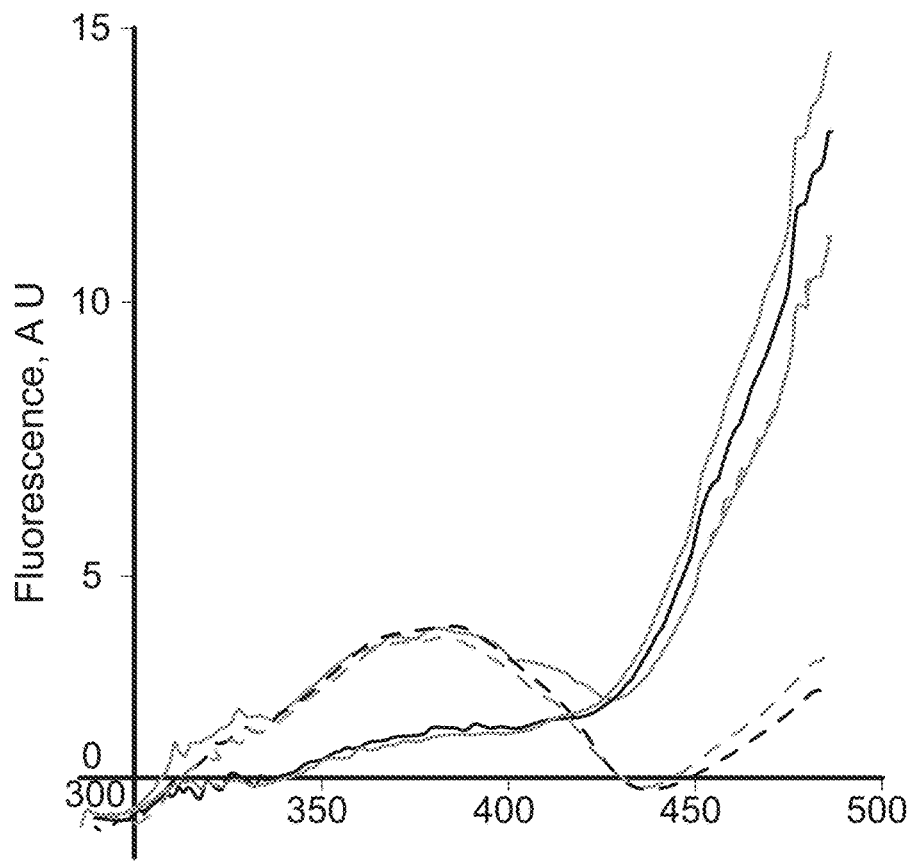
Figure 58C:
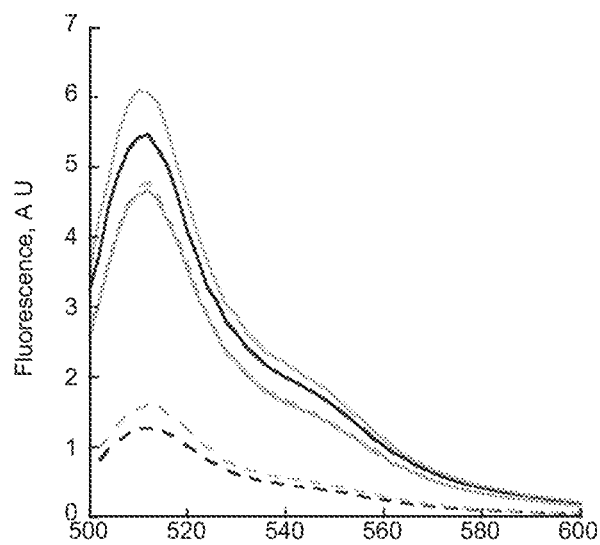
Figure 58D:
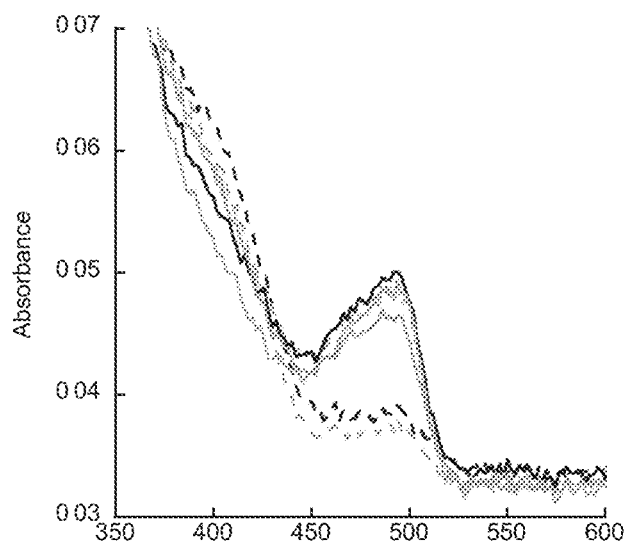
Figure 59E:
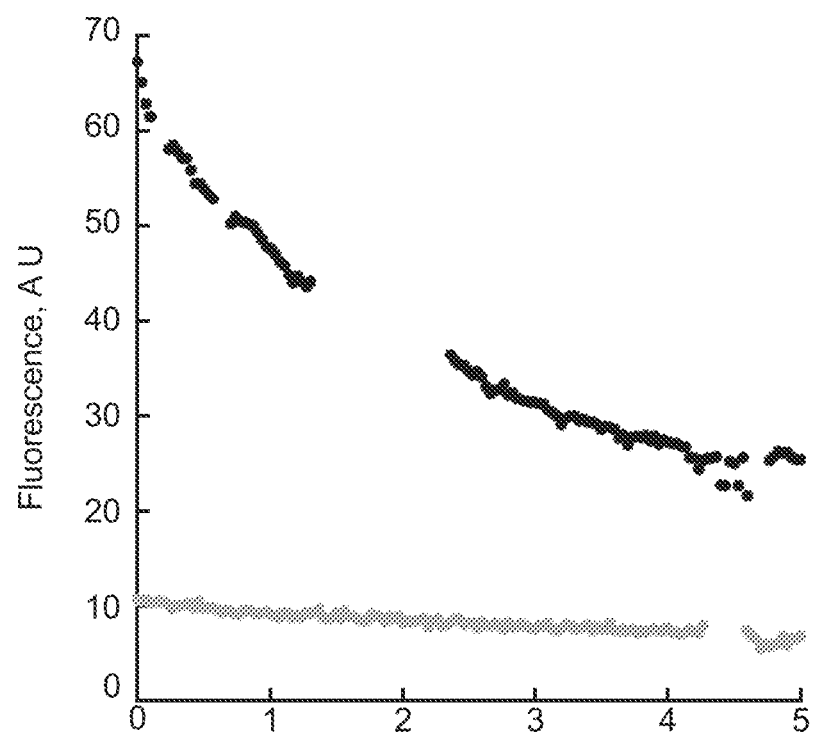

Replacement of circularly permuted eGFP with circularly permuted "superfolder" GFP (Pedelacq et al., 2006, Nat. Biotech., 24:79-88) (SF-iGluSnFR) yielded 5-fold higher soluble-protein expression levels in bacteria (0.5 µmol/1 L growth vs. 0.1 µmol/1 L). Circular dichroism indicates an increase in melting temperature transition ($T_m$) of ~5° C. (FIG. 57). The 2-photon cross-section and excitation, emission, and absorption spectra of SF-iGluSnFR are similar to the original (FIG. 58a-d). Head-to-head comparison of SF-iGluSnFR with original iGluSnFR in mouse somatosensory cortex shows substantially more robust expression by the former (FIG. 59a,b). Under typical imaging conditions (<20 mW, 130-nanosecond dwell time per pixel), SF-iGluSnFR is bright enough for repeated imaging, while original iGluSnFR is too dim (FIG. 59c,d). While a faster 2-photon in vivo photobleaching rate was observed for SF-iGluSnFR in somatosensory cortex (FIG. 59e), partially-bleached SF-iGluSnFR was still brighter than iGluSnFR. Thus, SF-iGluSnFR will have superior expression in vivo, where the quantity of deliverable DNA can be limiting.

Figure 61:
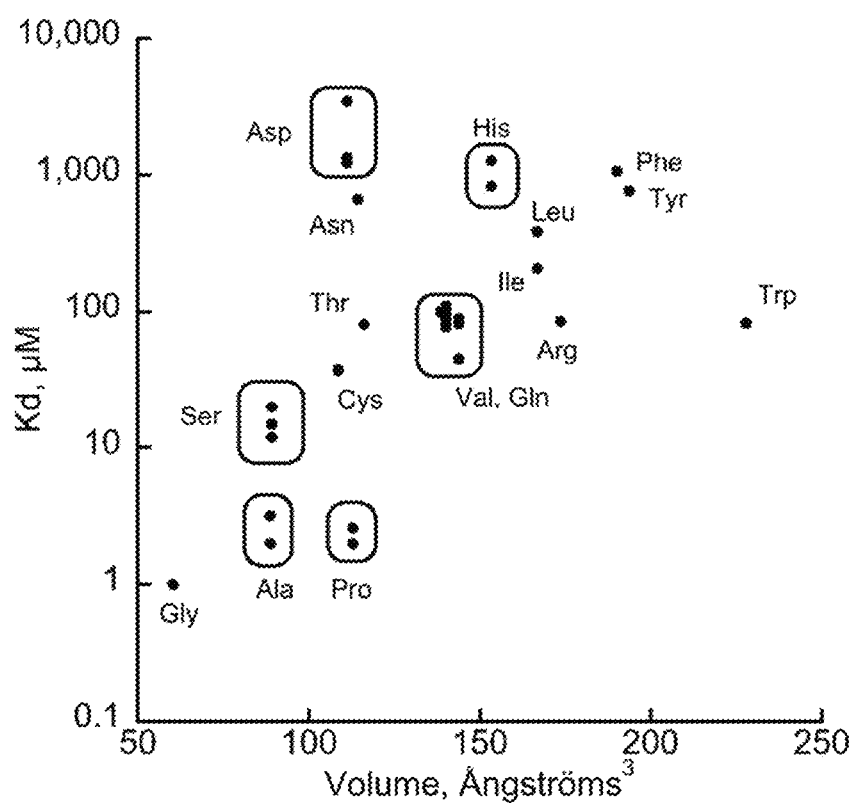
FIG. 61|Binding affinity screening. Pellets of bacterially expressed A184X variants of iGluSnFR were washed 5 times in PBS to remove bound glutamate. After freezing and thawing, pellets were clarified by centrifugation and titrated with glutamate to screen for their affinity for glutamate. There is a general trend of larger amino acids resulting in weaker affinity.

While the affinity of membrane-displayed iGluSnFR (4 µM) is adequate for some in vivo applications, tighter variants are needed for circumstances of limiting glutamate concentrations, such as at sparsely-firing synapses. Additionally, measuring glutamate release events with raster scanning microscopes requires variants with slower off-rates so that the decay time from glutamate binding is long enough to be sufficiently sampled at the operating frame rate for most experiments (typically <100 Hz). Replacement of eGFP with superfolder GFP increases the in vitro affinity of soluble SF-iGluSnFR two-fold compared to original iGluSnFR (40 µM vs. 80 FIG. 60a). To further modulate affinity, the conformational coupling between the open-closed equilibrium of bacterial periplasmic binding proteins (PBPs, e.g. the glutamate-binding protein in iGluSnFR) and their ligand-binding affinity (Marvin et al., 2001, Nat. Struct. Biol., 8:795-8) was exploited. Briefly, mutation of residues in the "hinge" of PBPs can allosterically alter affinity, without compromising the stereochemical integrity of the ligand-binding site. In a bacterial lysate assay, an A184X library of the iGluSnFR glutamate-binding domain (mutated to valine in the original iGluSnFR) was screened. Reversion to alanine or other small amino acids tightened affinity, while larger side chains weakened affinity (FIG. 61).

A184S was introduced into SF-iGluSnFR to generate a tighter variant. (Reversion A184A had a low ΔF/F.) Affinities of purified soluble protein were 7 µM and 40 µM for the A184S and A184V (unmutated from iGluSnFR) SF-iGluSnFR variants, respectively (FIG. 60a). The tighter affinity of the A184S variant arises from a slower off-rate (FIG. 60b). The affinity variants were re-cloned into an AAV vector containing an IgG secretion signal and a PDGFR transmembrane domain. Viral expression on cultured rat hippocampal neurons (AAV2/1.hSynapsin1.SF-iGluSnFR) yields glutamate affinities about an order of magnitude tighter than the soluble form (0.7 µM and 2 µM for A184S and A184V, respectively; FIG. 62). A similar increase in affinity upon membrane tethering was seen with the original sensor (Marvin et al., 2013, Nat. Methods, 10:162-70). Whole-field stimulation (50 Hz) of these cultures shows that their relative half-times of fluorescence decay parallel their in vitro kinetics, with all variants having faster decay than GCaMP6f (FIG. 63).

Figure 64:
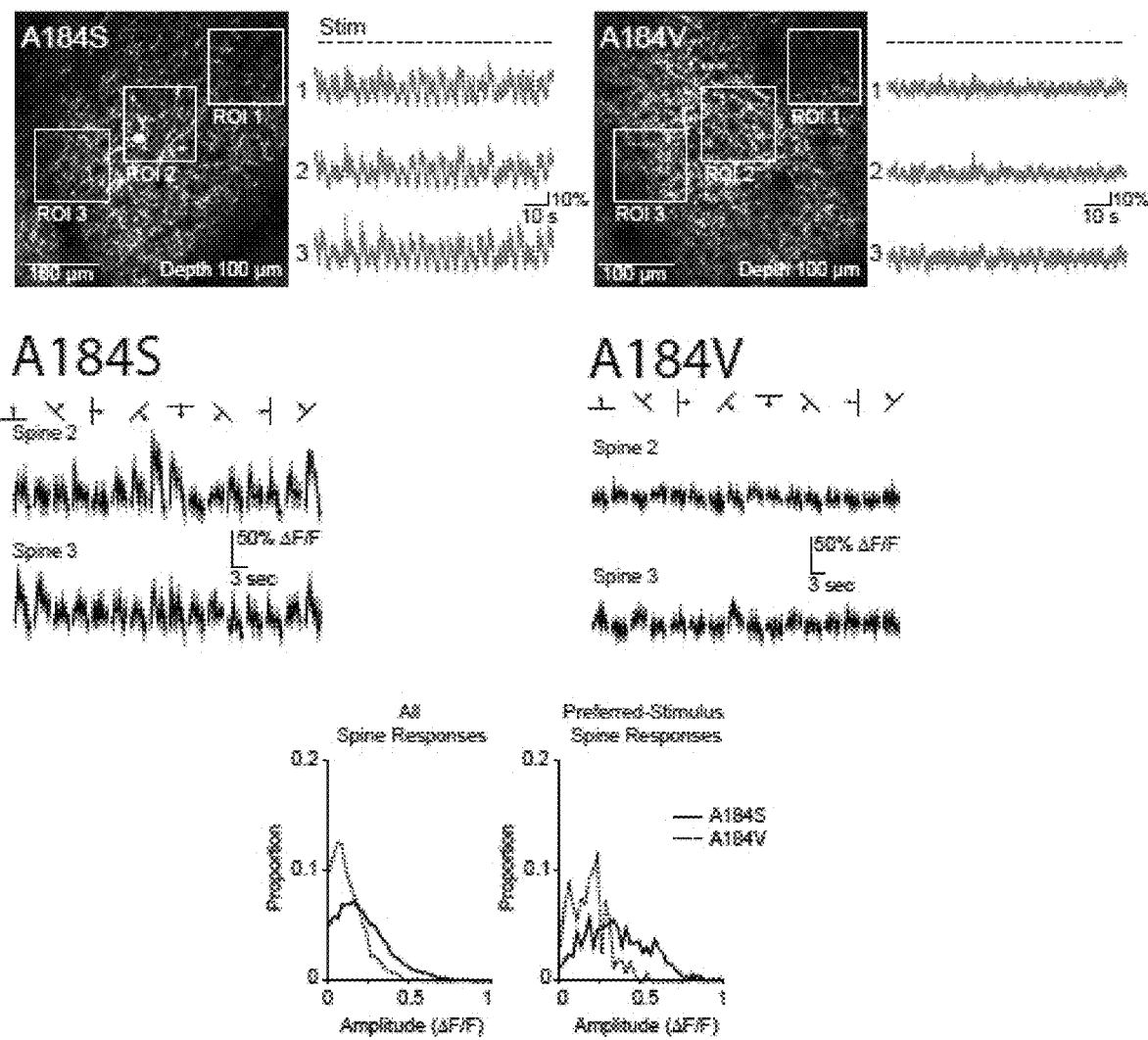
FIG. 64|Examples of individual responses for ROIs 1, 2, and 3 (top). Responses of individual Spines #2 and #3 (from FIG. 53) (middle). Histogram showing distribution of spine responses (bottom). Response amplitudes across individual trials were consistently greater for A184S than the A184V when examining all stimulus-evoked responses.
Figure 65A:
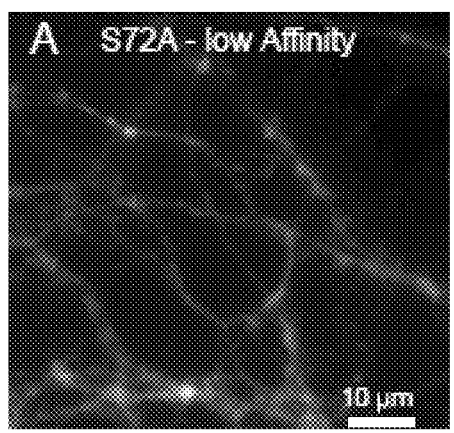
FIG. 65A-D|Mouse neuronal culture images. The fluorescent labeling pattern and intensity of primary hippocampal neurons transduced with AAV2/1.hSynapsin1. SF-iGluSnFR.S72A or with AAV2/1.hSynapsin1-SF-iGluSnFR.A184V at DIV4 and imaged at DIV13 looked qualitatively similar for both variants and as expected for a membrane targeted protein. To resolve fast stimulus associated changes in fluorescence, a time series of 100 frames at 60 Hz during a paired-pulse stimulation paradigm was acquired. Basal fluorescence before stimulation was clearly stronger for A184V, the high affinity sensor, leading to a higher SNR (FIG. 65A and FIG. 65C). However, when dividing each frame by an average of the pre-stimulus images for both variants of SF-iGluSnFR localized spots where fluorescence increases was observed (FIG. 65B, FIG. 65D, arrows), likely representing synaptic release sites. ROIs were defined based on these spots, and fluorescence within these ROIs (background subtracted) was averaged for every image in the time series.
Figure 65B:
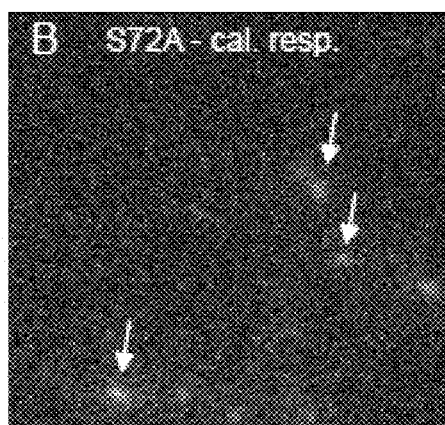
Figure 65C:
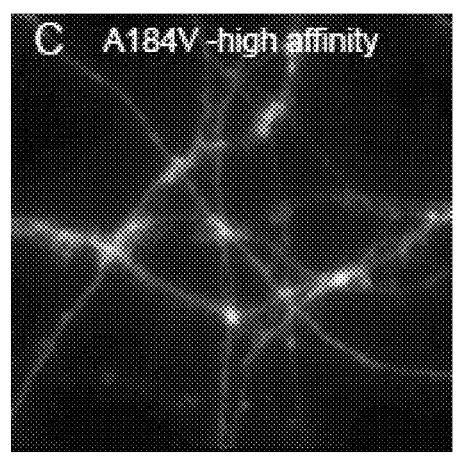
Figure 65D:
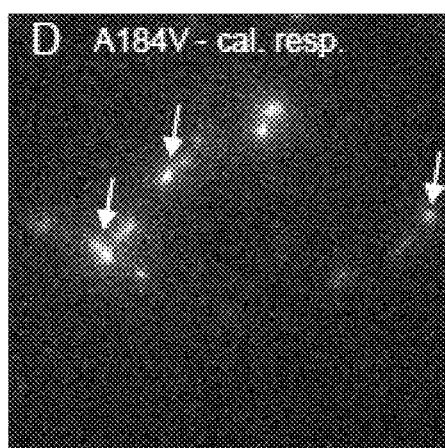
Figure 66A:
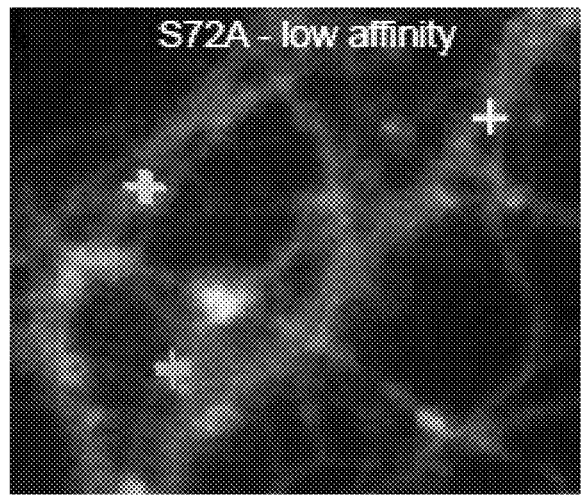
Figure 66B:
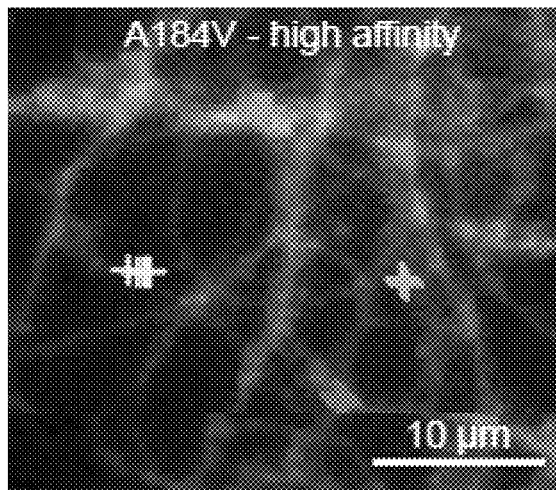
Figure 66C:
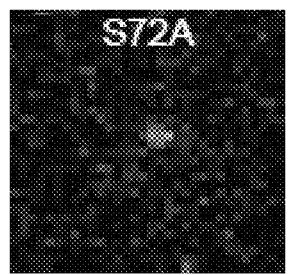
Figure 66D:
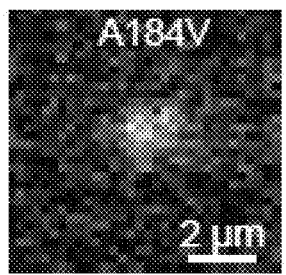
Figure 66E:
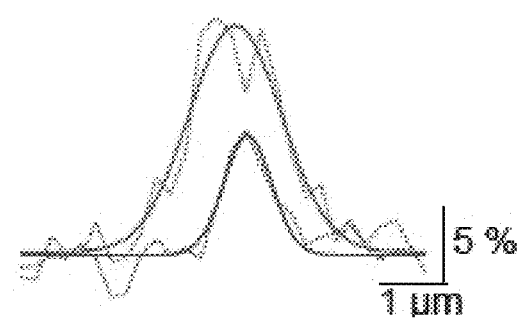
Figure 68A:
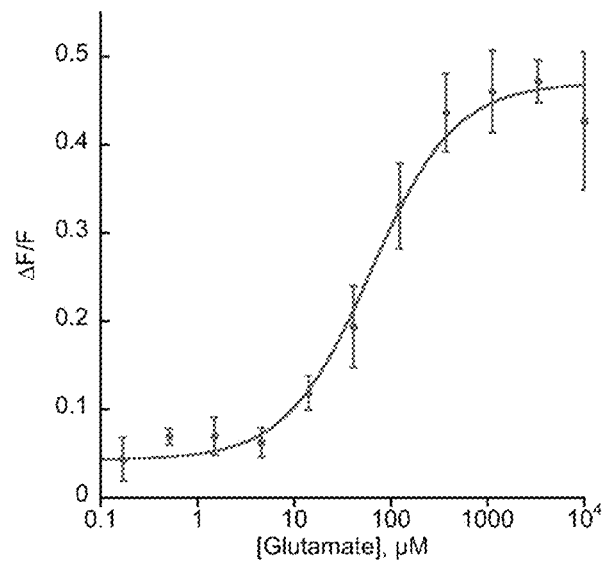
FIG. 68A-D|Characterization of soluble, purified SF-Azurite-iGluSnFR.
Figure 68B:
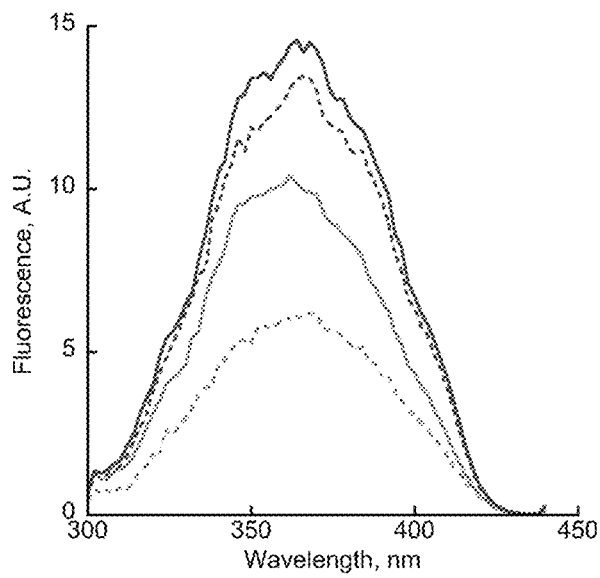
Figure 68C:
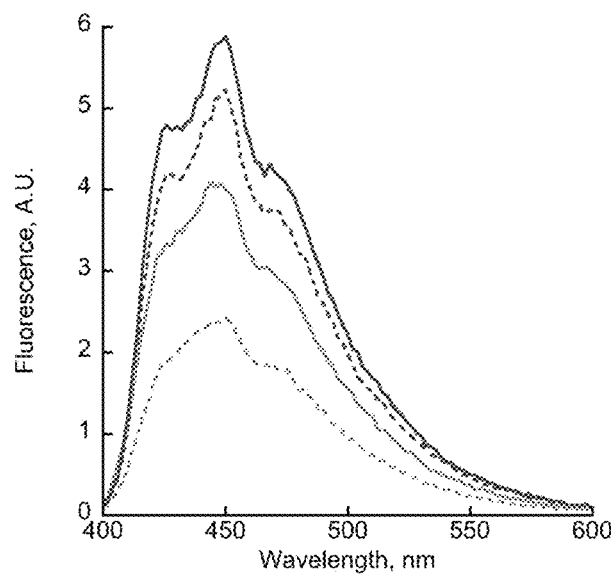
Figure 68D:
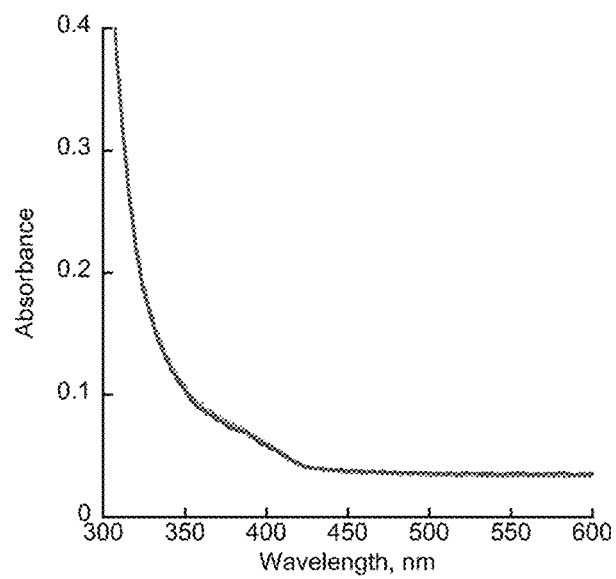
Figure 69A:
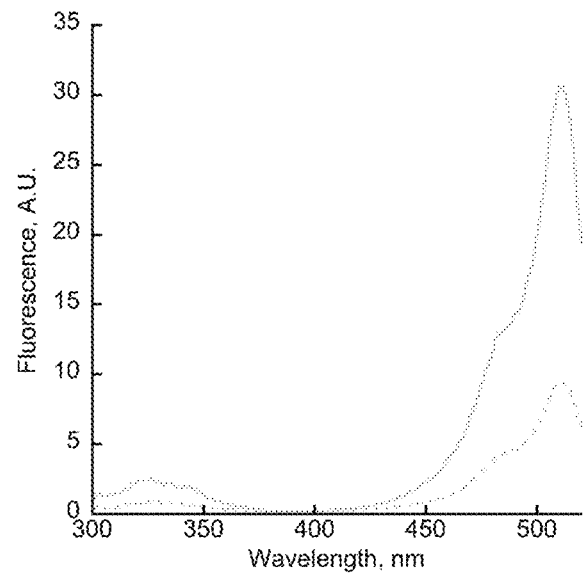
FIG. 69A-D|Spectra of SF-Venus-iGluSnFR. Excitation (FIG. 69A), emission (FIG. 69B), and absorbance (FIG. 69C) spectra of SF-Venus-iGluSnFR (yellow) with (solid line) and without (dashed line) glutamate.
Figure 69B:
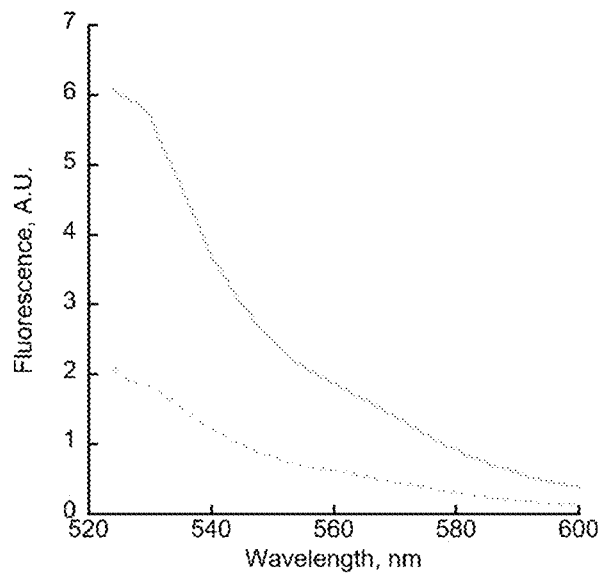
Figure 69C:
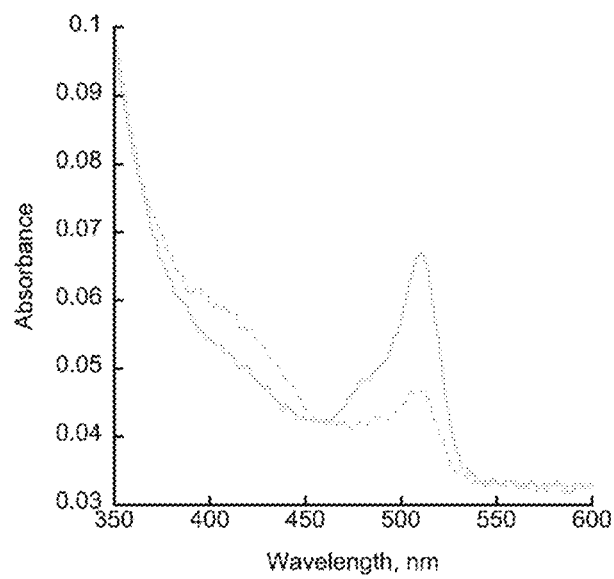
Figure 69D:
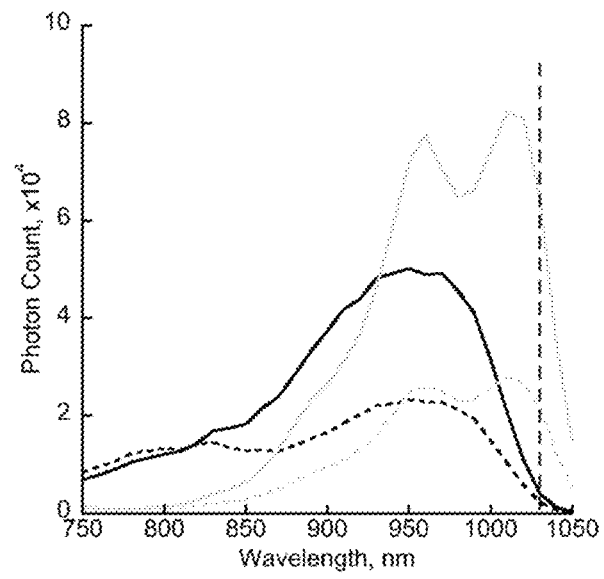

In vivo, the tighter/slower SF-iGluSnFR.A184S variant shows improved detection of stimulus-evoked glutamate release in the ferret visual cortex in response to presented drifting gratings (FIG. 53a,b). Peak amplitudes reached 30% ΔF/F for SF-iGluSnFR.A184S but only 5% ΔF/F for SF-iGluSnFR.A184V when imaged at 30 Hz. Greater ΔF/F of SF-iGluSnFR.A184S allows extraction of robust orientation tuning curves compared to SF-iGluSnFR.A184V. Enhanced sensitivity of the A184S variant also allowed orientation-selective responses to be resolved in individual dendritic spines (FIG. 53c,d). Synaptic glutamate release as measured with SF-iGluSnFR.A184S was not only strongly selective for visual stimuli, but response amplitudes across individual trials were consistently greater than the A184V variant when examining all stimulus-evoked responses (A184S median ΔF/F=16%, n=72 spines; A184V median ΔF/F=9%, n=22 spines; p=2e-115, Wilcoxon rank-sum test) or only preferred stimuli (A184S median ΔF/F=27%, n=72 spines; A184V median ΔF/F=14%, n=22 spines; p=9e-23, Wilcoxon rank-sum test) (FIG. 64).

While slow off-rate variants of SF-iGluSnFR are better for detecting individual synaptic events by temporal summation of fluorescence, faster off-rate variants are needed for temporal resolution spiking dynamics and at large synapses where glutamate clearance is limiting. A weaker variant of SF-iGluSnFR (S72A) was made by removing a hydrogen bond between the protein and glutamate. Soluble SF-iGluSnFR.S72A has 200 µM affinity for glutamate (FIG. 60a), arising from a combination of both slower on-rate and faster off-rate (FIG. 60b). In neuronal culture, S72A has an affinity of 35 µM, an order of magnitude weaker than its parent, A184V (FIG. 62).

Figure 54C:
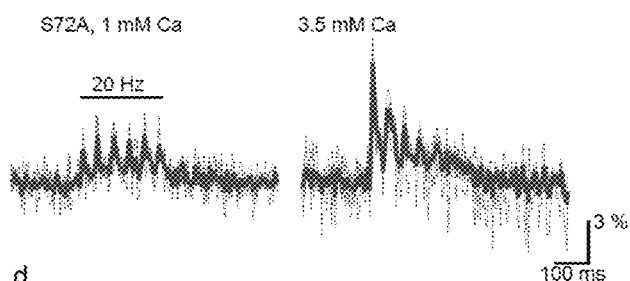
Figure 54D:
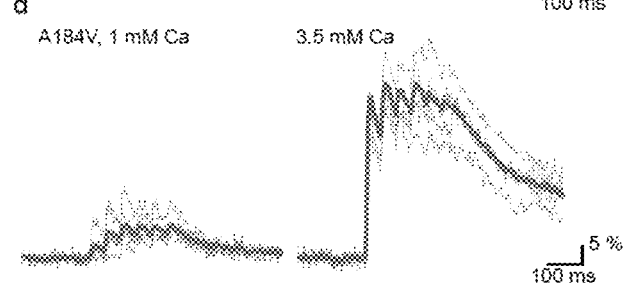

In rat neuronal culture, without buffer perfusion, fluorescence of the culture (not localized to specific structures) returns to baseline within 100 msec. of a single electrical stimulation for S72A, faster than A184V, A184S, or GCaMP6f (FIG. 63). In mouse neuronal culture (FIG. 65), the substantially faster off-rate of S72A provides enhanced temporal resolution of paired (20 Hz) electrical stimuli over the A184V variant (FIG. 54a,b), making it useful for assessing short-term synaptic plasticity. A train of 6 electrical pulses (20 Hz) in 1 mM extracellular $Ca^{2+}$ can be resolved as equal, individual release events by observation with S72A, while A184V yields an integrated signal (FIG. 54c,d). In 3.5 mM extracellular $Ca^{2+}$, vesicles are released with higher probability during the initial stimulation (Dodge et al., 1967, J. Physiol., 193:419-32). This can be observed by S72A, as reported by a reduction in fluorescence response as the train of field pulses progresses (FIG. 54c), while these differences are obscured by the slower decay of A184V (FIG. 54d). Thus, while S72A has a lower ΔF/F in response to the same amount of glutamate being released (due to weaker affinity), its faster kinetics provides enhanced temporal resolution of synaptic activity. Similarly, S72A provides enhanced spatial resolution of glutamate release over A184V (FIG. 66).

Figure 55A:
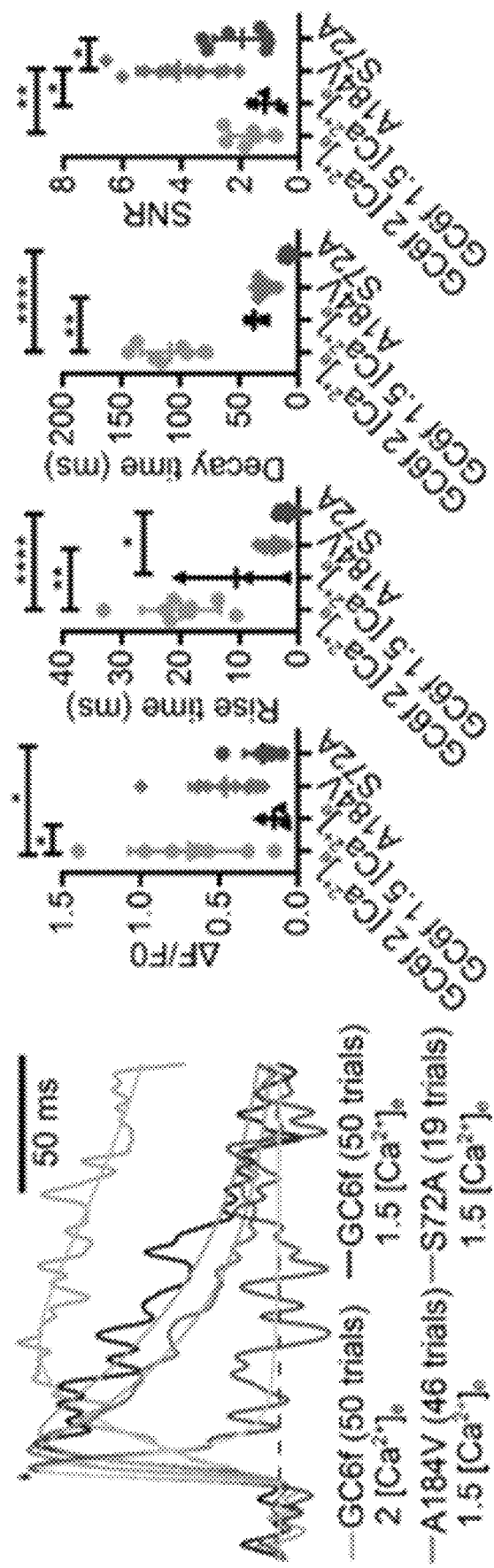
FIG. 55A-D|S72A variant shows faster bouton fluorescence signals resulting from single or trains of electrical stimulation mouse cerebellar brain slice.
Figure 55C:
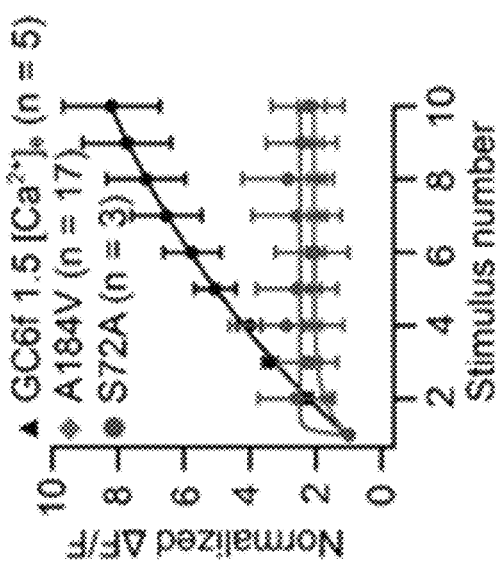
Figure 55D:
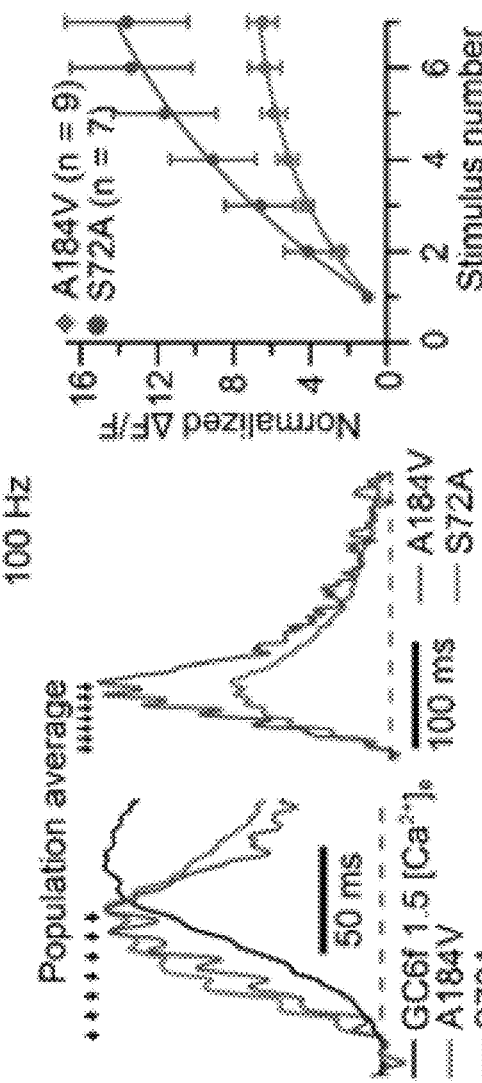
Figure 55B:
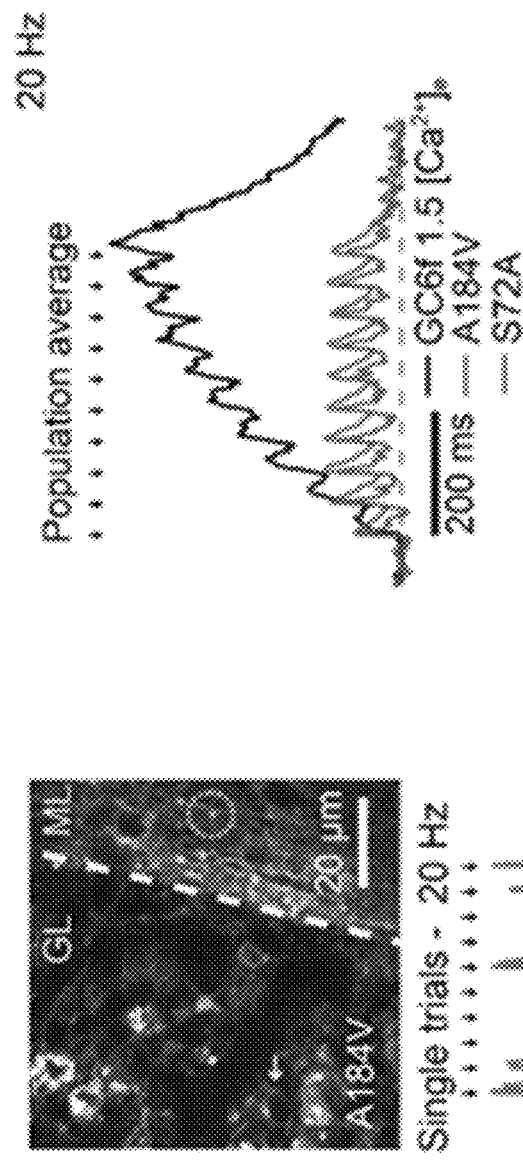

With fast rise and decay times, it was examined whether SF-iGluSnFR could be used as an alternative to GCaMP6f for monitoring neuronal activity in mouse cerebellar brain slice. Single cerebellar granule cell bouton responses to single action potentials (APs) could indeed be resolved using fast linescan detection (<1 ms per line; FIG. 55a), and were much faster than GCaMP6f rise and decay times at both 2 mM and 1.5 mM extracellular calcium. The S72A variant had by far the fastest response (S72 half decay 7.9±1.0 ms, A184V 28.1±1.6 ms, GCaMP6f 1.5 mM $[Ca^{2+}]_e$ 37.9±3.9 ms, GCaMP6f 1.5 mM $[Ca^{2+}]_e$ 108.6±8.8 ms). The signal-to-noise-ratios (SNRs) were best for A184V, but even S72A produced better SNRs than GCaMP6f under physiological extracellular calcium concentrations (1.5 mM). The superior SNR of A184V showed putative single vesicle release events in single trials (FIG. 55b). However, if many bouton responses are pooled and averaged for each trial, single spike detection at 20 Hz is feasible (see average trace, FIG. 55b). For 20 Hz stimuli, both the A184V and S72A variants produced little accumulation of bouton fluorescence after 10 stimuli as compared to GCaMP6f (FIG. 55c), similar to the dendritic responses in culture (FIG. 54). For 100 Hz train stimuli, discrete release events could be detected, in contrast to GCaMP6f (FIG. 55d). Note the poor temporal precision of the train response, in contrast to A184V and S72A. Thus both A184V and S72A enable a larger dynamic range of reported firing frequencies, with S72A providing the largest range due to its low affinity. Moreover, the fast kinetics of SF-iGluSnFR.A184V and SF-iGluSnFR.S72A could be used for a more reliable estimate of spike times (versus GCaMP6f), and are much better suited to high-frequency spike detection (>100 Hz) which is necessary for the high instantaneous firing rates of cerebellar granule cells (van Beugen et al., 2013, Frontiers in Neural Circuits, 7:95).

Figure 56A:
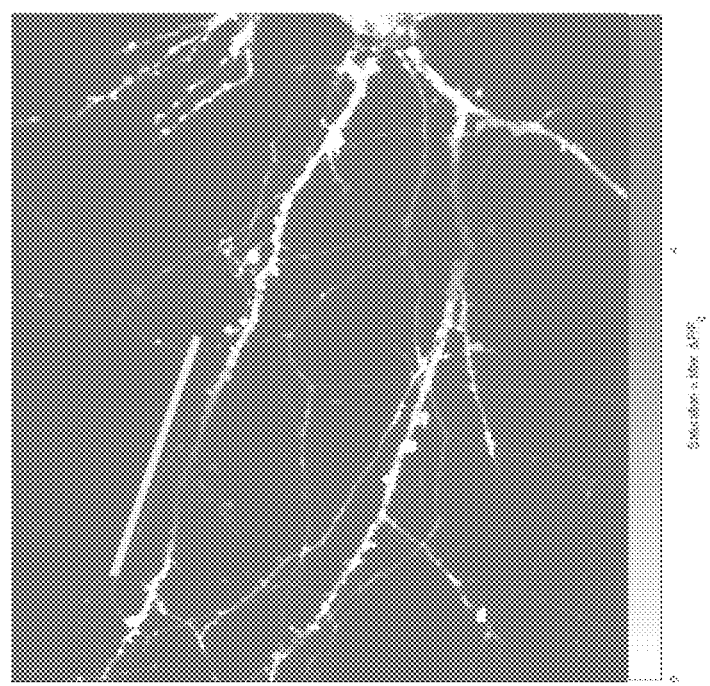
FIG. 56A-B|High-speed two photon imaging (1016 Hz frame rate) of a neuron expressing SF-Venus-iGluSnFR.
Figure 56B:
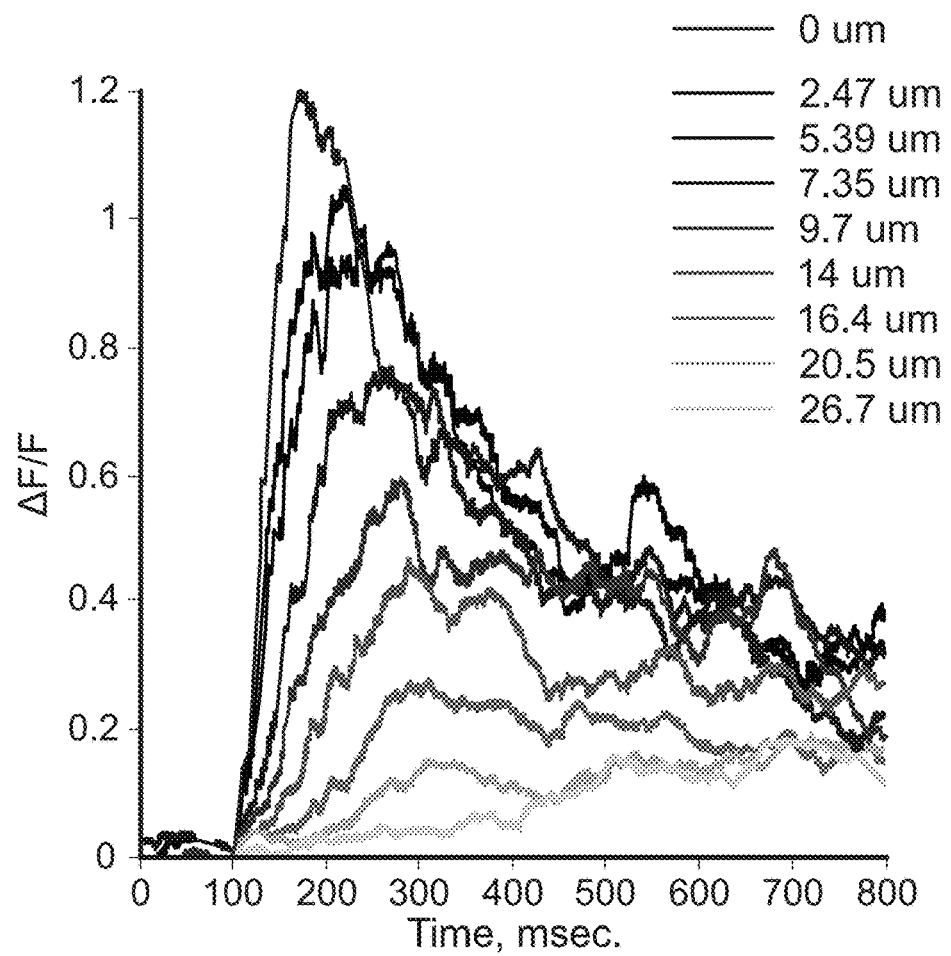

Introduction of chromophore mutations from GFP variants Azurite (Mena et al., 2006, Nat. Biotech., 24:1569-71) or Venus (Nagai et al., 2002, Nat. Biotech., 20:87-90) to SF-iGluSnFR led to functional blue and yellow versions, respectively. The former required re-optimization of the residues that link the FP with the glutamate-binding protein. The latter was a straightforward modular replacement. (Annotated amino acid sequences are given in FIG. 67). SF-Azurite-iGluSnFR has significantly lower ΔF/F (FIG. 68), perhaps a result of intrinsic differences in chromophore structure. SF-Venus-iGluSnFR has similar affinity and maximum fluorescence response to glutamate as SF-iGluSnFR, but with red-shifted excitation and emission spectra (FIG. 69). Importantly, its 2-photon excitation spectrum is sufficiently red-shifted to allow strong excitation at 1030 nm (FIG. 69), compatible with relatively inexpensive, powerful femtosecond fiber lasers (Tang et al., 2009, J. Biomed. Optics, 14:030508). These powerful lasers enable simultaneous excitation of many foci, enabling very fast (1016 Hz) large-area imaging by recording projections of the sample and computationally reconstructing images (Kazemipour, et al., 2018). In neuronal culture, two near-simultaneous pulses of glutamate uncaging can be resolved with both high spatial and temporal resolution by measuring fluorescence changes in a neuron expressing SF-Venus-iGluSnFR.A184V (FIG. 56).

The iGluSnFR variants described here increase the power of genetically encoded glutamate imaging. Affinity variants with altered kinetics broaden the range of observable glutamate release events. Chromatic mutants allow fast imaging with cheap lasers, and potential utility in multi-color imaging. Improved membrane targeting and photostability will be valuable in all applications.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 197
SEQ ID NO: 1            moltype = AA  length = 662
FEATURE                 Location/Qualifiers
source                  1..662
                        mol_type = protein
                        organism = synthetic construct
SEQUENCE: 1
MRGSHHHHHH GMASMTGGQQ MGRDLYDDDD KDRWGSKIEE GKLVIWINGD KGYNGLAEVG   60
KKFEKDTGIK VTVEHPDKLE EKFPQVAATG DGPDIIFWAH DRFGGYAQSG LLAEITPDKA  120
FQDKLYPFTW DAVRYNGKLI AYPIAVEALS LIYNKDLLPN PPKTWEEIPA LDKELKAKGK  180
SALMFNLQEP YFTWPLIAAD GGSHNVYIMA DKQKNGIKAN FKIRHNIEDG GVQLAYHYQQ  240
NTPIGDGPVL LPDNHYLSTQ SKLSKDPNEK RDHMVLLEFV TAAGITLGMD ELYKGGTGGS  300
MVSKGEELFT GVVPILVELD GDVNGHKFSV SGEGEGDATY GKLTLKFICT TGKLPVPWPT  360
LVTTLTYGVQ CFSRYPDHMK QHDFFKSAMP EGYIQERTIF FKDDGNYKTR AEVKFEGDTL  420
VNRIELKGID FKEDGNILGH KLEYNFNGGY AFKYENGKYD IKDVGVDNAG AKAGLTFLVD  480
LIKNKHMNAD TDYSIAEAAF NKGETAMTIN GPWAWSNIDT SKVNYGVTVL PTFKGQPSKP  540
FVGVLSAGIN AASPNKELAK EFLENYLLTD EGLEAVNKDK PLGAVALKSY EEELVKDPRI  600
AATMENAQKG EIMPNIPQMS AFWYAVRTAV INAASGRQTV DEDLKDAQTR ITKGSHHHHH  660
HG                                                                662

SEQ ID NO: 2            moltype = AA  length = 662
FEATURE                 Location/Qualifiers
source                  1..662
                        mol_type = protein
                        organism = synthetic construct
SEQUENCE: 2
MRGSHHHHHH GMASMTGGQQ MGRDLYDDDD KDRWGSKIEE GKLVIWINGD KGYNGLAEVG   60
KKFEKDTGIK VTVEHPDKLE EKFPQVAATG DGPDIIFWAH DRFGGYAQSG LLAEITPDKA  120
FQDKLYPFTW DAVRYNGKLI AYPIAVEALS LIYNKDLLPN PPKTWEEIPA LDKELKAKGK  180
SALMFNLQEP YFTWPLIAAD PPSYNVFIMA DKQKNGIKAN FKIRHNIEDG GVQLAYHYQQ  240
NTPIGDGPVL LPDNHYLSTQ SKLSKDPNEK RDHMVLLEFV TAAGITLGMD ELYKGGTGGS  300
MVSKGEELFT GVVPILVELD GDVNGHKFSV SGEGEGDATY GKLTLKFICT TGKLPVPWPT  360
LVTTLTYGVQ CFSRYPDHMK QHDFFKSAMP EGYIQERTIF FKDDGNYKTR AEVKFEGDTL  420
VNRIELKGID FKEDGNILGH KLEYNFNGGY AFKYENGKYD IKDVGVDNAG AKAGLTFLVD  480
LIKNKHMNAD TDYSIAEAAF NKGETAMTIN GPWAWSNIDT SKVNYGVTVL PTFKGQPSKP  540
FVGVLSAGIN AASPNKELAK EFLENYLLTD EGLEAVNKDK PLGAVALKSY EEELVKDPRI  600
AATMENAQKG EIMPNIPQMS AFWYAVRTAV INAASGRQTV DEDLKDAQTR ITKGSHHHHH  660
HG                                                                662

SEQ ID NO: 3            moltype = AA  length = 659
FEATURE                 Location/Qualifiers
source                  1..659
                        mol_type = protein
                        organism = synthetic construct
SEQUENCE: 3
MRGSHHHHHH GMASMTGGQQ MGRDLYDDDD KDRWGSKIEE GKLVIWINGD KGYNGLAEVG   60
KKFEKDTGIK VTVEHPDKLE EKFPQVAATG DGPDIIFWAH DRFGGYAQSG LLAEITPDKA  120
FQDKLYPFTW DAVRYNGKLI AYPIAVEALS LIYNKDLLPN PPKTWEEIPA LDKELKAKGK  180
SALMFNLQEP YFTWPLIAAD PCSHNVFIMA DKQKNGIKAN FKIRHNIEDG GVQLAYHYQQ  240
NTPIGDGPVL LPDNHYLSTQ SKLSKDPNEK RDHMVLLEFV TAAGITLGMD ELYKGGSMVS  300
KGEELFTGVV PILVELDGDV NGHKFSVSGE GEGDATYGKL TLKFICTTGK LPVPWPTLVT  360
TLTYGVQCFS RYPDHMKQHD FFKSAMPEGY IQERTIFFKD DGNYKTRAEV KFEGDTLVNR  420
```

```
IELKGIDFKE DGNILGHKLE YNFNGGYAFK YENGKYDIKD VGVDNAGAKA GLTFLVDLIK    480
NKHMNADTDY SIAEAAFNKG ETAMTINGPW AWSNIDTSKV NYGVTVLPTF KGQPSKPFVG    540
VLSAGINAAS PNKELAKEFL ENYLLTDEGL EAVNKDKPLG AVALKSYEEE LVDKPRIAAT    600
MENAQKGEIM PNIPQMSAFW YAVRTAVINA ASGRQTVDED LKDAQTRITK GSHHHHHHG     659

SEQ ID NO: 4            moltype = AA   length = 661
FEATURE                 Location/Qualifiers
source                  1..661
                        mol_type = protein
                        organism = synthetic construct
SEQUENCE: 4
MRGSHHHHHH GMASMTGGQQ MGRDLYDDDD KDRWGSKIEE GKLVIWINGD KGYNGLAEVG     60
KKFEKDTGIK VTVEHPDKLE EKFPQVAATG DGPDIIFWAH DRFGGYAQSG LLAEITPDKA    120
FQDKLYPFTW DAVRYNGKLI AYPIAVEALS LIYNKDLLPN PPKTWEEIPA LDKELKAKGK    180
SALMFNLQEP YFTWPLIAAD GGYAFKYENG GSHNVYIMAD KQKNGIKANF KIRHNIEDGG    240
VQLAYHYQQN TPIGDPVLL PDNHYLSTQS KLSKDPNEKR DHMVLLEFVT AAGITLGMDE     300
LYKGGTGGSM VSKGEELFTG VVPILVELDG DVNGHKFSVS GEGEGDATYG KLTLKFICTT    360
GKLPVPWPTL VTTLTYGVQC FSRYPDHMKQ HDFFKSAMPE GYIQERTIFF KDDGNYKTRA    420
EVKFEGDTLV NRIELKGIDF KEDGNILGHK LEYNFNGGKY DIKVGDNAG AKAGLTFLVD     480
LIKNKHMNAD TDYSIAEAAF NKGETAMTIN GPWAWSNIDT SKVNYGVTVL PTFKGQPSKP    540
FVGVLSAGIN AASPNKELAK EFLENYLLTD EGLEAVNKDK PLGAVALKSY EEELVDKPRI    600
AATMENAQKG EIMPNIPQMS AFWYAVRTAV INAASGQTVD EDLKDAQTRI TKGSHHHHHH    660
G                                                                    661

SEQ ID NO: 5            moltype = AA   length = 663
FEATURE                 Location/Qualifiers
source                  1..663
                        mol_type = protein
                        organism = synthetic construct
SEQUENCE: 5
MRGSHHHHHH GMASMTGGQQ MGRDLYDDDD KDRWGSKIEE GKLVIWINGD KGYNGLAEVG     60
KKFEKDTGIK VTVEHPDKLE EKFPQVAATG DGPDIIFWAH DRFGGYAQSG LLAEITPDKA    120
FQDKLYPFTW DAVRYNGKLI AYPIAVEALS LIYNKDLLPN PPKTWEEIPA LDKELKAKGK    180
SALMFNLQEP YFTWPLIAAD GGYAFKYENH LSHNVYIMAD KQKNGIKANF KIRHNIEDGG    240
VQLAYHYQQN TPIGDPVLL PDNHYLSTQS KLSKDPNEKR DHMVLLEFVT AAGITLGMDE     300
LYKGGTGGSM VSKGEELFTG VVPILVELDG DVNGHKFSVS GEGEGDATYG KLTLKFICTT    360
GKLPVPWPTL VTTLTYGVQC FSRYPDHMKQ HDFFKSAMPE GYIQERTIFF KDDGNYKTRA    420
EVKFEGDTLV NRIELKGIDF KEDGNILGHK LEYNFNGGKY DIKVGDNA GAKAGLTFLV      480
DLIKNKHMNA DTDYSIAEAA FNKGETAMTI NGPWAWSNID TSKVNYGVTV LPTFKGQPSK    540
PFVGVLSAGI NAASPNKELA KEFLENYLLT DEGLEAVNKD KPLGAVALKS YEEELVDKPR    600
IAATMENAQK GEIMPNIPQM SAFWYAVRTA VINAASGRQT VDEDLKDAQT RITKGSHHHH    660
HHG                                                                  663

SEQ ID NO: 6            moltype = AA   length = 655
FEATURE                 Location/Qualifiers
source                  1..655
                        mol_type = protein
                        organism = synthetic construct
SEQUENCE: 6
MRGSHHHHHH GMASMTGGQQ MGRDLYDDDD KDRWGSKIEE GKLVIWINGD KGYNGLAEVG     60
KKFEKDTGIK VTVEHPDKLE EKFPQVAATG DGPDIIFWAH DRFGGYAQSG LLAEITPDKA    120
FQDKLYPFTW DAVRYNGKLI AYPIAVEALS LIYNKDLLPN PPKTWEEIPA LDKELKAKGK    180
SALMFNLQEP YFTWPLIAAD GGYAFKYENG KYDIKDVGVD NAGAKAGLTF LVDLIKNKHM    240
NADTDYSIAE AAFNKGETAM TINGPWAWSN IDTSKVNYGV TVLPTFKGQP SKPFVGVLSA    300
GINAASPNKE LAKEFLENYL LTDEGLEAVN KDKPLGAVAL KSYEEELGGS HNVYIMADKQ    360
RNGIKANFKI RHNIEDGGVQ LAYHYQQNTP IGDPVLLPD NHYLSTQSKL SKDPNEKRDH     420
MVLLEFVTAA GITLGMDELY KGGTGGSMVS KGEELFTGVV PILVELDGDV NGHKFSVSGE    480
GEGDATYGKL TLKFICTTGK LPVPWPTLVT TLTYGVQCFS RYPDHMKQHD FFKSAMPEGY    540
IQERTIFFKD DGNYKTRAEV KFEGDTLVNR IELKGIDFKE DGNILGHKLE YNFNGGAKDP    600
RIAATMENAQ KGEIMPNIPQ MSAFWYAVRT AVINAASGRQ TVDEDLKDAQ TRITK         655

SEQ ID NO: 7            moltype = AA   length = 655
FEATURE                 Location/Qualifiers
source                  1..655
                        mol_type = protein
                        organism = synthetic construct
SEQUENCE: 7
MRGSHHHHHH GMASMTGGQQ MGRDLYDDDD KDRWGSKIEE GKLVIWINGD KGYNGLAEVG     60
KKFEKDTGIK VTVEHPDKLE EKFPQVAATG DGPDIIFWAH DRFGGYAQSG LLAEITPDKA    120
FQDKLYPFTW DAVRYNGKLI AYPIAVEALS LIYNKDLLPN PPKTWEEIPA LDKELKAKGK    180
SALMFNLQEP YFTWPLIAAD GGYAFKYENG KYDIKDVGVD NAGAKAGLTF LVDLIKNKHM    240
NADTDYSIAE AAFNKGETAM TINGPWAWSN IDTSKVNYGV TVLPTFKGQP SKPFVGVLSA    300
GINAASPNKE LAKEFLENYL LTDEGLEAVN KDKPLGAVAL KSYEEELGGS HNVYIMADKQ    360
RNGIKANFKI RHNIEDGGVQ LAYHYQQNTP IGDPVLLPD NHYLSTQSKL SKDPNEKRDH     420
MVLLEFVTAA GITLGMDELY KGGTGGSMVS KGEELFTGVV PILVELDGDV NGHKFSVSGE    480
GEGDATYGKL TLKFICTTGK LPVPWPTLVT TLTYGVQCFS RYPDHMKQHD FFKSAMPEGY    540
IQERTIFFKD DGNYKTRAEV KFEGDTLVNR IELKGIDFKE DGNILGHKLE YNFNPAKDP     600
RIAATMENAQ KGEIMPNIPQ MSAFWYAVRT AVINAASGRQ TVDEDLKDAQ TRITK         655
```

```
SEQ ID NO: 8              moltype = AA  length = 659
FEATURE                   Location/Qualifiers
source                    1..659
                          mol_type = protein
                          organism = synthetic construct
SEQUENCE: 8
MRGSHHHHHH GMASMTGGQQ MGRDLYDDDD KDRWGSKIEE GKLVIWINGD KGYNGLAEVG    60
KKFEKDTGIK VTVEHPDKLE EKFPQVAATG DGPDIIFWAH DRFGGYAQSG LLAEITPDKA   120
FQDKLYPFTW DAVRYNGKLI AYPIAVEALS LIYNKDLLPN PPKTWEEIPA LDKELKAKGK   180
SALMFNLQEP YFTWPLIAAD GGYAFKYENG KYDIKDVGVD NAGAKAGLTF LVDLIKNKHM   240
NADTDYSIAE AAFNKGETAM TINGPWAWSN IDTSKVNYGV TVLPTFKGQP SKPFVGVLSA   300
GINAASPNKE LAKEFLENYL LTDEGLEAVN KDKPLGAVAL KSYEEELVKD PRSHNVYIMA   360
DKQKNGIKAN FKIRHNIEDG GVQLAYHYQQ NTPIGDGPVL LPDNHYLSTQ SKLSKDPNEK   420
RDHMVLLEFV TAAGITLGMD ELYKGGTGGS MVSKGEELFT GVVPILVELD GDVNGHKFSV   480
SGEGEGDATY GKLTLKFICT TGKLPVPWPT LVTTLTYGVQ CFSRYPDHMK QHDFFKSAMP   540
EGYIQERTIF FKDDGNYKTR AEVKFEGDTL VNRIELKGID FKEDGNILGH KLEYNFNAAT   600
MENAQKGEIM PNIPQMSAFW YAVRTAVINA ASGRQTVDED LKDAQTRITK GSHHHHHHG    659

SEQ ID NO: 9              moltype = AA  length = 14
FEATURE                   Location/Qualifiers
VARIANT                   8..9
                          note = any amino acid
source                    1..14
                          mol_type = protein
                          organism = synthetic construct
SEQUENCE: 9
PLIAADGXXN VYIM                                                     14

SEQ ID NO: 10             moltype = AA  length = 13
FEATURE                   Location/Qualifiers
VARIANT                   7..8
                          note = any amino acid
source                    1..13
                          mol_type = protein
                          organism = synthetic construct
SEQUENCE: 10
PLIAADXXNV YIM                                                      13

SEQ ID NO: 11             moltype = AA  length = 15
FEATURE                   Location/Qualifiers
VARIANT                   9..10
                          note = any amino acid
source                    1..15
                          mol_type = protein
                          organism = synthetic construct
SEQUENCE: 11
PLIAADGGXX NVYIM                                                    15

SEQ ID NO: 12             moltype = AA  length = 15
FEATURE                   Location/Qualifiers
VARIANT                   8
                          note = any amino acid
source                    1..15
                          mol_type = protein
                          organism = synthetic construct
SEQUENCE: 12
PLIAADGXPN VYIMG                                                    15

SEQ ID NO: 13             moltype = AA  length = 15
FEATURE                   Location/Qualifiers
VARIANT                   9
                          note = any amino acid
source                    1..15
                          mol_type = protein
                          organism = synthetic construct
SEQUENCE: 13
PLIAADGIXN VYIMG                                                    15

SEQ ID NO: 14             moltype = AA  length = 15
FEATURE                   Location/Qualifiers
VARIANT                   8
                          note = any amino acid
source                    1..15
                          mol_type = protein
                          organism = synthetic construct
SEQUENCE: 14
PLIAADPXSH NVYIM                                                    15

SEQ ID NO: 15             moltype = AA  length = 15
```

```
FEATURE                 Location/Qualifiers
VARIANT                 7
                        note = any amino acid
source                  1..15
                        mol_type = protein
                        organism = synthetic construct
SEQUENCE: 15
PLIAADXPSH NVYIM                                                              15

SEQ ID NO: 16           moltype = AA  length = 15
FEATURE                 Location/Qualifiers
VARIANT                 7..8
                        note = any amino acid
source                  1..15
                        mol_type = protein
                        organism = synthetic construct
SEQUENCE: 16
PLIAADXXSH NVYIM                                                              15

SEQ ID NO: 17           moltype = AA  length = 15
FEATURE                 Location/Qualifiers
VARIANT                 7..8
                        note = any amino acid
source                  1..15
                        mol_type = protein
                        organism = synthetic construct
SEQUENCE: 17
PLIAADXXSH NVFIM                                                              15

SEQ ID NO: 18           moltype = AA  length = 15
FEATURE                 Location/Qualifiers
VARIANT                 8
                        note = any amino acid
source                  1..15
                        mol_type = protein
                        organism = synthetic construct
SEQUENCE: 18
PLIAADPXSH NVFIM                                                              15

SEQ ID NO: 19           moltype = AA  length = 15
FEATURE                 Location/Qualifiers
VARIANT                 8
                        note = any amino acid
source                  1..15
                        mol_type = protein
                        organism = synthetic construct
SEQUENCE: 19
PLIAADPXSY NVFIM                                                              15

SEQ ID NO: 20           moltype = AA  length = 15
FEATURE                 Location/Qualifiers
VARIANT                 7..8
                        note = any amino acid
source                  1..15
                        mol_type = protein
                        organism = synthetic construct
SEQUENCE: 20
PLIAADXXSY NVFIM                                                              15

SEQ ID NO: 21           moltype = AA  length = 15
FEATURE                 Location/Qualifiers
VARIANT                 8
                        note = any amino acid
source                  1..15
                        mol_type = protein
                        organism = synthetic construct
SEQUENCE: 21
PLIAADPXSY NVFIM                                                              15

SEQ ID NO: 22           moltype = AA  length = 15
FEATURE                 Location/Qualifiers
VARIANT                 7..8
                        note = any amino acid
source                  1..15
                        mol_type = protein
                        organism = synthetic construct
SEQUENCE: 22
PLIAADXXSY NVFIM                                                              15
```

```
SEQ ID NO: 23              moltype = AA  length = 15
FEATURE                    Location/Qualifiers
VARIANT                    8
                           note = any amino acid
VARIANT                    10
                           note = any amino acid
source                     1..15
                           mol_type = protein
                           organism = synthetic construct
SEQUENCE: 23
PLIAADPXSX NVYIM                                                              15

SEQ ID NO: 24              moltype = AA  length = 15
FEATURE                    Location/Qualifiers
VARIANT                    8
                           note = any amino acid
VARIANT                    11
                           note = any amino acid
source                     1..15
                           mol_type = protein
                           organism = synthetic construct
SEQUENCE: 24
PLIAADPXSH XVYIM                                                              15

SEQ ID NO: 25              moltype = AA  length = 15
FEATURE                    Location/Qualifiers
VARIANT                    8
                           note = any amino acid
VARIANT                    12
                           note = any amino acid
source                     1..15
                           mol_type = protein
                           organism = synthetic construct
SEQUENCE: 25
PLIAADPXSH NXYIM                                                              15

SEQ ID NO: 26              moltype = AA  length = 15
FEATURE                    Location/Qualifiers
VARIANT                    8
                           note = any amino acid
VARIANT                    13
                           note = any amino acid
source                     1..15
                           mol_type = protein
                           organism = synthetic construct
SEQUENCE: 26
PLIAADPXSH NVXIM                                                              15

SEQ ID NO: 27              moltype = AA  length = 16
FEATURE                    Location/Qualifiers
VARIANT                    8..9
                           note = any amino acid
source                     1..16
                           mol_type = protein
                           organism = synthetic construct
SEQUENCE: 27
KLEYNFNXXY AFKYEN                                                             16

SEQ ID NO: 28              moltype = AA  length = 15
FEATURE                    Location/Qualifiers
VARIANT                    8
                           note = any amino acid
source                     1..15
                           mol_type = protein
                           organism = synthetic construct
SEQUENCE: 28
KLEYNFNXYA FKYEN                                                              15

SEQ ID NO: 29              moltype = AA  length = 14
FEATURE                    Location/Qualifiers
source                     1..14
                           mol_type = protein
                           organism = synthetic construct
SEQUENCE: 29
KLEYNFNYAF KYEN                                                               14

SEQ ID NO: 30              moltype = AA  length = 14
FEATURE                    Location/Qualifiers
VARIANT                    7
```

```
                            note = any amino acid
source                      1..14
                            mol_type = protein
                            organism = synthetic construct
SEQUENCE: 30
KLEYNFXYAF KYEN                                                              14

SEQ ID NO: 31               moltype = AA   length = 14
FEATURE                     Location/Qualifiers
VARIANT                     6..7
                            note = any amino acid
source                      1..14
                            mol_type = protein
                            organism = synthetic construct
SEQUENCE: 31
KLEYNXXYAF KYEN                                                              14

SEQ ID NO: 32               moltype = AA   length = 14
FEATURE                     Location/Qualifiers
VARIANT                     7
                            note = any amino acid
source                      1..14
                            mol_type = protein
                            organism = synthetic construct
SEQUENCE: 32
KLEYNWXYAF KYEN                                                              14

SEQ ID NO: 33               moltype = AA   length = 14
FEATURE                     Location/Qualifiers
VARIANT                     6
                            note = any amino acid
source                      1..14
                            mol_type = protein
                            organism = synthetic construct
SEQUENCE: 33
KLEYNXKYAF KYEN                                                              14

SEQ ID NO: 34               moltype = AA   length = 16
FEATURE                     Location/Qualifiers
VARIANT                     9
                            note = any amino acid
source                      1..16
                            mol_type = protein
                            organism = synthetic construct
SEQUENCE: 34
KLEYNFNPXY AFKYEN                                                            16

SEQ ID NO: 35               moltype = AA   length = 16
FEATURE                     Location/Qualifiers
VARIANT                     8
                            note = any amino acid
source                      1..16
                            mol_type = protein
                            organism = synthetic construct
SEQUENCE: 35
KLEYNFNXPY AFKYEN                                                            16

SEQ ID NO: 36               moltype = AA   length = 15
FEATURE                     Location/Qualifiers
VARIANT                     7..8
                            note = any amino acid
source                      1..15
                            mol_type = protein
                            organism = synthetic construct
SEQUENCE: 36
AFKYENXXSH NVYIM                                                             15

SEQ ID NO: 37               moltype = AA   length = 16
FEATURE                     Location/Qualifiers
VARIANT                     8..9
                            note = any amino acid
source                      1..16
                            mol_type = protein
                            organism = synthetic construct
SEQUENCE: 37
KLEYNFNXXK YDIKDV                                                            16

SEQ ID NO: 38               moltype = AA   length = 15
FEATURE                     Location/Qualifiers
```

```
VARIANT                  7..8
                         note = any amino acid
source                   1..15
                         mol_type = protein
                         organism = synthetic construct
SEQUENCE: 38
KSYEELXXSH NVYIM                                                             15

SEQ ID NO: 39            moltype = AA  length = 15
FEATURE                  Location/Qualifiers
VARIANT                  8
                         note = any amino acid
source                   1..15
                         mol_type = protein
                         organism = synthetic construct
SEQUENCE: 39
KSYEELPXSH NVYIM                                                             15

SEQ ID NO: 40            moltype = AA  length = 15
FEATURE                  Location/Qualifiers
VARIANT                  7
                         note = any amino acid
source                   1..15
                         mol_type = protein
                         organism = synthetic construct
SEQUENCE: 40
KSYEELXPSH NVYIM                                                             15

SEQ ID NO: 41            moltype = AA  length = 16
FEATURE                  Location/Qualifiers
VARIANT                  8..9
                         note = any amino acid
source                   1..16
                         mol_type = protein
                         organism = synthetic construct
SEQUENCE: 41
KLEYNFNXXA KDPRIA                                                            16

SEQ ID NO: 42            moltype = AA  length = 16
FEATURE                  Location/Qualifiers
VARIANT                  9
                         note = any amino acid
source                   1..16
                         mol_type = protein
                         organism = synthetic construct
SEQUENCE: 42
KLEYNFNPXA KDPRIA                                                            16

SEQ ID NO: 43            moltype = AA  length = 16
FEATURE                  Location/Qualifiers
VARIANT                  8
                         note = any amino acid
source                   1..16
                         mol_type = protein
                         organism = synthetic construct
SEQUENCE: 43
KLEYNFNXPA KDPRIA                                                            16

SEQ ID NO: 44            moltype = AA  length = 15
FEATURE                  Location/Qualifiers
VARIANT                  8
                         note = any amino acid
source                   1..15
                         mol_type = protein
                         organism = synthetic construct
SEQUENCE: 44
ELAKDPRXSH NVYIM                                                             15

SEQ ID NO: 45            moltype = AA  length = 16
FEATURE                  Location/Qualifiers
VARIANT                  8..9
                         note = any amino acid
source                   1..16
                         mol_type = protein
                         organism = synthetic construct
SEQUENCE: 45
ELAKDPRXXS HNVYIM                                                            16

SEQ ID NO: 46            moltype = AA  length = 17
```

| FEATURE | Location/Qualifiers |
|---|---|
| VARIANT | 8..10 |
| | note = any amino acid |
| source | 1..17 |
| | mol_type = protein |
| | organism = synthetic construct |

SEQUENCE: 46
ELAKDPRXXX SHNVYIM                                                    17

| SEQ ID NO: 47 | moltype = AA  length = 15 |
|---|---|
| FEATURE | Location/Qualifiers |
| VARIANT | 8 |
| | note = any amino acid |
| source | 1..15 |
| | mol_type = protein |
| | organism = synthetic construct |

SEQUENCE: 47
KLEYNFNXAA TMENA                                                      15

| SEQ ID NO: 48 | moltype = AA  length = 16 |
|---|---|
| FEATURE | Location/Qualifiers |
| VARIANT | 8..9 |
| | note = any amino acid |
| source | 1..16 |
| | mol_type = protein |
| | organism = synthetic construct |

SEQUENCE: 48
KLEYNFNXXA ATMENA                                                     16

| SEQ ID NO: 49 | moltype = AA  length = 17 |
|---|---|
| FEATURE | Location/Qualifiers |
| VARIANT | 8..10 |
| | note = any amino acid |
| source | 1..17 |
| | mol_type = protein |
| | organism = synthetic construct |

SEQUENCE: 49
KLEYNFNXXX AATMENA                                                    17

| SEQ ID NO: 50 | moltype = AA  length = 671 |
|---|---|
| FEATURE | Location/Qualifiers |
| source | 1..671 |
| | mol_type = protein |
| | organism = synthetic construct |

SEQUENCE: 50
```
MRGSHHHHHH GMASMTGGQQ MGRDLYDDDD KDRWGSKIEE GKVVIWHAMQ PNELEVFQSL   60
AEEYMALCPE VEIVFEQKPN LEDALKAAIP TGQGPDLFIW AHDWIGKFAE AGLLEPIDEY  120
VTEDLLNEFA PMAQDAMQYK GHYYALPFAA ETVAIIYSKE MVSEPPKTFD EMKAIMEKYY  180
DPANEKYGIA WPINAYFISA IAQAFGGSHN VYIMADKQKN GIKANFKIRH NIEDGGVQLA  240
YHYQQNTPIG DGPVLLPDNH YLSTQSKLSK DPNEKRDHMV LLEFVTAAGI TLGMDELYKG  300
GTGGSMVSKG EELFTGVVPI LVELDGDVNG HKFSVSGEGE GDATYGKLTL KFICTTGKLP  360
VPWPTLVTTL TYGVQCFSRY PDHMKQHDFF KSAMPEGYIQ ERTIFFKDDG NYKTRAEVKF  420
EGDTLVNRIE LKGIDFKEDG NILGHKLEYN FNGGYYFDDK TEQPGLDKPE TIEGFKFFFT  480
EIWPYMAPTG DYNTQQSIFL EGRAPMMVNG PWSINDVKKA GINFGVVPLP PIIKDGKEYW  540
PRPYGGVKLI YFAAGIKNKD AAWKFAKWLT TSEESIKTLA LELGYIPVLT KVLDDPEIKN  600
DPVIYGFGQA VQHAYLMPKS PKMSAVWGGV DGAINEILQD PQNADIEGIL KKYQQEILNN  660
MQGSHHHHHH G                                                       671
```

| SEQ ID NO: 51 | moltype = AA  length = 671 |
|---|---|
| FEATURE | Location/Qualifiers |
| source | 1..671 |
| | mol_type = protein |
| | organism = synthetic construct |

SEQUENCE: 51
```
MRGSHHHHHH GMASMTGGQQ MGRDLYDDDD KDRWGSKIEE GKVVIWHAMQ PNELEVFQSL   60
AEEYMALCPE VEIVFEQKPN LEDALKAAIP TGQGPDLFIW AHDWIGKFAE AGLLEPIDEY  120
VTEDLLNEFA PMAQDAMQYK GHYYALPFAA ETVAIIYSKE MVSEPPKTFD EMKAIMEKYY  180
DPANEKYGIA WPINAYFISA IAQAFGGSHN VYIMADKQKN GIKANFKIRH NIEDGGVQLA  240
YHYQQNTPIG DGPVLLPDNH YLSTQSKLSK DPNEKRDHMV LLEFVTAAGI TLGMDELYKG  300
GTGGSMVSKG EELFTGVVPI LVELDGDVNG HKFSVSGEGE GDATYGKLTL KFICTTGKLP  360
VPWPTLVTTL TYGVQCFSRY PDHMKQHDFF KSAMPEGYIQ ERTIFFKDDG NYKTRAEVKF  420
EGDTLVNRIE LKGIDFKEDG NILGHKLEYN FNFEYYFDDK TEQPGLDKPE TIEGFKFFFT  480
EIWPYMAPTG DYNTQQSIFL EGRAPMMVNG PWSINDVKKA GINFGVVPLP PIIKDGKEYW  540
PRPYGGVKLI YFAAGIKNKD AAWKFAKWLT TSEESIKTLA LELGYIPVLT KVLDDPEIKN  600
DPVIYGFGQA VQHAYLMPKS PKMSAVWGGV DGAINEILQD PQNADIEGIL KKYQQEILNN  660
MQGSHHHHHH G                                                       671
```

| SEQ ID NO: 52 | moltype = AA  length = 662 |
|---|---|
| FEATURE | Location/Qualifiers |

```
source                  1..662
                        mol_type = protein
                        organism = synthetic construct
SEQUENCE: 52
MRGSHHHHHH GMASMTGGQQ MGRDLYDDDD KDRWGSKIEE GKVVIWHAMQ PNELEVFQSL    60
AEEYMALCPE VEIVFEQKPN LEDALKAAIP TGQGPDLFIW AHDWIGKFAE AGLLEPIDEY   120
VTEDLLNEFA PMAQDAMQYK GHYYALPFAA ETVAIIYSKE MVSEPPKTFD EMKAIMEKYY   180
DPANEKYGIA WPINAYFISA IAQAFGGYYF DDKTEQPGLD KPETIEGFKF FFTEIWPYMA   240
PTGDYNTQQS IFLEGRAPMM VNGPWSINDV KKAGINFGVV PLPPIIKDGK EYWPRPYGGV   300
KLIYFAAGIK NKDAAWKFAK WLTTSEESIK TLALELGYIP VLTKVLDDPE ISHNVYIMAD   360
KQKNGIKANF KIRHNIEDGG VQLAYHYQQN TPIGDGPVLL PDNHYLSTQS KLSKDPNEKR   420
DHMVLLEFVT AAGITLGMDE LYKGGTGGSM VSKGEELFTG VVPILVELDG DVNGHKFSVS   480
GEGEGDATYG KLTLKFICTT GKLPVPWPTL VTTLTYGVQC FSRYPDHMKQ HDFFKSAMPE   540
GYIQERTIFF KDDGNYKTRA EVKFEGDTLV NRIELKGIDF KEDGNILGHK LEYNFNKNDP   600
VIYGFGQAVQ HAYLMPKSPK MSAVWGGVDG AINEILQDPQ NADIEGILKK YQQEILNNMQ   660
GS                                                                 662

SEQ ID NO: 53           moltype = AA  length = 664
FEATURE                 Location/Qualifiers
source                  1..664
                        mol_type = protein
                        organism = synthetic construct
SEQUENCE: 53
MRGSHHHHHH GMASMTGGQQ MGRDLYDDDD KDRWGSKIEE GKVVIWHAMQ PNELEVFQSL    60
AEEYMALCPE VEIVFEQKPN LEDALKAAIP TGQGPDLFIW AHDWIGKFAE AGLLEPIDEY   120
VTEDLLNEFA PMAQDAMQYK GHYYALPFAA ETVAIIYSKE MVSEPPKTFD EMKAIMEKYY   180
DPANEKYGIA WPINAYFISA IAQAFGGYYF DDKTEQPGLD KPETIEGFKF FFTEIWPYMA   240
PTGDYNTQQS IFLEGRAPMM VNGPWSINDV KKAGINFGVV PLPPIIKDGK EYWPRPYGGV   300
KLIYFAAGIK NKDAAWKFAK WLTTSEESIK TLALELGYIP VLTKVLDDPE IPPSHNVYIM   360
ADKQKNGIKA NFKIRHNIED GGVQLAYHYQ QNTPIGDGPV LLPDNHYLST QSKLSKDPNE   420
KRDHMVLLEF VTAAGITLGM DELYKGGTGG SMVSKGEELF TGVVPILVEL DGDVNGHKFS   480
VSGEGEGDAT YGKLTLKFIC TTGKLPVPWP TLVTTLTYGV QCFSRYPDHM KQHDFFKSAM   540
PEGYIQERTI FFKDDGNYKT RAEVKFEGDT LVNRIELKGI DFKEDGNILG HKLEYNFNKN   600
DPVIYGFGQA VQHAYLMPKS PKMSAVWGGV DGAINEILQD PQNADIEGIL KKYQQEILNN   660
MQGS                                                               664

SEQ ID NO: 54           moltype = AA  length = 16
FEATURE                 Location/Qualifiers
VARIANT                 7..8
                        note = any amino acid
source                  1..16
                        mol_type = protein
                        organism = synthetic construct
SEQUENCE: 54
AIAQAFXXSH NVYIMA                                                   16

SEQ ID NO: 55           moltype = AA  length = 16
FEATURE                 Location/Qualifiers
VARIANT                 8
                        note = any amino acid
source                  1..16
                        mol_type = protein
                        organism = synthetic construct
SEQUENCE: 55
AIAQAFPXSH NVYIMA                                                   16

SEQ ID NO: 56           moltype = AA  length = 17
FEATURE                 Location/Qualifiers
VARIANT                 8..9
                        note = any amino acid
source                  1..17
                        mol_type = protein
                        organism = synthetic construct
SEQUENCE: 56
KLEYNFNXXY YFDDKTE                                                  17

SEQ ID NO: 57           moltype = AA  length = 14
FEATURE                 Location/Qualifiers
VARIANT                 7..8
                        note = any amino acid
source                  1..14
                        mol_type = protein
                        organism = synthetic construct
SEQUENCE: 57
VLDDPEXXHN VYIM                                                     14

SEQ ID NO: 58           moltype = AA  length = 16
FEATURE                 Location/Qualifiers
VARIANT                 8..9
```

```
                         note = any amino acid
source                   1..16
                         mol_type = protein
                         organism = synthetic construct
SEQUENCE: 58
VLDDPEIXXS HNVYIM                                                       16

SEQ ID NO: 59            moltype = AA  length = 14
FEATURE                  Location/Qualifiers
VARIANT                  7..8
                         note = any amino acid
source                   1..14
                         mol_type = protein
                         organism = synthetic construct
SEQUENCE: 59
KLEYNFXXND PVIY                                                         14

SEQ ID NO: 60            moltype = AA  length = 16
FEATURE                  Location/Qualifiers
VARIANT                  8
                         note = any amino acid
source                   1..16
                         mol_type = protein
                         organism = synthetic construct
SEQUENCE: 60
KLEYNFNXPK NDPVIY                                                       16

SEQ ID NO: 61            moltype = AA  length = 16
FEATURE                  Location/Qualifiers
VARIANT                  9
                         note = any amino acid
source                   1..16
                         mol_type = protein
                         organism = synthetic construct
SEQUENCE: 61
KLEYNFNPXK NDPVIY                                                       16

SEQ ID NO: 62            moltype = AA  length = 556
FEATURE                  Location/Qualifiers
source                   1..556
                         mol_type = protein
                         organism = synthetic construct
SEQUENCE: 62
MRGSHHHHHH GMASMTGGQQ MGRDLYDDDD KDRWGSAAGS TLDKIAKNGV IVVGHRESSV        60
PFSYYDNQQK VVGYSQDYSN AIVEAVKKKL NKPDLQVKLI PITSQNRIPL LQNGTFDFEC        120
GSTTNNVERQ KQAAFSDTIF VVGTRLLTKK GGDIKDFANL KDKAVVVTSG TTSEVLLNKL        180
NEEQKMNMRI ISAKDHGDSF RTLESGRAVA FMMDDVLLAG ERAKAKKPDN WEIVGKPQSQ        240
EAYGCMLRKD DPQFKKLMDD TIAQVQTSGE AEKWFDKWFK NPILVSHNVY IMADKQKNGI        300
KANFKIRHNI EDGGVQLAYH YQQNTPIGDG PVLLPDNHYL STQSKLSKDP NEKRDHMVLL        360
EFVTAAGITL GMDELYKGGT GGSMVSKGEE LFTGVVPILV ELDGDVNGHK FSVSGEGEGD        420
ATYGKLTLKF ICTTGKLPVP WPTLVTTLTY GVQCFSRYPD HMKQHDFFKS AMPEGYIQER        480
TIFFKDDGNY KTRAEVKFEG DTLVNRIELK GIDFKEDGNI LGHKLEYNFN NPLNMNFELS        540
DEMKALFKEP NDKALK                                                       556

SEQ ID NO: 63            moltype = AA  length = 556
FEATURE                  Location/Qualifiers
source                   1..556
                         mol_type = protein
                         organism = synthetic construct
SEQUENCE: 63
MRGSHHHHHH GMASMTGGQQ MGRDLYDDDD KDRWGSAAGS TLDKIAKNGV IVVGHRESSV        60
PFSYYDNQQK VVGYSQDYSN AIVEAVKKKL NKPDLQVKLI PITSQNRIPL LQNGTFDFEC        120
GSTTNNVERQ KQAAFSDTIF VVGTRLLTKK GGDIKDFANL KDKAVVVTSG TTSEVLLNKL        180
NEEQKMNMRI ISAKDHGDSF RTLESGRAVA FMMDDVLLAG ERAKAKKPDN WEIVGKPQSQ        240
EAYGCMLRKD DPQFKKLMDD TIAQVQTSGE AEKWFDKWFK NPILVSHNVY IMADKQKNGI        300
KANFKIRHNI EDGGVQLAYH YQQNTPIGDG PVLLPDNHYL STQSKLSKDP NEKRDHMVLL        360
EFVTAAGITL GMDELYKGGT GGSMVSKGEE LFTGVVPILV ELDGDVNGHK FSVSGEGEGD        420
ATYGKLTLKF ICTTGKLPVP WPTLVTTLTY GVQCFSRYPD HMKQHDFFKS AMPEGYIQER        480
TIFFKDDGNY KTRAEVKFEG DTLVNRIELK GIDFKEDGNI LGHKLEYNFN NPLNMNFELS        540
DEMKALFKEP NDKALK                                                       556

SEQ ID NO: 64            moltype = AA  length = 16
FEATURE                  Location/Qualifiers
VARIANT                  8
                         note = any amino acid
source                   1..16
                         mol_type = protein
                         organism = synthetic construct
SEQUENCE: 64
```

```
FKNPIPPXSH NVYIMA                                                16

SEQ ID NO: 65         moltype = AA  length = 17
FEATURE               Location/Qualifiers
VARIANT               8..9
                      note = any amino acid
source                1..17
                      mol_type = protein
                      organism = synthetic construct
SEQUENCE: 65
FKNPIPPXXS HNVYIMA                                               17

SEQ ID NO: 66         moltype = AA  length = 17
FEATURE               Location/Qualifiers
VARIANT               9
                      note = any amino acid
source                1..17
                      mol_type = protein
                      organism = synthetic construct
SEQUENCE: 66
FKNPIPPPXS HNVYIMA                                               17

SEQ ID NO: 67         moltype = AA  length = 17
FEATURE               Location/Qualifiers
VARIANT               8
                      note = any amino acid
source                1..17
                      mol_type = protein
                      organism = synthetic construct
SEQUENCE: 67
FKNPIPPXPS HNVYIMA                                               17

SEQ ID NO: 68         moltype = AA  length = 17
FEATURE               Location/Qualifiers
VARIANT               8..9
                      note = any amino acid
source                1..17
                      mol_type = protein
                      organism = synthetic construct
SEQUENCE: 68
KWFKNPIXXS HNVYIMA                                               17

SEQ ID NO: 69         moltype = AA  length = 16
FEATURE               Location/Qualifiers
VARIANT               8..9
                      note = any amino acid
source                1..16
                      mol_type = protein
                      organism = synthetic construct
SEQUENCE: 69
FKNPIPPXXN VYIMAD                                                16

SEQ ID NO: 70         moltype = AA  length = 16
FEATURE               Location/Qualifiers
VARIANT               8..9
                      note = any amino acid
source                1..16
                      mol_type = protein
                      organism = synthetic construct
SEQUENCE: 70
KWFKNPIXXN VYIMAD                                                16

SEQ ID NO: 71         moltype = AA  length = 15
FEATURE               Location/Qualifiers
VARIANT               8
                      note = any amino acid
source                1..15
                      mol_type = protein
                      organism = synthetic construct
SEQUENCE: 71
KLEYNFNXKN LNMNF                                                 15

SEQ ID NO: 72         moltype = AA  length = 16
FEATURE               Location/Qualifiers
VARIANT               8..9
                      note = any amino acid
source                1..16
                      mol_type = protein
                      organism = synthetic construct
```

```
SEQUENCE: 72
KLEYNFNXXK NLNMNF                                                           16

SEQ ID NO: 73           moltype = AA  length = 16
FEATURE                 Location/Qualifiers
VARIANT                 8
                        note = any amino acid
source                  1..16
                        mol_type = protein
                        organism = synthetic construct
SEQUENCE: 73
KLEYNFNXPK NLNMNF                                                           16

SEQ ID NO: 74           moltype = AA  length = 16
FEATURE                 Location/Qualifiers
VARIANT                 9
                        note = any amino acid
source                  1..16
                        mol_type = protein
                        organism = synthetic construct
SEQUENCE: 74
KLEYNFNPXK NLNMNF                                                           16

SEQ ID NO: 75           moltype = AA  length = 14
FEATURE                 Location/Qualifiers
VARIANT                 8..9
                        note = any amino acid
source                  1..14
                        mol_type = protein
                        organism = synthetic construct
SEQUENCE: 75
GHKLEYNXXL NMNF                                                             14

SEQ ID NO: 76           moltype = AA  length = 14
FEATURE                 Location/Qualifiers
VARIANT                 8..9
                        note = any amino acid
source                  1..14
                        mol_type = protein
                        organism = synthetic construct
SEQUENCE: 76
KLEYNFNXXL NMNF                                                             14

SEQ ID NO: 77           moltype = AA  length = 567
FEATURE                 Location/Qualifiers
source                  1..567
                        mol_type = protein
                        organism = synthetic construct
SEQUENCE: 77
MHHHHHHGSE EQEKALNFGI ISTESQQNLK PQWTPFLQDM EKKLGVKVNA FFAPDYAGII  60
QGMRFNKVDI AWYGNLSAME AVDRANGQVF AQTVAADGSS HNVYIMADKQ RNGIKANFKI  120
RHNIEDGGVQ LAYHYQQNTP IGDGPVLLPD NHYLSTQSKL SKDPNEKRDH MVLLEFVTAA  180
GITLGMDELY KGGTGGSMVS KGEELFTGVV PILVELDGDV NGHKFSVSGE GEGDATYGKL  240
TLKFICTTGK LPVPWPTLVT TLTYGVQCFS RYPDHMKQHD FFKSAMPEGY IQERTIFFKD  300
DGNYKTRAEV KFEGDTLVNR IELKGIDFKE DGNILGHKLE YNFNPGYWSV LIVNKDSPIN  360
NLNDLLAKRK DLTFGNGDPN STSGFLVPGY YVFAKNINIS ASDFKRTVNA GHETNALAVA  420
NKQVDVATNN TENLDKLKTS APEKLKELKV IWKSPLIPGD PIVWRKNLSE TTKDKIYDFF  480
MNYGKTPEEK AVLERLGWAP FRASSDLQLV PIRQLALFKE MQSVKDNKGL NEQDKLAKTT  540
AIQAQLDDLD RLNNALSAMS SVSKAVQ                                       567

SEQ ID NO: 78           moltype = AA  length = 566
FEATURE                 Location/Qualifiers
source                  1..566
                        mol_type = protein
                        organism = synthetic construct
SEQUENCE: 78
MHHHHHHGSE EQEKALNFGI ISTESQQNLK PQWTPFLQDM EKKLGVKVNA FFAPDYAGII  60
QGMRFNKVDI AWYGNLSAME AVDRANGQVF AQTVAADADN VYIMADKQRN GIKANFKIRH  120
NIEDGGVQLA YHYQQNTPIG DGPVLLPDNH YLSTQSKLSK SKDPNEKRDH MVLLEFVTAA  180
GITLGMDELY KGGTGGSMVS KGEELFTGVV PILVELDGDV NGHKFSVSGE GEGDATYGKL  240
TLKFICTTGK LPVPWPTLVT TLTYGVQCFS RYPDHMKQHD FFKSAMPEGY IQERTIFFKD  300
DGNYKTRAEV KFEGDTLVNR IELKGIDFKE DGNILGHKLE YNFNPGYWSV LIVNKDSPIN  360
NLNDLLAKRK DLTFGNGDPN STSGFLVPGY YVFAKNNISA GKTPEEKAVL ERLGWAPFRA  420
SSDLQLVPIR QLALFKEMQS VKDNKGLNEQ DKLAKTTAIQ AQLDDLDRRN NARSAMSSVS  480
NYGKTPEEKA VLERLGWAPF RASSDLQLVP IRQLALFKEM QSVKDNKGLN EQDKLAKTTA  540
IQAQLDDLDR LNNALSAMSS VSKAVQ                                       566

SEQ ID NO: 79           moltype = AA  length = 16
FEATURE                 Location/Qualifiers
```

```
source                   1..16
                         mol_type = protein
                         organism = synthetic construct
SEQUENCE: 79
QTVAADGSSH NVYIMA                                                                16

SEQ ID NO: 80            moltype = AA   length = 16
FEATURE                  Location/Qualifiers
VARIANT                  7..8
                         note = any amino acid
source                   1..16
                         mol_type = protein
                         organism = synthetic construct
SEQUENCE: 80
QTVAADXXSH NVYIMA                                                                16

SEQ ID NO: 81            moltype = AA   length = 16
FEATURE                  Location/Qualifiers
VARIANT                  7
                         note = any amino acid
source                   1..16
                         mol_type = protein
                         organism = synthetic construct
SEQUENCE: 81
QTVAADXPSH NVYIMA                                                                16

SEQ ID NO: 82            moltype = AA   length = 16
FEATURE                  Location/Qualifiers
VARIANT                  8
                         note = any amino acid
source                   1..16
                         mol_type = protein
                         organism = synthetic construct
SEQUENCE: 82
QTVAADPXSH NVYIMA                                                                16

SEQ ID NO: 83            moltype = AA   length = 14
FEATURE                  Location/Qualifiers
VARIANT                  7..8
                         note = any amino acid
source                   1..14
                         mol_type = protein
                         organism = synthetic construct
SEQUENCE: 83
QTVAADXXNV YIMA                                                                  14

SEQ ID NO: 84            moltype = AA   length = 16
FEATURE                  Location/Qualifiers
VARIANT                  7..8
                         note = any amino acid
source                   1..16
                         mol_type = protein
                         organism = synthetic construct
SEQUENCE: 84
QTVAADXXSH NVYIMA                                                                16

SEQ ID NO: 85            moltype = AA   length = 16
FEATURE                  Location/Qualifiers
VARIANT                  7..8
                         note = any amino acid
source                   1..16
                         mol_type = protein
                         organism = synthetic construct
SEQUENCE: 85
VFQTVAXXSH NVYIMA                                                                16

SEQ ID NO: 86            moltype = AA   length = 16
FEATURE                  Location/Qualifiers
source                   1..16
                         mol_type = protein
                         organism = synthetic construct
SEQUENCE: 86
HKLEYNFNPG YWSVLI                                                                16

SEQ ID NO: 87            moltype = AA   length = 18
FEATURE                  Location/Qualifiers
VARIANT                  9..10
                         note = any amino acid
source                   1..18
```

```
                        mol_type = protein
                        organism = synthetic construct
SEQUENCE: 87
HKLEYNFNXX PGYWSVLI                                                         18

SEQ ID NO: 88           moltype = AA   length = 16
FEATURE                 Location/Qualifiers
VARIANT                 7..8
                        note = any amino acid
source                  1..16
                        mol_type = protein
                        organism = synthetic construct
SEQUENCE: 88
HKLEYNXXPG YWSVLI                                                           16

SEQ ID NO: 89           moltype = AA   length = 16
FEATURE                 Location/Qualifiers
VARIANT                 9..10
                        note = any amino acid
source                  1..16
                        mol_type = protein
                        organism = synthetic construct
SEQUENCE: 89
HKLEYNFNXX YWSVLI                                                           16

SEQ ID NO: 90           moltype = AA   length = 16
FEATURE                 Location/Qualifiers
VARIANT                 10
                        note = any amino acid
source                  1..16
                        mol_type = protein
                        organism = synthetic construct
SEQUENCE: 90
HKLEYNFNPX YWSVLI                                                           16

SEQ ID NO: 91           moltype = AA   length = 678
FEATURE                 Location/Qualifiers
source                  1..678
                        mol_type = protein
                        organism = synthetic construct
SEQUENCE: 91
MRGSHHHHHH GMASMTGGQQ MGRDLYDDDD KDRWGSKLEI FSWWAGDEGP ALEALIRLYK           60
QKYPGVEVIN ATVTGGAGVN ARAVLKTRML GGDPPDTFQV HAGMELIGTW VVANRMEDLS          120
ALFRQEGWLQ AFPKGLIDLI SYKGGIWSVP VNIHRSNVMW YLPAKLKEWG VNPPRTWDEF          180
LATCQTLKQK GLEAPLALGE NWTQQHLWES VALAVLGPDD WNNLWNGKLK FTDPKAVRAW          240
EVFGRVLDCA NKDAAGLSWQ QAVDRVVQGK AAFNVMGDWA AGYMTTTLKL KPGTDFAWAP          300
SPGTQGVFMM LSDSFGLPKG AKNRQNAINW LRLVGSKEGQ DTFNPLKGSI AARLDSDPSK          360
YGGSHNVYIM ADKQRNGIKA NFKIRHNIED GGVQLAYHYQ QNTPIGDGPV LLPDNHYLST          420
QSKLSKDPNE KRDHMVLLEF VTAAGITLGM DELYKGGTGG SMVSKGEELF TGVVPILVEL          480
DGDVNGHKFS VSGEGEGDAT YGKLTLKFIC TTGKLPVPWP TLVTTLTYGV QCFSRYPDHM          540
KQHDFFKSAM PEGYIQERTI FFKDDGNYKT RAEVKFEGDT LVNRIELKGI DFKEDGNILG          600
HKLEYNFNNP NAYGQSAMRD WRSNRIVGSL VHGAVAPESF MSQFGTVMEI FLQTRNPQAA          660
ANAAQAIADQ VGLGRLGQ                                                        678

SEQ ID NO: 92           moltype = AA   length = 678
FEATURE                 Location/Qualifiers
source                  1..678
                        mol_type = protein
                        organism = synthetic construct
SEQUENCE: 92
MRGSHHHHHH GMASMTGGQQ MGRDLYDDDD KDRWGSKLEI FSWWAGDEGP ALEALIRLYK           60
QKYPGVEVIN ATVTGGAGVN ARAVLKTRML GGDPPDTFQV HAGMELIGTW VVANRMEDLS          120
ALFRQEGWLQ AFPKGLIDLI SYKGGIWSVP VNIHRSNVMW YLPAKLKEWG VNPPRTWDEF          180
LATCQTLKQK GLEAPLALGE NWTQQHLWES VALAVLGPDD WNNLWNGKLK FTDPKAVRAW          240
EVFGRVLDCA NKDAAGLSWQ QAVDRVVQGK AAFNVMGDWA AGYMTTTLKL KPGTDFAWAP          300
SPGTQGVFMM LSDSFGLPKG AKNRQNAINW LRLVGSKEGQ DTFNPLKGSI AARLDSDPSK          360
YPASHNVYIM ADKQRNGIKA NFKIRHNIED GGVQLAYHYQ QNTPIGDGPV LLPDNHYLST          420
QSKLSKDPNE KRDHMVLLEF VTAAGITLGM DELYKGGTGG SMVSKGEELF TGVVPILVEL          480
DGDVNGHKFS VSGEGEGDAT YGKLTLKFIC TTGKLPVPWP TLVTTLTYGV QCFSRYPDHM          540
KQHDFFKSAM PEGYIQERTI FFKDDGNYKT RAEVKFEGDT LVNRIELKGI DFKEDGNILG          600
HKLEYNFNNP NAYGQSAMRD WRSNRIVGSL VHGAVAPESF MSQFGTVMEI FLQTRNPQAA          660
ANAAQAIADQ VGLGRLGQ                                                        678

SEQ ID NO: 93           moltype = AA   length = 678
FEATURE                 Location/Qualifiers
source                  1..678
                        mol_type = protein
                        organism = synthetic construct
SEQUENCE: 93
```

```
MRGSHHHHHH GMASMTGGQQ MGRDLYDDDD KDRWGSKLEI FSWWAGDEGP ALEALIRLYK    60
QKYPGVEVIN ATVTGGAGVN ARAVLKTRML GGDPPDTFQV HAGMELIGTW VVANRMEDLS   120
ALFRQEGWLQ AFPKGLIDLI SYKGGIWSVP VNIHRSNVMW YLPAKLKEWG VNPPRTWDEF   180
LATCQTLKQK GLEAPLALGE NWTQQHLWES VALAVLGPDD WNNLWNGKLK FTDPKAVRAW   240
ARAVLKTRML GGDPPDTFQV AAGMELIGTW VVANRMEDLS ALFRQEGWLQ AFPKGLIDLI   300
SYKGGIWSVP VNIHRSNVMW AKNRQNAINW LRLVGSKEGQ DTFNPLKGSI AARLDSDPSK   360
YGGSHNVYIM ADKQRNGIKA NFKIRHNIED GGVQLAYHYQ QNTPIGDGPV LLPDNHYLST   420
QSKLSKDPNE KRDHMVLLEF VTAAGITLGM DELYKGGTGG SMVSKGEELF TGVVPILVEL   480
DGDVNGHKFS VSGEGEGDAT YGKLTLKFIC TTGKLPVPWP TLVTTLTYGV QCFSRYPDHM   540
KQHDFFKSAM PEGYIQERTI FFKDDGNYKT RAEVKFEGDT LVNRIELKGI DFKEDGNILG   600
HKLEYNFNNP NAYGQSAMRD WRSNRIVGSL VHGAVAPESF MSQFGTVMEI FLQTRNPQAA   660
ANAAQAIADQ VGLGRLGQ                                                 678

SEQ ID NO: 94             moltype = AA   length = 678
FEATURE                   Location/Qualifiers
source                    1..678
                          mol_type = protein
                          organism = synthetic construct
SEQUENCE: 94
MRGSHHHHHH GMASMTGGQQ MGRDLYDDDD KDRWGSKLEI FSWWAGDEGP ALEALIRLYK    60
QKYPGVEVIN ATVTGGAGVN ARAVLKTRML GGDPPDTFQV HAGMELIGTW VVANRMEDLS   120
ALFRQEGWLQ AFPKGLIDLI SYKGGIWSVP VNIHRSNVMW YLPAKLKEWG VNPPRTWDEF   180
LATCQTLKQK GLEAPLALGE NWTQQHLWES VALAVLGPDD WNNLWNGKLK FTDPKAVRAW   240
EVFGRVLDCA NKDAAGLSWQ QAVDRVVQGK AAFNVMGDWA AGYMTTTLKL KPGTDFAWAP   300
SPGTQGVFMM LSDSFGLPKG AKNRQNAINW LRLVGSKEGQ DTFNPLKGSI AARLDSDPSK   360
YGGSHNVYIM ADKQRNGIKA NFKIRHNIED GGVQLAYHYQ QNTPIGDGPV LLPDNHYLST   420
QSKLSKDPNE KRDHMVLLEF VTAAGITLGM DELYKGGTGG SMVSKGEELF TGVVPILVEL   480
DGDVNGHKFS VSGEGEGDAT YGKLTLKFIC TTGKLPVPWP TLVTTLTYGV QCFSRYPDHM   540
KQHDFFKSAM PEGYIQERTI FFKDDGNYKT RAEVKFEGDT LVNRIELKGI DFKEDGNILG   600
HKLEYNFNNP NAYGQSAMRD WRSNRIVGSL VAGAVAPESF MSQFGTVMEI FLQTRNPQAA   660
ANAAQAIADQ VGLGRLGQ                                                 678

SEQ ID NO: 95             moltype = AA   length = 16
FEATURE                   Location/Qualifiers
VARIANT                   8..9
                          note = any amino acid
source                    1..16
                          mol_type = protein
                          organism = synthetic construct
SEQUENCE: 95
DSDPSKYXXS HNVYIM                                                    16

SEQ ID NO: 96             moltype = AA   length = 16
FEATURE                   Location/Qualifiers
VARIANT                   9
                          note = any amino acid
source                    1..16
                          mol_type = protein
                          organism = synthetic construct
SEQUENCE: 96
DSDPSKYPXS HNVYIM                                                    16

SEQ ID NO: 97             moltype = AA   length = 16
FEATURE                   Location/Qualifiers
VARIANT                   8
                          note = any amino acid
source                    1..16
                          mol_type = protein
                          organism = synthetic construct
SEQUENCE: 97
DSDPSKYXPS HNVYIM                                                    16

SEQ ID NO: 98             moltype = AA   length = 16
FEATURE                   Location/Qualifiers
VARIANT                   8..9
                          note = any amino acid
source                    1..16
                          mol_type = protein
                          organism = synthetic construct
SEQUENCE: 98
RLDSDPSXXS HNVYIM                                                    16

SEQ ID NO: 99             moltype = AA   length = 14
FEATURE                   Location/Qualifiers
VARIANT                   8..9
                          note = any amino acid
source                    1..14
                          mol_type = protein
                          organism = synthetic construct
```

```
SEQUENCE: 99
DSDPSKYXXN VYIM                                                        14

SEQ ID NO: 100          moltype = AA  length = 16
FEATURE                 Location/Qualifiers
VARIANT                 8..9
                        note = any amino acid
source                  1..16
                        mol_type = protein
                        organism = synthetic construct
SEQUENCE: 100
KLEYNFNXXN AYGQSA                                                      16

SEQ ID NO: 101          moltype = AA  length = 16
FEATURE                 Location/Qualifiers
VARIANT                 7..8
                        note = any amino acid
source                  1..16
                        mol_type = protein
                        organism = synthetic construct
SEQUENCE: 101
KLEYNFXXPN AYGQSA                                                      16

SEQ ID NO: 102          moltype = AA  length = 16
FEATURE                 Location/Qualifiers
VARIANT                 8..9
                        note = any amino acid
source                  1..16
                        mol_type = protein
                        organism = synthetic construct
SEQUENCE: 102
GHKLEYNXXN AYGQSA                                                      16

SEQ ID NO: 103          moltype = AA  length = 16
FEATURE                 Location/Qualifiers
VARIANT                 8
                        note = any amino acid
source                  1..16
                        mol_type = protein
                        organism = synthetic construct
SEQUENCE: 103
KLEYNFNXPN AYGQSA                                                      16

SEQ ID NO: 104          moltype = AA  length = 16
FEATURE                 Location/Qualifiers
VARIANT                 9
                        note = any amino acid
source                  1..16
                        mol_type = protein
                        organism = synthetic construct
SEQUENCE: 104
KLEYNFNPXN AYGQSA                                                      16

SEQ ID NO: 105          moltype = AA  length = 396
FEATURE                 Location/Qualifiers
source                  1..396
                        mol_type = protein
                        organism = Escherichia coli
SEQUENCE: 105
MKIKTGARIL ALSALTTMMF SASALAKIEE GKLVIWINGD KGYNGLAEVG KKFEKDTGIK        60
VTVEHPDKLE EKFPQVAATG DGPDIIFWAH DRFGGYAQSG LLAEITPDKA FQDKLYPFTW       120
DAVRYNGKLI AYPIAVEALS LIYNKDLLPN PPKTWEEIPA LDKELKAKGK SALMFNLQEP       180
YFTWPLIAAD GGYAFKYENG KYDIKDVGVD NAGAKAGLTF LVDLIKNKHM NADTDYSIAE       240
AAFNKGETAM TINGPWAWSN IDTSKVNYGV TVLPTFKGQP SKPFVGVLSA GINAASPNKE       300
LAKEFLENYL LTDEGLEAVN KDKPLGAVAL KSYEEELAKD PRIAATMENA QKGEIMPNIP       360
QMSAFWYAVR TAVINAASGR QTVDEALKDA QTRITK                                396

SEQ ID NO: 106          moltype = AA  length = 434
FEATURE                 Location/Qualifiers
source                  1..434
                        mol_type = protein
                        organism = Pyrococcus furiosus
SEQUENCE: 106
MRRATYAFAL LAILVLGVVA SGCIGGGTTT PTQTSPATQP TTTQTPTQTE TQAVECGSGK        60
VVIWHAMQPN ELEVFQSLAE EYMALCPEVE IVFEQKPNLE DALKAAIPTG QGPDLFIWAH       120
DWIGKFAEAG LLEPIDEYVT EDLLNEFAPM AQDAMQYKGH YYALPFAAET VAIIYNKEMV       180
SEPPKTFDEM KAIMEKYYDP ANEKYGIAWP INAYFISAIA QAFGGYYFDD KTEQPGLDKP       240
ETIEGFKFFF TEIWPYMAPT GDYNTQQSIF LEGRAPMMVN GPWSINDVKK AGINFGVVPL       300
PPIIKDGKEY WPRPYGGVKL IYFAAGIKNK DAAWKFAKWL TTSEESIKTL ALELGYIPVL       360
```

```
TKVLDDPEIK NDPVIYGFGQ AVQHAYLMPK SPKMSAVWGG VDGAINEILQ DPQNADIEGI    420
LKKYQQEILN NMQG                                                      434

SEQ ID NO: 107          moltype = AA  length = 338
FEATURE                 Location/Qualifiers
source                  1..338
                        mol_type = protein
                        organism = Escherichia coli
SEQUENCE: 107
MNAKIIASLA FTSMFSLSTL LNPAYAEEQE KALNFGIIST ESQQNLKPQW TPFLQDMEKK     60
LGVKVNAFFA PDYAGIIQGM RFNKVDIAWY GNLSAMEAVD RANGQVFAQT VAADGSPGYW    120
SVLIVNKDSP INNLNDLLAK RKDLTFGNGD PNSTSGFLVP GYYVFAKNNI SASDFKRTVN    180
AGHETNALAV ANKQVDVATN NTENLDKLKT SAPEKLKELK VIWKSPLIPG DPIVWRKNLS    240
ETTKDKIYDF FMNYGKTPEE KAVLERLGWA PFRASSDLQL VPIRQLALFK EMQSVKDNKG    300
LNEQDKLAKT TAIQAQLDDL DRLNNALSAM SSVSKAVQ                            338

SEQ ID NO: 108          moltype = AA  length = 302
FEATURE                 Location/Qualifiers
source                  1..302
                        mol_type = protein
                        organism = Escherichia coli
SEQUENCE: 108
MQLRKPATAI LALALSAGLA QADDAAPAAG STLDKIAKNG VIVVGHRESS VPFSYYDNQQ     60
KVVGYSQDYS NAIVEAVKKK LNKPDLQVKL IPITSQNRIP LLQNGTFDFE CGSTTNNVER    120
QKQAAFSDTI FVVGTRLLTK KGGDIKDFAN LKDAVVVTS GTTSEVLLNK LNEEQKMNMR     180
IISAKDHGDS FRTLESGRAV AFMMDDALLA GERAKAKKPD NWEIVGKPQS QEAYGCMLRK    240
DDPQFKKLMD DTIAQVQTSG EAEKWFDKWF KNPIPPKNLN MNFELSDEMK ALFKEPNDKA    300
LN                                                                   302

SEQ ID NO: 109          moltype = AA  length = 414
FEATURE                 Location/Qualifiers
source                  1..414
                        mol_type = protein
                        organism = Thermus thermophilus
SEQUENCE: 109
MRKWLLAIGM VLGLSALAQG GKLEIFSWWA GDEGPALEAL IRLYKQKYPG VEVINATVTG     60
GAGVNARAVL KTRMLGGDPP DTFQVHAGME LIGTWVVANR MEDLSALFRQ EGWLQAFPKG    120
LIDLISYKGG IWSVPVNIHR SNVMWYLPAK LKEWGVNPPR TWDEFLATCQ TLKQKGLEAP    180
LALGENWTQQ HLWESVALAV LGPDDWNNLW NGKLKFTDPK AVRAWEVFGR VLDCANKDAA    240
GLSWQQAVDR VVQGKAAFNV MGDWAAGYMT TTLKLKPGTD FAWAPSPGTQ GVFMMLSDSF    300
GLPKGAKNRQ NAINWLRLVG SKEGQDTFNP LKGSIAARLD SDPSKYNAYG QSAMRDWRSN    360
RIVGSLVHGA VAPESFMSQF GTVMEIFLQT RNPQAAANAA QAIADQVGLG RLGQ          414

SEQ ID NO: 110          moltype = AA  length = 318
FEATURE                 Location/Qualifiers
source                  1..318
                        mol_type = protein
                        organism = Rhizobium meliloti
SEQUENCE: 110
MIRTLSLKFM LAGAVCMATL TAGSAFAAEP ESCGTVRFSD VGWTDITATT ATATTILEAL     60
GYETDVKVLS VPVTYTSLKN KDIDVFLGNW MPTMEADIAP YREDKSVETV RENLAGAKYT    120
LATNAKGAEL GIKDFKDIAA HKDELDGKIY GIEPGNDGNR LIIDMVEKGT FDLKGFEVVE    180
SSEQGMLAQV ARAEKSGDPI VFLGWEPHPM NANFKLTYLS GGDDVFGPNY GGATVHTNVR    240
AGYTTECPNV GKLLQNLSFS LQMENEIMGK ILNDGEDPEK AAAAWLKDNP QSIEPWLSGV    300
ATKDGGDGLA AVKAALGL                                                  318

SEQ ID NO: 111          moltype = AA  length = 249
FEATURE                 Location/Qualifiers
source                  1..249
                        mol_type = protein
                        organism = Geobacillus stearothermophilus
SEQUENCE: 111
MGGGRSTETS SSSGGDGGAT KKKVVVGTDA AFAPPFEYMQK GKIVGFDVDL LDAVMKAAGL    60
DYELKNIGWD PLFASLQSKE VDMGISGITI TDERKQSYDF SDPYFEATQV ILVKQGSPVK    120
NALDLKGTIG VQNATTGQEA AEKLFGKGPH IKKFETTVVA IMELLNGGVD AVITDNAVAN    180
EYVKNNPNKK LQVIEDPKNF ASEYYGMIFP KNSELKAKVD EALKNVINSG KYTEIYKKWF    240
GKEPKLDRL                                                            249

SEQ ID NO: 112          moltype = AA  length = 370
FEATURE                 Location/Qualifiers
source                  1..370
                        mol_type = protein
                        organism = Agrobacterium tumefaciens
SEQUENCE: 112
MKKSLLSAVA LTAMVAFGGS AWADVVIAVG APLTGPNAAF GAQIQKGAEQ AAKDINAAGG     60
INGEQIKIVL GDDVSDPKQG ISVANKFVAD GVKFVVGHFN SGVSIPASEV YAENGILEIT    120
PAATNPVFTE RGLWNTFRTC GRDDQQGGIA GKYLADHFKD AKVAIIHDKT PYGQGLADET    180
KKAANAAGVT EVMYEGVNVG DKDFSALISK MKEAGVSIIY WGGLHTEAGL IIRQAADQGL    240
KAKLVSGDGI VSNELASIAG DAVEGTLNTF GPDPTLRPEN KELVEKFKAA GFNPEAYTLY    300
```

```
SYAAMQAIAG AAKAAGSVEP EKVAEALKKG SFPTALGEIS FDEKGDPKLP GYVMYEWKKG    360
PDGKFTYIQQ                                                          370

SEQ ID NO: 113          moltype = AA  length = 367
FEATURE                 Location/Qualifiers
source                  1..367
                        mol_type = protein
                        organism = Escherichia coli
SEQUENCE: 113
MNIKGKALLA GCIALAFSNM ALAEDIKVAV VGAMSGPVAQ YGDQEFTGAE QAVADINAKG     60
GIKGNKLQIV KYDDACDPKQ AVAVANKVVN DGIKYVIGHL CSSSTQPASD IYEDEGILMI    120
TPAATAPELT ARGYQLILRT TGLDSDQGPT AAKYILEKVK PQRIAIVHDK QQYGEGLARA    180
VQDGLKKGNA NVVFFDGITA GEKDFSTLVA RLKKENIDFV YYGGYHPEMG QILRQARAAG    240
LKTQFMGPEG VANVSLSNIA GESAEGLLVT KPKNYDQVPA NKPIVDAIKA KKQDPSGAFV    300
WTTYAALQSL QAGLNQSDDP AEIAKYLKAN SVDTVMGPLT WDEKGDLKGF EFGVFDWHAN    360
GTATDAK                                                             367

SEQ ID NO: 114          moltype = AA  length = 677
FEATURE                 Location/Qualifiers
source                  1..677
                        mol_type = protein
                        organism = synthetic construct
SEQUENCE: 114
MRGSHHHHHH GMASMTGGQQ MGRDLYDDDD KDRWGSKLEI FSWWAGDEGP ALEALIRLYK     60
QKYPGVEVIN ATVTGGAGVN ARAVLKTRML GGDPPDTFQV AAGMELIGTW VVANRMEDLS    120
ALFRQEGWLQ AFPKGLIDLI SYKGGIWSVP VNIHRSNVMW YLPAKLKEWG VNPPRTWEFL    180
ATCQTLKQKG LEAPLALGEN WTQQHLWESV ALAVLGPDDW NNLWNGKLKF TDPKAVRAWE    240
VFGRVLDCAN KDAAGLSWQQ AVDRVVQGKA AFNVMGDWAA GYMTTTLKLK PGTDFAWAPS    300
PGTQGVFMMV SDSFGLPKGA KNRQNAINWL RLVGSKEGQD TFNPLKGSIA ARLDSDPSKY    360
PASHNVYIMA DKQRNGIKAN FKIRHNIEDG GVQLAYHYQQ NTPIGDGPVL LPDNHYLSTQ    420
SKLSKDPNEK RDHMVLLEFV TAAGITLGMD ELYKGGTGGS MVSKGEELFT GVVPILVELD    480
GDVNGHKFSV SGEGEGDATY GKLTLKFICT TGKLPVPWPT LVTTLTYGVQ CFSRYPDHMK    540
QHDFFKSAMP EGYIQERTIF FKDDGNYKTR AEVKFEGDTL VNRIELKGID FKEDGNILGH    600
KLEYNFNNPN AYGQSAMRDW RSNRIVGSLV AGAVAPESFM SQFGTVMEIF LQTRNPQAAA    660
NAAQAIADQV GLGRLGQ                                                  677

SEQ ID NO: 115          moltype = AA  length = 7
FEATURE                 Location/Qualifiers
VARIANT                 1
                        note = any amino acid
source                  1..7
                        mol_type = protein
                        organism = synthetic construct
SEQUENCE: 115
XPSHNVY                                                               7

SEQ ID NO: 116          moltype = AA  length = 7
FEATURE                 Location/Qualifiers
VARIANT                 1..2
                        note = any amino acid
source                  1..7
                        mol_type = protein
                        organism = synthetic construct
SEQUENCE: 116
XXSHNVY                                                               7

SEQ ID NO: 117          moltype = AA  length = 7
FEATURE                 Location/Qualifiers
VARIANT                 1..2
                        note = any amino acid
source                  1..7
                        mol_type = protein
                        organism = synthetic construct
SEQUENCE: 117
XXSHNVF                                                               7

SEQ ID NO: 118          moltype = AA  length = 7
FEATURE                 Location/Qualifiers
VARIANT                 2
                        note = any amino acid
source                  1..7
                        mol_type = protein
                        organism = synthetic construct
SEQUENCE: 118
PXSHNVF                                                               7

SEQ ID NO: 119          moltype = AA  length = 7
FEATURE                 Location/Qualifiers
VARIANT                 2
```

```
                      note = any amino acid
source                1..7
                      mol_type = protein
                      organism = synthetic construct
SEQUENCE: 119
PXSYNVF                                                                 7

SEQ ID NO: 120        moltype = AA  length = 7
FEATURE               Location/Qualifiers
VARIANT               1..2
                      note = any amino acid
source                1..7
                      mol_type = protein
                      organism = synthetic construct
SEQUENCE: 120
XXSYNVF                                                                 7

SEQ ID NO: 121        moltype = AA  length = 7
FEATURE               Location/Qualifiers
VARIANT               2
                      note = any amino acid
source                1..7
                      mol_type = protein
                      organism = synthetic construct
SEQUENCE: 121
PXSYNVF                                                                 7

SEQ ID NO: 122        moltype = AA  length = 7
FEATURE               Location/Qualifiers
VARIANT               1..2
                      note = any amino acid
source                1..7
                      mol_type = protein
                      organism = synthetic construct
SEQUENCE: 122
XXSYNVF                                                                 7

SEQ ID NO: 123        moltype = AA  length = 7
FEATURE               Location/Qualifiers
VARIANT               2
                      note = any amino acid
VARIANT               4
                      note = any amino acid
source                1..7
                      mol_type = protein
                      organism = synthetic construct
SEQUENCE: 123
PXSXNVY                                                                 7

SEQ ID NO: 124        moltype = AA  length = 7
FEATURE               Location/Qualifiers
VARIANT               2
                      note = any amino acid
VARIANT               5
                      note = any amino acid
source                1..7
                      mol_type = protein
                      organism = synthetic construct
SEQUENCE: 124
PXSHXVY                                                                 7

SEQ ID NO: 125        moltype = AA  length = 7
FEATURE               Location/Qualifiers
VARIANT               2
                      note = any amino acid
VARIANT               6
                      note = any amino acid
source                1..7
                      mol_type = protein
                      organism = synthetic construct
SEQUENCE: 125
PXSHNXY                                                                 7

SEQ ID NO: 126        moltype = AA  length = 7
FEATURE               Location/Qualifiers
VARIANT               2
                      note = any amino acid
VARIANT               7
                      note = any amino acid
```

| | | |
|---|---|---|
| source | 1..7<br>mol_type = protein<br>organism = synthetic construct | |
| SEQUENCE: 126<br>PXSHNVX | | 7 |
| SEQ ID NO: 127<br>SEQUENCE: 127<br>000 | moltype =   length = | |
| SEQ ID NO: 128<br>SEQUENCE: 128<br>000 | moltype =   length = | |
| SEQ ID NO: 129<br>SEQUENCE: 129<br>000 | moltype =   length = | |
| SEQ ID NO: 130<br>SEQUENCE: 130<br>000 | moltype =   length = | |
| SEQ ID NO: 131<br>SEQUENCE: 131<br>000 | moltype =   length = | |
| SEQ ID NO: 132<br>SEQUENCE: 132<br>000 | moltype =   length = | |
| SEQ ID NO: 133<br>SEQUENCE: 133<br>000 | moltype =   length = | |
| SEQ ID NO: 134<br>FEATURE<br>VARIANT<br><br>source | moltype = AA  length = 5<br>Location/Qualifiers<br>4<br>note = any amino acid<br>1..5<br>mol_type = protein<br>organism = synthetic construct | |
| SEQUENCE: 134<br>FNPXY | | 5 |
| SEQ ID NO: 135<br>FEATURE<br>VARIANT<br><br>source | moltype = AA  length = 5<br>Location/Qualifiers<br>3<br>note = any amino acid<br>1..5<br>mol_type = protein<br>organism = synthetic construct | |
| SEQUENCE: 135<br>FNXPY | | 5 |
| SEQ ID NO: 136<br>SEQUENCE: 136<br>000 | moltype =   length = | |
| SEQ ID NO: 137<br>SEQUENCE: 137<br>000 | moltype =   length = | |
| SEQ ID NO: 138<br>SEQUENCE: 138<br>000 | moltype =   length = | |
| SEQ ID NO: 139<br>SEQUENCE: 139<br>000 | moltype =   length = | |
| SEQ ID NO: 140<br>SEQUENCE: 140<br>000 | moltype =   length = | |
| SEQ ID NO: 141<br>SEQUENCE: 141<br>000 | moltype =   length = | |
| SEQ ID NO: 142 | moltype =   length = | |

```
SEQUENCE: 142
000

SEQ ID NO: 143          moltype =    length =
SEQUENCE: 143
000

SEQ ID NO: 144          moltype =    length =
SEQUENCE: 144
000

SEQ ID NO: 145          moltype =    length =
SEQUENCE: 145
000

SEQ ID NO: 146          moltype =    length =
SEQUENCE: 146
000

SEQ ID NO: 147          moltype = AA   length = 4
FEATURE                 Location/Qualifiers
source                  1..4
                        mol_type = protein
                        organism = synthetic construct
SEQUENCE: 147
NPCK                                                                   4

SEQ ID NO: 148          moltype = AA   length = 5
FEATURE                 Location/Qualifiers
VARIANT                 3
                        note = any amino acid
source                  1..5
                        mol_type = protein
                        organism = synthetic construct
SEQUENCE: 148
PPXSH                                                                  5

SEQ ID NO: 149          moltype = AA   length = 6
FEATURE                 Location/Qualifiers
VARIANT                 3..4
                        note = any amino acid
source                  1..6
                        mol_type = protein
                        organism = synthetic construct
SEQUENCE: 149
PPXXSH                                                                 6

SEQ ID NO: 150          moltype = AA   length = 6
FEATURE                 Location/Qualifiers
VARIANT                 4
                        note = any amino acid
source                  1..6
                        mol_type = protein
                        organism = synthetic construct
SEQUENCE: 150
PPPXSH                                                                 6

SEQ ID NO: 151          moltype = AA   length = 6
FEATURE                 Location/Qualifiers
VARIANT                 3
                        note = any amino acid
source                  1..6
                        mol_type = protein
                        organism = synthetic construct
SEQUENCE: 151
PPXPSH                                                                 6

SEQ ID NO: 152          moltype =    length =
SEQUENCE: 152
000

SEQ ID NO: 153          moltype =    length =
SEQUENCE: 153
000

SEQ ID NO: 154          moltype = AA   length = 5
FEATURE                 Location/Qualifiers
VARIANT                 3
                        note = any amino acid
```

```
                            -continued source                  1..5
                        mol_type = protein
                        organism = synthetic construct
SEQUENCE: 154
FNXKN                                                                   5

SEQ ID NO: 155          moltype = AA   length = 6
FEATURE                 Location/Qualifiers
VARIANT                 3..4
                        note = any amino acid
source                  1..6
                        mol_type = protein
                        organism = synthetic construct
SEQUENCE: 155
FNXXKN                                                                  6

SEQ ID NO: 156          moltype = AA   length = 6
FEATURE                 Location/Qualifiers
VARIANT                 3
                        note = any amino acid
source                  1..6
                        mol_type = protein
                        organism = synthetic construct
SEQUENCE: 156
FNXPKN                                                                  6

SEQ ID NO: 157          moltype = AA   length = 6
FEATURE                 Location/Qualifiers
VARIANT                 4
                        note = any amino acid
source                  1..6
                        mol_type = protein
                        organism = synthetic construct
SEQUENCE: 157
FNPXKN                                                                  6

SEQ ID NO: 158          moltype =    length =
SEQUENCE: 158
000

SEQ ID NO: 159          moltype = AA   length = 7
FEATURE                 Location/Qualifiers
source                  1..7
                        mol_type = protein
                        organism = synthetic construct
SEQUENCE: 159
NADGSSH                                                                 7

SEQ ID NO: 160          moltype = AA   length = 6
FEATURE                 Location/Qualifiers
VARIANT                 3..4
                        note = any amino acid
source                  1..6
                        mol_type = protein
                        organism = synthetic construct
SEQUENCE: 160
ADXXSH                                                                  6

SEQ ID NO: 161          moltype = AA   length = 6
FEATURE                 Location/Qualifiers
VARIANT                 3
                        note = any amino acid
source                  1..6
                        mol_type = protein
                        organism = synthetic construct
SEQUENCE: 161
ADXPSH                                                                  6

SEQ ID NO: 162          moltype = AA   length = 6
FEATURE                 Location/Qualifiers
VARIANT                 4
                        note = any amino acid
source                  1..6
                        mol_type = protein
                        organism = synthetic construct
SEQUENCE: 162
ADPXSH                                                                  6

SEQ ID NO: 163          moltype =    length =
```

```
SEQUENCE: 163
000

SEQ ID NO: 164        moltype = AA  length = 6
FEATURE               Location/Qualifiers
VARIANT               3..4
                      note = any amino acid
source                1..6
                      mol_type = protein
                      organism = synthetic construct
SEQUENCE: 164
ADXXSH                                                                    6

SEQ ID NO: 165        moltype = AA  length = 4
FEATURE               Location/Qualifiers
source                1..4
                      mol_type = protein
                      organism = synthetic construct
SEQUENCE: 165
FNPG                                                                      4

SEQ ID NO: 166        moltype = AA  length = 6
FEATURE               Location/Qualifiers
VARIANT               3..4
                      note = any amino acid
source                1..6
                      mol_type = protein
                      organism = synthetic construct
SEQUENCE: 166
FNXXPG                                                                    6

SEQ ID NO: 167        moltype =   length =
SEQUENCE: 167
000

SEQ ID NO: 168        moltype =   length =
SEQUENCE: 168
000

SEQ ID NO: 169        moltype =   length =
SEQUENCE: 169
000

SEQ ID NO: 170        moltype = AA  length = 6
FEATURE               Location/Qualifiers
VARIANT               3..4
                      note = any amino acid
source                1..6
                      mol_type = protein
                      organism = synthetic construct
SEQUENCE: 170
KYXXSH                                                                    6

SEQ ID NO: 171        moltype = AA  length = 6
FEATURE               Location/Qualifiers
VARIANT               4
                      note = any amino acid
source                1..6
                      mol_type = protein
                      organism = synthetic construct
SEQUENCE: 171
KYPXSH                                                                    6

SEQ ID NO: 172        moltype = AA  length = 6
FEATURE               Location/Qualifiers
VARIANT               3
                      note = any amino acid
source                1..6
                      mol_type = protein
                      organism = synthetic construct
SEQUENCE: 172
KYXPSH                                                                    6

SEQ ID NO: 173        moltype =   length =
SEQUENCE: 173
000

SEQ ID NO: 174        moltype =   length =
SEQUENCE: 174
```

```
000

SEQ ID NO: 175         moltype =    length =
SEQUENCE: 175
000

SEQ ID NO: 176         moltype = AA   length = 606
FEATURE                Location/Qualifiers
source                 1..606
                       mol_type = protein
                       organism = synthetic construct
SEQUENCE: 176
METDTLLLWV LLLWVPGSTG DRSAAGSTLD KIAKNGVIVV GHRESSVPFS YYDNQQKVVG    60
YSQDYSNAIV EAVKKKLNKP DLQVKLIPIT SQNRIPLLQN GTFDFECGST TNNVERQKQA   120
AFSDTIFVVG TRLLTKKGGD IKDFANLKDK AVVVTSGTTS EVLLNKLNEE QKMNMRIISA   180
KDHGDSFRTL ESGRAVAFMM DDVLLAGERA KAKKPDNWEI VGKPQSQEAY GCMLRKDDPQ   240
FKKLMDDTIA QVQTSGEAEK WFDKWFKNPI LVSHNVYITA DKQKNGIKAN FKIRHNVEDG   300
SVQLADHYQQ NTPIGDGPVL LPDNHYLSTQ SVLSKDPNEK RDHMVLLEFV TAAGITLGMD   360
ELYKGGTGGS MSKGEELFTG VVPILVELDG DVNGHKFSVR GEGEGDATNG KLTLKFICTT   420
GKLPVPWPTL VTTLTYGVQC FSRYPDHMKQ HDFFKSAMPE GYVQERTISF KDDGTYKTRA   480
EVKFEGDTLV NRIELKGIDF KEDGNILGHK LEYNFNNPLN MNFELSDEMK ALFKEPNDKA   540
LKLQVDEQKL ISEEDLNAVG QDTQEVIVVP HSLPFKVVVI SAILALVVLT IISLIILIML   600
WQKKPR                                                              606

SEQ ID NO: 177         moltype = AA   length = 606
FEATURE                Location/Qualifiers
source                 1..606
                       mol_type = protein
                       organism = synthetic construct
SEQUENCE: 177
METDTLLLWV LLLWVPGSTG DRSAAGSTLD KIAKNGVIVV GHRESSVPFS YYDNQQKVVG    60
YSQDYSNAIV EAVKKKLNKP DLQVKLIPIT SQNRIPLLQN GTFDFECGST TNNVERQKQA   120
AFSDTIFVVG TRLLTKKGGD IKDFANLKDK AVVVTSGTTS EVLLNKLNEE QKMNMRIISA   180
KDHGDSFRTL ESGRAVAFMM DDSLLAGERA KAKKPDNWEI VGKPQSQEAY GCMLRKDDPQ   240
FKKLMDDTIA QVQTSGEAEK WFDKWFKNPI LVSHNVYITA DKQKNGIKAN FKIRHNVEDG   300
SVQLADHYQQ NTPIGDGPVL LPDNHYLSTQ SVLSKDPNEK RDHMVLLEFV TAAGITLGMD   360
ELYKGGTGGS MSKGEELFTG VVPILVELDG DVNGHKFSVR GEGEGDATNG KLTLKFICTT   420
GKLPVPWPTL VTTLTYGVQC FSRYPDHMKQ HDFFKSAMPE GYVQERTISF KDDGTYKTRA   480
EVKFEGDTLV NRIELKGIDF KEDGNILGHK LEYNFNNPLN MNFELSDEMK ALFKEPNDKA   540
LKLQVDEQKL ISEEDLNAVG QDTQEVIVVP HSLPFKVVVI SAILALVVLT IISLIILIML   600
WQKKPR                                                              606

SEQ ID NO: 178         moltype = AA   length = 606
FEATURE                Location/Qualifiers
source                 1..606
                       mol_type = protein
                       organism = synthetic construct
SEQUENCE: 178
METDTLLLWV LLLWVPGSTG DRSAAGSTLD KIAKNGVIVV GHRESSVPFS YYDNQQKVVG    60
YSQDYSNAIV EAVKKKLNKP DLQVKLIPIT AQNRIPLLQN GTFDFECGST TNNVERQKQA   120
AFSDTIFVVG TRLLTKKGGD IKDFANLKDK AVVVTSGTTS EVLLNKLNEE QKMNMRIISA   180
KDHGDSFRTL ESGRAVAFMM DDVLLAGERA KAKKPDNWEI VGKPQSQEAY GCMLRKDDPQ   240
FKKLMDDTIA QVQTSGEAEK WFDKWFKNPI LVSHNVYITA DKQKNGIKAN FKIRHNVEDG   300
SVQLADHYQQ NTPIGDGPVL LPDNHYLSTQ SVLSKDPNEK RDHMVLLEFV TAAGITLGMD   360
ELYKGGTGGS MSKGEELFTG VVPILVELDG DVNGHKFSVR GEGEGDATNG KLTLKFICTT   420
GKLPVPWPTL VTTLTYGVQC FSRYPDHMKQ HDFFKSAMPE GYVQERTISF KDDGTYKTRA   480
EVKFEGDTLV NRIELKGIDF KEDGNILGHK LEYNFNNPLN MNFELSDEMK ALFKEPNDKA   540
LKLQVDEQKL ISEEDLNAVG QDTQEVIVVP HSLPFKVVVI SAILALVVLT IISLIILIML   600
WQKKPR                                                              606

SEQ ID NO: 179         moltype = AA   length = 606
FEATURE                Location/Qualifiers
source                 1..606
                       mol_type = protein
                       organism = synthetic construct
SEQUENCE: 179
METDTLLLWV LLLWVPGSTG DRSAAGSTLD KIAKNGVIVV GHRESSVPFS YYDNQQKVVG    60
YSQDYSNAIV EAVKKKLNKP DLQVKLIPIT SQNRIPLLQN GTFDFECGST TNNVERQKQA   120
AFSDTIFVVG TRLLTKKGGD IKDFANLKDK AVVVTSGTTS EVLLNKLNEE QKMNMRIISA   180
KDHGDSFRTL ESGRAVAFMM DDVLLAGERA KAKKPDNWEI VGKPQSQEAY GCMLRKDDPQ   240
FKKLMDDTIA QVQTSGEAEK WFDKWFKNPI LVSHNVYITA DKQKNGIKAN FKIRHNVEDG   300
SVQLADHYQQ NTPIGDGPVL LPDNHYLSYQ SVLSKDPNEK RDHMVLLEFV TAAGITLGMD   360
ELYKGGTGGS MSKGEELFTG VVPILVELDG DVNGHKFSVR GEGEGDATNG KLTLKLICTT   420
GKLPVPWPTL VTTLGYGVQC FARYPDHMKQ HDFFKSAMPE GYVQERTISF KDDGTYKTRA   480
EVKFEGDTLV NRIELKGIDF KEDGNILGHK LEYNFNNPLN MNFELSDEMK ALFKEPNDKA   540
LKLQVDEQKL ISEEDLNAVG QDTQEVIVVP HSLPFKVVVI SAILALVVLT IISLIILIML   600
WQKKPR                                                              606

SEQ ID NO: 180         moltype = AA   length = 606
```

```
FEATURE                 Location/Qualifiers
source                  1..606
                        mol_type = protein
                        organism = synthetic construct
SEQUENCE: 180
METDTLLLWV LLLWVPGSTG DRSAAGSTLD KIAKNGVIVV GHRESSVPFS YYDNQQKVVG   60
YSQDYSNAIV EAVKKKLNKP DLQVKLIPIT AQNRIPLLQN GTFDFECGST TNNVERQKQA  120
AFSDTIFVVG TRLLTKKGGD IKDFANLKDK AVVTSGTTS  EVLLNKLNEE QKMNMRIISA  180
KDHGDSFRTL ESGRAVAFMM DDSLLAGERA KAKKPDNWEI VGKPQSQEAY GCMLRKDDPQ  240
FKKLMDDTIA QVQTSGEAEK WFDKWFKNPI LVSHNVYITA DKQKNGIKAN FKIRHNVEDG  300
SVQLADHYQQ NTPIGDGPVL LPDNHYLSYQ SVLSKDPNEK RDHMVLLEFV TAAGITLGMD  360
ELYKGGTGGS MSKGEELFTG VVPILVELDG DVNGHKFSVR GEGEGDATNG KLTLKLICTT  420
GKLPVPWPTL VTTLGYGVQC FARYPDHMKQ HDFFKSAMPE GYVQERTISF KDDGTYKTRA  480
EVKFEGDTLV NRIELKGIDF KEDGNILGHK LEYNFNNPLN MNFELSDEMK ALFKEPNDKA  540
LKLQVDEQKL ISEEDLNAVG QDTQEVIVVP HSLPFKVVVI SAILALVVLT IISLIILIML  600
WQKKPR                                                              606

SEQ ID NO: 181          moltype = AA   length = 606
FEATURE                 Location/Qualifiers
source                  1..606
                        mol_type = protein
                        organism = synthetic construct
SEQUENCE: 181
METDTLLLWV LLLWVPGSTG DRSAAGSTLD KIAKNGVIVV GHRESSVPFS YYDNQQKVVG   60
YSQDYSNAIV EAVKKKLNKP DLQVKLIPIT SQNRIPLLQN GTFDFECGST TNNVERQKQA  120
AFSDTIFVVG TRLLTKKGGD IKDFANLKDK AVVTSGTTS  EVLLNKLNEE QKMNMRIISA  180
KDHGDSFRTL ESGRAVAFMM DDVLLAGERA KAKKPDNWEI VGKPQSQEAY GCMLRKDDPQ  240
FKKLMDDTIA QVQTSGEAEK WFDKWFKNPI LVSHNVYITA DKQKNGIKAN FKIRHNVEDG  300
SVQLADHYQQ NTPIGDGPVL LPDNHYLSYQ SVLSKDPNEK RDHMVLLEFV TAAGITLGMD  360
ELYKGGTGGS MSKGEELFTG VVPILVELDG DVNGHKFSVR GEGEGDATNG KLTLKLICTT  420
GKLPVPWPTL VTTLGYGVQC FARYPDHMKQ HDFFKSAMPE GYVQERTISF KDDGTYKTRA  480
EVKFEGDTLV NRIELKGIDF KEDGNILGHK LEYNFNNPLN MNFELSDEMK ALFKEPNDKA  540
LKLQVDEQKL ISEEDLNAVG QDTQEVIVVP HSLPFKVVVI SAILALVVLT IISLIILIML  600
WQKKPR                                                              606

SEQ ID NO: 182          moltype = AA   length = 606
FEATURE                 Location/Qualifiers
source                  1..606
                        mol_type = protein
                        organism = synthetic construct
SEQUENCE: 182
METDTLLLWV LLLWVPGSTG DRSAAGSTLD KIAKNGVIVV GHRESSVPFS YYDNQQKVVG   60
YSQDYSNAIV EAVKKKLNKP DLQVKLIPIT SQNRIPLLQN GTFDFECGST TNNVERQKQA  120
AFSDTIFVVG TRLLTKKGGD IKDFANLKDK AVVTSGTTS  EVLLNKLNEE QKMNMRIISA  180
KDHGDSFRTL ESGRAVAFMM DDVLLAGERA KAKKPDNWEI VGKPQSQEAY GCMLRKDDPQ  240
FKKLMDDTIA QVQTSGEAEK WFDKWFKNPI LGYHNIYITA DKQKNGIKAN FKIRHNVEDG  300
SVQLADHYQQ NTPIGDGPVL LPDNHYLSTQ SVLSKDPNEK RDHMVLLEFV TAAGITLGMD  360
ELYKGGTGGS MSKGEELFTG VVPILVELDG DVNGHKFSVR GEGEGDATNG KLTLKFICTT  420
GKLPVPWPTL VTTLSHGVQC FSRYPDHMKQ HDFFKSAMPE GYVQERTISF KDDGTYKTRA  480
EVKFEGDTLV NRIELKGIDF KEDGNILGHK LEYNFNEQLN MNFELSDEMK ALFKEPNDKA  540
LKLQVDEQKL ISEEDLNAVG QDTQEVIVVP HSLPFKVVVI SAILALVVLT IISLIILIML  600
WQKKPR                                                              606

SEQ ID NO: 183          moltype = AA   length = 728
FEATURE                 Location/Qualifiers
source                  1..728
                        mol_type = protein
                        organism = synthetic construct
SEQUENCE: 183
METDTLLLWV LLLWVPGSTG DRSKLEIFSW WAGDEGPALE ALIRLYKQKY PGVEVINATV   60
TGGAGVNARA VLKTRMLGGD PPDTFQVAAG MELIGTWVVA NRMEDLSALF RQEGWLQAFP  120
KGLIDLISYK GGIWSVPVNI HRSNVMWYLP AKLKEWGVNP PRTWDEFLAT CQTLKQKGLE  180
APLALGENWT QQHLWESVAL AVLGPDDWNN LWNGKLKFTD PKAVRAWEVF GRVLDCANKD  240
AAGLSWQQAV DRVVQGKAAF NVMGDWAAGY MTTTLKLKPG TDFAWAPSPG TQGVFMMLSD  300
SFGLPKGAKN RQNAINWLRL VGSKEGQDTF NPLKGSIAAR LDSDPSKYPA SHNVYITADK  360
QKNGIKANFK IRHNVEDGSV QLADHYQQNT PIGDGPVLLP DNHYLSTQSV LSKDPNEKRD  420
HMVLLEFVTA AGITLGMDEL YKGGTGGSMS KGEELFTGVV PILVELDGDV NGHKFSVRGE  480
GEGDATNGKL TLKFICTTGK LPVPWPTLVT TLTYGVQCFS RYPDHMKQHD FFKSAMPEGY  540
VQERTISFKD DGTYKTRAEV KFEGDTLVNR IELKGIDFKE DGNILGHKLE YNFNNPNAYG  600
QSAMRDWRSN RIVGSLVAGA VAPESFMSQF GTVMEIFLQT RNPQAAANAA QAIADQVGLG  660
RLGQLQVDEQ KLISEEDLNA VGQDTQEVIV VPHSLPFKVV VISAILALVV LTIISLIILI  720
MLWQKKPR                                                            728

SEQ ID NO: 184          moltype = AA   length = 650
FEATURE                 Location/Qualifiers
source                  1..650
                        mol_type = protein
                        organism = synthetic construct
SEQUENCE: 184
```

```
METDTLLLWV LLLWVPGSTG DRSESINFVS WGGSTQDAQK QAWADPFSKA SGITVVQDGP   60
TDYGKLKAMV ESGNVQWDVV DVEADFALRA AAEGLLEPLD FSVIQRDKID PRFVSDHGVG  120
SFLFSFVLGY NEGKLGASKP QDWTALFDTK TYPGKRALYK WPSPGVLELA LLADGVPADK  180
LYPLDLDRAF KKLDTIKKDI VWWGGGAQSQ QLLASGEVSM GQFWNGRIHA LQEDGAPVGV  240
SWKQNLVMAD ILVVPKGTKN KAAAMKFLAS ASSAKGQDDF SALTAYAPVN IDSVQRLDLA  300
QVRITADKQK NGIMANFKIR HNVEDGSVQL ADHYQQNTPI GDGPVLLPDN HYLSTQSVLS  360
KDPNEKRDHM VLLEFVTAAG ITLGMDELYK GGTGGSMSKG EELFTGVVPI LVELDGDVNG  420
HKFSVRGEGE GDATNGKLTL KFICTTGKLP VPWPTLVTTL TYGVQCFSRY PDHMKQHFF   480
KSAMPEGYVQ ERTISFKDDG TYKTRAEVKF EGDTLVNRIE LKGIDFKEDG NILGHKLEYN  540
WNANLAPNLP TAYVKDQITL DFAYWAKNGP AIATRWNEWL VKLQVDLQVD EQKLISEEDL  600
NAVGQDTQEV IVVPHSLPFK VVVISAILAL VVLTIISLII LIMLWQKKPR            650

SEQ ID NO: 185              moltype = AA  length = 560
FEATURE                     Location/Qualifiers
source                      1..560
                            mol_type = protein
                            organism = synthetic construct
SEQUENCE: 185
MHHHHHGYP YDVPDYAGAQ PARSANDTVV VGSIIFTEGI IVANMVAEMI EAHTDLKVVR   60
KLNLGGVNVN FEAIKRGGAN NGIDIYVEYT GHGLVDILGF PEPNVYITAD KQKNGIKANF  120
KIRHNVEDGS VQLADHYQQN TPIGDGPVLL PDNHYLSTQS VLSKDPNEKR DHMVLLEFVT  180
AAGITLGMDE LYKGGTGGSM SKGEELFTGV VPILVELDGD VNGHKFSVRG EGEGDATNGK  240
LTLKFICTTG KLPVPWPTLV TTLTYGVQCF SRYPDHMKQH DFFKSAMPEG YVQERTISFK  300
DDGTYKTRAE VKFEGDTLVN RIELKGIDFK EDGNILGHKL EYNFPPPATT DPEGAYETVK  360
KEYKRKWNIV WLKPLGFNNT YTLTVKDELA KQYNLKTFSD LAKISDKLIL GATMFFLEGP  420
DGYPGLQKLY NFKFKHTKSM DMGIRYTAID NNEVQVIDAW ATDGLLVSHK LKILEDDKAF  480
FPPYYAAPII RQDVLDKHPE LKDVLNKLAN QISLEEMQKL NYKVDGEGQD PAKVAKEFLK  540
EKGLILQVDE QKLISEEDLN                                             560

SEQ ID NO: 186              moltype = AA  length = 608
FEATURE                     Location/Qualifiers
source                      1..608
                            mol_type = protein
                            organism = synthetic construct
SEQUENCE: 186
METDTLLLWV LLLWVPGSTG DRSANDTVVV GSIIFTEGII VANMVAEMIE AHTDLKVVRK   60
LNLGGVNVNF EAIKRGGANN GIDIYVEYTG HGLVDILGFP EPNVYITADK QKNGIKANFK  120
IRHNVEDGSV QLADHYQQNT PIGDGPVLLP DNHYLSTQSV LSKDPNEKRD HMVLLEFVTA  180
AGITLGMDEL YKGGTGGSMS KGEELFTGVV PILVELDGDV NGHKFSVRGE GEGDATNGKL  240
TLKFICTTGK LPVPWPTLVT TLTYGVQCFS RYPDHMKQHD FFKSAMPEGY VQERTISFKD  300
DGTYKTRAEV KFEGDTLVNR IELKGIDFKE DGNILGHKLE YNFPPPATTD PEGAYETVKK  360
EYKRKWNIVW LKPLGFNNTY TLTVKDELAK QYNLKTFSDL AKISDKLILG ATMFFLEGPD  420
GYPGLQKLYN FKFKHTKSMD MGIRYTAIDN NEVQVIDAWA TDGLLVSHKL KILEDDKAFF  480
PPYYAAPIIR QDVLDKHPEL KDVLNKLANQ ISLEEMQKLN YKVDGEGQDP AKVAKEFLKE  540
KGLILQVDEQ KLISEEDLNA VGQDTQEVIV VPHSLPFKVV VISAILALVV LTIISLIILI  600
MLWQKKPR                                                          608

SEQ ID NO: 187              moltype = AA  length = 8
FEATURE                     Location/Qualifiers
source                      1..8
                            mol_type = protein
                            organism = synthetic construct
SEQUENCE: 187
PILVSHNV                                                            8

SEQ ID NO: 188              moltype = AA  length = 8
FEATURE                     Location/Qualifiers
source                      1..8
                            mol_type = protein
                            organism = synthetic construct
SEQUENCE: 188
PILGYHNV                                                            8

SEQ ID NO: 189              moltype = AA  length = 8
FEATURE                     Location/Qualifiers
source                      1..8
                            mol_type = protein
                            organism = synthetic construct
SEQUENCE: 189
YNFNNPLN                                                            8
```

```
SEQ ID NO: 190          moltype = AA   length = 8
FEATURE                 Location/Qualifiers
source                  1..8
                        mol_type = protein
                        organism = synthetic construct
SEQUENCE: 190
YNFNEQLN                                                                  8

SEQ ID NO: 191          moltype = AA   length = 5
FEATURE                 Location/Qualifiers
source                  1..5
                        mol_type = protein
                        organism = synthetic construct
SEQUENCE: 191
SHNVY                                                                     5

SEQ ID NO: 192          moltype = AA   length = 5
FEATURE                 Location/Qualifiers
source                  1..5
                        mol_type = protein
                        organism = synthetic construct
SEQUENCE: 192
LAQVR                                                                     5

SEQ ID NO: 193          moltype = AA   length = 5
FEATURE                 Location/Qualifiers
source                  1..5
                        mol_type = protein
                        organism = synthetic construct
SEQUENCE: 193
SFGFP                                                                     5

SEQ ID NO: 194          moltype = AA   length = 5
FEATURE                 Location/Qualifiers
source                  1..5
                        mol_type = protein
                        organism = synthetic construct
SEQUENCE: 194
SVLAP                                                                     5

SEQ ID NO: 195          moltype = AA   length = 5
FEATURE                 Location/Qualifiers
source                  1..5
                        mol_type = protein
                        organism = synthetic construct
SEQUENCE: 195
ANLAP                                                                     5

SEQ ID NO: 196          moltype = AA   length = 7
FEATURE                 Location/Qualifiers
VARIANT                 2
                        note = any amino acid
source                  1..7
                        mol_type = protein
                        organism = synthetic construct
SEQUENCE: 196
PXSHNVY                                                                   7

SEQ ID NO: 197          moltype = AA   length = 6
FEATURE                 Location/Qualifiers
source                  1..6
                        mol_type = protein
                        organism = synthetic construct
SEQUENCE: 197
HHHHHH                                                                    6
```

What is claimed is:

1. A recombinant peptide biosensor comprising an analyte-binding framework portion and a signaling portion, wherein the signaling portion is present within the framework portion at a site or amino acid position that undergoes a conformational change upon interaction of the framework portion with a defined, specific, or selected analyte, wherein the recombinant peptide biosensor comprises a amino acid sequence having at least 85% sequence identity to SEQ ID NO: 179.

2. The recombinant peptide biosensor of claim 1, wherein the recombinant peptide biosensor comprises an amino acid sequence having at least 90% sequence identity to SEQ ID NO:179.

3. The recombinant peptide biosensor of claim 1, wherein the recombinant peptide biosensor comprises an amino acid sequence having at least 95% sequence identity to SEQ ID NO:179.

4. The recombinant peptide biosensor of claim 1, wherein the recombinant peptide biosensor comprises an amino acid sequence having at least 99% sequence identity to SEQ ID NO:179.

5. The recombinant peptide biosensor of claim 1, wherein the recombinant peptide biosensor comprises the amino acid sequence of SEQ ID NO:179.

6. The recombinant peptide biosensor of claim 1, wherein signaling by the signaling portion detectably increases upon interaction of the framework portion with the analyte.

7. The recombinant peptide biosensor of claim 1, wherein signaling by the signaling portion detectably decreases upon interaction of the framework portion with the analyte.

8. The recombinant peptide biosensor of claim 1, wherein signaling by the signaling portion is proportional to the level of interaction between the framework portion and the analyte.

9. The recombinant peptide biosensor of claim 1, wherein the framework portion is a periplasmic binding protein (PBP) or a variant of a PBP.

10. The recombinant peptide biosensor of claim 1, wherein the signaling portion is a circularly permuted super fluorescent (SF) protein.

11. The recombinant peptide biosensor of claim 10, wherein the SF protein is selected from the group consisting of a green fluorescent protein, a yellow fluorescent protein, a red fluorescent protein, and a blue fluorescent protein.

12. The recombinant peptide biosensor of claim 1, wherein the analyte-binding framework portion binds specifically to glutamate.

13. The recombinant peptide biosensor of claim 1, comprising 10 or fewer conservative amino acid substitutions.

14. A nucleic acid encoding the recombinant peptide biosensor of claim 1.

15. A vector comprising the nucleic acid of claim 14.

16. A cell comprising the nucleic acid of claim 14.

17. A cell comprising the vector of claim 15.

18. A kit comprising the recombinant peptide biosensor of claim 1, the nucleic acid of claim 14, the vector of claim 15, or the cell of claim 16 or claim 17.

19. A recombinant peptide biosensor comprising an analyte-binding framework portion and a signaling portion, wherein the signaling portion is present within the framework portion at a site or amino acid position that undergoes a conformational change upon interaction of the framework portion with a defined, specific, or selected analyte, wherein the recombinant peptide biosensor comprises an amino acid sequence having at least 85% sequence identity to SEQ ID NO: 180.

20. The recombinant peptide biosensor of claim 19, wherein the recombinant peptide biosensor comprises an amino acid sequence having at least 90% sequence identity to SEQ ID NO:180.

21. The recombinant peptide biosensor of claim 19, wherein the recombinant peptide biosensor comprises an amino acid sequence having at least 95% sequence identity to SEQ ID NO:180.

22. The recombinant peptide biosensor of claim 19, wherein the recombinant peptide biosensor comprises an amino acid sequence having at least 99% sequence identity to SEQ ID NO:180.

23. The recombinant peptide biosensor of claim 19, wherein the recombinant peptide biosensor comprises the amino acid sequence of SEQ ID NO:180.

24. The recombinant peptide biosensor of claim 19, wherein signaling by the signaling portion detectably increases upon interaction of the framework portion with the analyte.

25. The recombinant peptide biosensor of claim 19, wherein signaling by the signaling portion detectably decreases upon interaction of the framework portion with the analyte.

26. The recombinant peptide biosensor of claim 19, wherein signaling by the signaling portion is proportional to the level of interaction between the framework portion and the analyte.

27. The recombinant peptide biosensor of claim 19, wherein the framework portion is a periplasmic binding protein (PBP) or a variant of a PBP.

28. The recombinant peptide biosensor of claim 19, wherein the signaling portion is a circularly permuted super fluorescent (SF) protein.

29. The recombinant peptide biosensor of claim 28, wherein the SF protein is selected from the group consisting of a green fluorescent protein, a yellow fluorescent protein, a red fluorescent protein, and a blue fluorescent protein.

30. The recombinant peptide biosensor of claim 19, wherein the analyte-binding framework portion binds specifically to glutamate.

31. The recombinant peptide biosensor of claim 19, comprising 10 or fewer conservative amino acid substitutions.

32. A nucleic acid encoding the recombinant peptide biosensor of claim 19.

33. A vector comprising the nucleic acid of claim 32.

34. A cell comprising the nucleic acid of claim 32.

35. A cell comprising the vector of claim 33.

36. A kit comprising the recombinant peptide biosensor of claim 19, the nucleic acid of claim 32, the vector of claim 33, or the cell of claim 34 or claim 35.

* * * * *